(12) United States Patent
Chobanian et al.

(10) Patent No.: US 10,059,667 B2
(45) Date of Patent: Aug. 28, 2018

(54) ANTIDIABETIC COMPOUNDS

(71) Applicants: MERCK SHARP & DOHME CORP., Rahway, NJ (US); Harry Chobanian, Kenilworth, NJ (US); Duane DeMong, Kenilworth, NJ (US); Yan Guo, Kenilworth, NJ (US); Zhiyong Hu, Kenilworth, NJ (US); Michael Miller, Kenilworth, NJ (US); Barbara Pio, Kenilworth, NJ (US); Christopher W. Plummer, Kenilworth, NJ (US); Dong Xiao, Kenilworth, NJ (US); Cangming Yang, Kenilworth, NJ (US); Rui Zhang, Kenilworth, NJ (US)

(72) Inventors: Harry Chobanian, Aberdeen, NJ (US); Duane DeMong, Somerset, NJ (US); Yan Guo, Westfield, NJ (US); Zhiyong Hu, Livingston, NJ (US); Michael Miller, Scotch Plains, NJ (US); Barbara Pio, West Orange, NJ (US); Christopher W. Plummer, Hoboken, NJ (US); Dong Xiao, Warren, NJ (US); Cangming Yang, South River, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/110,894

(22) PCT Filed: Feb. 3, 2015

(86) PCT No.: PCT/US2015/014153
§ 371 (c)(1),
(2) Date: Jul. 11, 2016

(87) PCT Pub. No.: WO2015/119899
PCT Pub. Date: Aug. 13, 2015

(65) Prior Publication Data
US 2016/0332968 A1 Nov. 17, 2016

Related U.S. Application Data

(60) Provisional application No. 61/936,597, filed on Feb. 6, 2014.

(51) Int. Cl.
*C07D 211/42* (2006.01)
*A61K 45/06* (2006.01)
(Continued)

(52) U.S. Cl.
CPC .......... *C07D 211/42* (2013.01); *A61K 31/366* (2013.01); *A61K 31/397* (2013.01); *A61K 31/40* (2013.01); *A61K 31/44* (2013.01); *A61K 31/4985* (2013.01); *A61K 45/06* (2013.01); *C07C 59/72* (2013.01); *C07C 217/52* (2013.01); *C07D 205/04* (2013.01); *C07D 205/12* (2013.01); *C07D 207/08* (2013.01); *C07D 207/10* (2013.01); *C07D 207/12* (2013.01); *C07D 209/52* (2013.01); *C07D 209/54* (2013.01); *C07D 211/22* (2013.01); *C07D 213/30* (2013.01); *C07D 213/64* (2013.01); *C07D 213/647* (2013.01); *C07D 213/65* (2013.01); *C07D 213/69* (2013.01); *C07D 231/20* (2013.01); *C07D 239/52* (2013.01); *C07D 265/30* (2013.01); *C07D 307/86* (2013.01); *C07D 307/88* (2013.01); *C07D 401/04* (2013.01); *C07D 491/056* (2013.01); *C07C 2601/02* (2017.05);
(Continued)

(58) Field of Classification Search
CPC .... C07D 211/42; C07D 59/72; C07D 217/52; C07D 205/04; C07D 205/12; C07D 207/08; C07D 207/10; C07D 207/12; A61K 31/366; A61K 31/397; A61K 31/40; A61K 31/44; A61K 31/4985; A61K 45/06
USPC ...................................................... 514/210.2
See application file for complete search history.

(56) References Cited

U.S. PATENT DOCUMENTS

2006/0160851 A1 7/2006 Ebdrup et al.
2007/0213364 A1 9/2007 Yasuma et al.
(Continued)

FOREIGN PATENT DOCUMENTS

CN 103030646 A 4/2013
EP 1930320 A1 6/2008
(Continued)

OTHER PUBLICATIONS

Brown S. P. et al., Discovery of AM-1638: A Potent and Orally Bioavailable GPR40/FFA1 Full Agonist, American Chemical Society, 2012, p. 726-730, vol. 3.
(Continued)

*Primary Examiner* — Yevgeny Valenrod
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

11 Claims, No Drawings

(51) Int. Cl.

| | | |
|---|---|---|
| A61K 31/366 | (2006.01) | |
| A61K 31/397 | (2006.01) | |
| A61K 31/40 | (2006.01) | |
| A61K 31/44 | (2006.01) | |
| C07D 231/20 | (2006.01) | |
| A61K 31/4985 | (2006.01) | |
| C07D 401/04 | (2006.01) | |
| C07D 239/52 | (2006.01) | |
| C07C 217/52 | (2006.01) | |
| C07D 205/04 | (2006.01) | |
| C07D 491/056 | (2006.01) | |
| C07D 265/30 | (2006.01) | |
| C07D 207/08 | (2006.01) | |
| C07D 207/10 | (2006.01) | |
| C07D 207/12 | (2006.01) | |
| C07D 209/52 | (2006.01) | |
| C07D 209/54 | (2006.01) | |
| C07D 211/22 | (2006.01) | |
| C07D 213/30 | (2006.01) | |
| C07D 213/64 | (2006.01) | |
| C07D 213/65 | (2006.01) | |
| C07D 213/69 | (2006.01) | |
| C07D 307/86 | (2006.01) | |
| C07D 307/88 | (2006.01) | |
| C07C 59/72 | (2006.01) | |
| C07D 205/12 | (2006.01) | |
| C07D 213/647 | (2006.01) | |

(52) U.S. Cl.
CPC ...... *C07C 2601/04* (2017.05); *C07C 2601/08* (2017.05); *C07C 2601/10* (2017.05)

(56) References Cited

U.S. PATENT DOCUMENTS

| | | |
|---|---|---|
| 2007/0265332 A1 | 11/2007 | Ge et al. |
| 2009/0186894 A1 | 7/2009 | Singh et al. |
| 2009/0275598 A1 | 11/2009 | Akerman et al. |
| 2012/0004187 A1 | 1/2012 | Keil et al. |
| 2013/0172248 A1 | 7/2013 | Defossa et al. |
| 2013/0252937 A1 | 9/2013 | Eckhardt et al. |
| 2016/0115128 A1* | 4/2016 | Aida ................ C07D 401/14 514/210.2 |

FOREIGN PATENT DOCUMENTS

| | | |
|---|---|---|
| EP | 1939189 A1 | 7/2008 |
| GB | 2498976 A | 7/2013 |
| WO | WO2004022551 A1 | 3/2004 |
| WO | WO2004041266 A1 | 5/2004 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006127503 A2 | 11/2006 |
| WO | WO2007033002 A1 | 3/2007 |
| WO | WO2007106469 A2 | 9/2007 |
| WO | WO2007123225 A1 | 11/2007 |
| WO | WO2007131619 A1 | 11/2007 |
| WO | WO2007131620 A1 | 11/2007 |
| WO | WO2007131621 A1 | 11/2007 |
| WO | WO2007131622 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030520 A1 | 3/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2008139987 A1 | 11/2008 |
| WO | WO2009038204 A1 | 3/2009 |
| WO | WO2009039942 A1 | 4/2009 |
| WO | WO2009039943 A1 | 4/2009 |
| WO | WO2009048527 A1 | 4/2009 |
| WO | WO2009054390 A1 | 4/2009 |
| WO | WO2009054423 A1 | 4/2009 |
| WO | WO2009054479 A1 | 4/2009 |
| WO | WO2009058237 A1 | 5/2009 |
| WO | WO2009111056 A1 | 9/2009 |
| WO | WO2010025424 A1 | 3/2010 |
| WO | WO2010045258 A2 | 4/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010123016 A1 | 10/2010 |
| WO | WO2010123017 A1 | 10/2010 |
| WO | WO2010143733 A1 | 12/2010 |
| WO | WO2011052756 A1 | 5/2011 |
| WO | WO2011066183 A1 | 6/2011 |
| WO | WO2012011125 A1 | 1/2012 |
| WO | WO2015020184 A1 | 2/2012 |
| WO | WO2012030566 A2 | 3/2012 |
| WO | WO02012046869 A1 | 4/2012 |
| WO | WO2012072691 A1 | 6/2012 |
| WO | WO2013025424 A1 | 2/2013 |
| WO | WO2013122028 A1 | 8/2013 |
| WO | WO2013122029 A1 | 8/2013 |
| WO | WO2013128378 A1 | 9/2013 |
| WO | WO2015119899 A1 | 8/2015 |

OTHER PUBLICATIONS

Houze, J. B. et al., 265—AMG 837: A potent, orally bioavailable, partial allosteric agonist of GPR40, MEDI, 2012, p. 1, Abstracts of Papers, 243rd ACS National Meeting & Exposition, San Diego, CA, Mar. 25-29, 2012.

Houze, J. B. et al., AMG 837: A potent, orally bioavailable GPR40 agonist, Bioorganic & Medicinal Chemistry Letters, 2012, p. 1267-1270, vol. 22.

International Search Report for PCT/US2015/014153 dated Apr. 21, 2015, 10 pages.

Lin, D. C. H. et al., Identification and Pharmacological Characterization of Multiple Allosteric Binding Sites on the Tree Fatty Acid 1 Receptor, Molecular Pharmacology, 2012, p. 843-859, vol. 82, No. 5.

Lin, D. D. H. et al., AMG 837: A Novel GPR40/FFA1 Agonist that Enhances Insulin Secretion and Lowers Glucose Levels in Rodents, PLoS ONE, 2011, p. 1-10, vol. 6, No. 11.

Luo, J. et al., A Potent Class of GPR40 Full Agonist Engages the EnteroInsular Axis to Promote Glucose Control in Rodents, PLOS ONE, 2012, p. 6-12, vol. 7, Issue 10.

Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.

Walsh S. P. et al., 3-Substituted 3-(4-aryloxyaryl)-propanoic acids as GPR40 agonists, Bioorganic & Medicinal Chemistry Letters, 2011, p. 3390-3394, vol. 21.

Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25.

Zhou, C. et al., Discovery of 5-aryloxy-2,4-thiazolidinediones as potent GPR40 agonists, Bioorganic & Medicinal Chemistry Letters, 2010, p. 1298-1301, vol. 20.

\* cited by examiner

ANTIDIABETIC COMPOUNDS

CROSS-REFERENCE TO RELATED APPLICATIONS

This application is a U.S. National Phase application under 35 U.S.C. § 371 of PCT Application No. PCT/US15/014153, filed on Feb. 3, 2015, which claims priority from and the benefit of U.S. Patent Application Ser. No. 61/936,597, filed Feb. 6, 2014.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body, however patients with Type 2 diabetes have a resistance to the effects of insulin in stimulating glucose and lipid metabolism in the insulin-sensitive muscle, liver and adipose tissues. These patients often have normal levels of insulin, and may have hyperinsulinemia (elevated plasma insulin levels), as they compensate for the reduced effectiveness of insulin by secreting increased amounts of insulin. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have Metabolic Syndrome, which is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic (as defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670). Patients with Metabolic Syndrome have an increased risk of developing the macrovascular and microvascular complications that occur with Type 2 diabetes, such as atherosclerosis and coronary heart disease.

There are several available treatments for Type 2 diabetes. Physical exercise and a reduction in dietary intake of calories often dramatically improve the diabetic condition and are the usual recommended first-line treatment of Type 2 diabetes and of pre-diabetic conditions associated with insulin resistance, however compliance with this treatment is generally very poor. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); and (5) inhibitors of incretin hormone degradation (DPP-4 inhibitors, such as sitagliptin, alogliptin, vildagliptin, linagliptin, denagliptin and saxagliptin).

The biguanides are a class of drugs that are widely used to treat Type 2 diabetes. The two best known biguanides, phenformin and metformin, cause some correction of hyperglycemia, but can induce lactic acidosis and nausea/diarrhea. Metformin has a lower risk of side effects than phenformin and is widely prescribed for the treatment of Type 2 diabetes.

The glitazones (e.g. 5-benzylthiazolidine-2,4-diones) can ameliorate hyperglycemia and other symptoms of Type 2 diabetes. Glitazones, such as rosiglitazone and pioglitazone, are peroxisome proliferator activated receptor (PPAR) gamma subtype agonists, and are modestly effective in reducing plasma glucose and HemoglobinA1C. The currently marketed compounds do not greatly improve lipid metabolism and may actually have a negative effect on the lipid profile.

Another widely used drug treatment involves the administration of insulin secretagogues, such as the sulfonylureas (e.g. tolbutamide, glipizide, and glimepiride). Sulfonylureas and related insulin secretagogues act by blocking the ATP-dependent K+ channel in β-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled.

Dipeptidyl peptidase IV (DPP-4) inhibitors (e.g., sitagliptin, alogliptin, vildagliptin, linagliptin, denagliptin and saxagliptin) provide a route to increase insulin secretion in response to food consumption.

Studies with DPP-4(−/−)-deficient mice and clinical trials with DPP-4 inhibitors indicate that DPP-4 inhibition increases the steady state concentrations of GLP-1 and GIP, resulting in improved glucose tolerance. As a result DPP-4 inhibitors have utility in the treatment of Type 2 diabetes, as well as numerous conditions that often accompany Type 2 diabetes, including Metabolic Syndrome, reactive hypoglycemia, and diabetic dyslipidemia.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., Nature, 422: 173 (2003); Briscoe, C. P. et al., J. Biol. Chem., 278: 11303 (2003); Kotarsky, K. et al., Biochem. Biophys. Res. Comm., 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight.

There is a need for potent GPR40 agonists that have pharmacokinetic and pharmacodynamic properties suitable for use as human pharmaceuticals.

G-protein-coupled receptor 40 (GPR40) agonists are disclosed in: WO 2004/022551, WO 2004/041266, WO 2005/051373, WO 2005/051890, WO 2005/063729, WO 2005/086661, WO 2005/087710, WO 2006/038738, WO 2006/083612, WO 2006/083781, WO 2006/127503, WO 2007/033002, WO 2007/101368, WO 2007/106469, WO 2007/123225, WO 2007/131619, WO 2007/131620, WO 2007/131621, WO 2007/131622, WO 2007/136572, WO 2007/136573, WO 2007/213364, WO 2008/001931, WO 2008/030520, WO 2008/030618, WO 2008/054674, WO 2008/054675, WO 2008/058237; WO 2008/066097, WO 2008/130514, WO 2008/139987, WO 2009/038204, WO 2009/039942, WO 2009/039943, WO 2009/048527, WO 2009/054390, WO 2009/054423, WO 2009/054479, WO 2009/058237, WO 2009/111056, WO 2010/025424, WO 2010/045258, WO 2010/085522, WO 2010/085525, WO 2010/085528, WO 2010/085528, WO 2010/091176, WO 2010/091176, WO 2010/123016, WO 2010/123017, WO 2010/143733, WO 2011/052756, WO 2011/066183, WO 2012/011125, WO 2012/030566, WO 2012/046869, WO 2012/072691, WO 2013/025424, WO 2013/104267, US 2007/0265332, US 2013/0252937, WO 2013/122028, WO 2013/122029, WO 2013/128378, US2013/0172248, CN 2013/103012343A, CN 2013/103145663A, CN 2012/10300982.7, CN 103030646 and GB 2498976.

GPR40 agonists are also disclosed in Walsh et al., Bioorganic & Medicinal Chemistry Letters (2011), 21(11), 3390-3394; Zhou et al., Bioorganic & Medicinal Chemistry Letters (2010), 20(3), 1298-1301; Tan et al., Diabetes (2008), 57(8), 2211-2219; Houze et al., Bioorganic & Medicinal Chemistry Letters (2012), 22(2), 1267-1270; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; and Houze et al., Abstracts of Papers, 243rd ACS National Meeting & Exposition, San Diego, Calif., USA Mar. 25-29, 2012, MEDI-265.

SUMMARY OF THE INVENTION

The present invention relates to novel substituted compounds of structural formula I:

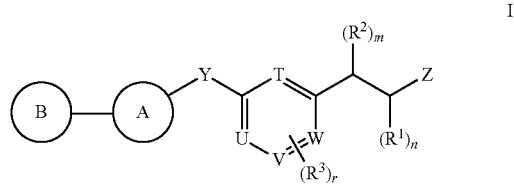

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

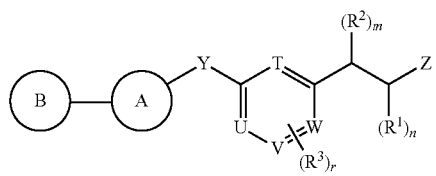

or a pharmaceutically acceptable salt thereof; wherein
A is selected from the group consisting of:
   (1) —$C_{3-9}$cycloalkyl,
   (2) —$C_{3-9}$cycloalkenyl,
   (3) —$C_{2-10}$cycloheteroalkyl, and
   (4) —$C_{2-10}$cycloheteroalkenyl,
wherein each cycloalkyl, cycloalkenyl, cycloheteroalkyl and cycloheteroalkenyl is unsubstituted or substituted with one, two or three substituents selected from $R^a$;
B is selected from the group consisting of:
   (1) —$(CH_2)_u$-aryl,
   (2) —$(CH_2)_u$-heteroaryl,
   (3) —$(CH_2)_u$-aryl-aryl,
   (4) —$(CH_2)_u$—$N(R^g)$—$(CH_2)_u$-aryl,
   (5) —$(CH_2)_u$—$N(R^g)$—$(CH_2)_u$-heteroaryl,
   (6) —$(CH_2)_u$—O—$(CH_2)_u$-aryl,
   (7) —$(CH_2)_u$—O—$(CH_2)_u$-aryl-aryl,
   (8) —$(CH_2)_u$—O—$(CH_2)_u$-heteroaryl,
   (9) —$(CH_2)_u$—$C_{3-6}$cycloalkyl,
   (10) —$(CH_2)_u$—O—$(CH_2)_u$—$C_{3-6}$cycloalkyl,
   (11) —$(CH_2)_u$—$C_{2-6}$cycloheteroalkyl, and
   (12) —$(CH_2)_u$—O—$(CH_2)_u$—$C_{2-6}$cycloheteroalkyl,
wherein each $CH_2$, cycloalkyl, cycloheteroalkyl, aryl and heteroaryl is unsubstituted or substituted with one, two, three, four or five substituents selected from $R^b$;
T is selected from the group consisting of:
   (1) CH,
   (2) N, and
   (3) N-oxide;
U is selected from the group consisting of:
   (1) CH,
   (2) N, and
   (3) N-oxide;
V is selected from the group consisting of:
   (1) CH,
   (2) N, and
   (3) N-oxide;
W is selected from the group consisting of:
   (1) CH,
   (2) N, and
   (3) N-oxide,
provided that no more than three of T, U, V and W are selected from N and N-oxide;
Y is selected from the group consisting of:
   (1) —$(CH_2)_x$O—,
   (2) —O—$(CH_2)_x$—,
   (3) —$(CH_2)_x$—$NR^f$—,
   (4) —$(CH_2)_x$—S—,
   (5) —$(CH_2)_x$—$CH_2$—,
   (6) —$(CH_2)_x$—C(O)—,
   (7) —$(CH_2)_x$—$CF_2$—, and
   (8) —$CF_2$—$(CH_2)_x$—,
wherein $CH_2$ is unsubstituted or substituted with one or two substituents selected from $R^i$;
Z is selected from the group consisting of:
   (1) —$C_{0-6}$alkyl-$CO_2H$,
   (2) —$C_{0-6}$alkyl-$CO_2R^j$,
   (3) —$C_{0-6}$alkyl-C(O)$NHR^h$,
   (4) —$C_{0-6}$alkyl-C(O)$NHSO_2R^h$,
   (5) —$C_{0-6}$alkyl-$SO_2NHC(O)R^h$,
   (6) —$C_{0-6}$alkyl-heteroaryl, and
   (7) —$C_{0-6}$alkyl-cycloheteroalkyl, wherein cycloheteroalkyl is selected from the group consisting of:

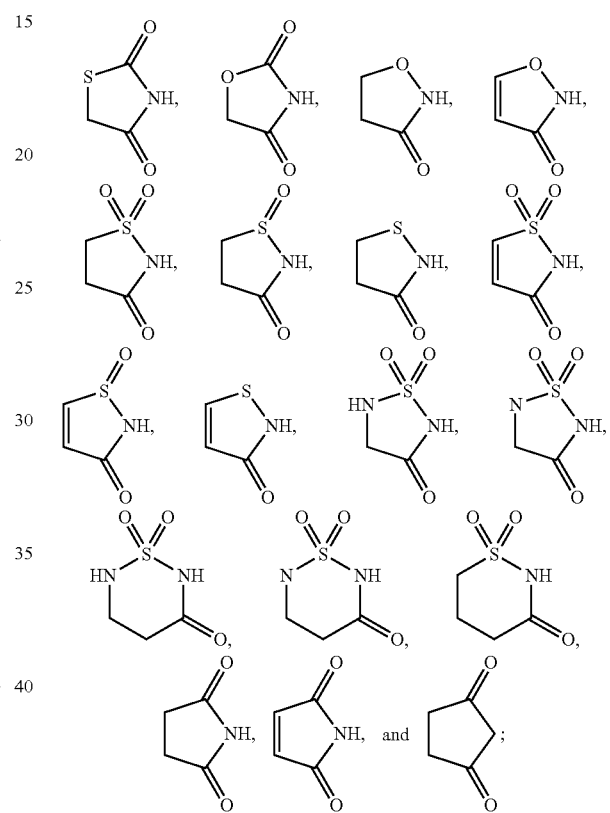

wherein each alkyl, cycloheteroalkyl and heteroaryl is unsubstituted or substituted with one to five substituents selected from $C_{1-6}$alkyl;
each $R^1$ is independently selected from the group consisting of:
   (1) hydrogen,
   (2) halogen,
   (3) —$(CH_2)_s$—$OC_{1-6}$alkyl,
   (4) —$(CH_2)_s$—OH,
   (5) —CN, and
   (6) —$C_{1-6}$alkyl,
wherein $CH_2$ and alkyl are unsubstituted or substituted with one, two or three halogens; each $R^2$ is independently selected from the group consisting of:
   (1) hydrogen,
   (2) —$(CH_2)_s$—O—$C_{1-6}$alkyl,
   (3) —$C_{1-6}$alkyl,
   (4) —$C_{3-6}$cycloalkyl, and
   (5) —$C_{2-4}$cycloheteroalkyl,
wherein each $CH_2$, alkyl, cycloalkyl and cycloheteroalkyl is unsubstituted or substituted with one, two or three substituents selected from halogen, OH, —$C_{1-6}$alkyl and —$OC_{1-6}$alkyl;

each $R^3$ is independently selected from the group consisting of:
- (1) hydrogen,
- (2) halogen,
- (3) $-(CH_2)_s-OC_{1-6}$alkyl,
- (4) $-(CH_2)_s-OH$,
- (5) $-CN$, and
- (6) $-C_{1-6}$alkyl, wherein $CH_2$ and alkyl are unsubstituted or substituted with one, two or three substituents selected from halogen, OH, and $OC_{1-6}$alkyl;

each $R^a$ is independently selected from the group consisting of:
- (1) $-C_{1-6}$alkyl,
- (2) halogen,
- (3) $-(CH_2)_u-OC_{1-6}$alkyl,
- (1) $-OR^e$,
- (2) $-S(O)_uR^e$,
- (3) $-S(O)_uNR^cR^d$,
- (4) $-N(R^c)S(O)_pR^e$,
- (5) $-NR^cR^d$,
- (6) $-C(O)R^e$,
- (7) $-OC(O)R^e$,
- (8) $-CO_2R^e$,
- (9) $-N(R^c)C(O)R^e$,
- (10) $-N(R^c)C(O)OR^e$,
- (11) $-N(R^c)C(O)NR^cR^d$,
- (12) $-C(O)NR^cR^d$,
- (13) $-CN$,
- (14) $-CF_3$,
- (15) $-OCF_3$,
- (16) $-OCHF_2$,
- (17) $-(CH_2)_r$aryl,
- (18) $-(CH_2)_r$heteroaryl,
- (19) $-(CH_2)_r-C_{3-6}$cycloalkyl,
- (20) $-(CH_2)_r-C_{3-6}$cycloalkenyl,
- (21) $-(CH_2)_r-C_{2-5}$cycloheteroalkyl, and
- (22) $-(CH_2)_r-O-(CH_2)_r-C_{3-6}$cycloalkyl, wherein each $CH_2$, alkyl, cycloalkyl, cycloalkenyl, cycloheteroalkyl, aryl and heteroaryl is unsubstituted or substituted with one to four substituents selected from: halogen, $-C_{1-6}$alkyl, $-(CH_2)_w-OH$, $-O-C_{1-6}$alkyl, $-CF_3$, $-CN$, $-(CH_2)_v-C_{3-6}$cycloalkyl, SH, and $-SO_2-C_{1-6}$alkyl;

each $R^b$ is independently selected from the group consisting of:
- (1) $-C_{1-10}$alkyl,
- (2) $-C_{2-10}$alkenyl,
- (3) $-(CH_2)_v-CF_3$,
- (4) $-O(CH_2)_vCF_3$,
- (5) $-OCHF_2$,
- (6) $-S(CH_2)_vCF_3$,
- (7) $-(CH_2)_vSC_{1-10}$alkyl,
- (8) halogen,
- (9) oxo,
- (10) $-(CH_2)_vCN$,
- (11) $-(CH_2)_vOH$,
- (12) $-(CH_2)_vOC_{1-10}$alkyl,
- (13) $-(CH_2)_vOC_{2-10}$alkenyl,
- (14) $-O-(CH_2)_vOC_{1-10}$alkyl,
- (15) $-(CH_2)_v-O-(CH_2)_vC_{3-6}$cycloalkyl,
- (16) $-(CH_2)_v-O-(CH_2)_vC_{2-10}$cycloheteroalkyl,
- (17) $-(CH_2)_v-O-(CH_2)_v$-aryl,
- (18) $-(CH_2)_v-O-(CH_2)_v$-heteroaryl,
- (19) $-(CH_2)_v\ O(CH_2)_vN(R^c)S(O)_qR^e$,
- (20) $-(CH_2)_v\ O(CH_2)_vS(O)_qR^e$,
- (21) $-(CH_2)_v\ O(CH_2)_vS(O)_qNR^cR^d$,
- (22) $-(CH_2)_v\ O(CH_2)_vNR^cR^d$,
- (23) $-C(O)R^e$,
- (24) $-OC(O)R^e$,
- (25) $-CO_2R^e$,
- (26) $-C(O)NR^cR^d$,
- (27) $-N(R^c)C(O)R^e$,
- (28) $-N(R^c)C(O)OR^e$,
- (29) $-N(R^c)C(O)NR^cR^d$,
- (30) $-N(R^c)S(O)_qR^e$,
- (31) $-S(O)_qR^e$,
- (32) $-S(O)_qNR^cR^d$,
- (33) $-NR^cR^d$,
- (34) $-O(CH_2)_vO-C_{3-6}$cycloalkyl,
- (35) $-O(CH_2)_vO-C_{2-5}$cycloheteroalkyl,
- (36) $-O(CH_2)_vO$-aryl,
- (37) $-O(CH_2)_vO$-heteroaryl,
- (38) $-(CH_2)_vC_{3-6}$cycloalkyl,
- (39) $-(CH_2)_vC_{2-10}$cycloheteroalkyl,
- (40) $-(CH_2)_v$-aryl, and
- (41) $-(CH_2)_v$-heteroaryl, wherein each CH, $CH_2$, alkyl, alkenyl, cycloalkyl, cycloheteroalkyl, aryl and heteroaryl is unsubstituted or substituted with one, two or three substituents selected from: halogen, $-C_{1-6}$alkyl, $-(CH_2)_w-OH$, $-O-C_{1-6}$alkyl, $-CF_3$, $-CN$, $-(CH_2)_v-C_{3-6}$cycloalkyl, SH, and $-SO_2-C_{1-6}$alkyl;

each $R^c$ is independently selected from the group consisting of:
- (1) hydrogen,
- (2) $C_{1-10}$alkyl,
- (3) $C_{3-6}$cycloalkyl,
- (4) $C_{2-5}$ cycloheteroalkyl,
- (5) aryl, and
- (6) heteroaryl, wherein each alkyl, cycloalkyl, cycloheteroalkyl, aryl and heteroaryl is unsubstituted or substituted with one to three substituents selected from $C_{1-6}$alkyl;

each $R^d$ is independently selected from the group consisting of:
- (1) hydrogen,
- (2) $C_{1-10}$alkyl,
- (3) $C_{3-6}$cycloalkyl,
- (4) $C_{2-5}$ cycloheteroalkyl,
- (5) aryl, and
- (6) heteroaryl, wherein each alkyl, cycloalkyl, cycloheteroalkyl, aryl and heteroaryl is unsubstituted or substituted with one to three substituents selected from $C_{1-6}$alkyl;

each $R^e$ is independently selected from the group consisting of:
- (1) hydrogen,
- (2) $C_{1-10}$alkyl,
- (3) $C_{3-6}$cycloalkyl,
- (4) $C_{2-5}$ cycloheteroalkyl,
- (5) aryl, and
- (6) heteroaryl, wherein each alkyl, cycloalkyl, cycloheteroalkyl, aryl and heteroaryl is unsubstituted or substituted with one to three substituents selected from $C_{1-6}$alkyl;

each $R^f$ is independently selected from the group consisting of:
- (1) hydrogen,
- (2) $C_{1-6}$alkyl, and
- (3) $C_{3-6}$cycloalkyl;

each $R^g$ is independently selected from the group consisting of:
(1) hydrogen,
(2) halogen,
(3) $C_{1-6}$alkyl, and
(4) $C_{3-6}$cycloalkyl;
each $R^h$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) $C_{3-6}$ cycloalkyl-$C_{1-10}$alkyl-,
(6) —$C_{2-5}$cycloheteroalkyl,
(7) $C_{2-5}$ cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-,
wherein alkyl, alkenyl, cycloalkyl, cycloheteroalkyl, aryl and heteroaryl are unsubstituted or substituted with one to four substituents selected from $C_{1-6}$alkyl;
each $R^1$ is independently selected from the group consisting of:
(1) hydrogen,
(2) halogen,
(3) —$C_{1-6}$alkyl,
(4) —$(CH_2)_s$—O—$C_{1-6}$alkyl,
(5) —$(CH_2)_s$OH,
(6) —$N(R^c)S(O)_2R^e$,
(7) —$S(C_{1-6}$alkyl),
(8) —$(CH_2)_sSO_2C_{1-6}$alkyl,
(9) —$(CH_2)_sSO_2$—$(CH_2)_t$—$C_{3-6}$cycloalkyl,
(10) —$S(O)_2NR^cR^d$,
(11) —$NR^cR^d$,
(12) —$C(O)R^e$,
(13) —$OC(O)R^e$,
(14) —$CO_2R^e$,
(15) —$(CH_2)_sCN$,
(16) —$C(O)NR^cR^d$,
(17) —$N(R^c)C(O)R^e$,
(18) —$N(R^c)C(O)OR^e$,
(19) —$N(R^c)C(O)NR^cR^d$,
(20) —$CF_3$,
(21) —$OCF_3$,
(22) —$OCHF_2$,
(23) —$C_{3-6}$cycloalkyl, and
(24) —$C_{2-5}$ cycloheteroalkyl,
wherein each $CH_2$, alkyl, cycloalkyl and cycloheteroalkyl is unsubstituted or substituted with one, two, three or four substituents selected from: —$C_{1-6}$alkyl and halogen;
each $R^j$ is independently selected from the group consisting of:
(1) —$C_{1-6}$alkyl,
(2) —$C_{3-6}$cycloalkyl, and
(3) -aryl-$C_{1-6}$alkyl,
wherein each alkyl, cycloalkyl and aryl is unsubstituted or substituted with one to three substituents selected from $R^k$;
each $R^k$ is independently selected from the group consisting of:
(1) —$C_{1-6}$alkyl,
(2) —$OR^e$,
(3) —$N(R^c)S(O)_pR^e$,
(4) halogen,
(5) —$S(O)_pR^e$,
(6) —$S(O)_pNR^cR^d$,
(7) —$NR^cR^d$,
(8) —$C(O)R^e$,
(9) —$OC(O)R^e$,
(10) —$CO_2R^e$,
(11) —$CN$,
(12) —$C(O)NR^cR^d$,
(13) —$N(R^c)C(O)R^e$,
(14) —$N(R^c)C(O)OR^e$,
(15) —$N(R^c)C(O)NR^cR^d$,
(16) —$CF_3$,
(17) —$OCF_3$,
(18) —$OCHF_2$,
(19) —$C_{3-6}$cycloalkyl, and
(20) —$C_{2-5}$ cycloheteroalkyl;
n is independently selected from: 1 and 2;
m is independently selected from: 1 and 2;
each p is independently selected from: 0, 1 and 2;
each q is independently selected from: 0, 1 and 2;
each r is independently selected from: 1, 2, 3 and 4;
each s is independently selected from: 0, 1, 2 and 3;
each t is independently selected from: 0, 1, 2, 3 and 4;
each u is independently selected from: 0, 1, 2 and 3;
each v is independently selected from: 0, 1, 2, 3 and 4;
each w is independently selected from: 0, 1, 2 and 3; and
each x is independently selected from: 0, 1 and 2.

The present invention is also concerned with novel compounds of structural Formula I:

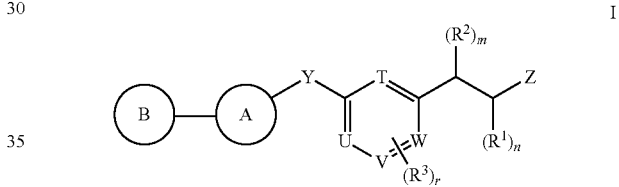

or a pharmaceutically acceptable salt thereof; wherein
A is selected from the group consisting of:
(1) —$C_{3-9}$cycloalkyl,
(2) —$C_{3-9}$cycloalkenyl,
(3) —$C_{2-10}$cycloheteroalkyl, and
(4) —$C_{2-10}$cycloheteroalkenyl,
wherein each cycloalkyl, cycloalkenyl, cycloheteroalkyl and cycloheteroalkenyl is unsubstituted or substituted with one, two or three substituents selected from $R^a$;
B is selected from the group consisting of:
(1) —$(CH_2)_u$-aryl,
(2) —$(CH_2)_u$-heteroaryl,
(3) —$(CH_2)_u$-aryl-aryl,
(4) —$(CH_2)_u$—$N(R^g)$—$(CH_2)_u$-aryl,
(5) —$(CH_2)_u$—$N(R^g)$—$(CH_2)_u$-heteroaryl,
(6) —$(CH_2)_u$—O—$(CH_2)_u$-aryl,
(7) —$(CH_2)_u$—O—$(CH_2)_u$-heteroaryl,
(8) —$(CH_2)_u$—$C_{3-6}$cycloalkyl,
(9) —$(CH_2)_u$—O—$(CH_2)_u$—$C_{3-6}$cycloalkyl,
(10) —$(CH_2)_u$—$C_{2-6}$cycloheteroalkyl, and
(11) —$(CH_2)_u$—O—$(CH_2)_u$—$C_{2-6}$cycloheteroalkyl,
wherein each $CH_2$, cycloalkyl, cycloheteroalkyl, aryl and heteroaryl is unsubstituted or substituted with one, two, three, four or five substituents selected from $R^b$;
T is selected from the group consisting of:
(1) CH,
(2) N, and
(3) N-oxide;

U is selected from the group consisting of:
 (1) CH,
 (2) N, and
 (3) N-oxide;
V is selected from the group consisting of:
 (1) CH,
 (2) N, and
 (3) N-oxide;
W is selected from the group consisting of:
 (1) CH,
 (2) N, and
 (3) N-oxide,
provided that no more than three of T, U, V and W are selected from N and N-oxide;
Y is selected from the group consisting of:
 (1) —(CH$_2$)$_x$O—,
 (2) —O—(CH$_2$)$_x$—,
 (3) —(CH$_2$)$_x$—NR$^f$—,
 (4) —(CH$_2$)$_x$—S—,
 (5) —(CH$_2$)$_x$—CH$_2$—,
 (6) —(CH$_2$)$_x$—C(O)—,
 (7) —(CH$_2$)$_x$—CF$_2$—, and
 (8) —CF$_2$—(CH$_2$)$_x$—,
wherein CH$_2$ is unsubstituted or substituted with one or two substituents selected from R$^i$;
Z is selected from the group consisting of:
 (1) —C$_{0-6}$alkyl-CO$_2$H,
 (2) —C$_{0-6}$alkyl-CO$_2$R$^j$,
 (3) —C$_{0-6}$alkyl-C(O)NHR$^h$,
 (4) —C$_{0-6}$alkyl-C(O)NHSO$_2$R$^h$,
 (5) —C$_{0-6}$alkyl-SO$_2$NHC(O)R$^h$,
 (6) —C$_{0-6}$alkyl-heteroaryl, and
 (7) —C$_{0-6}$alkyl-cycloheteroalkyl, wherein cycloheteroalkyl is selected from the group consisting of:

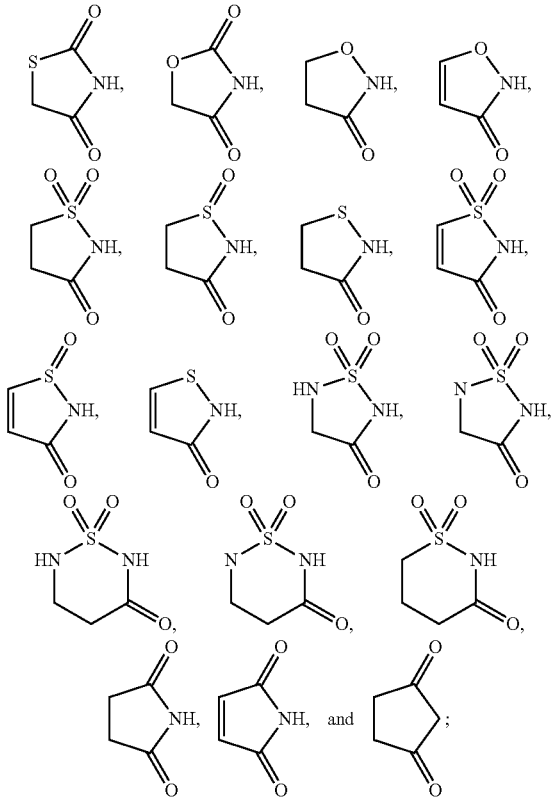

wherein each alkyl, cycloheteroalkyl and heteroaryl is unsubstituted or substituted with one to five substituents selected from C$_{1-6}$alkyl;
each R$^1$ is independently selected from the group consisting of:
 (1) hydrogen,
 (2) halogen,
 (3) —(CH$_2$)$_s$—OC$_{1-6}$alkyl,
 (4) —(CH$_2$)$_s$—OH,
 (5) —CN, and
 (6) —C$_{1-6}$alkyl,
wherein CH$_2$ and alkyl are unsubstituted or substituted with one, two or three halogens;
each R$^2$ is independently selected from the group consisting of:
 (1) hydrogen,
 (2) —(CH$_2$)$_s$—O—C$_{1-6}$alkyl,
 (3) —C$_{1-6}$alkyl,
 (4) —C$_{3-6}$cycloalkyl, and
 (5) —C$_{2-4}$cycloheteroalkyl,
wherein each CH$_2$, alkyl, cycloalkyl and cycloheteroalkyl is unsubstituted or substituted with one, two or three substituents selected from halogen, OH, —C$_{1-6}$alkyl and —OC$_{1-6}$alkyl;
each R$^3$ is independently selected from the group consisting of:
 (1) hydrogen,
 (2) halogen,
 (3) —(CH$_2$)$_s$—OC$_{1-6}$alkyl,
 (4) —(CH$_2$)$_s$—OH,
 (5) —CN, and
 (6) —C$_{1-6}$alkyl,
wherein CH$_2$ and alkyl are unsubstituted or substituted with one, two or three substituents selected from halogen, OH, and OC$_{1-6}$alkyl;
each R$^a$ is independently selected from the group consisting of:
 (1) —C$_{1-6}$alkyl,
 (2) halogen,
 (3) —(CH$_2$)$_u$—OC$_{1-6}$alkyl,
 (4) —OR$^e$,
 (5) —S(O)$_u$R$^e$,
 (6) —S(O)$_u$NR$^c$R$^d$,
 (7) —N(R$^c$)S(O)$_p$R$^e$,
 (8) —NR$^c$R$^d$,
 (9) —C(O)R$^e$,
 (10) —OC(O)R$^e$,
 (11) —CO$_2$R$^e$,
 (12) —N(R$^c$)C(O)R$^e$,
 (13) —N(R$^c$)C(O)OR$^e$,
 (14) —N(R$^c$)C(O)NR$^c$R$^d$,
 (15) —C(O)NR$^c$R$^d$,
 (16) —CN,
 (17) —CF$_3$,
 (18) —OCF$_3$,
 (19) —OCHF$_2$,
 (20) —(CH$_2$)$_r$aryl,
 (21) —(CH$_2$)$_r$heteroaryl,
 (22) —(CH$_2$)$_r$—C$_{3-6}$cycloalkyl,
 (23) —(CH$_2$)$_r$—C$_{3-6}$cycloalkenyl,
 (24) —(CH$_2$)$_r$—C$_{2-5}$cycloheteroalkyl, and
 (25) —(CH$_2$)$_r$—O—(CH$_2$)$_r$—C$_{3-6}$cycloalkyl,
wherein each CH$_2$, alkyl, cycloalkyl, cycloalkenyl, cycloheteroalkyl, aryl and heteroaryl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl;

each $R^b$ is independently selected from the group consisting of:
(1) —$C_{1-10}$alkyl,
(2) —$C_{2-10}$alkenyl,
(3) —$(CH_2)_v$—$CF_3$,
(4) —$O(CH_2)_vCF_3$,
(5) —$OCHF_2$,
(6) —$S(CH_2)_vCF_3$,
(7) —$(CH_2)_vSC_{1-10}$alkyl,
(8) halogen,
(9) —$(CH_2)_v$CN,
(10) —$(CH_2)_v$OH
(11) —$(CH_2)_v$$OC_{1-10}$alkyl,
(12) —$(CH_2)_v$$OC_{2-10}$alkenyl,
(13) —O—$(CH_2)_v$$OC_{1-10}$alkyl,
(14) —$(CH_2)_v$—O—$(CH_2)_v$$C_{3-6}$cycloalkyl,
(15) —$(CH_2)_v$—O—$(CH_2)_v$$C_{2-10}$cycloheteroalkyl,
(16) —$(CH_2)_v$—O—$(CH_2)_v$-aryl,
(17) —$(CH_2)_v$—O—$(CH_2)_v$-heteroaryl,
(18) —$(CH_2)_v$ $O(CH_2)_vN(R^c)S(O)_qR^e$,
(19) —$(CH_2)_v$ $O(CH_2)_vS(O)_qR^e$,
(20) —$(CH_2)_v$ $O(CH_2)_vS(O)_qNR^cR^d$,
(21) —$(CH_2)_v$ $O(CH_2)_vNR^cR^d$,
(22) —$C(O)R^e$,
(23) —$OC(O)R^e$,
(24) —$CO_2R^e$,
(25) —$C(O)NR^cR^d$,
(26) —$N(R^c)C(O)R^e$,
(27) —$N(R^c)C(O)OR^e$,
(28) —$N(R^c)C(O)NR^cR^d$,
(29) —$N(R^c)S(O)_qR^e$,
(30) —$S(O)_qR^e$,
(31) —$S(O)_qNR^cR^d$,
(32) —$NR^cR^d$,
(33) —$O(CH_2)_vO$—$C_{3-6}$cycloalkyl,
(34) —$O(CH_2)_vO$—$C_{2-5}$cycloheteroalkyl,
(35) —$O(CH_2)_vO$-aryl,
(36) —$O(CH_2)_vO$-heteroaryl,
(37) —$(CH_2)_vC_{3-6}$cycloalkyl,
(38) —$(CH_2)_vC_{2-10}$cycloheteroalkyl,
(39) —$(CH_2)_v$-aryl, and
(40) —$(CH_2)_v$-heteroaryl, wherein each CH, $CH_2$, alkyl, alkenyl, cycloalkyl, cycloheteroalkyl, aryl and heteroaryl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl;

each $R^c$ is independently selected from the group consisting of:
(1) hydrogen,
(2) $C_{1-10}$alkyl,
(3) $C_{3-6}$cycloalkyl,
(4) $C_{2-5}$ cycloheteroalkyl,
(5) aryl, and
(6) heteroaryl,
wherein each alkyl, cycloalkyl, cycloheteroalkyl, aryl and heteroaryl is unsubstituted or substituted with one to three substituents selected from $C_{1-6}$alkyl;

each $R^d$ is independently selected from the group consisting of:
(1) hydrogen,
(2) $C_{1-10}$alkyl,
(3) $C_{3-6}$cycloalkyl,
(4) $C_{2-5}$ cycloheteroalkyl,
(5) aryl, and
(6) heteroaryl,
wherein each alkyl, cycloalkyl, cycloheteroalkyl, aryl and heteroaryl is unsubstituted or substituted with one to three substituents selected from $C_{1-6}$alkyl;

each $R^e$ is independently selected from the group consisting of:
(1) hydrogen,
(2) $C_{1-10}$alkyl,
(3) $C_{3-6}$cycloalkyl,
(4) $C_{2-5}$ cycloheteroalkyl,
(5) aryl, and
(6) heteroaryl,
wherein each alkyl, cycloalkyl, cycloheteroalkyl, aryl and heteroaryl is unsubstituted or substituted with one to three substituents selected from $C_{1-6}$alkyl;

each $R^f$ is independently selected from the group consisting of:
(1) hydrogen,
(2) $C_{1-6}$alkyl, and
(3) $C_{3-6}$cycloalkyl;

each $R^g$ is independently selected from the group consisting of:
(1) hydrogen,
(2) halogen,
(3) $C_{1-6}$alkyl, and
(4) $C_{3-6}$cycloalkyl;

each $R^h$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) $C_{3-6}$ cycloalkyl-$C_{1-10}$alkyl-,
(6) —$C_{2-5}$cycloheteroalkyl,
(7) $C_{2-5}$ cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-,
wherein alkyl, alkenyl, cycloalkyl, cycloheteroalkyl, aryl and heteroaryl are unsubstituted or substituted with one to four substituents selected from $C_{1-6}$alkyl;

each $R^i$ is independently selected from the group consisting of:
(1) hydrogen,
(2) halogen,
(3) —$C_{1-6}$alkyl,
(4) —$(CH_2)_s$—O—$C_{1-6}$alkyl,
(5) —$(CH_2)_s$OH,
(6) —$N(R^c)S(O)_2R^e$,
(7) —$S(C_{1-6}$alkyl),
(8) —$(CH_2)_sSO_2C_{1-6}$alkyl,
(9) —$(CH_2)_sSO_2$—$(CH_2)_t$—$C_{3-6}$cycloalkyl,
(10) —$S(O)_2NR^cR^d$,
(11) —$NR^cR^d$,
(12) —$C(O)R^e$,
(13) —$OC(O)R^e$,
(14) —$CO_2R^e$,
(15) —$(CH_2)_s$CN,
(16) —$C(O)NR^cR^d$,
(17) —$N(R^c)C(O)R^e$,
(18) —$N(R^c)C(O)OR^e$,
(19) —$N(R^c)C(O)NR^cR^d$,
(20) —$CF_3$,
(21) —$OCF_3$,

(22) —OCHF$_2$,
(23) —C$_{3-6}$cycloalkyl, and
(24) —C$_{2-5}$ cyclohetroalkyl,
wherein each CH$_2$, alkyl, cycloalkyl and cycloheteroalkyl is unsubstituted or substituted with one, two, three or four substituents selected from: —C$_{1-6}$alkyl and halogen;
each R$^j$ is independently selected from the group consisting of:
(1) —C$_{1-6}$alkyl,
(2) —C$_{3-6}$cycloalkyl, and
(3) -aryl-C$_{1-6}$alkyl,
wherein each alkyl, cycloalkyl and aryl is unsubstituted or substituted with one to three substituents selected from R$^k$;
each R$^k$ is independently selected from the group consisting of:
(1) —C$_{1-6}$alkyl,
(2) —OR$^e$,
(3) —N(R$^c$)S(O)$_p$R$^e$,
(4) halogen,
(5) —S(O)$_p$R$^e$,
(6) —S(O)$_p$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —N(R$^c$)C(O)R$^e$,
(14) —N(R$^c$)C(O)OR$^e$,
(15) —N(R$^c$)C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$ cyclohetroalkyl;
each n is independently selected from: 1 and 2;
each m is independently selected from: 1 and 2;
each p is independently selected from: 0, 1 and 2;
each q is independently selected from: 0, 1 and 2;
each r is independently selected from: 1, 2, 3 and 4;
each s is independently selected from: 0, 1, 2 and 3;
each t is independently selected from: 0, 1, 2, 3 and 4;
each u is independently selected from: 0, 1, 2 and 3;
each v is independently selected from: 0, 1, 2, 3 and 4;
each w is independently selected from: 0, 1, 2 and 3; and
each x is independently selected from: 0, 1 and 2.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In another embodiment of the present invention, A is selected from the group consisting of: —C$_{3-6}$cycloalkyl, —C$_{3-6}$cycloalkenyl, —C$_{2-10}$cycloheteroalkyl, and —C$_{2-10}$cycloheteroalkenyl, wherein each cycloalkyl, cycloalkenyl, cycloheteroalkyl and cycloheteroalkenyl is unsubstituted or substituted with one, two or three substituents selected from R$^a$.

In another embodiment of the present invention, A is selected from the group consisting of: —C$_{3-9}$cycloalkyl, —C$_{3-9}$cycloalkenyl, and —C$_{2-10}$cycloheteroalkyl, wherein each cycloalkyl, cycloalkenyl and cycloheteroalkyl is unsubstituted or substituted with one, two or three substituents selected from R$^a$. In a class of this embodiment, A is selected from the group consisting of: cyclopropyl, cyclobutyl, cyclopentyl, cyclopentenyl, pyrrolidine, piperidine, azetidine, morpholine, 2-azaspiro[3.3]heptane, octahydrocyclopenta[c]pyrrole, and 6-azaspiro[3,4]octane, wherein each cycloalkyl, cycloalkenyl and cycloheteroalkyl is unsubstituted or substituted with one, two or three substituents selected from R$^a$.

In another embodiment of the present invention, A is selected from the group consisting of: —C$_{3-9}$cycloalkyl and —C$_{2-10}$cycloheteroalkyl, wherein each cycloalkyl and cycloheteroalkyl is unsubstituted or substituted with one, two or three substituents selected from R$^a$. In a class of this embodiment of the present invention, A is selected from the group consisting of: —C$_{3-6}$cycloalkyl and —C$_{2-10}$cycloheteroalkyl, wherein each cycloalkyl and cycloheteroalkyl is unsubstituted or substituted with one, two or three substituents selected from R$^a$. In another class of this embodiment, A is selected from the group consisting of: cyclopropyl, cyclobutyl, cyclopentyl, pyrrolidine, piperidine, azetidine, morpholine, 2-azaspiro[3.3]heptane, octahydrocyclopenta [c]pyrrole, and 6-azaspiro[3,4]octane, wherein A is unsubstituted or substituted with one, two or three substituents selected from R$^a$.

In another embodiment of the present invention, A is —C$_{3-9}$cycloalkyl, wherein each cycloalkyl is unsubstituted or substituted with one, two or three substituents selected from R$^a$. In a class of this embodiment of the present invention, A is —C$_{3-6}$cycloalkyl, wherein each cycloalkyl is unsubstituted or substituted with one, two or three substituents selected from R$^a$. In another class of this embodiment, A is selected from the group consisting of: cyclopropyl, cyclobutyl, and cyclopentyl, wherein each cycloalkyl is unsubstituted or substituted with one, two or three substituents selected from R$^a$.

In another embodiment of the present invention, A is —C$_{2-10}$cycloheteroalkyl, wherein each cycloheteroalkyl is unsubstituted or substituted with one, two or three substituents selected from R$^a$. In a class of this embodiment, A is selected from the group consisting of: pyrrolidine, piperidine, azetidine, morpholine, 2-azaspiro[3.3]heptane, octahydrocyclo-penta-[c]pyrrole, and 6-azaspiro[3,4]octane, wherein A is unsubstituted or substituted with one, two or three substituents selected from R$^a$. In another class of this embodiment, A is selected from the group consisting of: piperidine, azetidine, and octahydrocyclopenta[c]pyrrole, wherein A is unsubstituted or substituted with one, two or three substituents selected from R$^a$.

In another embodiment of the present invention, B is selected from the group consisting of: —(CH$_2$)$_u$-aryl, —(CH$_2$)$_u$-heteroaryl, —(CH$_2$)$_u$-aryl-aryl, —(CH$_2$)$_u$—N(R$^g$)—(CH$_2$)$_u$-aryl, —(CH$_2$)$_u$—N(R$^g$)—(CH$_2$)$_u$-heteroaryl, —(CH$_2$)$_u$—O—(CH$_2$)$_u$-aryl, —(CH$_2$)$_u$—O—(CH$_2$)$_u$-aryl-aryl, —(CH$_2$)$_u$—O—(CH$_2$)$_u$-heteroaryl, —(CH$_2$)$_u$—C$_{3-6}$cycloalkyl, —(CH$_2$)$_u$—O—(CH$_2$)$_u$—C$_{3-6}$cycloalkyl, —(CH$_2$)$_u$—C$_{2-6}$cycloheteroalkyl, and —(CH$_2$)$_u$—O—(CH$_2$)$_u$—C$_{2-6}$cycloheteroalkyl, wherein each CH$_2$, cycloalkyl, cycloheteroalkyl, aryl and heteroaryl is unsubstituted or substituted with one, two, three, four or five substituents selected from R$^b$. In a class of this embodiment of the present invention, B is selected from the group consisting of: —(CH$_2$)$_u$-aryl, —(CH$_2$)$_u$-heteroaryl, —(CH$_2$)$_u$-aryl-aryl, —(CH$_2$)$_u$—N(R$^g$)—(CH$_2$)$_u$-aryl, —(CH$_2$)$_u$—N(R$^g$)—(CH$_2$)$_u$-heteroaryl, —(CH$_2$)$_u$—O—(CH$_2$)$_u$-aryl, —(CH$_2$)$_u$—O—(CH$_2$)$_u$-aryl-aryl, —(CH$_2$)$_u$—O—(CH$_2$)$_u$-heteroaryl, —(CH$_2$)$_u$—C$_{3-6}$cycloalkyl, —(CH$_2$)$_u$—O—(CH$_2$)$_u$—C$_{3-6}$cycloalkyl, —(CH$_2$)$_u$—C$_{2-6}$cycloheteroalkyl, and —(CH$_2$)$_u$—O—(CH$_2$)$_u$—C$_{2-6}$cycloheteroalkyl, wherein each —(CH$_2$)$_u$, cycloalkyl, cycloheteroalkyl, aryl and heteroaryl is unsubstituted or substituted with one, two, three, four or five substituents selected from $R^b$.

In another embodiment of the present invention, B is selected from the group consisting of: —(CH$_2$)$_u$-aryl, —(CH$_2$)$_u$-heteroaryl, —(CH$_2$)$_u$—NR$^g$(CH$_2$)$_u$-aryl, —(CH$_2$)$_u$—O—(CH$_2$)$_u$-aryl, —(CH$_2$)$_u$—O—(CH$_2$)$_u$-aryl-aryl, and —(CH$_2$)$_u$—O—(CH$_2$)$_u$-heteroaryl, wherein each (CH$_2$)$_u$, aryl and heteroaryl is unsubstituted or substituted with one, two, three, four or five substituents selected from $R^b$.

In a class of this embodiment, B is selected from the group consisting of: —(CH$_2$)$_u$-aryl, -heteroaryl, —N(R$^g$)—(CH$_2$)$_u$-aryl, —O—CH$_2$aryl, —O-aryl, —O-aryl-aryl, and —O-heteroaryl, wherein each —(CH$_2$)$_u$, aryl and heteroaryl is unsubstituted or substituted with one, two, three, four or five substituents selected from $R^b$.

In another class of this embodiment, B is selected from the group consisting of: -phenyl, —CH$_2$-phenyl, —CH(CH$_3$)-phenyl, —CH(CH$_2$CH$_3$)-phenyl, pyridine, —NHCH$_2$-phenyl, —O—CH$_2$phenyl, —O-phenyl, —O-(1-oxo-1,3-dihydroisobenzofuran), —O-(2,3-dihydrobenzofuran), —O— phenyl-phenyl, —O-pyridine, —O-pyrimidine, —O-pyrazole, and —O-(2,3-dihydro-[1,4]dioxino[2,3-b]pyridine), wherein each B is unsubstituted or substituted with one, two, or three substituents selected from $R^b$.

In another embodiment of the present invention, B is selected from the group consisting of: —(CH$_2$)$_u$-aryl, —(CH$_2$)$_u$-heteroaryl, —(CH$_2$)$_u$-aryl-aryl, —(CH$_2$)$_u$—N(R$^g$)—(CH$_2$)$_u$-aryl, —(CH$_2$)$_u$—N(R$^g$)—(CH$_2$)$_u$-heteroaryl, —(CH$_2$)$_u$—O—(CH$_2$)$_u$-aryl, —(CH$_2$)$_u$—O—(CH$_2$)$_u$-heteroaryl, —(CH$_2$)$_u$—C$_{3-6}$cycloalkyl, —(CH$_2$)$_u$—O—(CH$_2$)$_u$—C$_{3-6}$cycloalkyl, —(CH$_2$)$_u$—C$_{2-6}$cycloheteroalkyl, and —(CH$_2$)$_u$—O—(CH$_2$)$_u$—C$_{2-6}$cycloheteroalkyl, wherein each CH$_2$, cycloalkyl, cycloheteroalkyl, aryl and heteroaryl is unsubstituted or substituted with one, two, three, four or five substituents selected from $R^b$.

In another embodiment of the present invention, B is selected from the group consisting of: —(CH$_2$)$_u$-aryl, —(CH$_2$)$_u$-heteroaryl, —(CH$_2$)$_u$—N(R$^g$)—(CH$_2$)$_u$-aryl, —(CH$_2$)$_u$—O—(CH$_2$)$_u$-aryl, and —(CH$_2$)$_u$—O—(CH$_2$)$_u$-heteroaryl, wherein each CH$_2$, aryl and heteroaryl is unsubstituted or substituted with one, two, three, four or five substituents selected from $R^b$.

In another embodiment of the present invention, B is selected from the group consisting of: —(CH$_2$)$_u$-aryl, —(CH$_2$)$_u$-heteroaryl, —(CH$_2$)$_u$—N(R$^g$)—(CH$_2$)$_u$-aryl, and —(CH$_2$)$_u$—O—(CH$_2$)$_u$-aryl, wherein each CH$_2$, aryl and heteroaryl is unsubstituted or substituted with one, two, three, four or five substituents selected from $R^b$. In a class of this embodiment, B is selected from the group consisting of: —(CH$_2$)$_u$-aryl, -heteroaryl, —N(R$^g$)—(CH$_2$)$_u$-aryl, —O—CH$_2$aryl, and —O-aryl, wherein each CH$_2$, aryl and heteroaryl is unsubstituted or substituted with one, two, three, four or five substituents selected from $R^b$. In another class of this embodiment, B is selected from the group consisting of: -phenyl, —CH$_2$-phenyl, —CH(CH$_3$)-phenyl, —CH(CH$_2$CH$_3$)-phenyl, pyridine, —NHCH$_2$-phenyl, —O—CH$_2$phenyl, and —O-phenyl, wherein each B is unsubstituted or substituted with one, two, three, four or five substituents selected from $R^b$.

In another embodiment of the present invention, B is selected from the group consisting of: —(CH$_2$)$_u$-aryl, and -heteroaryl, wherein each CH$_2$, aryl and heteroaryl is unsubstituted or substituted with one, two, three, four or five substituents selected from $R^b$. In a class of this embodiment, B is selected from the group consisting of: -phenyl, —CH$_2$-phenyl, —CH(CH$_3$)-phenyl, —CH(CH$_2$CH$_3$)-phenyl and pyridine, wherein each B is unsubstituted or substituted with one, two, three, four or five substituents selected from $R^b$.

In another embodiment of the present invention, B is —(CH$_2$)$_u$-aryl, wherein each CH$_2$ and aryl is unsubstituted or substituted with one, two, three, four or five substituents selected from $R^b$. In a class of this embodiment, B is selected from the group consisting of: -phenyl, —CH$_2$-phenyl, —CH(CH$_3$)-phenyl and —CH(CH$_2$CH$_3$)-phenyl, wherein each CH$_2$ and phenyl is unsubstituted or substituted with one, two, three, four or five substituents selected from $R^b$.

In another embodiment of the present invention, B is -heteroaryl, wherein each heteroaryl is unsubstituted or substituted with one, two, three, four or five substituents selected from $R^b$. In a class of this embodiment, B is pyridine, wherein each pyridine is unsubstituted or substituted with one, two, three, four or five substituents selected from $R^b$.

In another embodiment of the present invention, T is selected from the group consisting of: CH, N and N-oxide. In a class of this embodiment, T is selected from the group consisting of: CH and N. In another class of this embodiment, T is CH. In another class of this embodiment, T is N or N-oxide. In another class of this embodiment, T is N. In another class of this embodiment, T is N-oxide.

In another embodiment of the present invention, U is selected from the group consisting of: CH, N and N-oxide. In a class of this embodiment, U is selected from the group consisting of: CH and N. In another class of this embodiment, U is CH. In another class of this embodiment, U is N or N-oxide. In another class of this embodiment, U is N. In another class of this embodiment, U is N-oxide.

In another embodiment of the present invention, V is selected from the group consisting of: CH, N and N-oxide. In a class of this embodiment, V is selected from the group consisting of: CH and N. In another class of this embodiment, V is CH. In another class of this embodiment, V is N or N-oxide. In another class of this embodiment, V is N. In another class of this embodiment, V is N-oxide.

In another embodiment of the present invention, W is selected from the group consisting of: CH, N and N-oxide. In a class of this embodiment, W is selected from the group consisting of: CH and N. In another class of this embodiment, W is CH. In another class of this embodiment, W is N or N-oxide. In another class of this embodiment, W is N. In another class of this embodiment, W is N-oxide.

In another embodiment of the present invention, T, U, V and W are CH.

In another embodiment of the present invention, T, U, V and W are selected from the group consisting of: CH, N, and N-oxide, provided no more than three of T, U, V and W are selected from N and N-oxide. In another embodiment of the present invention, T, U, V and W are selected from the group consisting of: CH and N, provided that no more than three of T, U, V and W are N.

In another embodiment of the present invention, T, U, V and W are selected from the group consisting of: CH, N, and N-oxide, provided no more than two of T, U, V and W are selected from N and N-oxide. In another embodiment of the present invention, T, U, V and W are selected from the group consisting of: CH and N, provided that no more than two of T, U, V and W are N.

In another embodiment of the present invention, T, U, V and W are selected from the group consisting of: CH, N, and N-oxide, provided that two of T, U, V and W are selected from N and N-oxide. In another embodiment of the present invention, T, U, V and W are selected from the group consisting of: CH and N, provided that two of T, U, V and W are N.

In another embodiment of the present invention, T, U, V and W are selected from the group consisting of: CH, N, and N-oxide, provided that one of T, U, V and W is selected from N and N-oxide. In another embodiment of the present invention, T, U, V and W are selected from the group consisting of: CH and N, provided that one of T, U, V and W is N.

In another embodiment of the present invention, Y is selected from the group consisting of: —$(CH_2)_xO$—, —O—$(CH_2)_x$—, —$(CH_2)_x$—$NR^f$—, —$(CH_2)_x$—S—, —$(CH_2)_x$—$CH_2$—, —$(CH_2)_x$—C(O)—, —$(CH_2)_x$—$CF_2$—, and —$CF_2$—$(CH_2)_x$—, wherein $CH_2$ is unsubstituted or substituted with one or two substituents selected from $R^i$.

In another embodiment of the present invention, Y is selected from the group consisting of: —$(CH_2)_xO$—, —$(CH_2)_x$—$NR^f$—, —$(CH_2)_x$—S—, —$(CH_2)_x$—$CH_2$—, —$(CH_2)_x$—C(O)—, —$(CH_2)_x$—$CF_2$—, and —$CF_2$—$(CH_2)_x$—, wherein $CH_2$ is unsubstituted or substituted with one or two substituents selected from $R^i$.

In another embodiment of the present invention, Y is selected from the group consisting of: —$(CH_2)_xO$—, —$(CH_2)_x$—$NR^f$—, —$(CH_2)_x$—S—, —$(CH_2)_x$—$CH_2$—, —$(CH_2)_x$—C(O)— and —$(CH_2)_x$—$CF_2$—, wherein $CH_2$ is unsubstituted or substituted with one or two substituents selected from $R^i$.

In another embodiment of the present invention, Y is selected from the group consisting of: —$(CH_2)_xO$—, —$(CH_2)_x$—$NR^f$—, —$(CH_2)_x$—S—, —$(CH_2)_x$—$CH_2$—, and —$(CH_2)_x$—C(O)—, wherein $CH_2$ is unsubstituted or substituted with one or two substituents selected from $R^i$.

In another embodiment of the present invention, Y is selected from the group consisting of: —$(CH_2)_xO$—, —$(CH_2)_x$—$NR^f$—, —$(CH_2)_x$—S—, and —$(CH_2)_x$—C(O)—, wherein $CH_2$ is unsubstituted or substituted with one or two substituents selected from $R^i$.

In another embodiment of the present invention, Y is selected from the group consisting of: —$(CH_2)_xO$—, —$(CH_2)_x$—$NR^f$—, and —$(CH_2)_x$—S—, wherein $CH_2$ is unsubstituted or substituted with one or two substituents selected from $R^i$.

In another embodiment of the present invention, Y is selected from: —O—, —$(CH_2)_xO$— and —O—$(CH_2)_x$—, wherein $CH_2$ is unsubstituted or substituted with one or two substituents selected from $R^i$. In a class of this embodiment, Y is selected from: —O—, —$CH_2$—O—, and —O—$CH_2$— wherein $CH_2$ is unsubstituted or substituted with one or two substituents selected from $C_{1-6}$alkyl.

In another embodiment of the present invention, Y is selected from: —$(CH_2)_xO$— and —O—$(CH_2)_x$—, wherein $CH_2$ is unsubstituted or substituted with one or two substituents selected from $R^i$. In a class of this embodiment, Y is selected from: —$CH_2$—O—, and —O—$CH_2$—, wherein $CH_2$ is unsubstituted or substituted with one or two substituents selected from $C_{1-6}$alkyl. In another class of this embodiment, Y is selected from: —$CH_2$—O—, and —O—$CH_2$—.

In another embodiment of the present invention, Y is selected from: —O—$(CH_2)_x$, wherein $CH_2$ is unsubstituted or substituted with one or two substituents selected from $R^i$. In a class of this embodiment, Y is —O—$CH_2$—, wherein $CH_2$ is unsubstituted or substituted with one or two substituents selected from $C_{1-6}$alkyl. In another class of this embodiment, Y is —O—$CH_2$—.

In another embodiment of the present invention, Y is —$(CH_2)_xO$—, wherein $CH_2$ is unsubstituted or substituted with one or two substituents selected from $R^i$. In a class of this embodiment, Y is —$(CH_2)_xO$—, wherein $CH_2$ is unsubstituted or substituted with one or two substituents selected from $C_{1-6}$alkyl. In a subclass of this class, $CH_2$ is unsubstituted or substituted with one or two substituents selected from $CH_3$. In another class of this embodiment, Y is selected from the group consisting of: —O—, —$CH_2$O—, —$CH_2CH_2$O— and —$CH(CH_3)$O—. In another class of this embodiment, Y is selected from the group consisting of: —O—, —$CH_2$O— and —$CH(CH_3)$O—. In another class of this embodiment, Y is —$CH_2$O—. In another class of this embodiment, Y is —$CH(CH_3)$O—. In another class of this embodiment, Y is —O—.

In another embodiment of the present invention, Y is selected from: —O— and —$CH_2$—O—, wherein $CH_2$ is unsubstituted or substituted with one or two substituents selected from $R^i$. In a class of this embodiment, Y is selected from: —O— and —$CH_2$—O—, wherein $CH_2$ is unsubstituted or substituted with one or two substituents selected from $C_{1-6}$alkyl. In another class of this embodiment, Y is —$CH(CH_3)$O—. In another class of this embodiment, Y is selected from the group consisting of: —O—, —$CH_2$O—, and —$CH(CH_3)$O—. In another class of this embodiment, Y is —$CH(CH_3)$O—. In another class of this embodiment, Y is —$CH_2$—O—. In another class of this embodiment, Y is —O—.

In another embodiment of the present invention, Z is selected from the group consisting of: —$C_{0-6}$alkyl-$CO_2$H, —$C_{0-6}$alkyl-$CO_2R^j$, —$C_{0-6}$alkyl-C(O)$NHR^h$, —$C_{0-6}$alkyl-C(O)NHSO$_2R^h$, —$C_{0-6}$alkyl-SO$_2$NHC(O)$R^h$, —$C_{0-6}$alkyl-heteroaryl, and —$C_{0-6}$alkyl-cycloheteroalkyl, wherein cycloheteroalkyl is selected from the group consisting of:

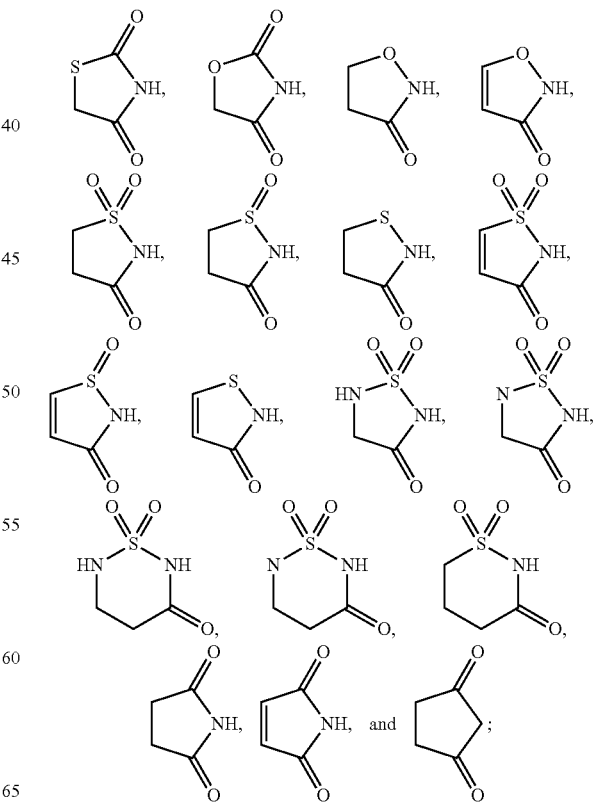

wherein each alkyl, cycloheteroalkyl and heteroaryl is unsubstituted or substituted with one to five substituents selected from $C_{1-6}$alkyl.

In another embodiment of the present invention, Z is selected from the group consisting of: —$C_{0-6}$alkyl —$CO_2H$, —$C_{0-6}$alkyl-$CO_2R^j$, —$C_{0-6}$alkyl-$C(O)NHR^h$, —$C_{0-6}$alkyl-$C(O)NHSO_2R^h$, —$C_{0-6}$alkyl-$SO_2NHC(O)R^h$, —$C_{0-6}$alkyl-heteroaryl, and a cycloheteroalkyl selected from the group consisting of:

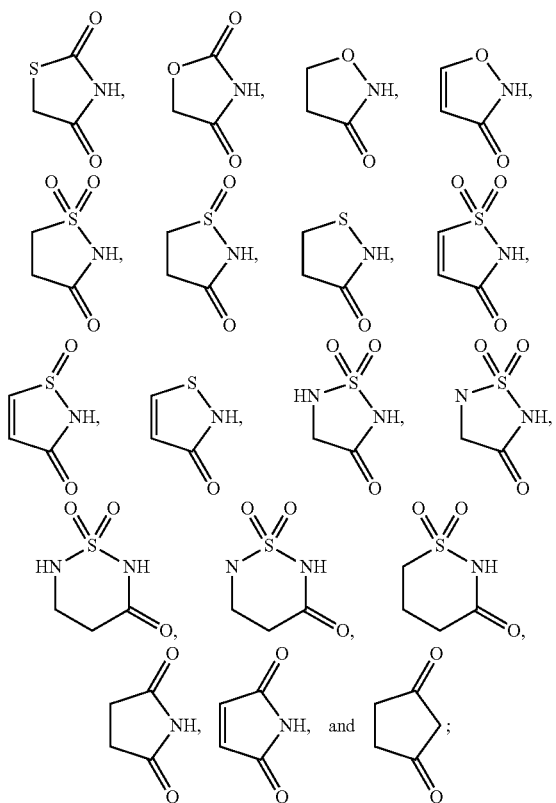

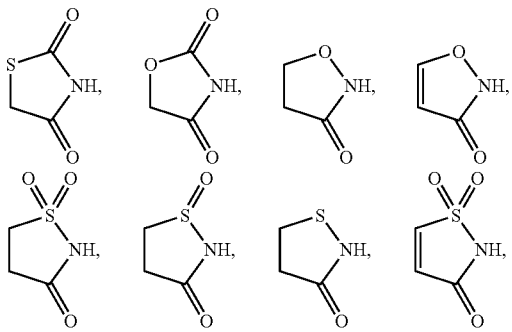

wherein each alkyl, cycloheteroalkyl and heteroaryl is unsubstituted or substituted with one to five substituents selected from $C_{1-6}$alkyl.

In another embodiment of the present invention, Z is selected from the group consisting of: —$CO_2H$, —$CO_2R^j$, —$C(O)NHR^h$, —$C(O)NHSO_2R^h$, —$SO_2NHC(O)R^h$, -heteroaryl, and a cycloheteroalkyl selected from the group consisting of:

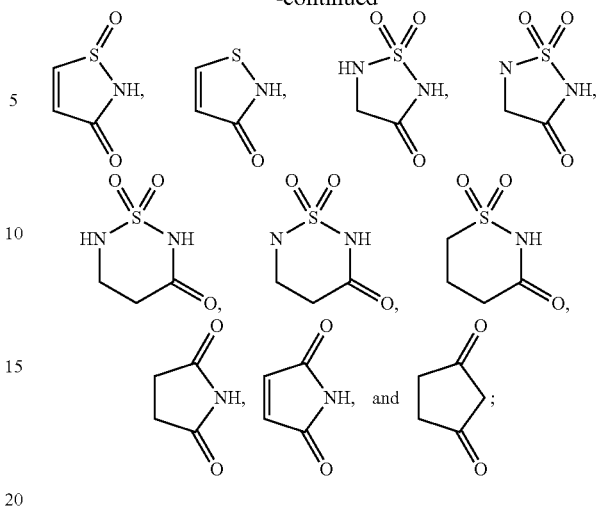

wherein each alkyl, cycloheteroalkyl and heteroaryl is unsubstituted or substituted with one to five substituents selected from $C_{1-6}$alkyl.

In another embodiment of the present invention, Z is selected from the group consisting of: —$C_{0-6}$alkyl —$CO_2H$, —$C_{0-6}$alkyl-$CO_2R^j$, —$C_{0-6}$alkyl-$C(O)NHR^h$, —$C_{0-6}$alkyl-$C(O)NHSO_2R^h$, —$C_{0-6}$alkyl-$SO_2NHC(O)R^h$, and —$C_{0-6}$alkyl-heteroaryl, wherein each alkyl, cycloheteroalkyl and heteroaryl is unsubstituted or substituted with one to five substituents selected from $C_{1-6}$alkyl.

In another embodiment of the present invention, Z is selected from the group consisting of: —$CO_2H$, —$CO_2R^j$, —$C(O)NHR^h$, —$C(O)NHSO_2R^h$, —$SO_2NHC(O)R^h$, and —$C_{0-6}$alkyl-heteroaryl, wherein each alkyl, cycloheteroalkyl and heteroaryl is unsubstituted or substituted with one to five substituents selected from $C_{1-6}$alkyl.

In another embodiment of the present invention, Z is —$C_{0-6}$alkyl-cycloheteroalkyl, wherein cycloheteroalkyl is selected from the group consisting of:

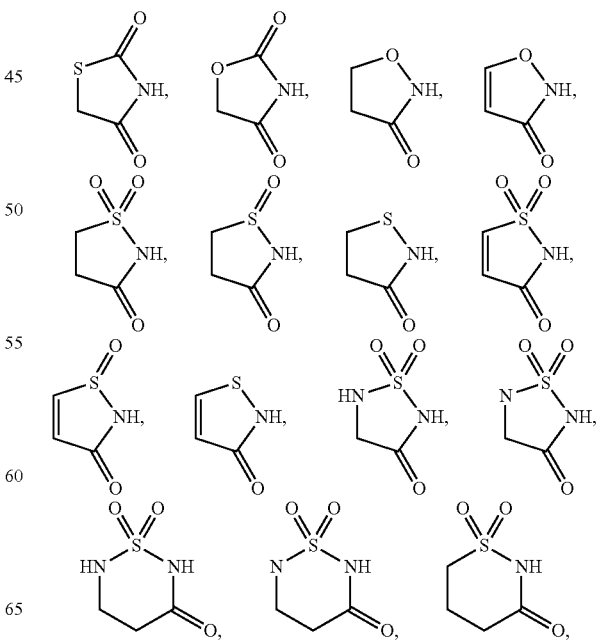

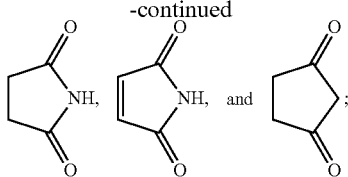

wherein each cycloheteroalkyl is unsubstituted or substituted with one to five substituents selected from $C_{1-6}$alkyl.

In another embodiment of the present invention, Z is a cycloheteroalkyl selected from the group consisting of:

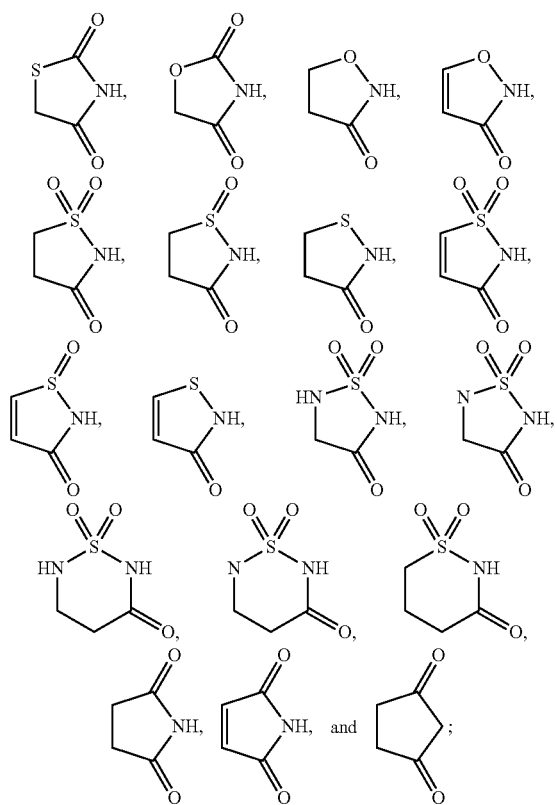

wherein each cycloheteroalkyl is unsubstituted or substituted with one to five substituents selected from $C_{1-6}$alkyl.

In another embodiment of the present invention, Z is selected from the group consisting of: —$C_{0-6}$alkyl—$CO_2H$, —$C_{0-6}$alkyl-$CO_2R^j$, —$C_{0-6}$alkyl-$C(O)NHR^h$, —$C_{0-6}$alkyl-C(O)NHSO_2R^h$ and —$C_{0-6}$alkyl-SO_2NHC(O)R^h$, wherein each alkyl, is unsubstituted or substituted with one to five substituents selected from $C_{1-6}$alkyl.

In another embodiment of the present invention, Z is selected from the group consisting of: —$C_{0-6}$alkyl-$CO_2H$, and —$C_{0-6}$alkyl-$CO_2R^j$, wherein each alkyl is unsubstituted or substituted with one to five substituents selected from $C_{1-6}$alkyl.

In another embodiment of the present invention, Z is —$C_{0-6}$alkyl-$CO_2H$, wherein each alkyl is unsubstituted or substituted with one to five substituents selected from $C_{1-6}$alkyl.

In another embodiment of the present invention, Z is —$CO_2H$.

In another embodiment of the present invention, $R^1$ is selected from the group consisting of: hydrogen, halogen, —$(CH_2)_s$—$OC_{1-6}$alkyl, —$(CH_2)_s$—OH, —CN, and —$C_{1-6}$alkyl, wherein $CH_2$ and alkyl are unsubstituted or substituted with one, two or three halogens. In a class of this embodiment, $R^1$ is selected from the group consisting of: hydrogen, halogen, —$(CH_2)_s$—$OC_{1-6}$alkyl, —$(CH_2)_s$—OH, —CN, and —$C_{1-6}$alkyl, wherein —$(CH_2)_s$— and alkyl are unsubstituted or substituted with one, two or three halogens.

In another embodiment of the present invention, $R^1$ is selected from the group consisting of: halogen, —$(CH_2)_s$—$OC_{1-6}$alkyl, —$(CH_2)_s$—OH, —CN, and —$C_{1-6}$alkyl, wherein $CH_2$ and alkyl are unsubstituted or substituted with one, two or three halogens. In a class of this embodiment, $R^1$ is selected from the group consisting of: halogen, —$(CH_2)_s$—$OC_{1-6}$alkyl, —$(CH_2)_s$—OH, —CN, and —$C_{1-6}$alkyl, wherein —$(CH_2)_s$— and alkyl are unsubstituted or substituted with one, two or three halogens.

In another embodiment of the present invention, $R^1$ is selected from the group consisting of: hydrogen, halogen, —$OC_{1-6}$alkyl, —OH, —CN, and —$C_{1-6}$alkyl, wherein alkyl is unsubstituted or substituted with one, two or three halogens.

In another embodiment of the present invention, $R^1$ is selected from the group consisting of: halogen, —$OC_{1-6}$alkyl, —OH, —CN, and —$C_{1-6}$alkyl, wherein alkyl is unsubstituted or substituted with one, two or three halogens.

In another embodiment of the present invention, $R^1$ is selected from the group consisting of: hydrogen, halogen, and —$C_{1-6}$alkyl, wherein alkyl is unsubstituted or substituted with one, two or three halogens.

In another embodiment of the present invention, $R^1$ is selected from the group consisting of: halogen, and —$C_{1-6}$alkyl, wherein alkyl is unsubstituted or substituted with one, two or three halogens.

In another embodiment of the present invention, $R^1$ is selected from the group consisting of: hydrogen, and —$C_{1-6}$alkyl, wherein alkyl is unsubstituted or substituted with one, two or three halogens. In a class of this embodiment, $R^1$ is hydrogen or —$CH_3$.

In another embodiment of the present invention, $R^1$ is —$C_{1-6}$alkyl, wherein alkyl is unsubstituted or substituted with one, two or three halogens. In a class of this embodiment, $R^1$ is —$CH_3$.

In another embodiment of the present invention, $R^1$ is hydrogen.

In another embodiment of the present invention, $R^2$ is selected from the group consisting of: hydrogen, —$(CH_2)_s$—O—$C_{1-6}$alkyl, —$C_{1-6}$alkyl, —$C_{3-6}$cycloalkyl and —$C_{2-4}$cycloheteroalkyl, wherein each $CH_2$, alkyl, cycloalkyl and cycloheteroalkyl is unsubstituted or substituted with one, two or three substituents selected from halogen, OH, —$C_{1-6}$alkyl and $OC_{1-6}$alkyl. In a class of this embodiment, $R^2$ is selected from the group consisting of: hydrogen, —$(CH_2)_s$—O—$C_{1-6}$alkyl, —$C_{1-6}$alkyl, —$C_{3-6}$cycloalkyl and —$C_{2-4}$cycloheteroalkyl, wherein each —$(CH_2)_s$—, alkyl, cycloalkyl and cycloheteroalkyl is unsubstituted or substituted with one, two or three substituents selected from halogen, OH, —$C_{1-6}$alkyl and $OC_{1-6}$alkyl.

In another embodiment of the present invention, $R^2$ is selected from the group consisting of: —$(CH_2)_s$—O—$C_{1-6}$alkyl, —$C_{1-6}$alkyl, —$C_{3-6}$cycloalkyl and —$C_{2-4}$cycloheteroalkyl, wherein each $CH_2$, alkyl, cycloalkyl and cycloheteroalkyl is unsubstituted or substituted with one, two or three substituents selected from halogen, OH, —$C_{1-6}$alkyl and $OC_{1-6}$alkyl. In a class of this embodiment, $R^2$ is selected from the group consisting of: —$(CH_2)_s$—O—$C_{1-6}$alkyl, —$C_{1-6}$alkyl, —$C_{3-6}$cycloalkyl and —$C_{2-4}$cycloheteroalkyl, wherein each —$(CH_2)_s$—, alkyl, cycloalkyl and cycloheteroalkyl is unsubstituted or substituted with one, two or three substituents selected from halogen, OH, —$C_{1-6}$alkyl and $OC_{1-6}$alkyl.

In another embodiment of the present invention, $R^2$ is selected from the group consisting of: hydrogen, —O—$C_{1-6}$alkyl, —$C_{1-6}$alkyl, —$C_{3-6}$cycloalkyl and —$C_{2-4}$cycloheteroalkyl, wherein each $CH_2$, alkyl, cycloalkyl and cycloheteroalkyl is unsubstituted or substituted with one, two or three substituents selected from halogen, OH, —$C_{1-6}$alkyl and $OC_{1-6}$alkyl. In another embodiment of the present invention, $R^2$ is selected from the group consisting of: hydrogen, —O—$C_{1-6}$alkyl, —$C_{1-6}$alkyl, —$C_{3-6}$cycloalkyl and —$C_{2-4}$cycloheteroalkyl, wherein each alkyl, cycloalkyl and cycloheteroalkyl is unsubstituted or substituted with one, two or three substituents selected from halogen, OH, —$C_{1-6}$alkyl and $OC_{1-6}$alkyl.

In another embodiment of the present invention, $R^2$ is selected from the group consisting of: —O—$C_{1-6}$alkyl, —$C_{1-6}$alkyl, —$C_{3-6}$cycloalkyl and —$C_{2-4}$cycloheteroalkyl, wherein each $CH_2$, alkyl, cycloalkyl and cycloheteroalkyl is unsubstituted or substituted with one, two or three substituents selected from halogen, OH, —$C_{1-6}$alkyl and $OC_{1-6}$alkyl. In another embodiment of the present invention, $R^2$ is selected from the group consisting of: —O—$C_{1-6}$alkyl, —$C_{1-6}$alkyl, —$C_{3-6}$cycloalkyl and —$C_{2-4}$cycloheteroalkyl, wherein each alkyl, cycloalkyl and cycloheteroalkyl is unsubstituted or substituted with one, two or three substituents selected from halogen, OH, —$C_{1-6}$alkyl and $OC_{1-6}$alkyl.

In another embodiment of the present invention, $R^2$ is selected from the group consisting of: hydrogen, —$C_{1-6}$alkyl, and —$C_{3-6}$cycloalkyl, wherein each alkyl and cycloalkyl is unsubstituted or substituted with one, two or three substituents selected from halogen, OH, —$C_{1-6}$alkyl and $OC_{1-6}$alkyl.

In another embodiment of the present invention, $R^2$ is selected from the group consisting of: —$C_{1-6}$alkyl, and —$C_{3-6}$cycloalkyl, wherein each alkyl and cycloalkyl is unsubstituted or substituted with one, two or three substituents selected from halogen, OH, —$C_{1-6}$alkyl and $OC_{1-6}$alkyl.

In another embodiment of the present invention, $R^2$ is selected from the group consisting of: hydrogen and —$C_{1-6}$alkyl, wherein alkyl is unsubstituted or substituted with one, two or three substituents selected from halogen, OH, —$C_{1-6}$alkyl and $OC_{1-6}$alkyl.

In another embodiment of the present invention, $R^2$ is —$C_{1-6}$alkyl, wherein alkyl is unsubstituted or substituted with one, two or three substituents selected from halogen, OH, —$C_{1-6}$alkyl and $OC_{1-6}$alkyl.

In another embodiment of the present invention, $R^2$ is —$C_{3-6}$cycloalkyl, wherein cycloalkyl is unsubstituted or substituted with one, two or three substituents selected from halogen, OH, —$C_{1-6}$alkyl and $OC_{1-6}$alkyl. In a class of this embodiment, $R^2$ is cyclopropyl, wherein cyclopropyl is unsubstituted or substituted with one, two or three substituents selected from halogen, OH, —$C_{1-6}$alkyl and $OC_{1-6}$alkyl. In another class of this embodiment, $R^2$ is cyclopropyl.

In another embodiment of the present invention, $R^2$ is hydrogen.

In another embodiment of the present invention, $R^3$ is selected from the group consisting of: hydrogen, halogen, —$(CH_2)_s$—$OC_{1-6}$alkyl, —$(CH_2)_s$—OH, —CN, and —$C_{1-6}$alkyl, wherein $CH_2$ and alkyl are unsubstituted or substituted with one, two or three substituents selected from halogen, OH, and $OC_{1-6}$alkyl. In a class of this embodiment, $R^3$ is selected from the group consisting of: hydrogen, halogen, —$(CH_2)_s$—$OC_{1-6}$alkyl, —$(CH_2)_s$—OH, —CN, and —$C_{1-6}$alkyl, wherein —$(CH_2)_s$— and alkyl are unsubstituted or substituted with one, two or three substituents selected from halogen, OH, and $OC_{1-6}$alkyl.

In another embodiment of the present invention, $R^3$ is selected from the group consisting of: hydrogen, halogen, —$OC_{1-6}$alkyl, —OH, —CN, and —$C_{1-6}$alkyl, wherein alkyl is unsubstituted or substituted with one, two or three substituents selected from halogen, OH, and $OC_{1-6}$alkyl. In another embodiment of the present invention, $R^3$ is selected from the group consisting of: hydrogen, halogen, and —$C_{1-6}$alkyl, wherein alkyl is unsubstituted or substituted with one, two or three substituents selected from halogen, OH, and $OC_{1-6}$alkyl.

In another embodiment of the present invention, $R^3$ is selected from the group consisting of: hydrogen, and halogen. In a class of this embodiment of the present invention, $R^3$ is selected from the group consisting of: hydrogen, Cl and F. In another class of this embodiment of the present invention, $R^3$ is selected from the group consisting of: hydrogen and F.

In another embodiment of the present invention, $R^3$ is —$C_{1-6}$alkyl, wherein alkyl is unsubstituted or substituted with one, two or three substituents selected from halogen, OH, and $OC_{1-6}$alkyl.

In another embodiment of the present invention, $R^3$ is halogen. In a class of this embodiment, $R^3$ is Cl or F. In another embodiment of the present invention, $R^3$ is hydrogen.

In another embodiment of the present invention, $R^a$ is selected from the group consisting of: —$C_{1-6}$alkyl, halogen, —$(CH_2)_u$—$OC_{1-6}$alkyl, —$OR^e$, —$S(O)_uR^e$, —$S(O)_u$N$R^cR^d$, —$N(R^c)S(O)_pR^e$, —$NR^cR^d$, —$C(O)R^e$, —$OC(O)R^e$, —$CO_2R^e$, —$N(R^c)C(O)R^e$, —$N(R^c)C(O)OR^e$, —$N(R^c)C(O)NR^cR^d$, —$C(O)NR^cR^d$, —CN, —$CF_3$, —$OCF_3$, —$OCHF_2$, —$(CH_2)_t$aryl, —$(CH_2)_t$heteroaryl, —$(CH_2)_r$—$C_{3-6}$cycloalkyl, —$(CH_2)_r$—$C_{3-6}$cycloalkenyl, —$(CH_2)_r$—$C_{2-5}$cycloheteroalkyl and —$(CH_2)_r$—O—$(CH_2)_r$—$C_{3-6}$cycloalkyl, wherein each CH, $CH_2$, alkyl, cycloalkyl, cycloalkenyl, cycloheteroalkyl, aryl and heteroaryl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^a$ is selected from the group consisting of: —$C_{1-6}$alkyl, halogen, —$(CH_2)_u$—$OC_{1-6}$alkyl, —$OR^e$, —$S(O)_uR^e$, —$S(O)_u$N$R^cR^d$, —$N(R^c)S(O)_pR^e$, —$NR^cR^d$, —$C(O)R^e$, —$OC(O)R^e$, —$CO_2R^e$, —$N(R^c)C(O)R^e$, —$N(R^c)C(O)OR^e$, —$N(R^c)C(O)NR^cR^d$, —$C(O)NR^cR^d$, —CN, —$CF_3$, —$OCF_3$, —$OCHF_2$, —$(CH_2)_t$aryl, —$(CH_2)_t$heteroaryl, —$(CH_2)_r$—$C_{3-6}$cycloalkyl, —$(CH_2)_r$—$C_{3-6}$cycloalkenyl, —$(CH_2)_r$—$C_{2-5}$cycloheteroalkyl and —$(CH_2)_r$—O—$(CH_2)_r$—$C_{3-6}$cycloalkyl, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl, and wherein each —$(CH_2)_r$, —$(CH_2)_u$, alkyl, cycloalkyl, cycloalkenyl, cycloheteroalkyl, aryl and heteroaryl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^a$ is selected from the group consisting of: —$C_{1-6}$alkyl, halogen, —$(CH_2)_u$—$OC_{1-6}$alkyl, —$OR^e$, —$S(O)_uR^e$, —$S(O)_u$N-

$R^cR^d$, —$N(R^c)S(O)_pR^e$, —$NR^cR^d$, —$C(O)R^e$, —$OC(O)R^e$, —$CO_2R^e$, —$N(R^c)C(O)R^e$, —$N(R^c)C(O)OR^e$, —$N(R^c)C(O)NR^cR^d$, —$C(O)NR^cR^d$, —CN, —$CF_3$, —$OCF_3$, —$OCHF_2$, —$(CH_2)_r$aryl, —$(CH_2)_r$heteroaryl, —$(CH_2)_r$—$C_{3-6}$cycloalkyl, —$(CH_2)_r$—$C_{3-6}$cycloalkenyl, —$(CH_2)_r$—$C_{2-5}$cycloheteroalkyl and —$(CH_2)_r$—O—$(CH_2)_r$—$C_{3-6}$cycloalkyl, wherein each CH, $CH_2$, alkyl, cycloalkyl, cycloalkenyl, cycloheteroalkyl, aryl and heteroaryl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In another class of this embodiment, $R^a$ is selected from the group consisting of: —$C_{1-6}$alkyl, halogen, —$(CH_2)_u$—$OC_{1-6}$alkyl, —$OR^e$, —$S(O)_uR^e$, —$S(O)_uNR^cR^d$, —$N(R^c)S(O)_pR^e$, —$NR^cR^d$, —$C(O)R^e$, —$OC(O)R^e$, —$CO_2R^e$, —$N(R^c)C(O)R^e$, —$N(R^c)C(O)OR^e$, —$N(R^c)C(O)NR^cR^d$, —$C(O)NR^cR^d$, —CN, —$CF_3$, —$OCF_3$, —$OCHF_2$, —$(CH_2)_r$aryl, —$(CH_2)_r$heteroaryl, —$(CH_2)_r$—$C_{3-6}$cycloalkyl, —$(CH_2)_r$—$C_{3-6}$cycloalkenyl, —$(CH_2)_r$—$C_{2-5}$cycloheteroalkyl and —$(CH_2)_r$—O—$(CH_2)_r$—$C_{3-6}$cycloalkyl, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl, and wherein each $(CH_2)_r$, $(CH_2)_u$, alkyl, cycloalkyl, cycloalkenyl, cycloheteroalkyl, aryl and heteroaryl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl.

In another embodiment of the present invention, $R^a$ is selected from the group consisting of: —$C_{1-6}$alkyl, halogen, —$(CH_2)_u$—$OC_{1-6}$alkyl, —$OR^e$, —$S(O)_uR^e$, —$S(O)_uNR^cR^d$, —$N(R^c)S(O)_pR^e$, —$NR^cR^d$, —$C(O)R^e$, —$OC(O)R^e$, —$CO_2R^e$, —$N(R^c)C(O)R^e$, —$N(R^c)C(O)OR^e$, —$N(R^c)C(O)NR^cR^d$, —$C(O)NR^cR^d$, —CN, —$CF_3$, —$OCF_3$, —$OCHF_2$, —$(CH_2)_r$aryl, —$(CH_2)_r$heteroaryl, —$(CH_2)_r$—$C_{3-6}$cycloalkyl, —$(CH_2)_r$—$C_{3-6}$cycloalkenyl and —$(CH_2)_r$—$C_{2-5}$cycloheteroalkyl, wherein each CH, $CH_2$, alkyl, cycloalkyl, cycloalkenyl, cycloheteroalkyl, aryl and heteroaryl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^a$ is selected from the group consisting of: —$C_{1-6}$alkyl, halogen, —$(CH_2)_u$—$OC_{1-6}$alkyl, —$OR^e$, —$S(O)_uR^e$, —$S(O)_uNR^cR^d$, —$N(R^c)S(O)_pR^e$, —$NR^cR^d$, —$C(O)R^e$, —$OC(O)R^e$, —$CO_2R^e$, —$N(R^c)C(O)R^e$, —$N(R^c)C(O)OR^e$, —$N(R^c)C(O)NR^cR^d$, —$C(O)NR^cR^d$, —CN, —$CF_3$, —$OCF_3$, —$OCHF_2$, —$(CH_2)_r$aryl, —$(CH_2)_r$heteroaryl, —$(CH_2)_r$—$C_{3-6}$cycloalkyl, —$(CH_2)_r$—$C_{3-6}$cycloalkenyl and —$(CH_2)_r$—$C_{2-5}$cycloheteroalkyl, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl, and wherein each —$(CH_2)_u$—, —$(CH_2)_r$, alkyl, cycloalkyl, cycloalkenyl, cycloheteroalkyl, aryl and heteroaryl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl.

In another embodiment of the present invention, $R^a$ is selected from the group consisting of: —$C_{1-6}$alkyl, halogen, —$(CH_2)_u$—$OC_{1-6}$alkyl, —$OR^e$, —$S(O)_uR^e$, —$S(O)_uNR^cR^d$, —$N(R^c)S(O)_pR^e$, —$NR^cR^d$, —$C(O)R^e$, —$OC(O)R^e$, —$CO_2R^e$, —$N(R^c)C(O)R^e$, —$N(R^c)C(O)OR^e$, —$N(R^c)C(O)NR^cR^d$, —$C(O)NR^cR^d$, —CN, —$CF_3$, —$OCF_3$, and —$OCHF_2$, wherein each CH, $CH_2$ and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^a$ is selected from the group consisting of: —$C_{1-6}$alkyl, halogen, —$(CH_2)_u$—$OC_{1-6}$alkyl, —$OR^e$, —$S(O)_uR^e$, —$S(O)_uNR^cR^d$, —$N(R^c)S(O)_pR^e$, —$NR^cR^d$, —$C(O)R^e$, —$OC(O)R^e$, —$CO_2R^e$, —$N(R^c)C(O)R^e$, —$N(R^c)C(O)OR^e$, —$N(R^c)C(O)NR^cR^d$, —$C(O)NR^cR^d$, —CN, —$CF_3$, —$OCF_3$, and —$OCHF_2$, wherein each CH, $CH_2$ and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In another class of this embodiment, $R^a$ is selected from the group consisting of: —$C_{1-6}$alkyl, halogen, —$(CH_2)_u$—$OC_{1-6}$alkyl, —$OR^e$, —$S(O)_uR^e$, —$S(O)_uNR^cR^d$, —$N(R^c)S(O)_pR^e$, —$NR^cR^d$, —$C(O)R^e$, —$OC(O)R^e$, —$CO_2R^e$, —$N(R^c)C(O)R^e$, —$N(R^c)C(O)OR^e$, —$N(R^c)C(O)NR^cR^d$, —$C(O)NR^cR^d$, —CN, —$CF_3$, —$OCF_3$, and —$OCHF_2$, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl, and each —$(CH_2)_u$— and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl.

In another embodiment of the present invention, $R^a$ is selected from the group consisting of: —$C_{1-6}$alkyl, halogen, —$(CH_2)_u$—$OC_{1-6}$alkyl, —$OR^e$, —$NR^cR^d$, —$CO_2R^e$, —CN, —$CF_3$, —$OCF_3$, and —$OCHF_2$, wherein each CH, $CH_2$ and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^a$ is selected from the group consisting of: —$C_{1-6}$alkyl, halogen, —$(CH_2)_u$—$OC_{1-6}$alkyl, —$OR^e$, —$NR^cR^d$, —$CO_2R^e$, —CN, —$CF_3$, —$OCF_3$, and —$OCHF_2$, wherein each CH, $CH_2$ and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In another class of this embodiment, $R^a$ is selected from the group consisting of: —$C_{1-6}$alkyl, halogen, —$(CH_2)_u$—$OC_{1-6}$alkyl, —$OR^e$, —$NR^cR^d$, —$CO_2R^e$, —CN, —$CF_3$, —$OCF_3$, and —$OCHF_2$, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl, and each —$(CH_2)_u$ and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl.

In another embodiment of the present invention, $R^a$ is selected from the group consisting of: —$C_{1-6}$alkyl, halogen, —$(CH_2)_u$—$OC_{1-6}$alkyl, —$OR^e$, —CN, —$CF_3$, —$OCF_3$, and —$OCHF_2$, wherein each CH, $CH_2$ and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^a$ is selected from the group consisting of: —$C_{1-6}$alkyl, halogen, —$(CH_2)_u$—$OC_{1-6}$alkyl, —$OR^e$, —CN, —$CF_3$, —$OCF_3$, and —$OCHF_2$, wherein each CH, $CH_2$ and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In another class of this embodiment, $R^a$ is selected from the group consisting of: —$C_{1-6}$alkyl, halogen, —$(CH_2)_u$—$OC_{1-6}$alkyl, —$OR^e$, —CN, —$CF_3$, —$OCF_3$, and —$OCHF_2$, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl, and each —$(CH_2)_u$— and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl.

In another embodiment of the present invention, $R^a$ is selected from the group consisting of: —$C_{1-6}$alkyl, halogen, —$OC_{1-6}$alkyl, —CN, —$CF_3$, —$OCF_3$, and —$OCHF_2$, wherein each CH, $CH_2$ and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^a$ is selected from the group consisting of: —$C_{1-6}$alkyl, halogen, —$OC_{1-6}$alkyl, —CN, —$CF_3$, —$OCF_3$, and —$OCHF_2$, wherein each CH, $CH_2$ and alkyl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl.

In another embodiment of the present invention, $R^a$ is selected from the group consisting of: —$C_{1-6}$alkyl, and halogen, wherein alkyl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^a$ is selected from the group consisting of: —$C_{1-6}$alkyl and halogen, wherein alkyl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In another class of this embodiment, $R^a$ is selected from the group consisting of: —$C_{1-6}$alkyl and halogen. In another class of this embodiment, $R^a$ is selected from the group consisting of: —$CH_3$ and F.

In another embodiment of the present invention, $R^a$ is —$C_{1-6}$alkyl, wherein each alkyl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^a$ is —$C_{1-6}$alkyl, wherein each alkyl is unsubstituted or substituted with one to four substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In another class of this embodiment, $R^a$ is —$C_{1-6}$alkyl. In a class of this embodiment, $R^a$ is —$CH_3$.

In another embodiment of the present invention, $R^a$ is halogen. In one class of this embodiment, $R^a$ is F.

In another embodiment of the present invention, $R^b$ is selected from the group consisting of: —$C_{1-10}$alkyl, —$(CH_2)_v$—$CF_3$, —$O(CH_2)_v CF_3$, —$OCHF_2$, halogen, oxo, —$(CH_2)_v OH$, —$(CH_2)_v OC_{1-10}$alkyl, —$(CH_2)_v$—O—$(CH_2)_v C_{3-6}$cycloalkyl, and —$(CH_2)_v C_{3-6}$cycloalkyl, wherein each CH, $CH_2$, alkyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In another embodiment of the present invention, $R^b$ is selected from the group consisting of: —$C_{1-10}$alkyl, —$(CH_2)_v$—$CF_3$, —$O(CH_2)_v CF_3$, —$OCHF_2$, halogen, oxo, —$(CH_2)_v OH$, —$(CH_2)_v OC_{1-10}$alkyl, —$(CH_2)_v$—O—$(CH_2)_v C_{3-6}$cycloalkyl, and —$(CH_2)_v C_{3-6}$cycloalkyl, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl, and each —$(CH_2)_v$—, alkyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl.

In another embodiment of the present invention, $R^b$ is selected from the group consisting of: —$C_{1-10}$alkyl, —$CF_3$, —$OCF_3$, —$OCHF_2$, halogen, oxo, —OH, —$OC_{1-10}$alkyl, —O—$C_{3-6}$cycloalkyl, and —$C_{3-6}$cycloalkyl.

In another embodiment of the present invention, $R^b$ is selected from the group consisting of: —$CH_3$, —$CF_3$, —$OCF_3$, —O—$CHF_2$, Cl, F, oxo, —OH, —$OCH_3$, —O—$CH_2CH_3$, —O—$CH(CH_3)_2$, —O— cyclopropyl, and cyclopropyl.

In another embodiment of the present invention, $R^b$ is selected from the group consisting of: —$C_{1-10}$alkyl, —$C_{2-10}$alkenyl, —$(CH_2)_v$—$CF_3$, —$O(CH_2)_v CF_3$, —$OCHF_2$, —$S(CH_2)_v CF_3$, —$(CH_2)_v SC_{1-10}$alkyl, halogen, —$(CH_2)_v CN$, —$(CH_2)_v OH$, —$(CH_2)_v OC_{1-10}$alkyl, —$(CH_2)_v OC_{2-10}$alkenyl, —O—$(CH_2)_v OC_{1-10}$alkyl, —$(CH_2)_v$—O—$(CH_2)_v C_{3-6}$cycloalkyl, —$(CH_2)_v$—O—$(CH_2)_v C_{2-10}$cycloheteroalkyl, —$(CH_2)_v$—O—$(CH_2)_v$-aryl, —$(CH_2)_v$—O—$(CH_2)_v$-heteroaryl, —$(CH_2)_v$—$O(CH_2)_v N(R^c)S(O)_q R^e$, —$(CH_2)_v O(CH_2)_v S(O)_q R^e$, —$(CH_2)_v O(CH_2)_v S(O)_q NR^c R^d$, —$(CH_2)_v O(CH_2)_v NR^c R^d$, —$C(O)R^e$, —$OC(O)R^e$, —$CO_2 R^e$, —$C(O)NR^c R^d$, —$N(R^c)C(O)R^e$, —$N(R^c)C(O)OR^e$, —$N(R^c)C(O)NR^c R^d$, —$N(R^c)S(O)_q R^e$, —$S(O)_q R^e$, —$S(O)_q NR^c R^d$, —$NR^c R^d$, —$O(CH_2)_v O$—$C_{3-6}$cycloalkyl, —$O(CH_2)_v O$—$C_{2-5}$ cycloheteroalkyl, —$O(CH_2)_v O$-aryl, —$O(CH_2)_v O$-heteroaryl, —$(CH_2)_v C_{3-6}$cycloalkyl, —$(CH_2)_v C_{2-10}$cycloheteroalkyl, —$(CH_2)_v$-aryl, and —$(CH_2)_v$-heteroaryl, wherein each CH, $CH_2$, alkyl, alkenyl, cycloalkyl, cycloheteroalkyl, aryl and heteroaryl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^b$ is selected from the group consisting of: —$C_{1-10}$alkyl, —$C_{2-10}$alkenyl, —$(CH_2)_v$—$CF_3$, —$O(CH_2)_v CF_3$, —$OCHF_2$, —$S(CH_2)_v CF_3$, —$(CH_2)_v SC_{1-10}$alkyl, halogen, —$(CH_2)_v CN$, —$(CH_2)_v OH$, —$(CH_2)_v OC_{1-10}$alkyl, —$(CH_2)_v OC_{2-10}$alkenyl, —O—$(CH_2)_v OC_{1-10}$alkyl, —$(CH_2)_v$—O—$(CH_2)_v C_{3-6}$cycloalkyl, —$(CH_2)_v$—O—$(CH_2)_v C_{2-10}$cycloheteroalkyl, —$(CH_2)_v$—O—$(CH_2)_v$-aryl, —$(CH_2)_v$—O—$(CH_2)_v$-heteroaryl, —$(CH_2)_v$—$O(CH_2)_v N(R^c)S(O)_q R^e$, —$(CH_2)_v O(CH_2)_v S(O)_q R^e$, —$(CH_2)_v O(CH_2)_v S(O)_q NR^c R^d$, —$(CH_2)_v O(CH_2)_v NR^c R^d$, —$C(O)R^e$, —$OC(O)R^e$, —$CO_2 R^e$, —$C(O)NR^c R^d$, —$N(R^c)C(O)R^e$, —$N(R^c)C(O)OR^e$, —$N(R^c)C(O)NR^c R^d$, —$N(R^c)S(O)_q R^e$, —$S(O)_q R^e$, —$S(O)_q NR^c R^d$, —$NR^c R^d$, —$O(CH_2)_v O$—$C_{3-6}$cycloalkyl, —$O(CH_2)_v O$—$C_{2-5}$ cycloheteroalkyl, —$O(CH_2)_v O$-aryl, —$O(CH_2)_v O$-heteroaryl, —$(CH_2)_v C_{3-6}$cycloalkyl, —$(CH_2)_v C_{2-10}$cycloheteroalkyl, —$(CH_2)_v$-aryl, and —$(CH_2)_v$-heteroaryl, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl, and each —$(CH_2)_v$—, alkyl, alkenyl, cycloalkyl, cycloheteroalkyl, aryl and heteroaryl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl.

In another embodiment of the present invention, $R^b$ is selected from the group consisting of: —$C_{1-10}$alkyl, —$C_{2-10}$alkenyl, —$(CH_2)_v$—$CF_3$, —$O(CH_2)_v CF_3$, —$OCHF_2$, —$S(CH_2)_v CF_3$, —$(CH_2)_v SC_{1-10}$alkyl, halogen, —$(CH_2)_v CN$, —$(CH_2)_v OH$, —$(CH_2)_v OC_{1-10}$alkyl, —$(CH_2)_v OC_{2-10}$alkenyl, —O—$(CH_2)_v OC_{1-10}$alkyl, —$(CH_2)_v$—O—$(CH_2)_v C_{3-6}$cycloalkyl, —$(CH_2)_v$—O—$(CH_2)_v C_{2-10}$cycloheteroalkyl, —$(CH_2)_v$—O—$(CH_2)_v$-aryl, —$(CH_2)_v$—O—$(CH_2)_v$-heteroaryl, —$(CH_2)_v$ O$(CH_2)_v$N-$R^c R^d$, —$CO_2 R^e$, —$NR^c R^d$, —$O(CH_2)_v O$—$C_{3-6}$cycloalkyl, —$O(CH_2)_v O$—$C_{2-5}$cycloheteroalkyl, —$O(CH_2)_v O$-aryl, —$O(CH_2)_v O$-heteroaryl, —$(CH_2)_v C_{3-6}$cycloalkyl, —$(CH_2)_v C_{2-10}$cycloheteroalkyl, —$(CH_2)_v$-aryl, and —$(CH_2)_v$-heteroaryl, wherein each CH, $CH_2$, alkyl, alkenyl, cycloalkyl, cycloheteroalkyl, aryl and heteroaryl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl.

In another embodiment of the present invention, $R^b$ is selected from the group consisting of: —$C_{1-10}$alkyl, —$C_{2-10}$alkenyl, —$(CH_2)_v$—$CF_3$, —$O(CH_2)_v CF_3$, —$OCHF_2$, —$S(CH_2)_v CF_3$, —$(CH_2)_v SC_{1-10}$alkyl, halogen, —$(CH_2)_v CN$, —$(CH_2)_v OH$, —$(CH_2)_v OC_{1-10}$alkyl, —$(CH_2)_v OC_{2-10}$alkenyl, —$(CH_2)_v$—O—$(CH_2)_v C_{3-6}$cycloalkyl, —$(CH_2)_v$—O—$(CH_2)_v C_{2-10}$cycloheteroalkyl, —$(CH_2)_v$—O—$(CH_2)_v$-aryl, —$(CH_2)_v$—O—$(CH_2)_v$-heteroaryl, —$CO_2 R^e$, —$NR^c R^d$, —$(CH_2)_v C_{3-6}$cycloalkyl, —$(CH_2)_v C_{2-10}$cycloheteroalkyl, —$(CH_2)_v$-aryl, and —$(CH_2)_v$-heteroaryl, wherein each CH, $CH_2$, alkyl, alkenyl, cycloalkyl, cycloheteroalkyl, aryl and heteroaryl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^b$ is selected from the group consisting of: —$C_{1-10}$alkyl, —$C_{2-10}$alkenyl, —$(CH_2)_v$—$CF_3$, —$O(CH_2)_v CF_3$, —$OCHF_2$, —$S(CH_2)_v CF_3$, —$(CH_2)_v SC_{1-10}$alkyl, halogen, —$(CH_2)_v CN$, —$(CH_2)_v OH$, —$(CH_2)_v OC_{1-10}$alkyl, —$(CH_2)_v OC_{2-10}$alkenyl, —$(CH_2)_v$—O—$(CH_2)_v C_{3-6}$cycloalkyl, —$(CH_2)_v$—O—$(CH_2)_v C_{2-10}$cycloheteroalkyl, —$(CH_2)_v$—O—$(CH_2)_v$-aryl, —$(CH_2)_v$—O—$(CH_2)_v$-heteroaryl, —$CO_2 R^e$, —$NR^c R^d$, —$(CH_2)_v C_{3-6}$cycloalkyl, —$(CH_2)_v C_{2-10}$cycloheteroalkyl, —$(CH_2)_v$-aryl, and —$(CH_2)_v$-heteroaryl, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl, and each —$(CH_2)_v$—, alkyl, alkenyl, cycloalkyl, cycloheteroalkyl, aryl and heteroaryl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl.

In another embodiment of the present invention, $R^b$ is selected from the group consisting of: —$C_{1-10}$alkyl, —$C_{2-10}$alkenyl, —$(CH_2)_v$—$CF_3$, —$O(CH_2)_v CF_3$, —$OCHF_2$, halogen, —$(CH_2)_v CN$, —$(CH_2)_v OH$, —$(CH_2)_v OC_{1-10}$alkyl, —$CO_2 R^e$, —$NR^c R^d$, —$(CH_2)_v C_{3-6}$cycloalkyl, —$(CH_2)_v C_{2-10}$cycloheteroalkyl, —$(CH_2)_v$-aryl, and —$(CH_2)_v$-heteroaryl, wherein each CH, $CH_2$, alkyl, alkenyl, cycloalkyl, cycloheteroalkyl, aryl and heteroaryl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl.

In another embodiment of the present invention, $R^b$ is selected from the group consisting of: —$C_{1-10}$alkyl, —$C_{2-10}$alkenyl, —$(CH_2)_v$—$CF_3$, —$O(CH_2)_v CF_3$, —$OCHF_2$, halogen, —$(CH_2)_v CN$, —$(CH_2)_v OH$, —$(CH_2)_v OC_{1-10}$alkyl, and —$(CH_2)_v C_{3-6}$cycloalkyl, wherein each CH, $CH_2$, alkyl, alkenyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In a class of this embodiment, $R^b$ is selected from the group consisting of: —$C_{1-10}$alkyl, —$C_{2-10}$alkenyl, —$(CH_2)_v$—$CF_3$, —$O(CH_2)_v CF_3$, —$OCHF_2$, halogen, —$(CH_2)_v CN$, —$(CH_2)_v OH$, —$(CH_2)_v OC_{1-10}$alkyl, and —$(CH_2)_v C_{3-6}$cycloalkyl, wherein each CH is unsubstituted or substituted with one substituent selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl, and each —$(CH_2)_v$—, alkyl, alkenyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl.

In another embodiment of the present invention, $R^b$ is selected from the group consisting of: —$C_{1-10}$alkyl, —$(CH_2)_v$—$CF_3$, —$O(CH_2)_v CF_3$, halogen, —$(CH_2)_v OC_{1-10}$alkyl, and —$(CH_2)_v C_{3-6}$cycloalkyl, wherein each $CH_2$, alkyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl. In another embodiment of the present invention, $R^b$ is selected from the group consisting of: —$C_{1-10}$alkyl, —$(CH_2)_v$—$CF_3$, —$O(CH_2)_v CF_3$, halogen, —$(CH_2)_v OC_{1-10}$alkyl, and —$(CH_2)_v C_{3-6}$cycloalkyl, wherein each $CH_2$, alkyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In a class of this embodiment, $R^b$ is selected from the group consisting of: —$C_{1-10}$alkyl, —$(CH_2)_v$—$CF_3$, —$O(CH_2)_v CF_3$, halogen, —$(CH_2)_v OC_{1-10}$alkyl, and —$(CH_2)_v C_{3-6}$cycloalkyl, wherein each —$(CH_2)_v$, alkyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl.

In another embodiment of the present invention, $R^b$ is selected from the group consisting of: —$C_{1-10}$alkyl, —$CF_3$, —$O(CH_2)_v CF_3$, halogen, —$OC_{1-10}$alkyl, and —$C_{3-6}$cycloalkyl, wherein each $CH_2$, alkyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl.

In another embodiment of the present invention, $R^b$ is selected from the group consisting of: —$C_{1-10}$alkyl, —$CF_3$, —$O(CH_2)_v CF_3$, halogen, —$OC_{1-10}$alkyl, and —$C_{3-6}$cycloalkyl, wherein each $CH_2$, alkyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In a class of this embodiment, $R^b$ is selected from the group consisting of: —$C_{1-10}$alkyl, —$CF_3$, —$O(CH_2)_vCF_3$, halogen, —$OC_{1-10}$alkyl, and —$C_{3-6}$cycloalkyl, wherein each $(CH_2)_v$, alkyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl.

In another embodiment of the present invention, $R^b$ is selected from the group consisting of: —$C_{1-10}$alkyl, —$CF_3$, —$O(CH_2)_vCF_3$, halogen, —$OC_{1-10}$alkyl, and —$C_{3-6}$cycloalkyl. In another embodiment of the present invention, $R^b$ is selected from the group consisting of: —$CH_3$, —$CH_2CH_3$, —$CF_3$, —$OCF_3$, F, Cl, —$OCH_3$, and cyclopropyl, wherein each $CH_2$, alkyl and cycloalkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In another embodiment of the present invention, $R^b$ is selected from the group consisting of: —$CH_3$, —$CH_2CH_3$, —$CF_3$, —$OCF_3$, F, Cl, —$OCH_3$, and cyclopropyl.

In another embodiment of the present invention, $R^b$ is selected from the group consisting of: —$C_{1-10}$alkyl, and —$CF_3$, wherein each alkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl.

In another embodiment of the present invention, $R^b$ is selected from the group consisting of: —$C_{1-10}$alkyl and —$CF_3$, wherein each alkyl is unsubstituted or substituted with one, two or three substituents selected from: halogen, —$C_{1-6}$alkyl, —$(CH_2)_w$—OH, —O—$C_{1-6}$alkyl, —$CF_3$, —CN, SH, and —$SO_2$—$C_{1-6}$alkyl. In a class of this embodiment, $R^b$ is selected from the group consisting of: —$CH_3$, —$CH_2CH_3$ and —$CF_3$. In another class of this embodiment, $R^b$ is independently selected from the group consisting of: —$CH_3$ and —$CF_3$.

In another embodiment of the present invention, $R^c$ is selected from the group consisting of: hydrogen, $C_{1-10}$alkyl, $C_{3-6}$cycloalkyl, $C_{2-5}$cycloheteroalkyl, aryl, and heteroaryl, wherein each alkyl, cycloalkyl, cycloheteroalkyl, aryl and heteroaryl is unsubstituted or substituted with one to three substituents selected from $C_{1-6}$alkyl. In another embodiment of the present invention, $R^c$ is selected from the group consisting of: hydrogen, $C_{1-10}$alkyl, $C_{3-6}$cycloalkyl and $C_{2-5}$cycloheteroalkyl, wherein each alkyl, cycloalkyl and cycloheteroalkyl is unsubstituted or substituted with one to three substituents selected from $C_{1-6}$alkyl.

In another embodiment of the present invention, $R^c$ is selected from the group consisting of: aryl and heteroaryl, wherein each aryl and heteroaryl is unsubstituted or substituted with one to three substituents selected from $C_{1-6}$alkyl. In another embodiment of the present invention, $R^c$ is selected from the group consisting of: hydrogen and $C_{1-10}$alkyl, wherein each alkyl is unsubstituted or substituted with one to three substituents selected from $C_{1-6}$alkyl.

In another embodiment of the present invention, $R^c$ is $C_{1-10}$alkyl, wherein each alkyl is unsubstituted or substituted with one to three substituents selected from $C_{1-6}$alkyl.

In another embodiment of the present invention, $R^c$ is hydrogen

In another embodiment of the present invention, $R^d$ is selected from the group consisting of: hydrogen, $C_{1-10}$alkyl, $C_{3-6}$cycloalkyl, $C_{2-5}$cycloheteroalkyl, aryl, and heteroaryl, wherein each alkyl, cycloalkyl, cycloheteroalkyl, aryl and heteroaryl is unsubstituted or substituted with one to three substituents selected from $C_{1-6}$alkyl. In another embodiment of the present invention, $R^d$ is selected from the group consisting of: hydrogen, $C_{1-10}$alkyl, $C_{3-6}$cycloalkyl and $C_{2-5}$cycloheteroalkyl, wherein each alkyl, cycloalkyl and cycloheteroalkyl is unsubstituted or substituted with one to three substituents selected from $C_{1-6}$alkyl.

In another embodiment of the present invention, $R^d$ is selected from the group consisting of: aryl and heteroaryl, wherein each aryl and heteroaryl is unsubstituted or substituted with one to three substituents selected from $C_{1-6}$alkyl. In another embodiment of the present invention, $R^d$ is selected from the group consisting of: hydrogen and $C_{1-10}$alkyl, wherein each alkyl is unsubstituted or substituted with one to three substituents selected from $C_{1-6}$alkyl.

In another embodiment of the present invention, $R^d$ is $C_{1-10}$alkyl, wherein each alkyl is unsubstituted or substituted with one to three substituents selected from $C_{1-6}$alkyl.

In another embodiment of the present invention, $R^d$ is hydrogen.

In another embodiment of the present invention, $R^e$ is selected from the group consisting of: hydrogen, $C_{1-10}$alkyl, $C_{3-6}$cycloalkyl, $C_{2-5}$cycloheteroalkyl, aryl, and heteroaryl, wherein each alkyl, cycloalkyl, cycloheteroalkyl, aryl and heteroaryl is unsubstituted or substituted with one to three substituents selected from $C_{1-6}$alkyl. In another embodiment of the present invention, $R^e$ is selected from the group consisting of: hydrogen, $C_{1-10}$alkyl, $C_{3-6}$cycloalkyl and $C_{2-5}$cycloheteroalkyl, wherein each alkyl, cycloalkyl and cycloheteroalkyl is unsubstituted or substituted with one to three substituents selected from $C_{1-6}$alkyl.

In another embodiment of the present invention, $R^e$ is selected from the group consisting of: aryl and heteroaryl, wherein each aryl and heteroaryl is unsubstituted or substituted with one to three substituents selected from $C_{1-6}$alkyl. In another embodiment of the present invention, $R^e$ is selected from the group consisting of: hydrogen and $C_{1-10}$alkyl, wherein each alkyl is unsubstituted or substituted with one to three substituents selected from $C_{1-6}$alkyl.

In another embodiment of the present invention, $R^e$ is $C_{1-10}$alkyl, wherein each alkyl is unsubstituted or substituted with one to three substituents selected from $C_{1-6}$alkyl.

In another embodiment of the present invention, $R^e$ is hydrogen

In another embodiment of the present invention, $R^f$ is selected from the group consisting of: hydrogen, $C_{1-6}$alkyl and $C_{3-6}$cycloalkyl. In another embodiment of the present invention, $R^f$ is selected from the group consisting of: hydrogen and $C_{1-6}$alkyl.

In another embodiment of the present invention, $R^f$ is $C_{1-6}$alkyl.

In another embodiment of the present invention, $R^f$ is hydrogen.

In another embodiment of the present invention, $R^g$ is selected from the group consisting of: hydrogen, halogen, $C_{1-6}$alkyl, and $C_{3-6}$cycloalkyl. In another embodiment of the present invention, $R^g$ is selected from the group consisting of: hydrogen, halogen and $C_{1-6}$alkyl. In another embodiment of the present invention, $R^g$ is selected from the group consisting of: hydrogen and $C_{1-6}$alkyl.

In another embodiment of the present invention, $R^g$ is $C_{1-6}$alkyl.

In another embodiment of the present invention, $R^g$ is hydrogen.

In another embodiment of the present invention, $R^h$ is selected from the group consisting of: hydrogen, —$C_{1-10}$alkyl, —$C_{2-10}$ alkenyl, —$C_{3-6}$ cycloalkyl, $C_{3-6}$ cycloalkyl-$C_{1-10}$alkyl-, —$C_{2-5}$cycloheteroalkyl, $C_{2-5}$cycloheteroalkyl-$C_{1-10}$alkyl-, aryl, heteroaryl, aryl-$C_{1-10}$alkyl-, and heteroaryl-$C_{1-10}$alkyl-, wherein alkyl, alkenyl, cycloalkyl, cycloheteroalkyl, aryl and heteroaryl are unsubstituted or substituted with one to four substituents selected from $C_{1-6}$alkyl. In another embodiment of the present invention, $R^h$ is selected from the group consisting of: —$C_{1-10}$alkyl, —$C_{2-10}$ alkenyl, —$C_{3-6}$ cycloalkyl, $C_{3-6}$ cycloalkyl-$C_{1-10}$alkyl-, —$C_{2-5}$cycloheteroalkyl, $C_{2-5}$ cycloheteroalkyl-$C_{1-10}$alkyl-, aryl, heteroaryl, aryl-$C_{1-10}$alkyl-, and heteroaryl-$C_{1-10}$ alkyl-, wherein alkyl, alkenyl, cycloalkyl, cycloheteroalkyl, aryl and heteroaryl are unsubstituted or substituted with one to four substituents selected from $C_{1-6}$alkyl.

In another embodiment of the present invention, $R^h$ is selected from the group consisting of: —$C_{1-10}$alkyl, —$C_{2-10}$ alkenyl, —$C_{3-6}$ cycloalkyl, —$C_{2-5}$cycloheteroalkyl, aryl, and heteroaryl, wherein alkyl, alkenyl, cycloalkyl, cycloheteroalkyl, aryl and heteroaryl are unsubstituted or substituted with one to four substituents selected from $C_{1-6}$alkyl. In another embodiment of the present invention, $R^h$ is selected from the group consisting of: —$C_{1-10}$alkyl, aryl, and heteroaryl, wherein alkyl, aryl and heteroaryl are unsubstituted or substituted with one to four substituents selected from $C_{1-6}$alkyl.

In another embodiment of the present invention, $R^h$ is —$C_{1-10}$alkyl, wherein alkyl is unsubstituted or substituted with one to four substituents selected from $C_{1-6}$alkyl. In another embodiment of the present invention, $R^h$ is selected from the group consisting of: aryl and heteroaryl, wherein aryl and heteroaryl are unsubstituted or substituted with one to four substituents selected from $C_{1-6}$alkyl.

In another embodiment of the present invention, $R^h$ is aryl, wherein aryl is unsubstituted or substituted with one to four substituents selected from $C_{1-6}$alkyl.

In another embodiment of the present invention, $R^h$ is heteroaryl, wherein heteroaryl is unsubstituted or substituted with one to four substituents selected from $C_{1-6}$alkyl.

In another embodiment of the present invention, $R^h$ is hydrogen.

In another embodiment of the present invention, $R^i$ is selected from the group consisting of: hydrogen, halogen, —$C_{1-6}$alkyl, —$(CH_2)_s$—O—$C_{1-6}$alkyl, —$(CH_2)_s$OH, —$N(R^c)S(O)_2R^e$, —$S(C_{1-6}$alkyl), —$(CH_2)_sSO_2C_{1-6}$alkyl, —$(CH_2)_sSO_2$—$(CH_2)_t$—$C_{3-6}$cycloalkyl, —$S(O)_2NR^cR^d$, —$NR^cR^d$, —$C(O)R^e$, —$OC(O)R^e$, —$CO_2R^e$, —$(CH_2)_sCN$, —$C(O)NR^cR^d$, —$N(R^c)C(O)R^e$, —$N(R^c)C(O)OR^e$, —$N(R^c)C(O)NR^cR^d$, —$CF_3$, —$OCF_3$, —$OCHF_2$, —$C_{3-6}$cycloalkyl, and —$C_{2-5}$cycloheteroalkyl, wherein each $CH_2$, alkyl, cycloalkyl and cycloheteroalkyl is unsubstituted or substituted with one, two, three or four substituents selected from: —$C_{1-6}$alkyl and halogen. In another embodiment of the present invention, $R^i$ is selected from the group consisting of: hydrogen, halogen, —$C_{1-6}$alkyl, —$(CH_2)_s$—O—$C_{1-6}$alkyl, —$(CH_2)_s$OH, —$N(R^c)S(O)_2R^e$, —$S(C_{1-6}$alkyl), —$(CH_2)_sSO_2C_{1-6}$alkyl, —$(CH_2)_sSO_2$—$(CH_2)_t$—$C_{3-6}$cycloalkyl, —$S(O)_2NR^cR^d$, —$NR^cR^d$, —$C(O)R^e$, —$OC(O)R^e$, —$CO_2R^e$, —$(CH_2)_sCN$, —$C(O)NR^cR^d$, —$N(R^c)C(O)R^e$, —$N(R^c)C(O)OR^e$, —$N(R^c)C(O)NR^cR^d$, —$CF_3$, —$OCF_3$, —$OCHF_2$, —$C_{3-6}$cycloalkyl, and —$C_{2-5}$cycloheteroalkyl, wherein each —$(CH_2)_s$—, —$(CH_2)_t$—, alkyl, cycloalkyl and cycloheteroalkyl is unsubstituted or substituted with one, two, three or four substituents selected from: —$C_{1-6}$alkyl and halogen. In another embodiment of the present invention, $R^1$ is selected from the group consisting of: hydrogen, halogen, —$C_{1-6}$alkyl, —$(CH_2)_s$—O—$C_{1-6}$alkyl, —$(CH_2)_s$OH, —$N(R^c)S(O)_2R^e$, —$S(C_{1-6}$alkyl), —$(CH_2)_sSO_2C_{1-6}$alkyl, —$S(O)_2NR^cR^d$, —$NR^cR^d$, —$C(O)R^e$, —$OC(O)R^e$, —$CO_2R^e$, —$(CH_2)_sCN$, —$C(O)NR^cR^d$, —$N(R^c)C(O)R^e$, —$N(R^c)C(O)OR^e$, —$N(R^c)C(O)NR^cR^d$, —$CF_3$, —$OCF_3$, and —$OCHF_2$, wherein each $CH_2$ and alkyl is unsubstituted or substituted with one, two, three or four substituents selected from: —$C_{1-6}$alkyl and halogen. In a class of this embodiment, $R^i$ is selected from the group consisting of: hydrogen, halogen, —$C_{1-6}$alkyl, —$(CH_2)_s$—O—$C_{1-6}$alkyl, —$(CH_2)_s$OH, —$N(R^c)S(O)_2R^e$, —$S(C_{1-6}$alkyl), —$(CH_2)_sSO_2C_{1-6}$alkyl, —$S(O)_2NR^cR^d$, —$NR^cR^d$, —$C(O)R^e$, —$OC(O)R^e$, —$CO_2R^e$, —$(CH_2)_sCN$, —$C(O)NR^cR^d$, —$N(R^c)C(O)R^e$, —$N(R^c)C(O)OR^e$, —$N(R^c)C(O)NR^cR^d$, —$CF_3$, —$OCF_3$, and —$OCHF_2$, wherein each —$(CH_2)_s$— and alkyl is unsubstituted or substituted with one, two, three or four substituents selected from: —$C_{1-6}$alkyl and halogen.

In another embodiment of the present invention, $R^i$ is selected from the group consisting of: hydrogen, halogen, —$C_{1-6}$alkyl, —$(CH_2)_s$—O—$C_{1-6}$alkyl, —$(CH_2)_s$OH, —$S(C_{1-6}$alkyl), —$NR^cR^d$, —$CO_2R^e$, —$(CH_2)_sCN$, —$CF_3$, —$OCF_3$, and —$OCHF_2$, wherein each $CH_2$ and alkyl is unsubstituted or substituted with one, two, three or four substituents selected from: —$C_{1-6}$alkyl and halogen.

In another embodiment of the present invention, $R^i$ is selected from the group consisting of: hydrogen, halogen, —$C_{1-6}$alkyl, —$(CH_2)_s$—O—$C_{1-6}$alkyl, —$(CH_2)_s$OH, —$(CH_2)_sCN$, —$CF_3$, —$OCF_3$, and —$OCHF_2$, wherein each $CH_2$ and alkyl is unsubstituted or substituted with one, two, three or four substituents selected from: —$C_{1-6}$alkyl and halogen. In a class of this embodiment, $R^i$ is selected from the group consisting of: hydrogen, halogen, —$C_{1-6}$alkyl, —$(CH_2)_s$—O—$C_{1-6}$alkyl, —$(CH_2)_s$OH, —$(CH_2)_sCN$, —$CF_3$, —$OCF_3$, and —$OCHF_2$, wherein each —$(CH_2)_s$— and alkyl is unsubstituted or substituted with one, two, three or four substituents selected from: —$C_{1-6}$alkyl and halogen.

In another embodiment of the present invention, $R^i$ is selected from the group consisting of: hydrogen, halogen, and —$C_{1-6}$alkyl, wherein alkyl is unsubstituted or substituted with one, two, three or four substituents selected from: —$C_{1-6}$alkyl and halogen. In another embodiment of the present invention, $R^i$ is selected from the group consisting of: hydrogen and —$C_{1-6}$alkyl, wherein alkyl is unsubstituted or substituted with one, two, three or four substituents selected from: —$C_{1-6}$alkyl and halogen. In a class of this embodiment, $R^i$ is selected from the group consisting of: hydrogen and —$CH_3$. In another embodiment of the present invention, $R^i$ is —$C_{1-6}$alkyl, wherein each alkyl is unsubstituted or substituted with one, two, three or four substituents selected from: —$C_{1-6}$alkyl and halogen. In a class of this embodiment, $R^i$ is —$C_{1-6}$alkyl. In another class of this embodiment, $R^i$ is —$CH_3$.

In another embodiment of the present invention, $R^i$ is hydrogen.

In another embodiment of the present invention, $R^j$ is selected from the group consisting of: —$C_{1-6}$alkyl, —$C_{3-6}$cycloalkyl, and -aryl-$C_{1-6}$alkyl, wherein each alkyl, cycloalkyl and aryl is unsubstituted or substituted with one to three substituents selected from $R^k$.

In another embodiment of the present invention, $R^j$ is selected from the group consisting of: —$C_{1-6}$alkyl and —$C_{3-6}$cycloalkyl, wherein each alkyl and cycloalkyl is unsubstituted or substituted with one to three substituents selected from $R^k$.

In another embodiment of the present invention, $R^j$ is —$C_{1-6}$alkyl, wherein each alkyl is unsubstituted or substituted with one to three substituents selected from $R^k$.

In another embodiment of the present invention, $R^k$ is selected from the group consisting of: —$C_{1-6}$alkyl, —$OR^e$, —$N(R^c)S(O)_pR^e$, halogen, —$S(O)_pR^e$, —$S(O)_pNR^cR^d$, —$NR^cR^d$, —$C(O)R^e$, —$OC(O)R^e$, —$CO_2R^e$, —$CN$, —C(O)NR$^c$R$^d$, —N(R$^c$)C(O)R$^e$, —N(R$^c$)C(O)OR$^e$, —N(R$^c$)C(O)NR$^c$R$^d$, —CF$_3$, —OCF$_3$, —OCHF$_2$, —C$_{3-6}$cycloalkyl, and —C$_{2-5}$cycloheteroalkyl.

In another embodiment of the present invention, R$^k$ is selected from the group consisting of: —C$_{1-6}$alkyl, —OR$^e$, —N(R$^c$)S(O)$_p$R$^e$, halogen, —S(O)$_p$R$^e$, —S(O)$_p$NR$^c$R$^d$, —NR$^c$R$^d$, —C(O)R$^e$, —OC(O)R$^e$, —CO$_2$R$^e$, —CN, —C(O)NR$^c$R$^d$, —N(R$^c$)C(O)R$^e$, —N(R$^c$)C(O)OR$^e$, —N(R$^c$)C(O)NR$^c$R$^d$, —CF$_3$, —OCF$_3$, and —OCHF$_2$.

In another embodiment of the present invention, R$^k$ is selected from the group consisting of: —C$_{1-6}$alkyl, —OR$^e$, halogen, —NR$^c$R$^d$, —CO$_2$R$^e$, —CN, —CF$_3$, —OCF$_3$, and —OCHF$_2$. In another embodiment of the present invention, R$^k$ is selected from the group consisting of: —C$_{1-6}$alkyl, —OR$^e$, halogen, —NR$^c$R$^d$, —CN, —CF$_3$, —OCF$_3$, and —OCHF$_2$.

In another embodiment of the present invention, R$^k$ is selected from the group consisting of: —C$_{1-6}$alkyl, —OR$^e$, halogen, —CN, —CF$_3$, —OCF$_3$, and —OCHF$_2$.

In another embodiment of the present invention, R$^k$ is selected from the group consisting of: —C$_{1-6}$alkyl and halogen. In a class of this embodiment, R$^k$ is —C$_{1-6}$alkyl. In another class of this embodiment, R$^k$ is halogen.

In another embodiment of the present invention, n is 1 or 2. In another class of this embodiment, n is 1. In another class of this embodiment, n is 2.

In another embodiment of the present invention, m is 1 or 2. In another class of this embodiment, m is 1. In another class of this embodiment, m is 2.

In another embodiment of the present invention, p is 0, 1 or 2. In another embodiment of the present invention, p is 1 or 2. In another embodiment of the present invention, p is 0 or 2. In another embodiment of the present invention, p is 0 or 1. In another embodiment of the present invention, p is 0. In another embodiment of the present invention, p is 1. In another embodiment of the present invention, p is 2.

In another embodiment of the present invention, q is 0, 1 or 2. In another embodiment of the present invention, q is 1 or 2. In another embodiment of the present invention, p is 0 or 2. In another embodiment of the present invention, q is 0 or 1. In another embodiment of the present invention, q is 0. In another embodiment of the present invention, q is 1. In another embodiment of the present invention, q is 2.

In another embodiment of the present invention, r is 1, 2, 3 or 4. In a class of this embodiment, r is 1, 2 or 3. In another class of this embodiment, r is 1 or 3. In a class of this embodiment, r is 1 or 2. In a class of this embodiment, r is 1 or 4. In another class of this embodiment, r is 2 or 3. In another class of this embodiment, r is 2 or 4. In another class of this embodiment, r is 3 or 4. In another class of this embodiment, r is 1. In another class of this embodiment, r is 2. In another class of this embodiment, r is 3. In another class of this embodiment, r is 4.

In another embodiment of the present invention, s is 0, 1, 2 or 3. In another embodiment of the present invention, s is 0, 1 or 2. In another embodiment of the present invention, s is 0, 1 or 3. In another embodiment of the present invention, s is 0, 2 or 3. In another embodiment of the present invention, s is 0 or 2. In another embodiment of the present invention, s is 0 or 1. In another embodiment of the present invention, s is 0 or 3. In another embodiment of the present invention, s is 1, 2 or 3. In another embodiment of the present invention, s is 1 or 3. In another embodiment of the present invention, s is 1 or 2. In another embodiment of the present invention, s is 2 or 3. In another embodiment of the present invention, s is 0. In another embodiment of the present invention, s is 1. In another embodiment of the present invention, s is 2. In another embodiment of the present invention, s is 3.

In another embodiment of the present invention, t is 0, 1, 2, 3 or 4. In a class of this embodiment, t is 0, 1, 2 or 3. In another class of this embodiment, t is 0, 1 or 2. In another embodiment of the present invention, t is 1, 2, 3 or 4. In a class of this embodiment, t is 1, 2 or 3. In a class of this embodiment, t is 1 or 3. In a class of this embodiment, t is 1 or 2. In a class of this embodiment, t is 1 or 4. In another class of this embodiment, t is 0 or 1. In another class of this embodiment, t is 0 or 2. In another class of this embodiment, t is 0 or 3. In another class of this embodiment, t is 0 or 4. In another class of this embodiment, t is 0. In another class of this embodiment, t is 1. In another class of this embodiment, t is 2. In another class of this embodiment, t is 3. In another class of this embodiment, t is 4.

In another embodiment of the present invention, u is 0, 1, 2 or 3. In another embodiment of the present invention, u is 0, 1 or 2. In another embodiment of the present invention, u is 0, 1 or 3. In another embodiment of the present invention, u is 0, 2 or 3. In another embodiment of the present invention, u is 0 or 2. In another embodiment of the present invention, u is 0 or 1. In another embodiment of the present invention, u is 0 or 3. In another embodiment of the present invention, u is 1, 2 or 3. In another embodiment of the present invention, u is 1 or 3. In another embodiment of the present invention, u is 1 or 2. In another embodiment of the present invention, u is 2 or 3. In another embodiment of the present invention, u is 0. In another embodiment of the present invention, u is 1. In another embodiment of the present invention, u is 2. In another embodiment of the present invention, u is 3.

In another embodiment of the present invention, v is 0, 1, 2, 3 or 4. In a class of this embodiment, v is 0, 1, 2 or 3. In another class of this embodiment, v is 0, 1 or 2. In another embodiment of the present invention, v is 1, 2, 3 or 4. In a class of this embodiment, v is 1, 2 or 3. In a class of this embodiment, v is 1 or 3. In a class of this embodiment, v is 1 or 2. In a class of this embodiment, v is 1 or 4. In another class of this embodiment, v is 0 or 1. In another class of this embodiment, v is 0 or 2. In another class of this embodiment, v is 0 or 3. In another class of this embodiment, v is 0 or 4. In another class of this embodiment, t is 0. In another class of this embodiment, v is 1. In another class of this embodiment, v is 2. In another class of this embodiment, v is 3. In another class of this embodiment, v is 4.

In another embodiment of the present invention, w is 0, 1, 2 or 3. In another embodiment of the present invention, w is 0, 1 or 2. In another embodiment of the present invention, w is 0, 1 or 3. In another embodiment of the present invention, w is 0, 2 or 3. In another embodiment of the present invention, w is 0 or 2. In another embodiment of the present invention, w is 0 or 1.

In another embodiment of the present invention, w is 0 or 3. In another embodiment of the present invention, w is 1, 2 or 3. In another embodiment of the present invention, w is 1 or 3. In another embodiment of the present invention, w is 1 or 2. In another embodiment of the present invention, w is 2 or 3. In another embodiment of the present invention, w is 0. In another embodiment of the present invention, w is 1. In another embodiment of the present invention, w is 2. In another embodiment of the present invention, w is 3.

In another embodiment of the present invention, x is 0, 1 or 2. In another embodiment of the present invention, x is 1 or 2. In another embodiment of the present invention, x is 0 or 2. In another embodiment of the present invention, x is 0 or 1. In another embodiment of the present invention, x is 0. In another embodiment of the present invention, x is 1. In another embodiment of the present invention, x is 2.

In another embodiment of the present invention, the invention relates to compounds of structural formula Ia:

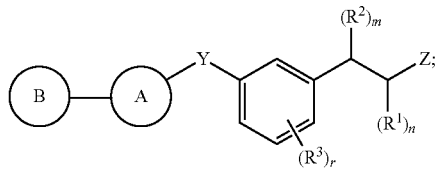

Ia or a pharmaceutically acceptable salt thereof.

In another embodiment of the present invention, the invention relates to compounds of structural formula Ib:

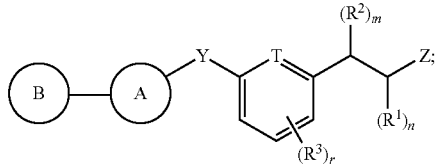

Ib or a pharmaceutically acceptable salt thereof.

In another embodiment of the present invention, the invention relates to compounds of structural formula Ic:

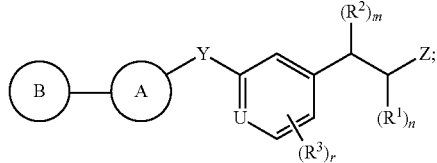

Ic or a pharmaceutically acceptable salt thereof.

In another embodiment of the present invention, the invention relates to compounds of structural formula Id:

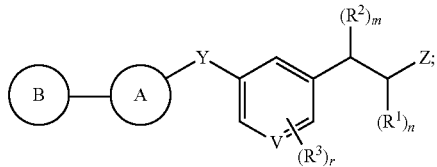

Id or a pharmaceutically acceptable salt thereof.

In another embodiment of the present invention, the invention relates to compounds of structural formula Ie:

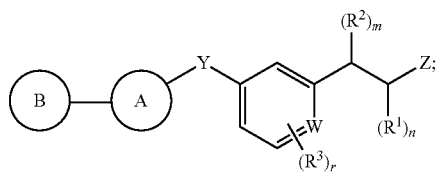

Ie or a pharmaceutically acceptable salt thereof.

In another embodiment of the present invention, the invention relates to compounds of structural formula If:

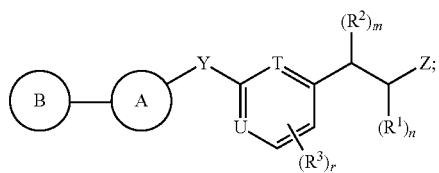

If or a pharmaceutically acceptable salt thereof.

In another embodiment of the present invention, the invention relates to compounds of structural formula Ig:

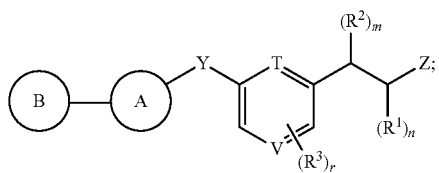

Ig or a pharmaceutically acceptable salt thereof.

In another embodiment of the present invention, the invention relates to compounds of structural formula Ih:

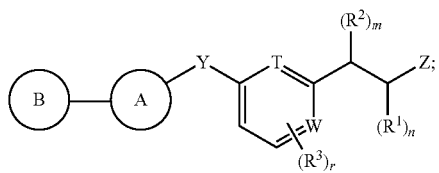

Ih or a pharmaceutically acceptable salt thereof.

In another embodiment of the present invention, the invention relates to compounds of structural formula Ii:

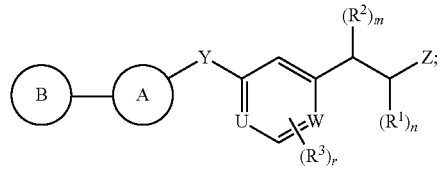

Ii or a pharmaceutically acceptable salt thereof.

In another embodiment of the present invention, the invention relates to compounds of structural formula Ij:

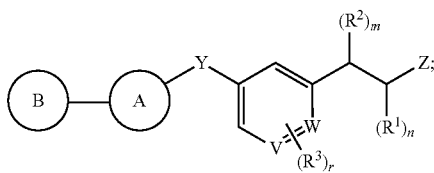

or a pharmaceutically acceptable salt thereof.

In one embodiment of the present invention, the compounds of formula I have the absolute stereochemistry at the two stereogenic carbon centers as indicated in the compound of structural formula Ik:

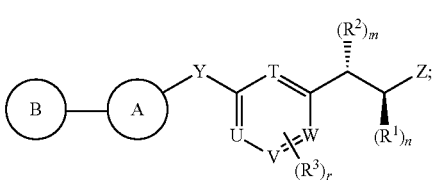

wherein n is 1; and pharmaceutically acceptable salts thereof.

In one embodiment of the present invention, the compounds of formula I have the absolute stereochemistry at the two stereogenic carbon centers as indicated in the compound of structural formula Il:

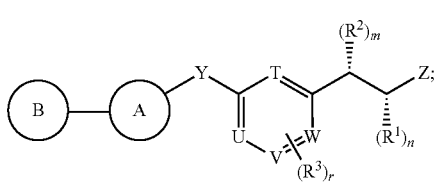

wherein n is 1; and pharmaceutically acceptable salts thereof.

The compound of structural formula I includes the compounds of structural formulas Ia, Ib, Ic, Id, Ie, If, Ig, Ih, Ii, Ij, Ik and Il, and pharmaceutically acceptable salts, hydrates and solvates thereof.

Another embodiment of the present invention relates to compounds of structural formula I wherein:
T, U, V and W are CH;
A is selected from the group consisting of:
  (1) —$C_{3-6}$cycloalkyl,
  (2) —$C_{3-6}$cycloalkenyl, and
  (3) —$C_{2-10}$cycloheteroalkyl,
wherein each cycloalkyl, cycloalkenyl and cycloheteroalkyl is unsubstituted or substituted with one, two or three substituents selected from $R^a$;
B is selected from the group consisting of:
  (1) —$(CH_2)_u$-aryl,
  (2) —$(CH_2)_u$-heteroaryl,
  (3) —$(CH_2)_u$—$NR^g(CH_2)_u$-aryl,
  (4) —$(CH_2)_u$—O—$(CH_2)_u$-aryl,
  (5) —$(CH_2)_u$—O—$(CH_2)_u$-aryl-aryl, and
  (6) —$(CH_2)_u$—O—$(CH_2)_u$-heteroaryl,
wherein each $CH_2$, aryl and heteroaryl is unsubstituted or substituted with one, two, three, four or five substituents selected from $R^b$;
Y is selected from: —O—, —$(CH_2)_xO$— and —O—$(CH_2)_x$, wherein $CH_2$ is unsubstituted or substituted with one or two substituents selected from $R^i$;
Z is selected from the group consisting of:
  (1) —$C_{0-6}$alkyl-$CO_2H$, and
  (2) —$C_{0-6}$alkyl-$CO_2R^j$,
wherein each alkyl is unsubstituted or substituted with one to five substituents selected from $C_{1-6}$alkyl;
$R^1$ is selected from the group consisting of:
  (1) hydrogen,
  (2) halogen, and
  (3) —$C_{1-6}$alkyl,
wherein alkyl is unsubstituted or substituted with one, two or three halogens;
$R^2$ is selected from the group consisting of:
  (1) hydrogen,
  (2) —$C_{1-6}$alkyl, and
  (3) —$C_{3-6}$cycloalkyl,
wherein each alkyl and cycloalkyl is unsubstituted or substituted with one, two or three substituents selected from halogen, OH, —$C_{1-6}$alkyl and —$OC_{1-6}$alkyl;
$R^3$ is hydrogen;
or a pharmaceutically acceptable salt thereof.

In a class of this embodiment, B is selected from the group consisting of: —$(CH_2)_u$-aryl, —$(CH_2)_u$-heteroaryl, —$(CH_2)_u$—$NR^g(CH_2)_u$-aryl, —$(CH_2)_u$—O—$(CH_2)_u$-aryl, —$(CH_2)_u$—O—$(CH_2)_u$-aryl-aryl, and —$(CH_2)_u$—O—$(CH_2)_u$-heteroaryl, wherein each —$(CH_2)_u$—, aryl and heteroaryl is unsubstituted or substituted with one, two, three, four or five substituents selected from $R^b$;

Another embodiment of the present invention relates to compounds of structural formula I wherein:
T, U, V and W are CH;
A is selected from the group consisting of:
  (1) —$C_{3-6}$cycloalkyl,
  (2) —$C_{3-6}$cycloalkenyl, and
  (3) —$C_{2-10}$cycloheteroalkyl,
wherein each cycloalkyl, cycloalkenyl and cycloheteroalkyl is unsubstituted or substituted with one, two or three substituents selected from $R^a$;
B is selected from the group consisting of:
  (1) —$(CH_2)_u$-aryl,
  (2) —$(CH_2)_u$-heteroaryl,
  (3) —$(CH_2)_u$—$NR^g(CH_2)_u$-aryl, and
  (4) —$(CH_2)_u$—O—$(CH_2)_u$-aryl,
wherein each $CH_2$, aryl and heteroaryl is unsubstituted or substituted with one, two, three, four or five substituents selected from $R^b$;
Y is —$(CH_2)_xO$—, wherein $CH_2$ is unsubstituted or substituted with one or two substituents selected from $R^i$;
Z is selected from the group consisting of:
  (1) —$C_{0-6}$alkyl-$CO_2H$, and
  (2) —$C_{0-6}$alkyl-$CO_2R^j$,
wherein each alkyl is unsubstituted or substituted with one to five substituents selected from $C_{1-6}$alkyl;
$R^1$ is selected from the group consisting of:
  (1) hydrogen,
  (2) halogen, and
  (3) —$C_{1-6}$alkyl,
wherein alkyl is unsubstituted or substituted with one, two or three halogens;
$R^2$ is selected from the group consisting of:
  (1) hydrogen,
  (2) —$C_{1-6}$alkyl, and
  (3) —$C_{3-6}$cycloalkyl, wherein each alkyl and cycloalkyl is unsubstituted or substituted with one, two or three substituents selected from halogen, OH, —C$_{1-6}$alkyl and —OC$_{1-6}$alkyl;

R$^3$ is hydrogen;

or a pharmaceutically acceptable salt thereof.

Another embodiment of the present invention relates to compounds of structural formula I wherein:

T, U, V and W are CH;

A is —C$_{2-10}$ cycloheteroalkyl, wherein each cycloheteroalkyl is unsubstituted or substituted with one, two or three substituents selected from R$^a$;

B is selected from the group consisting of:
  (1) —(CH$_2$)$_u$-aryl, and
  (2) -heteroaryl, wherein each CH$_2$, aryl and heteroaryl is unsubstituted or substituted with one, two, three, four or five substituents selected from R$^b$;

Y is selected from: —O— and —CH$_2$—O—, wherein CH$_2$ is unsubstituted or substituted with one or two substituents selected from C$_{1-6}$alkyl;

Z is —CO$_2$H;

R$^1$ is selected from the group consisting of:
  (1) hydrogen, and
  (2) —C$_{1-6}$alkyl, wherein alkyl is unsubstituted or substituted with one, two or three halogens;

R$^2$ is —C$_{3-6}$cycloalkyl, wherein cycloalkyl is unsubstituted or substituted with one, two or three substituents selected from halogen, OH, —C$_{1-6}$alkyl and —OC$_{1-6}$alkyl;

R$^3$ is hydrogen;

or a pharmaceutically acceptable salt thereof.

Illustrative, but non-limiting, examples of the compounds of the present invention that are useful as agonists of G-protein-coupled receptor 40 (GPR40) are the following compounds:

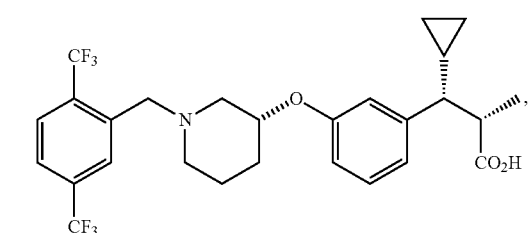

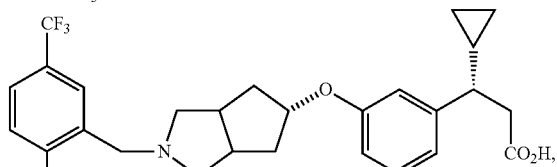

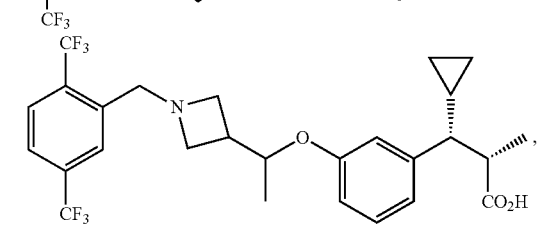

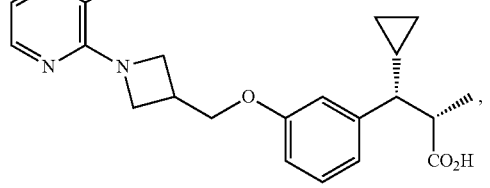

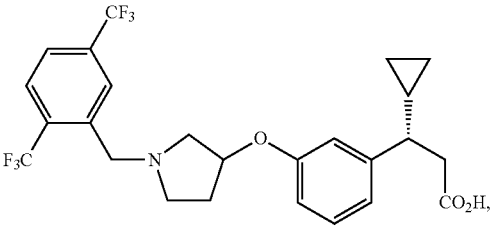

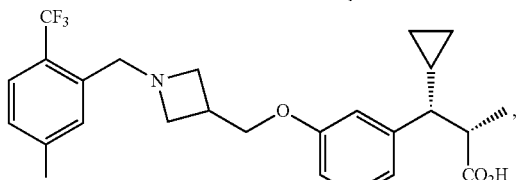

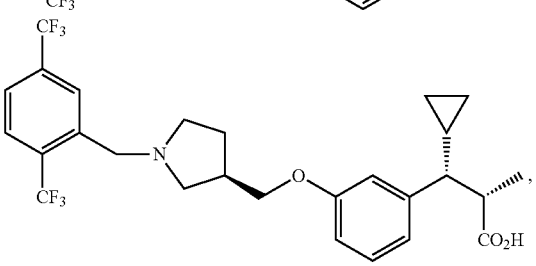

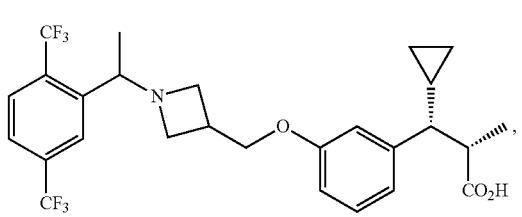

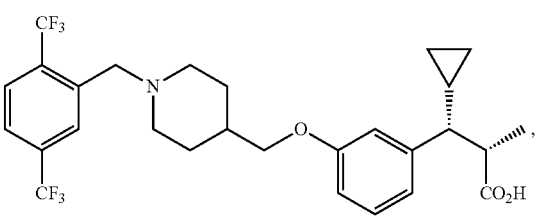

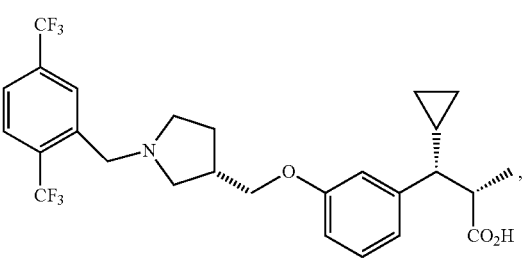

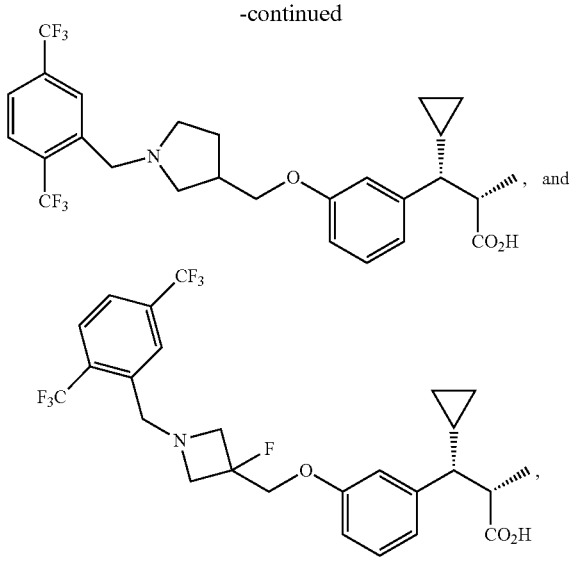

or a pharmaceutically acceptable salt thereof.

Although the specific stereochemistries described herein are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)—$.

"Oxo" is $=O$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. In one embodiment of the present invention, alkyl is methyl.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is 2-methyl-1-propenyl.

"Alkynyl" means carbon chains which contain at least one carbon-carbon triple bond, and which may be linear or branched or combinations thereof, unless otherwise defined. Examples of alkynyl include ethynyl, propargyl, 3-methyl-1-pentynyl, 2-heptynyl and the like. In one embodiment, alkynyl is $—C_2$alkyne-$CH_3$.

"Cycloalkyl" means a saturated monocyclic, bicyclic or bridged carbocyclic ring, having a specified number of carbon atoms. Examples of cycloalkyl include cyclopropyl, cyclobutyl, cyclopentyl, cyclohexyl, cycloheptyl, and the like. In one embodiment of the present invention, cycloalkyl is selected from: cyclopropane, cyclobutane, cyclopentane and cyclohexane. In one embodiment of the present invention, cycloalkyl is selected from: cyclopropane, cyclobutane, and cyclopentane. In another embodiment, cycloalkyl is selected from: cyclopropyl and cyclobutyl. In another embodiment of the present invention, cycloalkyl is cyclopropyl.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like. In one embodiment of the present invention, cycloalkenyl is cyclopentenyl.

"Cycloheteroalkyl" means a saturated or partly unsaturated non-aromatic monocyclic, bicyclic, sprio or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran, hexose, pentose, isosorbide and isomannide, dianhydromannitol, 1,4:3,6-dianhydromannitol, 1, 4:3, 6-dianhydro[D]mannitol, hexahydrofuro[3,2-b]furan, and 2,3,3a,5,6,6a-hexahydrofuro[3,2-b]furan. In one embodiment of the present invention, cycloheteroalkyl is pyrrolidine, piperidine, azetidine, morpholine, 3-azaspiro [3.3]heptane, octahydrocyclopenta[c]pyrrole and 6-azaspiro [3,4]octane.

"Cycloheteroalkenyl" means a nonaromatic monocyclic, bicyclic or bridged carbocyclic ring or ring system containing at least one double bond and containing at least one heteroatom selected from N, NH, S and O.

"Aryl" means a monocyclic, bicyclic or tricyclic carbocyclic aromatic ring or ring system containing 5-14 carbon atoms, wherein at least one of the rings is aromatic. Aryl includes compounds in which the aromatic ring is fused to a non aromatic ring, including but not limited to, a cycloalkyl, cycloalkenyl, cycloheteroalkyl and cyclohetreroalkenyl ring. Examples of aryl include phenyl and naphthyl. Another example of aryl is dihydrobenzofuran. In one embodiment of the present invention, aryl is phenyl. In another embodiment of the present invention, aryl is phenyl, 1-oxo-1,3-dihydro-isobenzofuran, and 2,3-dihydrobenzofuran. In another embodiment of the present invention, aryl is 1-oxo-1,3-dihydroisobenzofuran, and 2,3-dihydrobenzofuran. In another embodiment of the present invention, aryl is 1-oxo-1,3-dihydroisobenzofuran. In another embodiment of the present invention, aryl is 2,3-dihydrobenzofuran.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, indole, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzpyrazole (or indazole), benzothiophenyl (including S-oxide and dioxide), furo(2,3-b)pyridyl, quinolyl, indolyl, isoquinolyl, quinazolinyl, dibenzofuranyl, and the like. In one embodiment of the present invention, heteroaryl is selected from: pyridine, pyrazole, thiazole, thiophene, pyrrole, triazole, indazole and indole. In another embodiment of the present invention, heteroaryl is selected from pyrazole, thiazole, thiophene, pyrrole, triazole, indazole and indole. In another embodiment of the present invention, heteroaryl is pyridine. In another embodiment, heteroaryl is tetrazolyl. In another embodiment of the present invention, heteroaryl is 2,3-dihydro-[1,4]dioxino[2,3-b]pyridine. In another embodiment of the present invention, heteroaryl is pyridine, pyrimidine, pyrazole and 2,3-dihydro-[1,4]dioxino[2,3-b]pyridine. In another embodiment of the present invention, heteroaryl is pyridine, pyrimidine and pyrazole.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to:

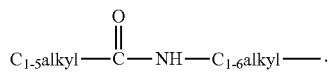

For example, $-NR^cS(O)_pR^e$ is equivalent to $-N(R^c)S(O)_pR^e$, and $-NR^cC(O)R^e$ is equivalent to $-N(R^c)C(O)R^e$.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1H$), deuterium ($^2H$), and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases:

(1) non-insulin dependent diabetes mellitus (Type 2 diabetes);
(2) hyperglycemia;
(3) insulin resistance;
(4) Metabolic Syndrome;
(5) obesity;
(6) hypercholesterolemia;
(7) hypertriglyceridemia (elevated levels of triglyceride-rich-lipoproteins);
(8) mixed or diabetic dyslipidemia;
(9) low HDL cholesterol;
(10) high LDL cholesterol;
(11) hyper apo-B liproteinemia; and
(12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases:

(1) Type 2 diabetes, and specifically hyperglycemia associated with Type 2 diabetes;
(2) Metabolic Syndrome;
(3) obesity; and
(4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hyperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a human or other mammalian subject or patient in need of treatment. Other medical uses of the compounds of the present invention are described herein.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dyslipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to a human or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy:

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients that may be administered separately or in the same pharmaceutical composition in combination with a compound of the formulas described herein include, but are not limited to:

(1) dipeptidyl peptidase-IV (DPP-4) inhibitors (e.g., sitagliptin, alogliptin, linagliptin, vildagliptin, saxagliptin, teneligliptin, omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof;

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, MR 1704, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, ertugliflozin, canagliflozin, BI-10773, PF-04971729, remogloflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof;

(37) GPR 120 agonists (such as KDT501).

Other suitable active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, THO318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promoters such as those disclosed in WO 03/007990; (21) fixed combinations of PPAR γ agonists and metformin such as AVANDAMET; (22) PPAR pan agonists such as GSK 677954; (23) GPR40 agonists (G-protein coupled receptor 40) also called SNORF 55 such as BG 700, and those disclosed in WO 04/041266, 04/022551, 03/099793; (24) GPR119 agonists (G-protein coupled receptor 119, also called RUP3; SNORF 25) such as RUP3, HGPRBMY26, PFI 007; (25) adenosine receptor 2B antagonists such as ATL-618, AT1-802, E3080, and the like; (26) camitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as ASP1941, SGLT-3, empagliflozin, dapagliflozin, ertugliflozin, canagliflozin, BI-10773, PF-04971729, remogloflozin, TS-071, tofogliflozin, ipragliflozin, LX-4211, AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methyl-pyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)methoxy)phenyl)iso, 5-(4-((3-(2-methyl-6-(3-hydroxypropoxy)pyridine-3-yl)-2-methylphenyl)methoxy)phenyl)isothiazole-3-ol 1-oxide, and 5-[4-[[3-[4-(3-aminopropoxy)-2,6 dimethylphenyl]phenyl]-methoxy]phenyl]-isothiazole-3-ol 1-oxide), and those disclosed in WO 11/078371.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin, atorvastatin or rosuvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A—cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTCO179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlortalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as alacepril, benazepril; captopril; ceronapril, cilazapril; delapril; enalapril; fosinopril; imidapril; losinopril; moveltipril; quinapril; quinaprilat; ramipril; perindopril; perindropril; quanipril; spirapril; temocapril; trandolapril, and zofenopril, and the like; (5) neutral endopeptidase inhibitors such as omapatrilat, cadoxatril, ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists, which may be in free acid, free base, salt or prodrug form, such as candesartan, eprosartan, irbesartan, losartan, olmesartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XENO10, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/ REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as taranabant, rimonabant (Accomplia Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vemalis), NESSO$_{327}$ (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/ antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552, 524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY 161503 (Biovitrum), R-1065, VR1065 (Vemalis/Roche) YM 348; and those disclosed in U.S. Pat. No. 3,914,250; and PCT Publications 01/66,548, 02/36,596, 02/48,124, 02/10,169, 02/44,152; 02/51,844, 02/40456, 02/40,457, 03/05,7698, 05/000,849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) 33 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC 1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. No. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), saxagliptin, alogliptin, NVP-DPP728, vildagliptin, P93/01, TSL 225, TMC-2A/2B/2C, FE 999011, P9310/K364, VIP 0177, SDZ 274-444, GSK 823093, E 3024, SYR 322, TSO21, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune)Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC 162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC 137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, rosuvastatin, sitagliptin, omarigliptin, metformin, sibutramine, orlistat, Qnexa, topiramate, naltrexone, bupriopion, phentermine, losartan, losartan with hydrochlorothiazide, canagliflozin, dapagliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

LIST OF ABBREVIATIONS

Ac is acetyl; AcO is acetoxy; Ac$_2$O is acetic anhydride; AcOH is acetic acid; Alk is alkyl; APCI is atmospheric pressure chemical ionization; aq or aq. is aqueous; Ar is aryl; atm is atmosphere; Boc or BOC is tert-butoxycarbonyl; Bn-O is phenyl-CH$_2$—O or benzyloxy; Br is broad; BSA is bis(trimethylsilyl)acetamide; BuLi is n-butyllithium; Bu$_3$P is tributylphosphine; t-BuOK is potassium tert-butoxide; NaOtBu is sodium tert-butoxide; ° C. is degrees celsius; Cbz is benzyloxycarbonyl; conc or conc. is concentrated; d is doublet; DAST is (diethylamino)sulfur trifluoride; dba is dibenzylideneacetone; DIAD is diisopropyl azodicarboxylate; DCM is dichloromethane; DIPEA is N,N-diisopropylethylamine; DME is dimethoxyethane; DMAP is 4-dimethylaminopyridine; DMF is N,N-dimethyl-formamide; DMSO is dimethylsulfoxide; DMT-silica is silica-dimercaptotriazine; dppf is 1,1'-Bis(diphenyl-phosphino)ferrocene; ESI is electrospray ionization; EA or EtOAc is ethyl acetate; Et is ethyl; EtMgBr is ethyl magnesium bromide; EtOH is ethanol; eq is equivalent; g is gram(s); h or hr or hrs is hour(s); HEPES is [4-(2-hydroxyethyl)-1-piperazineethanesulfonic acid], hex is hexanes; HPLC is high pressure liquid chromatography; HOAc or AcOH is acetic acid; kg is kilogram(s); IPA is isopropanol; IPAc is isopropyl acetate; KOH ispotassium hydroxide; KOAc is potassium acetate; KOTMS is potassium trimethyl-silanolate; L is liter; LAH is lithium aluminum hydride; M is molar; LC/MS or LCMS is liquid chromatography-mass spectroscopy; LDA is lithium diisopropyl amide; LiOH is lithium hydroxide; m is multiplet; Me is methyl; MeI is methyl iodide; MeO is methoxy; m-CPBA, MCPBA, or mCPBA is meta chloroperbenzoic acid; mL is milliliter; min or mins is minute(s); mol is mole(s); mmol is mmole(s); mg is milligram(s); MeMgBr is methyl magnesium bromide; MeCN is acetonitrile; MeOH is methyl alcohol or methanol; MgSO$_4$ is magnesium sulfate; MPLC is medium pressure liquid chromatography; MS is mass spectroscopy; MsCl or Ms-Cl is methane sulfonyl chloride; N is normal; Na(AcO)$_3$BH is sodium triacetoxy borohydride; NaOH is sodium hydroxide; NaOtBu is sodium tert-butoxide; Na$_2$SO$_4$ is sodium sulfate; NH$_4$OAc is ammonium acetate; NBS is N-bromo succinamide; NiCl$_2$DME is nickel (II) chloride dimethoxyethane adduct; NIS is N-iodo succinamide; NMO is 4-methyl morpholine N-oxide; NMP is 1-methyl-2-pyrrolidinone; NMR is nuclear magnetic resonance spectroscopy; paraform is para-formaldehyde; PE is petroleum ether; PG is protecting group; P(Cy)$_3$ is tricyclohexyl phosphine; Pd$_2$(dba)$_3$ is tris(dibenzylideneacetone)-dipalladium(0); Pd[P(t-Bu)$_3$]$_2$ is bis(tri-tert-butylphosphine)palladium (0); Pd(dppf)Cl$_2$ is [1,1'-bis(diphenylphosphino)-ferrocene]dichloro-palladium (II); PMB is para-methoxybenzyl; PMBCl is para-methoxybenzyl chloride; precat is precatalyst; prep is preparative; prep. TLC or prep-TLC, or prep TLC is preparative thin layer chromatography; RBF is round bottom flask; RCM is ring closing metathesis reaction; rt or r.t. or RT is room temperature; s is singlet; sat or sat. is saturated; SFC is supercritical fluid chromatography; S-Phos is 2-Dicyclohexylphosphino-2',6'-dimethoxybiphenyl; S-Phos(Pd) is chloro(2-dicyclohexyl-phosphino-2',6'-dimethoxy-1,1'-biphenyl)[2-(2-aminoethylphenyl)]-palladium(II) [CAS-No. 1028206-58-7]; S-Phos precatalyst $2^{nd}$ generation is Chloro(2-dicyclohexyl-phosphino-2',6'-dimethoxy-1,1'-biphenyl)[2-(2'-amino-1,1'-biphenyl)]palladium(II), SPhos-Pd-G2 is 2nd generation S-Phos precatalyst [CAS-No. 1375325-64-6]; t is triplet; TBAF is tetrabutylammonium fluoride; TBSCl is tert-butyl dimethylsilyl chloride; TBTU is N,N,N',N'-Tetramethyl-O-(benzotriazol-1-yl)uronium tetrafluoroborate; TEA is triethyl amine; THF is tetrahydrofuran; Ti(OiPr)$_4$ is titanium isopropoxide; TFA is trifluoroacetic acid; Tf$_2$O is trifluoromethanesulfonic anhydride; TLC is thin-layer chromatography; TosCl is p-toluene sulfonyl chloride; pTSA, pTsOH and TsOH is p-toluenesulfonic acid; RuCl[(S,S)-TsDPEN] (mesitylene) is [N-[(1S,2S)-2-(Amino-κN)-1,2-diphenylethyl]-4-methylbenzenesulfonamidato-κN]chloro [(1,2,3,4,5,6-η)-1,3,5-trimethylbenzene]-ruthenium; xphos or XPhos is 2-Dicyclohexylphosphino-2',4',6'-triisopropyl-biphenyl; and v/v is volume/volume.

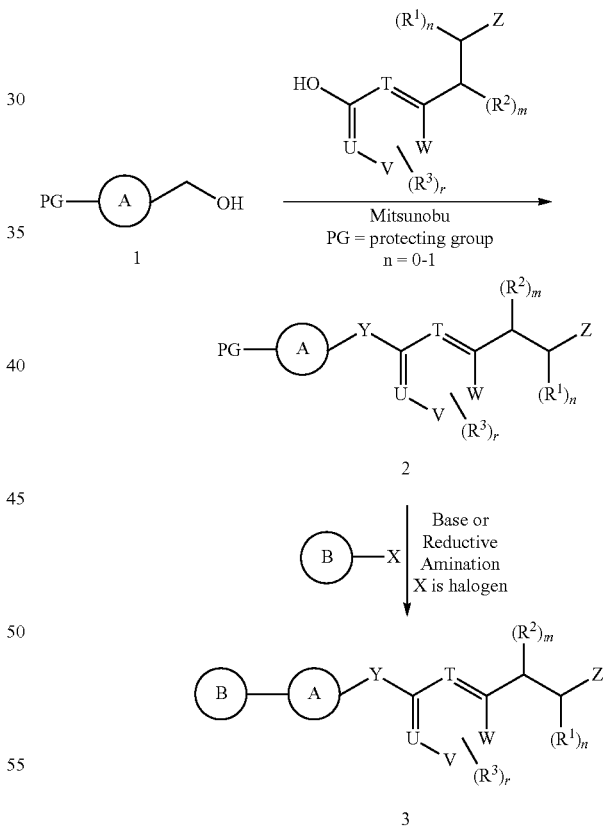

GENERAL SCHEME

An alcohol like compound 1 can be Mitsonobu coupled to a phenol giving rise to a compound 2. The PG is generally deprotected through standard methods and coupled to B. B can be coupled through an alkylation or reductive amination giving rise to compound such as 3.

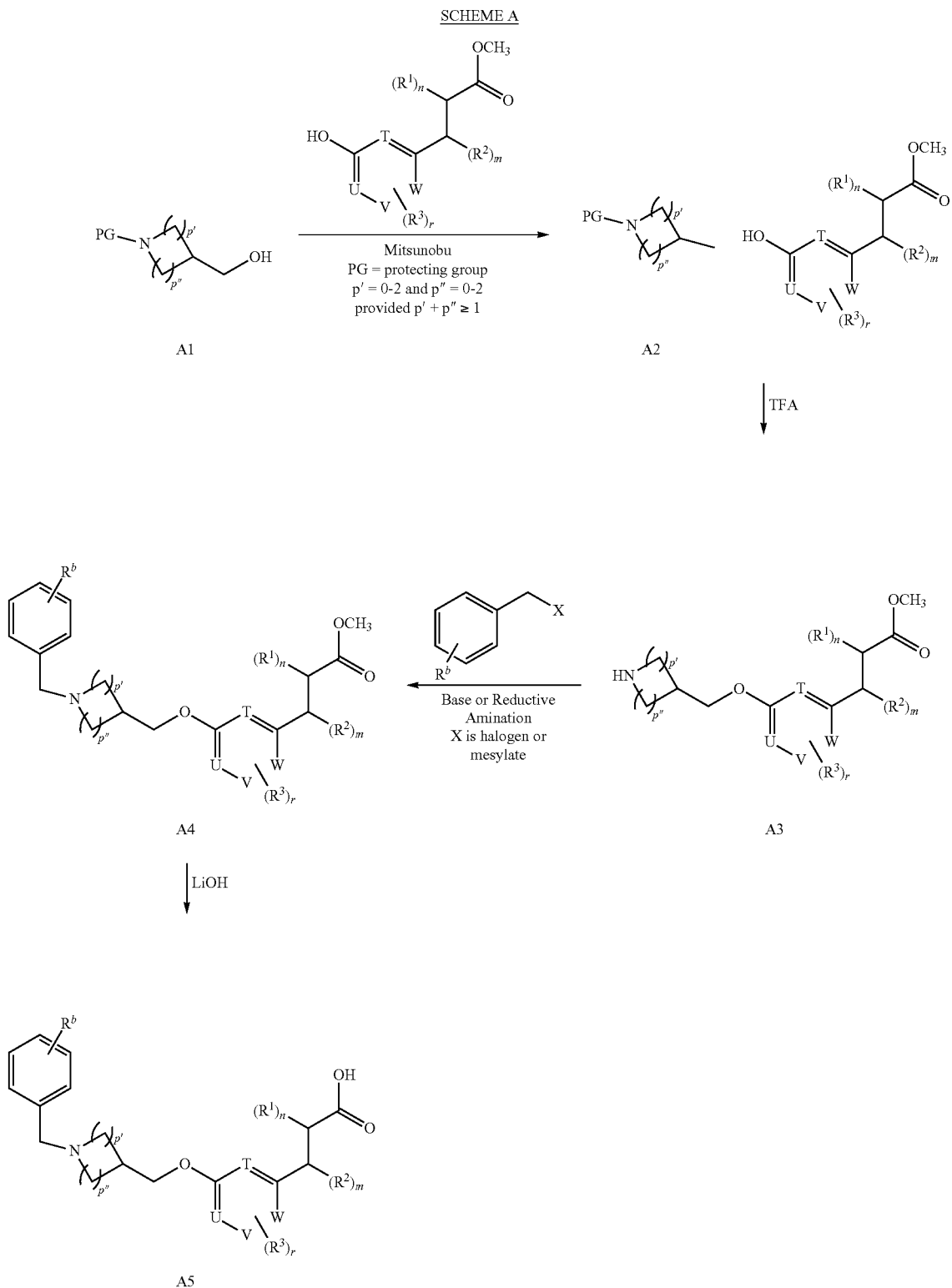

SCHEME A

A general approach to compound A5 is outlined in Scheme A. Alcohol A1 can be coupled to a phenol via a Mitsunobu reaction to afford compound A3. Subsequent alkylation or reductive amination affords compound A4. The ester present in compound A4 can be hydrolyzed with a mixture of aqueous lithium hydroxide, and the like, in solvents such as methanol or THF to afford carboxylic acid A5.

SCHEME B

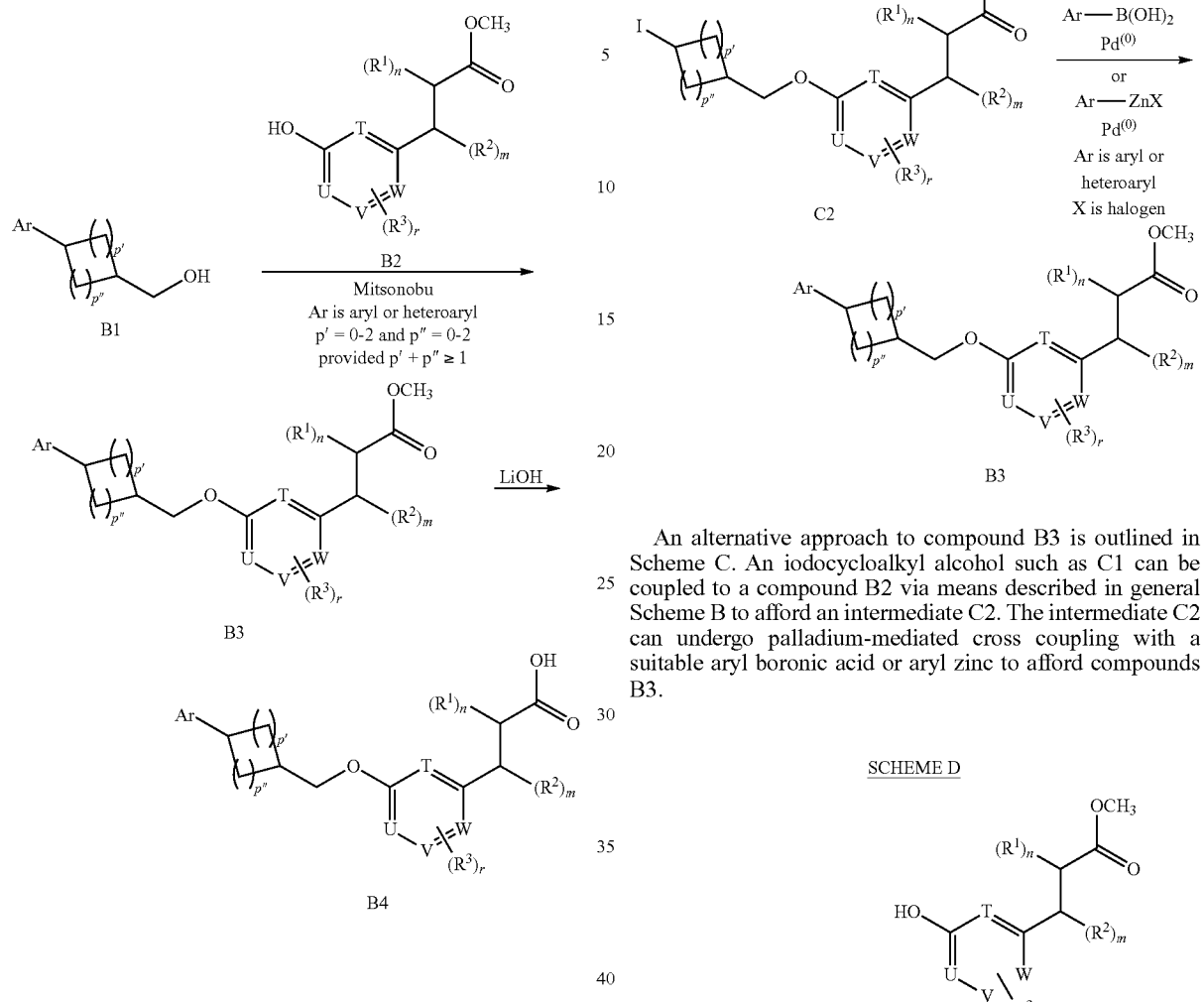

A general approach to compound B4 is outlined in Scheme B. Alcohol B1 can be coupled to B2 via a Mitsunobu reaction using tri-n-butylphosphine and the like, 1,1'-(azodicarbonyl)dipiperidine and the like in a solvent such as THF to afford compound B3. The ester present in compound B3 can be hydrolyzed with a mixture of aqueous lithium hydroxide and the like in solvents such as methanol, THF and the like to afford carboxylic acid B4.

SCHEME C

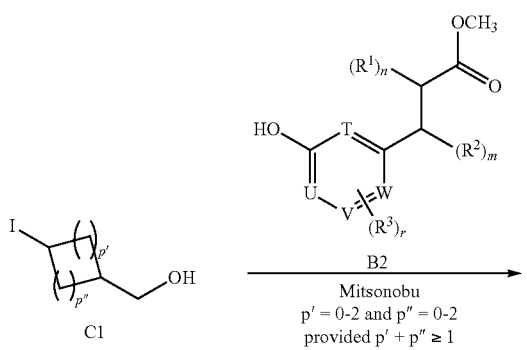

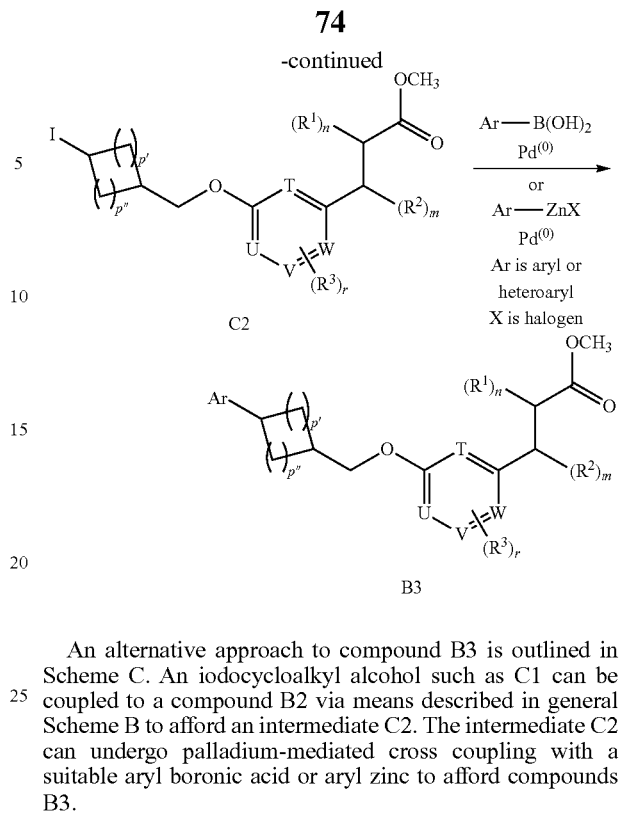

An alternative approach to compound B3 is outlined in Scheme C. An iodocycloalkyl alcohol such as C1 can be coupled to a compound B2 via means described in general Scheme B to afford an intermediate C2. The intermediate C2 can undergo palladium-mediated cross coupling with a suitable aryl boronic acid or aryl zinc to afford compounds B3.

SCHEME D

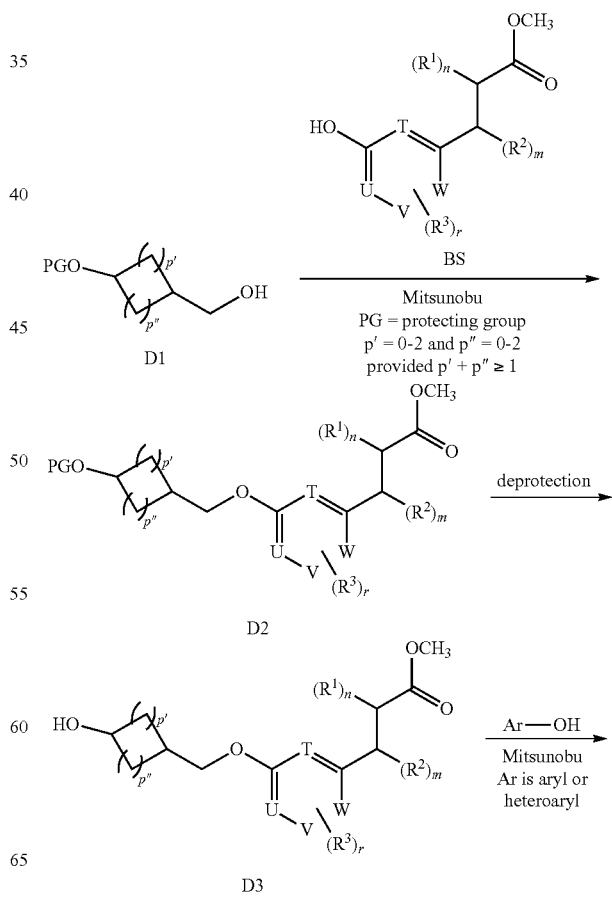

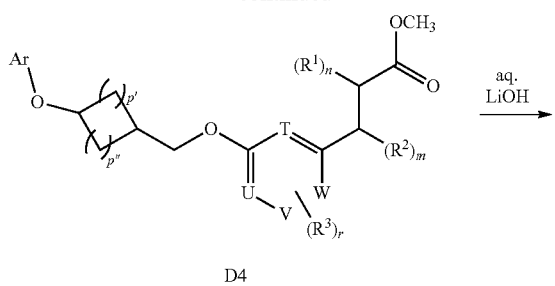

D4

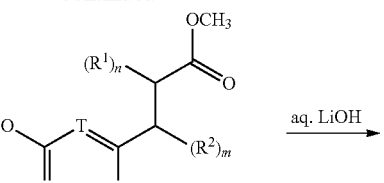

E3

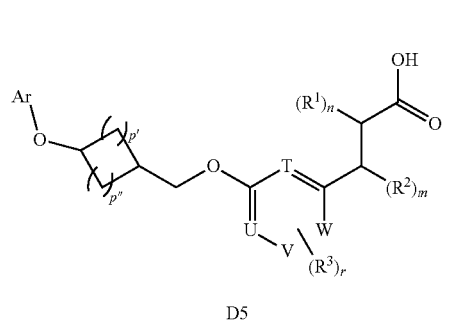

D5

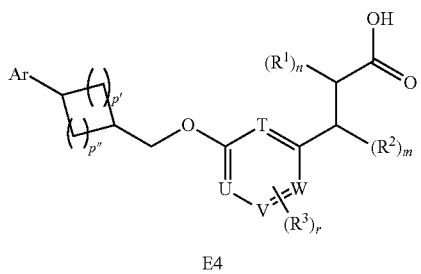

E4

Scheme D outlines the preparation of compound D5. A suitably mono-protected diol such as D1, wherein PG is benzyl or TBS and the like is coupled with B2 via a method such as that outlined in general Scheme B to afford intermediate D2. Removal of the protecting group via a method such as hydrogenation in the presence of a palladium catalyst (in the instance when PG is benzyl) or a method such as tetrabutylammonium fluoride in THF (in the instance when PG is TBS) will afford the alcohol D3. Coupling of a suitable aryl alcohol with intermediate D3 under Mitsunobu conditions such as those described in General Scheme B will afford compounds D4, which can be hydrolyzed to afford carboxylic acids D5.

Compound E1 can be treated with iodine in the presence of triphenylphosphine and the like and imidazole and the like to afford iodide E2. The intermediate E2 can undergo palladium-mediated cross coupling with a suitable aryl boronic acid or aryl zinc to afford intermediate E3. Hydrolysis of intermediate E3 can afford carboxylic acids E4.

SCHEME F

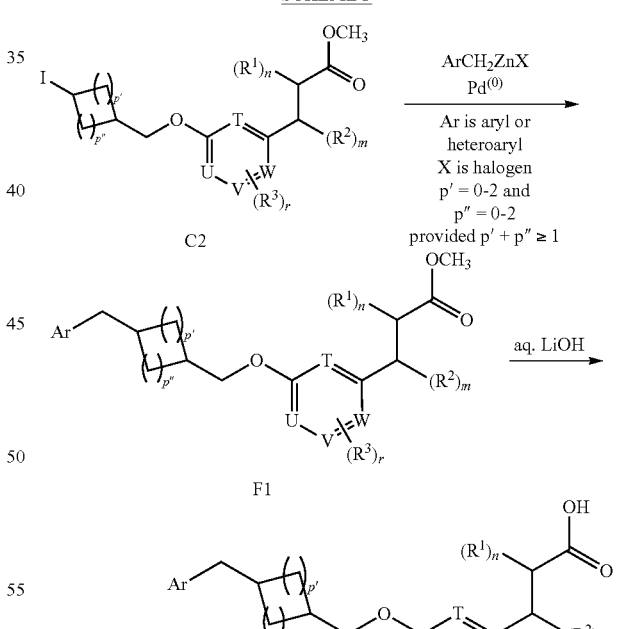

SCHEME E

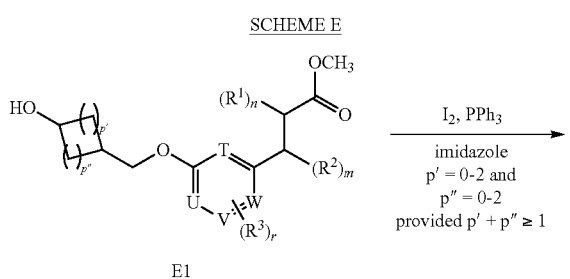

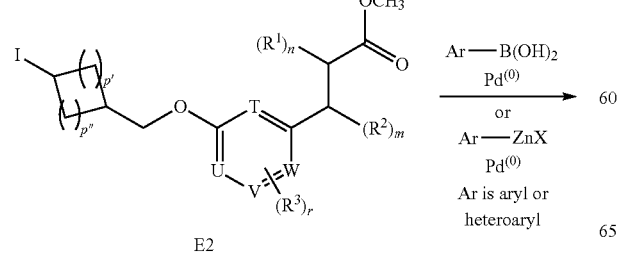

Compound C2 can also undergo palladium-mediated cross coupling with a suitable arylmethylzinc to afford intermediate F1, which can be hydrolyzed to afford carboxylic acid F2.

SCHEME G

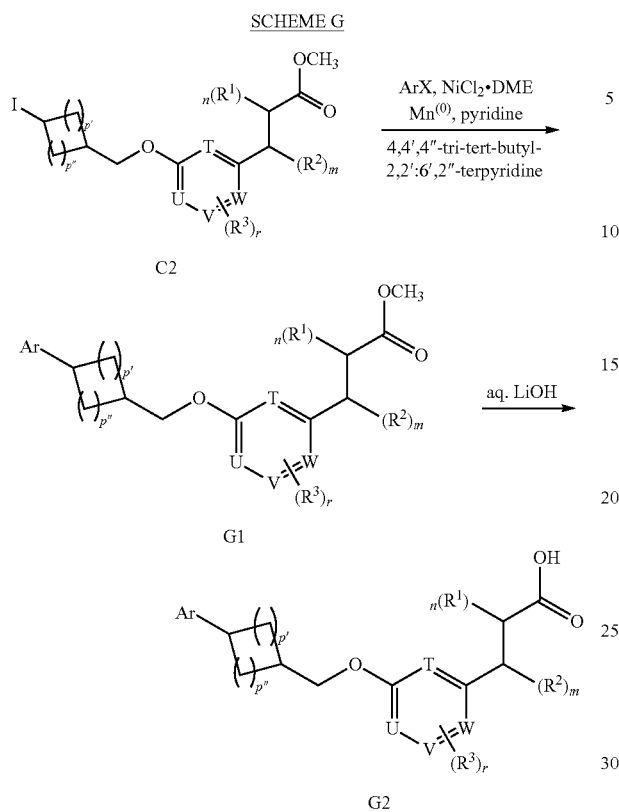

Ar is aryl or heteroaryl
X is halogen
p' = 0-2 and
p" = 0-2
provided p' + p" ≥ 1

Compound C2 can undergo cross coupling with a suitable aryl or heteroaryl halide in the presence of NiCl$_2$.DME, manganese, pyridine and 4,4',4"-tri-tert-butyl-2,2':6',2"-terpyridine in a solvent, such as N,N-dimethylacetamide, and at a temperature at or around 100° C. to afford compound G1. Hydrolysis of G1 with an aqueous solution of LiOH in a solvent, such as MeOH and/or THF, affords carboxylic acid G2.

Intermediate 1

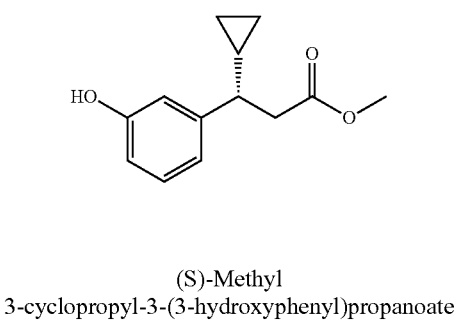

(S)-Methyl 3-cyclopropyl-3-(3-hydroxyphenyl)propanoate

The title compound was prepared according to the procedure disclosed in *ACS Med. Chem. Lett.* 2012, 3, 726-730.

Intermediates 2 and 3

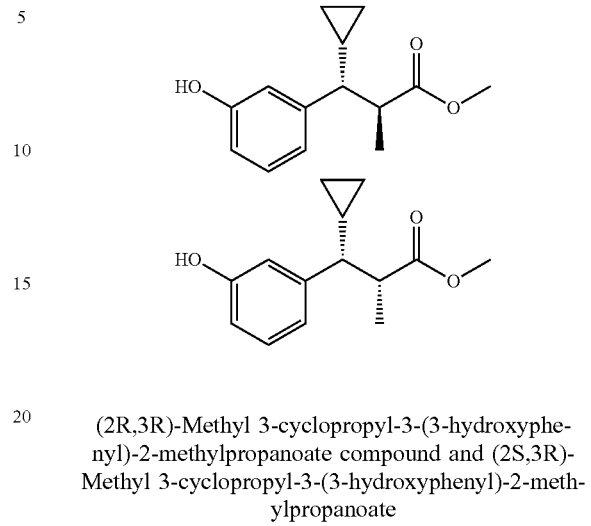

(2R,3R)-Methyl 3-cyclopropyl-3-(3-hydroxyphenyl)-2-methylpropanoate compound and (2S,3R)-Methyl 3-cyclopropyl-3-(3-hydroxyphenyl)-2-methylpropanoate Step A: To a solution of (S)-methyl 3-cyclopropyl-3-(3-hydroxyphenyl)propanoate (23.6 g, 101 mmol) in DMF (200 mL) was added TBSCl (15.9 g, 106 mmol), followed by imidazole (13.7 g, 201 mmol). The mixture was stirred at rt for 1 h, then diluted with saturated brine solution and extracted with hexanes (2×200 mL). The combined organic layers were dried over MgSO$_4$, filtered and concentrated giving rise to give the title compound, which was used immediately in the next step.

Step B: A solution of (S)-methyl 3-(3-((tert-butyldimethylsilyl)oxy)phenyl)-3-cyclopropylpropanoate (2 g, 6.0 mmol) in THF (30 mL) was cooled to −78° C. Then LDA (4.5 mL, 9 mmol, 2.0 M) was added. After 30 minutes, MeI (0.9 mL, 15 mmol) was added dropwise to the reaction mixture. Then the reaction was warmed to rt and poured into saturated aqueous Na$_2$S$_2$O$_3$ (50 mL). The aqueous layer was extracted with EtOAc (2×50 mL). The combined organic layers were dried over MgSO$_4$, filtered and concentrated to give an oil. The oil was purified using an ISCO 120 g cartridge (0-30% EtOAc:hexanes) to give a (1:2) mixture of (2R,3R)-methyl 3-(3-((tert-butyldimethyl-silyl)oxy)phenyl)-3-cyclopropyl-2-methylpropanoate and (2S,3R)-methyl 3-(3-((tert-butyl-dimethylsilyl)oxy)phenyl)-3-cyclopropyl-2-methylpropanoate.

Step C: A solution of the (1:2) mixture of (2R,3R)-methyl 3-(3-((tert-butyldimethyl-silyl)oxy)phenyl)-3-cyclopropyl-2-methylpropanoate and (2S,3R)-methyl 3-(3-((tert-butyldimethylsilyl)oxy)phenyl)-3-cyclopropyl-2-methylpropanoate (7.8 g, 22.2 mmol) in THF (80 mL) was cooled to 0° C. Then KOtBu solution (44 mL, 44.6 mmol, 1.0M in THF) was added to effect epimerization. After 20 minutes, the reaction was quenched with 1N HCl (200 mL), and the resulting aqueous layer was extracted with EtOAc (250 mL). The organic layer was removed, dried, filtered and concentrated to give an oil. The resulting crude oil was diluted with THF (40 mL) and treated with TBAF (33 mL, 33 mmol, 1.0 M THF) and stirred at rt until the reaction was complete. Then the reaction was diluted with brine and extracted with EtOAc (200 mL). The organic layer was removed, dried, filtered and concentrated to give a crude oil. The crude oil was purified an ISCO 330 g cartridge (0-40% EtOAc: Hexanes) to give a 3:1 mixture of (2R,3R)-methyl 3-(3-

((tert-butyldimethylsilyl)oxy)phenyl)-3-cyclopropyl-2-methylpropanoate and (2S,3R)-methyl 3-(3-((tert-butyldimethylsilyl)oxy)phenyl)-3-cyclopropyl-2-methylpropanoate.

Step D: Separation of the diastereomers in the 3:1 mixture of (2R,3R)-methyl 3-(3-((tert-butyldimethylsilyl)oxy)phenyl)-3-cyclopropyl-2-methylpropanoate and (2S,3R)-methyl 3-(3-((tert-butyldimethylsilyl)oxy)phenyl)-3-cyclopropyl-2-methylpropanoate was performed by SFC (IC, 50×250 mm, 10% IPA/CO$_2$, 200 mL/min, 35° C., 100 bar, 220 nm, 100 mg/mL in 15:1 IPA:DCM) to give Intermediate 2 and Intermediate 3.

Intermediate 2: $^1$H NMR (500 MHz, CDCl$_3$) δ 7.2 (m, 1H), 6.70 (m, 3H), 3.76 (s, 3H), 2.82 (m, 1H), 1.90 (m, 1H), 1.05 (m, 1H), 0.96 (d, 3H), 0.56 (m, 1H), 0.30 (m, 2H), 0.01 (m, 1H).

Intermediate 3: $^1$H NMR (500 MHz, CD$_3$OD) δ 7.24 (m, 1H), 6.70 (m, 3H), 3.40 (s, 3H), 2.98 (m, 1H), 2.15 (m, 1H), 1.35 (d, 3H), 1.25 (m, 1H), 0.75 (m, 1H), 0.45 (m, 2H), 0.1 (m, 1H).

Intermediate 4

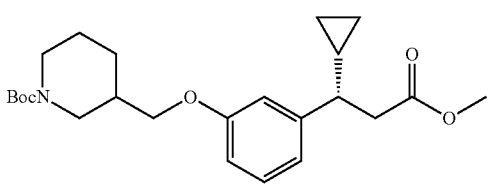 [SMILES: COC(=O)C[C@H](c1cccc(OCC2CCCN(C(=O)OC(C)(C)C)C2)c1)C1CC1]

tert-Butyl 3-((3-((S)-1-cyclopropyl-3-methoxy-3-oxopropyl)phenoxy)methyl)piperidine-1-carboxylate To Intermediate 1 (200 mg, 0.908 mmol) and tert-butyl 3-(bromomethyl)-piperidine-1-carboxylate (303 mg, 1.1 mmol) in CH$_3$CN (10 mL) at rt was added K$_2$CO$_3$ (188 mg, 1.4 mmol). The resulting mixture was stirred at 80° C. for 144 h. Then the reaction was diluted with H$_2$O, and extracted with EtOAc (3×50 mL). The combined organic layers were washed with brine, dried over MgSO$_4$, filtered, concentrated and purified by ISCO (24 g, 0-20% EtOAc/hexanes) to give the title compound LC/MS: m/e 418.34 (M+H)$^+$.

Intermediate 5

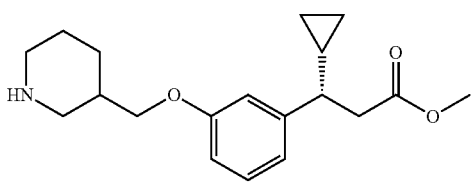 [SMILES: COC(=O)C[C@H](c1cccc(OCC2CCCNC2)c1)C1CC1]

(3S)-Methyl 3-cyclopropyl-3-(3-(piperidin-3-ylmethoxy)phenyl)propanoate

To a solution of Intermediate 4 (239 mg, 0.572 mmol) in CH$_2$Cl$_2$ (10 mL) at rt was added TFA (0.4 mL, 5.7 mmol). The reaction was stirred at rt for 1 h, then concentrated to dryness to give the title compound as an oil. LC/MS: m/e 318.29 (M+H)$^+$.

Intermediate 6

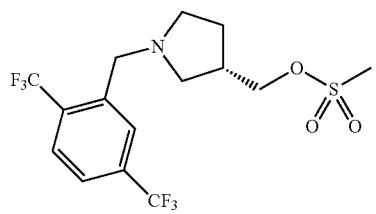 [SMILES: CS(=O)(=O)OC[C@H]1CCN(Cc2cc(C(F)(F)F)ccc2C(F)(F)F)C1]

(S)-(1-(2,5-bis(trifluoromethyl)benzyl)pyrrolidin-3-yl)methyl methanesulfonate

Step A: To a solution of (S)-pyrrolidin-3-ylmethanol (106 mg, 1.0 mmol) in DMF (2 mL) at rt was added 2,5-bis-trifluoromethylbenzyl bromide (322 mg, 1.0 mmol) and K$_2$CO$_3$ (290 mg, 2.1 mmol). The resulting mixture was stirred at rt for 12 h, then diluted with H$_2$O (10 mL), and extracted with EtOAc (3×15 mL). The combined organic layers were washed with brine, dried over MgSO$_4$, filtered, concentrated and purified by MPLC (ISCO, 24 g, 0-30% EtOAc/hexanes) to give (S)-(1-(2,5 bis(trifluoromethyl)benzyl)-pyrrolidin-3-yl)methanol.

Step B: (S)-(1-(2,5-bis(trifluoromethyl)benzyl)pyrrolidin-3-yl)methanol (100 mg, 0.306 mmol) was dissolved in DCM (4 mL) and the solution was cooled to 0° C. Then TEA (0.085 mL, 0.60 mmol) was added, followed by MsCl (0.025 mL, 0.30 mmol). The cooling bath was removed and the mixture was stirred at rt for 2 h. The mixture was then partitioned between DCM and water. The organic layer was separated, dried over MgSO$_4$, concentrated and purified by MPLC (ISCO 24 g, 0-30% EtOAc/hexanes) to give the title compound. LC/MS: m/e 406.47 (M+H)$^+$.

Intermediate 7

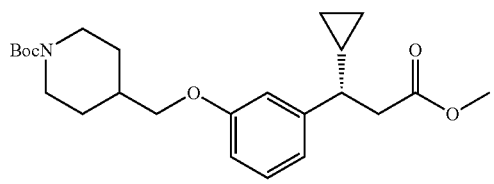 [SMILES: COC(=O)C[C@H](c1cccc(OCC2CCN(C(=O)OC(C)(C)C)CC2)c1)C1CC1]

(S)-tert-Butyl 4-((3-(1-cyclopropyl-3-methoxy-3-oxopropyl)phenoxy)methyl)piperidine-1-carboxylate A solution of N—BOC-4-piperidinemethanol (311 mg, 1.4 mmol), Intermediate 1 (212 mg, 0.9 mmol) and PPh$_3$ (642 mg, 1.9 mmol) in DCM (4 mL) was purged with N$_2$, followed by addition of DIAD (0.3 mL, 1.9 mmol). The reaction was stirred at rt for 12 h, then filtered through a pad of Celite™. The resulting filtrate was concentrated to dryness and purified by ISCO MPLC (24 g, 0-30% EtOAc/hexanes) to give the title compound as a colorless oil.
LC/MS: m/e 418.41 (M+H)$^+$.

Intermediate 8

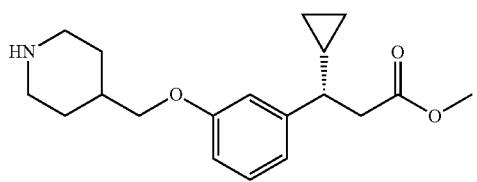 [SMILES: COC(=O)C[C@H](c1cccc(OCC2CCNCC2)c1)C1CC1]

(S)-Methyl 3-cyclopropyl-3-(3-(piperidin-4-yl-methoxy)phenyl)propanoate

Intermediate 8 was prepared in an analogous manner to Intermediate 5, starting with Intermediate 7. LC/MS: m/e 318.30 (M+H)$^+$.

Intermediate 9

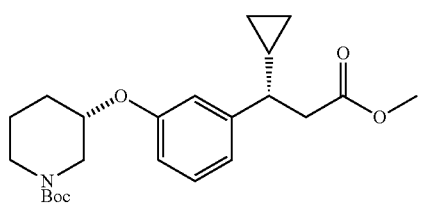 [SMILES: COC(=O)C[C@H](c1cccc(O[C@H]2CCCN(C(=O)OC(C)(C)C)C2)c1)C1CC1]

(S)-tert-Butyl 3-(3-((S)-1-cyclopropyl-3-methoxy-3-oxopropyl)phenoxy)piperidine-1-carboxylate Intermediate 9 was prepared in an analogous manner to Intermediate 7, starting with (S)-tert-butyl 3-hydroxypiperidine-1-carboxylate. LC/MS: m/e 479.43 (M+H)$^+$. $^1$H NMR (500 MHz; CDCl$_3$): δ 7.37 (d, J=7.8 Hz, 1H), 7.24 (d, J=7.5 Hz, 1H), 7.07 (t, J=8.6 Hz, 1H), 6.89 (m, 1H), 6.80 (m, 1H), 5.34 (t, 6.0 Hz, 1H), 4.11 (dt, J=6.9 Hz and 7.5 Hz, 1H), 3.80 (s, 3H), 3.16 (m, 1H), 2.91 (m, 1H), 2.60 (m, 1H), 2.02 (m, 1H).

Intermediate 10

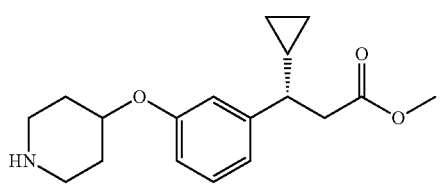 [SMILES: COC(=O)C[C@H](c1cccc(OC2CCNCC2)c1)C1CC1]

(S)-Methyl 3-cyclopropyl-3-(3-(piperidin-4-yloxy)phenyl)propanoate

Intermediate 10 was prepared in an analogous manner to Intermediate 5, starting with Intermediate 9. LC/MS: m/e 304.29 (M+H)$^+$.

Intermediate 11

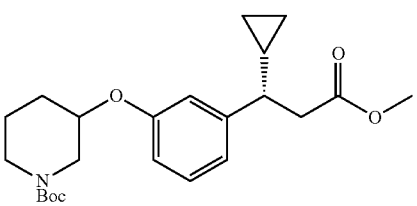 [SMILES: COC(=O)C[C@H](c1cccc(OC2CCCN(C(=O)OC(C)(C)C)C2)c1)C1CC1]

tert-Butyl 3-(3-((S)-1-cyclopropyl-3-methoxy-3-oxopropyl)phenoxy)piperidine-1-carboxylate Intermediate 11 was prepared in an analogous manner to Intermediate 4, starting with 1-BOC-3-hydroxypiperidine. LC/MS: m/e 404.39 (M+H)$^+$.

Intermediate 12

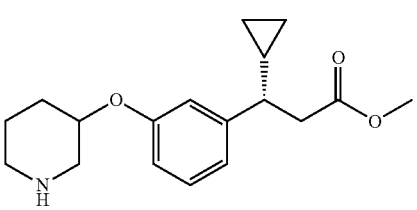 [SMILES: COC(=O)C[C@H](c1cccc(OC2CCCNC2)c1)C1CC1]

(3S)-Methyl 3-cyclopropyl-3-(3-(piperidin-3-yloxy)phenyl)propanoate

Intermediate 12 was prepared in an analogous manner to Intermediate 5, starting with Intermediate 11. LC/MS: m/e 304.33 (M+H)$^+$.

Intermediate 13

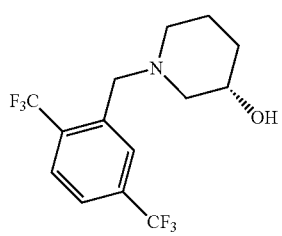 [SMILES: O[C@H]1CCCN(Cc2cc(C(F)(F)F)ccc2C(F)(F)F)C1]

(S)-1-(2,5-Bis(trifluoromethyl)benzyl)piperidin-3-ol

To a solution of (S)-piperidin-3-ol hydrochloride (100 mg, 0.7 mmol) in DMF (2 mL) at rt was added 2,5-bistrifluoromethylbenzyl bromide (223 mg, 0.7 mmol) and K$_2$CO$_3$ (301 mg, 2.2 mmol). The resulting mixture was stirred at rt for 12 h, then diluted with H$_2$O (10 mL), and extracted with EtOAc (3×15 mL). The combined organic layers were washed with brine, dried over MgSO$_4$, filtered, concentrated and purified by MPLC (ISCO 24 g, 0-30%

EtOAc/hexanes) to give the title compound as a colorless oil. LC/MS: m/e 328.24 (M+H)⁺.

Intermediate 14

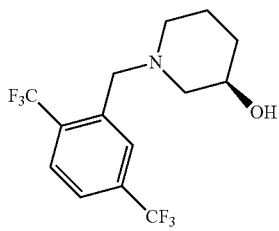 [SMILES: O[C@@H]1CCCN(Cc2cc(C(F)(F)F)ccc2C(F)(F)F)C1]

(R)-1-(2,5-Bis(trifluoromethyl)benzyl)piperidin-3-ol

To a solution of (R)-piperidin-3-ol hydrochloride (100 mg, 0.7 mmol) in DMF (2 mL) at rt was added 2,5-bistrifluoromethylbenzyl bromide (223 mg, 0.7 mmol) and K₂CO₃ (301 mg, 2.2 mmol). The resulting mixture was stirred at rt for 12 h, then diluted with H₂O (10 mL), and extracted with EtOAc (3×15 mL). The combined organic layers were washed with brine, dried over MgSO₄, filtered, concentrated and purified by MPLC (ISCO 24 g, 0-30% EtOAc/hexanes) to give the title compound as a colorless oil. LC/MS: m/e 328.24 (M+H)⁺.

Intermediate 15

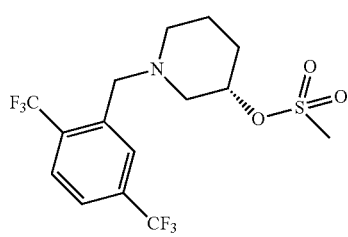 [SMILES: CS(=O)(=O)O[C@H]1CCCN(Cc2cc(C(F)(F)F)ccc2C(F)(F)F)C1]

(S)-1-(2,5-bis(trifluoromethyl)benzyl)piperidin-3-yl methanesulfonate

Intermediate 13 (188 mg, 0.60 mmol) was dissolved in DCM (6 mL) and the solution was cooled to 0° C. TEA (0.16 mL, 1.1 mmol) was added, followed by MsCl (0.05 mL, 0.6 mmol). The cooling bath was removed and the mixture was stirred at rt for 2 h. The mixture was partitioned between CH₂Cl₂ and water. The organic layer was dried over MgSO₄ and concentrated and purified by ISCO MPLC (24 g, 0-15% EtOAc/hexanes) to give rise to a colorless oil. LC/MS: m/e 406.26 (M+H)⁺.

Intermediate 16

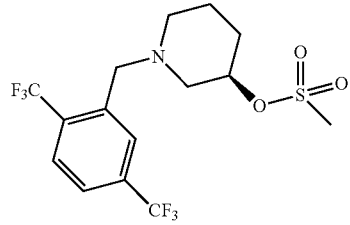 [SMILES: CS(=O)(=O)O[C@@H]1CCCN(Cc2cc(C(F)(F)F)ccc2C(F)(F)F)C1]

(R)-1-(2,5-bis(trifluoromethyl)benzyl)piperidin-3-yl methanesulfonate

Intermediate 16 was prepared in an identical manner to Intermediate 15, starting with Intermediate 14. LC/MS: m/e 406.26 (M+H)⁺.

Intermediate 17

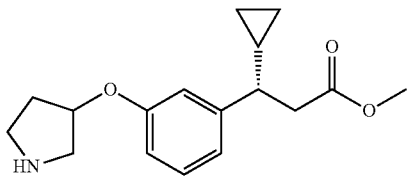 [SMILES: COC(=O)C[C@H](c1cccc(OC2CCNC2)c1)C1CC1]

(3S)-Methyl 3-cyclopropyl-3-(3-(pyrrolidin-3-yloxy)phenyl)propanoate

Intermediate 17 was prepared in an analogous manner to Intermediates 4 and 5, starting with tert-butyl 3-(3-((S)-1-cyclopropyl-3-methoxy-3-oxopropyl)phenoxy)pyrrolidine-1-carboxylate and Intermediate 1. LC/MS: m/e 290.16 (M+H)⁺.

Intermediate 18

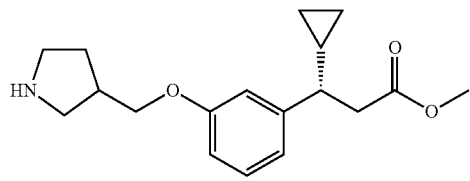 [SMILES: COC(=O)C[C@H](c1cccc(OCC2CCNC2)c1)C1CC1]

(3S)-Methyl 3-cyclopropyl-3-(3-(pyrrolidin-3-yl-methoxy)phenyl)propanoate

Intermediate 18 was prepared in an analogous manner to Intermediates 4 and 5, starting with tert-butyl 3-(3-((S)-1-cyclopropyl-3-methoxy-3-oxopropyl)phenoxy)pyrrolidine-1-carboxylate and Intermediate 1. LC/MS: m/e 304.26 (M+H)⁺.

Intermediate 19

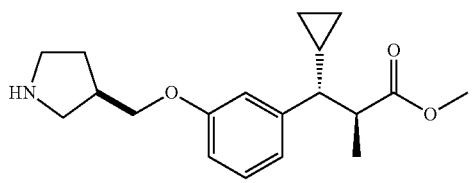

(2S,3R)-Methyl 3-cyclopropyl-2-methyl-3-(3-((R)-pyrrolidin-3-ylmethoxy)phenyl)-propanoate Intermediate 19 was prepared in an analogous manner to Intermediates 4 and 5, starting with (R)-tert-butyl 3-(hydroxymethyl)pyrrolidine-1-carboxylate and Intermediate 2. LC/MS: m/e 318.50 (M+H)$^+$.

Intermediate 20

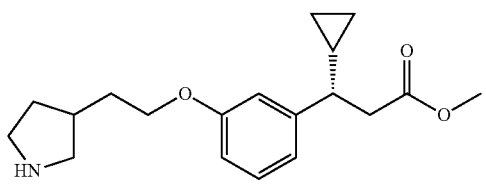 [SMILES: COC(=O)C[C@H](c1cccc(OCCC2CCNC2)c1)C1CC1]

(3S)-Methyl 3-cyclopropyl-3-(3-(2-(pyrrolidin-3-yl)ethoxy)phenyl)propanoate

Intermediate 20 was prepared in an analogous manner to Intermediates 4 and 5, starting with tert-butyl 3-(2-hydroxyethyl)pyrrolidine-1-carboxylate and Intermediate 1. LC/MS: m/e 318.31 (M+H)$^+$.

Intermediate 21A and 21B

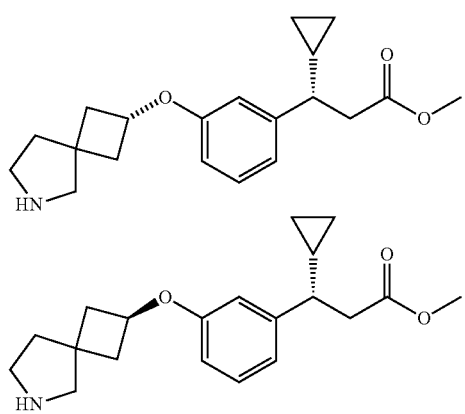

(3S)-Methyl 3-(3-(6-azaspiro[3.4]octan-2-yloxy)phenyl)-3-cyclopropylpropanoate and (S)-methyl 3-(3-(6-azaspiro[3.4]octan-2-yloxy)phenyl)-3-cyclopropylpropanoate Intermediates 21A and 21B were prepared in an analogous manner to Intermediates 4 and 5, starting with racemic tert-butyl 2-hydroxy-6-azaspiro[3.4]octane-6-carboxylate and Intermediate 1. 22A: LC/MS: m/e 330.50 (M+H)$^+$. 22B: LC/MS: m/e 330.50 (M+H)$^+$.

Intermediate 22

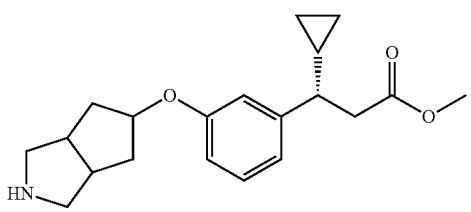 [SMILES: COC(=O)C[C@H](c1cccc(OC2CC3CNCC3C2)c1)C1CC1]

(3S)-Methyl 3-cyclopropyl-3-(3-((octahydrocyclopenta[c]pyrrol-5-yl)oxy)phenyl)propanoate Intermediate 22 was prepared in an analogous manner to Intermediates 4 and 5, starting with tert-butyl 5-hydroxyhexahydrocyclopenta[c]pyrrole-2(1H)-carboxylate and Intermediate 1.
LC/MS: m/e 330.34 (M+H)$^+$.

Intermediate 23

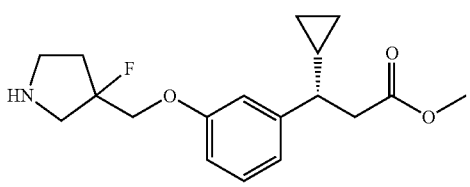 [SMILES: COC(=O)C[C@H](c1cccc(OCC2(F)CCNC2)c1)C1CC1]

(3S)-Methyl 3-cyclopropyl-3-(3-((3-fluoropyrrolidin-3-yl)methoxy)phenyl)propanoate Intermediate 23 was prepared in an analogous manner to Intermediates 4 and 5, starting with tert-butyl 3-(bromomethyl)-3-fluoropyrrolidine-1-carboxylate and Intermediate 1.
LC/MS: m/e 322.29 (M+H)$^+$.

Intermediate 24

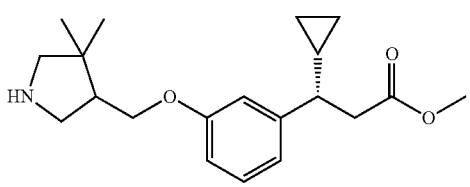 [SMILES: COC(=O)C[C@H](c1cccc(OCC2CNCC2(C)C)c1)C1CC1]

(3S)-Methyl 3-cyclopropyl-3-(3-((4,4-dimethylpyrrolidin-3-yl)methoxy)-phenyl)propanoate Intermediate 24 was prepared in an analogous manner to Intermediates 4 and 5, starting with tert-butyl 4-(hydroxymethyl)-3,3-dimethylpyrrolidine-1-carboxylate and Intermediate 1.
LC/MS: m/e 332.31 (M+H)$^+$.

Intermediate 25

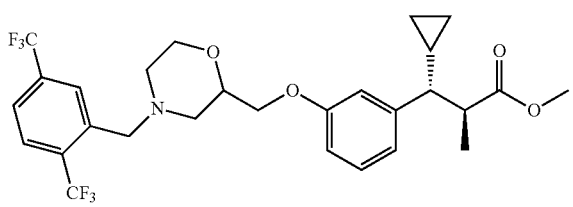 [SMILES: COC(=O)[C@@H](C)[C@H](c1cccc(OCC2CN(Cc3cc(C(F)(F)F)ccc3C(F)(F)F)CCO2)c1)C1CC1]

(2S,3R)-methyl 3-(3-((4-(2,5-bis(trifluoromethyl)benzyl)morpholin-2-yl)methoxy)-phenyl)-3-cyclopropyl-2-methylpropanoate Step A: To morpholin-2-ylmethanol (60 mg, 0.5 mmol) in DMF (1 mL) at rt was added 2,5,-bistrifluoromethylbenzyl bromide (157 mg, 0.5 mmol) and $K_2CO_3$ (142 mg, 1.0 mmol). The resulting mixture was stirred at rt overnight, diluted with $H_2O$ (4 mL), extracted with EtOAc (3×10 mL). The combined extracts were washed with brine, dried over $MgSO_4$, filtered, concentrated and purified by MPLC (ISCO 24 g, 0-30% EtOAc/hexanes) to give rise to (4-(2,5-bis(trifluoromethyl)benzyl)morpholin-2-yl)methanol. LC/MS: m/e 344.26 $(M+H)^+$.

Step B: A solution of (4-(2,5-bis(trifluoromethyl)benzyl)morpholin-2-yl)methanol (137 mg, 0.4 mmol), Intermediate 2 (66 mg, 0.3 mmol) and $PPh_3$ (190 mg, 0.6 mmol) in DCM (2 mL) was purged with $N_2$. Then DIAD (0.1 mL, 0.6 mmol) was and the reaction was stirred at rt for 12 h. The reaction was then filtered through a pad of Celite™. The resulting filtrate was concentrated to dryness and purified by MPLC (ISCO 24 g, 0-15% EtOAc/hexanes) to give rise to the title compound. LC/MS: m/e 560.46 $(M+H)^+$.

Intermediate 26

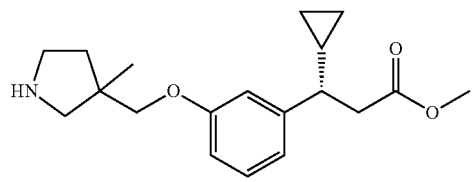 [SMILES: COC(=O)C[C@H](c1cccc(OCC2(C)CCNC2)c1)C1CC1]

(3S)-Methyl 3-cyclopropyl-3-(3-((3-methylpyrrolidin-3-yl)methoxy)phenyl)propanoate Intermediate 26 was prepared in an analogous manner to Intermediates 4 and 5, starting with tert-butyl 3-(hydroxymethyl)-3-methylpyrrolidine-1-carboxylate and Intermediate 1.

LC/MS: m/e 318.33 $(M+H)^+$.

Intermediate 27

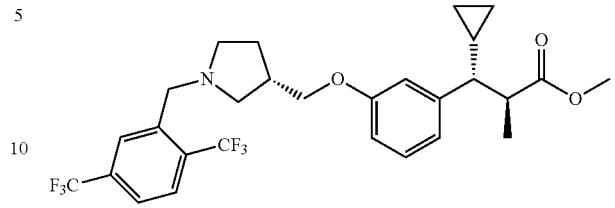

(2S,3R)-Methyl 3-(3-(((S)-1-(2,5-bis(trifluoromethyl)benzyl)pyrrolidin-3-yl)methoxy)phenyl)-3-cyclopropyl-2-methylpropanoate To a solution of (2S,3R)-methyl 3-cyclopropyl-3-(3-hydroxyphenyl)-2-methylpropanoate (40 mg, 0.17 mmol) in DMF (2 mL) at rt was added $Cs_2CO_3$ (111 mg, 0.34 mmol). The reaction was stirred at rt for 10 min, followed by the addition of Intermediate 6 (69 mg, 0.17 mmol). The resulting mixture was stirred at 50° C. for 48 h, then diluted with $H_2O$ (15 mL), and extracted with EtOAc (3×15 mL). The combined organic layers were washed with brine, dried over $MgSO_4$, filtered, concentrated and purified by MPLC (ISCO 24 g, 0-15% EtOAc/hexanes) to give the title compound as a colorless oil. LC/MS: m/e 544.40 $(M+H)^+$.

Intermediate 28

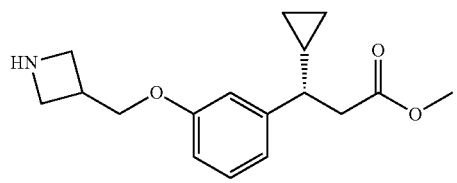 [SMILES: COC(=O)C[C@H](c1cccc(OCC2CNC2)c1)C1CC1]

(S)-Methyl 3-(3-(azetidin-3-ylmethoxy)phenyl)-3-cyclopropylpropanoate

Intermediate 28 was prepared in an analogous manner to Intermediates 4 and 5, starting with tert-butyl 3-(hydroxymethyl)azetidine-1-carboxylate and Intermediate 1. LC/MS: m/e 290.22 $(M+H)^+$.

Intermediate 29

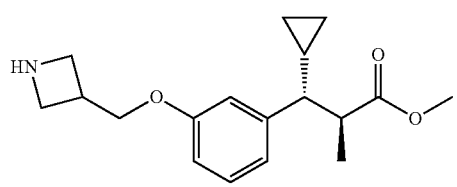 [SMILES: COC(=O)[C@@H](C)[C@H](c1cccc(OCC2CNC2)c1)C1CC1]

(2S,3R)-Methyl 3-(3-(azetidin-3-ylmethoxy)phenyl)-3-cyclopropyl-2-methylpropanoate Intermediate 29 was prepared in an analogous manner to Intermediates 4 and 5, starting with tert-butyl 3-(hydroxymethyl)azetidine-1-carboxylate and Intermediate 2. LC/MS: m/e 304.35 (M+H)+.

Intermediate 30

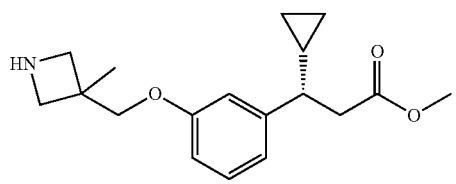 [SMILES: COC(=O)C[C@H](c1cccc(OCC2(C)CNC2)c1)C1CC1]

(S)-Methyl 3-cyclopropyl-3-(3-((3-methylazetidin-3-yl)methoxy)phenyl)propanoate

Intermediate 30 was prepared in an analogous manner to Intermediates 4 and 5, starting with tert-butyl 3-(hydroxymethyl)-3-methylazetidine-1-carboxylate and Intermediate 1. LC/MS: m/e 304.27 (M+H)+.

Intermediate 31

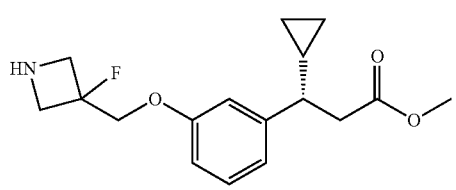 [SMILES: COC(=O)C[C@H](c1cccc(OCC2(F)CNC2)c1)C1CC1]

(S)-Methyl 3-cyclopropyl-3-(3-((3-fluoroazetidin-3-yl)methoxy)phenyl)propanoate

Intermediate 31 was prepared in an analogous manner to Intermediates 4 and 5, starting with tert-butyl 3-fluoro-3-(hydroxymethyl)azetidine-1-carboxylate and Intermediate 1. LC/MS: m/e 308.27 (M+H)+.

Intermediate 32

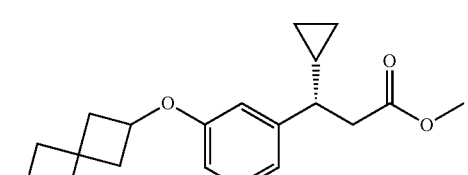

(S)-Methyl 3-(3-(2-azaspiro[3.3]heptan-6-yloxy)phenyl)-3-cyclopropylpropanoate

Intermediate 32 was prepared in an analogous manner to Intermediates 4 and 5, starting with tert-butyl 6-hydroxy-2-azaspiro[3.3]heptane-2-carboxylate and Intermediate 1. LC/MS: m/e 316.30 (M+H)+.

Intermediate 33

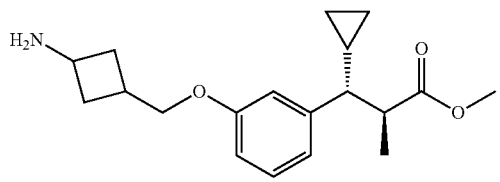 [SMILES: COC(=O)[C@@H](C)[C@H](c1cccc(OCC2CC(N)C2)c1)C1CC1]

(2S,3R)-Methyl 3-(3-((3-aminocyclobutyl)methoxy)phenyl)-3-cyclopropyl-2-methylpropanoate Intermediate 33 was prepared in an analogous manner to Intermediates 4 and 5, starting with tert-butyl (3-(hydroxymethyl)cyclobutyl)carbamate and Intermediate 2. LC/MS: m/e 318.33 (M+H)+.

Intermediate 34

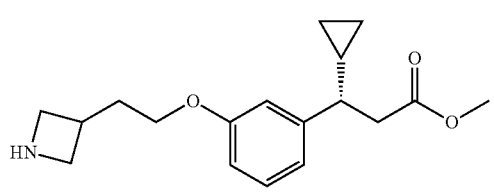 [SMILES: COC(=O)C[C@H](c1cccc(OCCC2CNC2)c1)C1CC1]

(S)-Methyl 3-(3-(2-(azetidin-3-yl)ethoxy)phenyl)-3-cyclopropylpropanoate

Intermediate 34 was prepared in an analogous manner to Intermediate 4 and 5 starting with tert-butyl 3-(2-hydroxyethyl)azetidine-1-carboxylate coupled to Intermediate 1. LC/MS: m/e 304.31 (M+H)+.

Intermediate 35

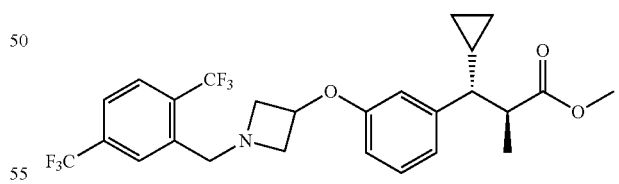

(2S,3R)-Methyl 3-(3-((1-(2,5-bis(trifluoromethyl)benzyl)azetidin-3-yl)oxy)phenyl)-3-cyclopropyl-2-methylpropanoate Step A: To a solution of 3-hydroxyazetidine hydrochloride (300 mg, 2.7 mmol, Aldrich) in DMF (4 mL) at rt was added 2,5-bis(trifluoromethyl)benzyl bromide (841 mg, 2.7 mmol) and $K_2CO_3$ (1.1 g, 8.2 mmol). The resulting slurry was stirred at rt for 12 h, then diluted with $H_2O$ (20 mL), and extracted with EtOAc (3×50 mL). The combined organic layers were washed with brine, dried over MgSO₄, filtered, concentrated and purified by MPLC (ISCO 40 g, 0-30% EtOAc/hexanes) to give 1-(2,5-bis(trifluoro-methyl)benzyl) azetidin-3-ol as a colorless oil.

Step B: 1-(2,5-bis(trifluoromethyl)benzyl)azetidin-3-ol (100 mg, 0.3 mmol) was dissolved in DCM (4 mL) and the resulting solution was cooled to 0° C. Then TEA (0.093 ml, 0.668 mmol) was added, followed by MsCl (0.03 mL, 0.4 mmol). The cooling bath was removed and the reaction was stirred at rt for 2 h. Then the reaction was partitioned between DCM and water (10 mL). The organic layer was separated, dried over MgSO₄, concentrated and purified by MPLC (ISCO 24 g, 0-30% EtOAc/hexanes) to give 1-(2,5-bis(trifluoromethyl)benzyl)azetidin-3-yl methanesulfonate as a colorless oil.

Step C: To a solution of Intermediate 2 (47 mg, 0.2 mmol) in DMF (2 mL) at rt was added Cs₂CO₃ (131 mg, 0.4 mmol) followed by 1-(2,5-bis(trifluoromethyl)benzyl)-azetidin-3-yl methanesulfonate (79 mg, 0.2 mmol). The resulting mixture was heated to 50° C. for 48 h, then diluted with H₂O (10 mL) and extracted with EtOAc (3×50 mL). The combined organic layers were washed with brine, dried over MgSO₄, filtered, concentrated and purified by MPLC (ISCO 24 g, 0-15% EtOAc/hexanes) to afford the title compound as a colorless oil. LC/MS: m/e 516.40 (M+H)⁺.

Intermediate 36

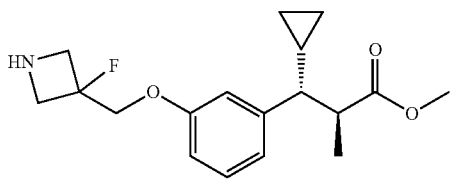 [SMILES: COC(=O)[C@@H](C)[C@H](c1cccc(OCC2(F)CNC2)c1)C1CC1]

(2S,3R)-Methyl 3-cyclopropyl-3-(3-((3-fluoroazetidin-3-yl)methoxy)phenyl)-2-methylpropanoate Intermediate 36 was prepared in an analogous manner to Intermediates 4 and 5 starting with tert-butyl 3-fluoro-3-(hydroxymethyl)azetidine-1-carboxylate and Intermediate 2.

LC/MS: m/e 322.31 (M+H)⁺.

Intermediate 37

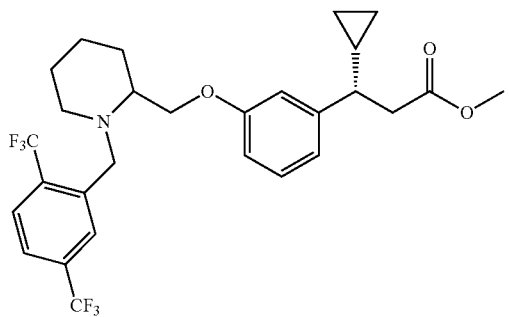 [SMILES: COC(=O)C[C@H](c1cccc(OCC2CCCCN2Cc2cc(C(F)(F)F)ccc2C(F)(F)F)c1)C1CC1]

(3S)-Methyl 3-(3-((1-(2,5-bis(trifluoromethyl)benzyl)piperidin-2-yl)methoxy)phenyl)-3-cyclopropylpropanoate Intermediate 37 was prepared in an analogous manner to Intermediate 35, starting with piperidin-2-yl methanol and Intermediate 1. LC/MS: m/e 544.69 (M+H)⁺.

Intermediate 38

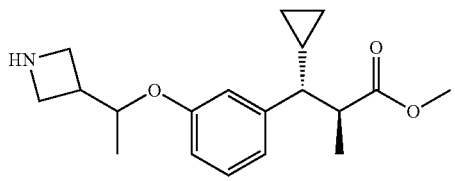 [SMILES: COC(=O)[C@@H](C)[C@H](c1cccc(OC(C)C2CNC2)c1)C1CC1]

(2S,3R)-Methyl 3-(3-(1-(azetidin-3-yl)ethoxy)phenyl)-3-cyclopropyl-2-methylpropanoate Step A: To a solution of tert-butyl 3-acetylazetidine-1-carboxylate (1 g, 5.0 mmol) in MeOH (25 mL) at rt was added NaBH₄ (0.095 g, 2.5 mmol). The resulting solution was stirred at rt for 1 h. Then the solution was concentrated to dryness and purified by MPLC (ISCO 40 g, 0-30% EtOAc/hexanes) to give tert-butyl 3-(1-hydroxyethyl)azetidine-1-carboxylate as a colorless oil.

Step B: A solution of tert-butyl 3-(1-hydroxyethyl)azetidine-1-carboxylate (73 mg, 0.4 mmol), Intermediate 2 (57 mg, 0.2 mmol) and PPh₃ (162 mg, 0.487 mmol) in DCM (2 mL) was treated with DIAD (0.095 mL, 0.5 mmol). The reaction was stirred at rt for 12 h, then concentrated to dryness and purified by MPLC (ISCO 12 g, 0-30% EtOAc/hexanes) to give tert-butyl 3-(1-(3-((1R,2S)-1-cyclopropyl-3-methoxy-2-methyl-3-oxopropyl)phenoxy)ethyl)azetidine-1-carboxylate as a colorless oil.

STEP C: The BOC group of the product of Step B was removed according to the BOC removal procedure for Intermediate 5 to give the title compound. LC/MS: m/e 318.56 (M+H)⁺.

Intermediate 39

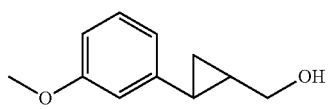

(2-(3-Methoxyphenyl)cyclopropyl)methanol

Step A: A mixture of 3-methoxybenzaldehyde (50 g, 367 mmol), malonic acid (57.3 g, 551 mmol), piperidine (3.6 mL) and pyridine (39.8 g, 503 mmol) was heated to reflux for 2 h. Then the reaction solution was quenched with ice water and concentrated HCl. The resulting white precipitate was filtered off and washed with 1N HCl, water, 95% EtOH, and MeOH to give (E)-3-(3-methoxyphenyl)acrylic acid.

Step B: A mixture of (E)-3-(3-methoxyphenyl)acrylic acid (60 g, 0.337 mol) in SOCl₂ (74 mL, 1.01 mol) was heated to 80° C. for 2 h. The excess SOCl₂ was removed to give (E)-3-(3-methoxyphenyl)acryloyl chloride.

Step C: To a solution of NaOH (53.9 g, 1.35 mol) in ether (500 mL) and water (675 mL) was added N,O-Dimethylhydroxylamine (98.5 g, 1.01 mol) in portions at 0° C. Then a solution of (E)-3-(3-methoxyphenyl)acryloyl chloride (66.5 g, 0.338 mol) in ether (100 mL) was added dropwise at 0° C. The resulting solution was stirred at rt for 2 h. Then the organic layer was separated and the aqueous layer was extracted with Et₂O. The combined organic layers were washed with water, brine, dried over anhydrous Na₂SO₄, filtered and concentrated to afford (E)-N-methoxy-3-(3-methoxyphenyl)-N-methylacrylamide.

Step D: To a solution of trimethyllsulfoxonium iodide (138.3 g, 0.673 mol) in DMSO (350 mL) was added NaH (16.2 g, 0.673 mol) in portions at rt under a nitrogen atmosphere. The mixture was stirred at rt for 1 h, followed by the dropwise addition of a solution of (E)-N-methoxy-3-(3-methoxyphenyl)-N-methyl acrylamide (74.5 g, 0.337 mol) in DMSO (100 mL). The reaction mixture was stirred at rt overnight, then quenched with saturated NH₄Cl (500 mL). The organic layer was separated, washed with water and brine, dried over Na₂SO₄, filtered and concentrated under vacuum to give N-methoxy-2-(3-methoxyphenyl)-N-methylcyclopropanecarboxamide.

Step E: A mixture of N-methoxy-2-(3-methoxyphenyl)-N-methylcyclopropane-carboxamide (75 g, 0.319 mol) and NaOH (15.3 g, 0.383 mol) in EtOH (155 mL) and water (155 mL) was heated to 80° C. overnight. Then the solvent was removed under vacuum to give a residue. The residue was dissolved in water and the solution was acidified to pH=4, and extracted with ether. The combined ether extracts were washed with water, brine, dried over sodium sulphate, filtered, and concentrated. The resulting residue was re-crystallized from petroleum ether to afford 2-(3-methoxyphenyl) cyclopropanecarboxylic acid.

Step F: 2-(3-methoxyphenyl)cyclopropanecarboxylic acid (1 g, 5.20 mmol) was dissolved in tetrahydrofuran (10 ml) and BH₃THF (7.80 ml, 7.80 mmol, 1 M THF solution) was added dropwise at 0° C. under N₂. After gas evolution ceased, the reaction was allowed to stir at rt for 30 min, then quenched by the slow addition of water (20 mL). After gas evolution ceased, added EtOAc (30 mL) was added to the reaction mixture. Then the organic layer was separated, dried over MgSO₄, and evaporated to give the crude product. The crude product was purified by ISCO (40 g, 0~40% EtOAc in hexane) to afford (2-(3-methoxyphenyl)cyclopropyl)methanol.

Intermediate 40

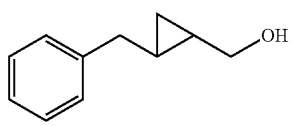 [SMILES: OCC1CC1Cc1ccccc1]

(2-Benzylcyclopropyl)methanol

Ethyl-2-benzylcyclopropanecarboxylate (963 mg, 4.71 mmol) was dissolved in anhydrous tetrahydrofuran (10 mL) and the mixture was cooled to −78° C. and stirred for 5 minutes. Then LAH (9.43 mL, 9.43 mmol, 1 M THF) was added over 5 minutes. The reaction mixture was slowly warmed to rt and stirred at rt for 3 h. Then the reaction was quenched with Rochelle salt solution (15 mL), and extracted with EtOAc (2×30 mL). The combined organic layers were separated, and concentrated. The resulting residue was re-dissolved in DCM, and purified by ISCO (0~60% EtOAc in hexane) to afford (2-benzylcyclopropyl)methanol.

Intermediate 41

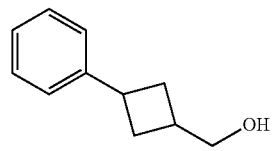 [SMILES: OCC1CC(c2ccccc2)C1]

(3-Phenylcyclobutyl)methanol

Step A: To a solution of bromobenzene (110.2 g, 0.702 mol) in THF (800 mL) was added dropwise n-BuLi (288 mL, 0.719 moL) at −78° C. under N₂. Then the reaction was stirred at −78° C. for 1 hour, followed by the dropwise addition of a solution of 3-oxocyclobutanecarboxylic acid (40 g, 0.351 moL) in THF (100 mL). The resulting solution was stirred at −78° C. for 2 hours, then quenched with saturated NH₄Cl solution and extracted with ethyl acetate. The organic layer was separated, washed with brine, dried over anhydrous Na₂SO₄, filtered and concentrated to give 3-hydroxy-3-phenylcyclobutanecarboxylic acid.

Step B: To a solution of 3-hydroxy-3-phenylcyclobutanecarboxylic acid (50 g, 260 mmol) in DMF (300 mL) was added K₂CO₃ (43 g, 312 mmol) and MeI (44 g, 312 mmol). The reaction mixture was stirred at 50° C. overnight. The reaction was diluted with water and extracted with EtOAc. The organic layer was washed with brine, dried over anhydrous Na₂SO₄, filtered and concentrated to give methyl 3-hydroxy-3-phenylcyclobutanecarboxylate.

Step C: To a solution of methyl 3-hydroxy-3-phenylcyclobutanecarboxylate (43 g, 208.7 mmol) in TFA (300 mL) was added dropwise Et₃SiH (158 g, 1.25 mol) at 0° C. The resulting solution was stirred at rt overnight. The reaction was concentrated to give a crude oil, which was purified by column silica gel chromatography to afford methyl 3-phenylcyclobutanecarboxylate.

Step D: To a solution of methyl 3-phenylcyclobutanecarboxylate (30 g, 158 mmol) in 1:1 THF/H₂O (300 mL) was added portionwise LiOH (11.4 g, 473.6 mmol) at 0° C. The resulting solution was stirred at rt for 4 hours. The reaction was extracted with dichloromethane. The aqueous layer was adjusted to pH 1 with 3N HCl aqueous solution and extracted with ethyl acetate. The EtOAc layer was washed with brine, dried over anhydrous Na₂SO₄, filtered and concentrated to give 3-phenylcyclobutanecarboxylic acid.

Step E: 3-Phenylcyclobutanecarboxylic acid (991 mg, 5.62 mmol) was dissolved in tetrahydrofuran (10 ml) and borane-tetrahydrofuran complex (8.44 ml, 8.44 mmol) (1.0 M THF solution) was added dropwise at 0° C. under N₂. After gas evolution ceased, the reaction was allowed to stir at rt for 30 minutes, then quenched by the slow addition of water (10 mL).

After gas evolution ceased, EtOAc (30 mL) was added. The layers were separated, and the organic layer was dried over MgSO₄, filtered and evaporated. The resulting crude material was purified by ISCO (0~40% EtOAc in hexane) to afford (3-phenylcyclobutyl)methanol.

Intermediate 42

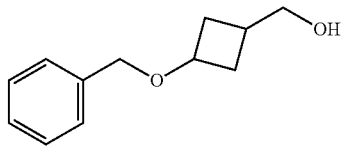 [SMILES: OCC1CC(OCc2ccccc2)C1]

(3-(Benzyloxy)cyclobutyl)methanol

3-Benzyloxy-cyclobutanecarboxylic acid (1 g, 4.85 mmol) was dissolved in THF (10 mL) and BH$_3$THF (7.27 ml, 7.27 mmol, 1 M THF solution) was added dropwise at 0° C. under N$_2$ atmosphere. After gas evolution ceased, the reaction was allowed to stir at rt for 30 min, and then quenched by the slow addition of water (10 mL). After gas evolution ceased, EtOAc (30 mL) was added. The organic layer was separated, dried over MgSO$_4$, and evaporated. The resulting crude material was purified by ISCO (0~70% EtOAc in hexane) to afford (3-(benzyloxy)cyclobutyl)methanol.

Intermediate 43

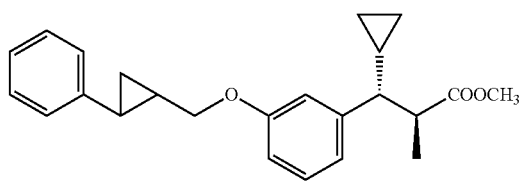 [SMILES: COC(=O)[C@@H](C)[C@H](c1cccc(OCC2CC2c2ccccc2)c1)C1CC1]

(2S,3R)-Methyl 3-cyclopropyl-2-methyl-3-(3-((2-phenylcyclopropyl) methoxy)phenyl) propanoate Intermediate 2 (50 mg, 0.2 mmol), (2-phenylcyclopropyl)methanol (127 mg, 0.8 mmol) and Bu$_3$P (0.2 mL, 0.8 mmol) were dissolved in THF (3 mL). The mixture was stirred at rt for 5 minutes, then 1,1'-(azodicarbonyl)dipiperidine (215 mg, 0.8 mmol) was added portionwise. The reaction mixture was stirred at 50° C. overnight. The reaction was then evaporated, re-dissolved in DCM (5 mL) and purified by ISCO (0~30% EtOAc in hexane) to afford the title compound.

Intermediate 44

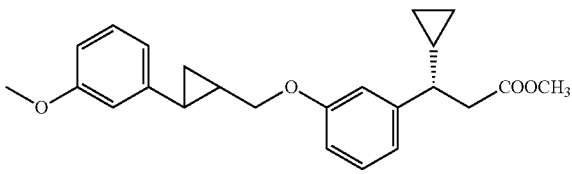 [SMILES: COC(=O)C[C@H](c1cccc(OCC2CC2c2cccc(OC)c2)c1)C1CC1]

(3S)-Methyl 3-cyclopropyl-3-(3-((2-(3-methoxyphenyl)cyclopropyl) methoxy)phenyl) propanoate Intermediate 44 was prepared in an analogous manner to Intermediate 43, starting with Intermediate 39 coupled with Intermediate 1.

Intermediate 45

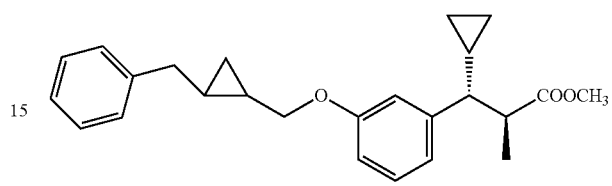

(2S,3R)-Methyl 3-(3-((2-benzylcyclopropyl) methoxy)phenyl)-3-cyclopropyl-2-methylpropanoate Intermediate 45 was prepared in an analogous manner to Intermediate 43, starting with Intermediate 40 coupled with Intermediate 2.

Intermediate 46

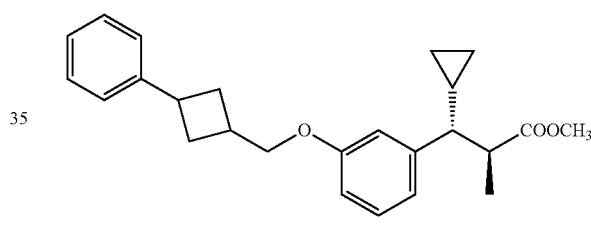

(2S,3R)-Methyl 3-cyclopropyl-2-methyl-3-(3-((3-phenylcyclobutyl) methoxy)phenyl) propanoate Intermediate 46 was prepared in an analogous manner to Intermediate 43, starting with Intermediate 41 coupled with Intermediate 2.

Intermediate 47

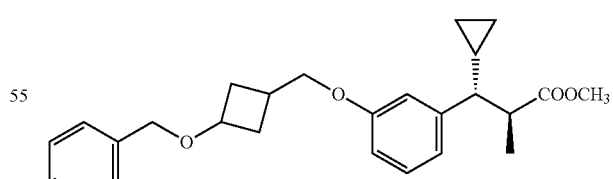

(2S,3R)-Methyl 3-(3-((3-(benzyloxy)cyclobutyl) methoxy)phenyl)-3-cyclopropyl-2-methylpropanoate Intermediate 47 was prepared in an analogous manner to Intermediate 43, starting with Intermediate 42 coupled with Intermediate 2.

Intermediate 48

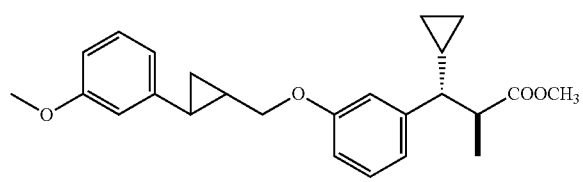 [SMILES: COC(=O)[C@@H](C)[C@H](c1cccc(OCC2CC2c2cccc(OC)c2)c1)C1CC1]

(2S,3R)-Methyl 3-cyclopropyl-3-(3-((2-(3-methoxyphenyl)cyclopropyl)methoxy)phenyl)-2-methylpropanoate Intermediate 48 was prepared in an analogous manner to Intermediate 43 starting with Intermediate 39 coupled with Intermediate 2.

Intermediate 49

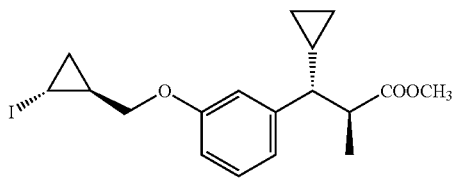 [SMILES: COC(=O)[C@@H](C)[C@H](c1cccc(OC[C@@H]2C[C@H]2I)c1)C1CC1]

(2S,3R)-Methyl 3-cyclopropyl-3-(33-(((1S,2R)-2-iodocyclopropyl)methoxy)phenyl)-2-methylpropanoate Intermediate 49 was prepared in an analogous manner to Intermediate 4 starting with ((1S,2R)-2-iodocyclopropyl)methanol and Intermediate 2.

Intermediate 50

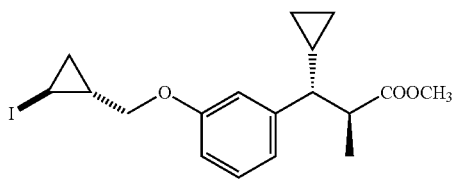

(2S,3R)-Methyl 3-cyclopropyl-3-(3-(((1R,2S)-2-iodocyclopropyl)methoxy)phenyl)-2-methylpropanoate Intermediate 50 was prepared in an analogous manner to Intermediate 4, starting with ((1R,2S)-2-iodocyclopropyl)methanol and Intermediate 2.

Intermediate 51

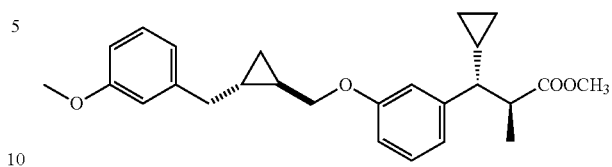

(2S,3R)-Methyl 3-cyclopropyl-3-(3-(((1R,2S)-2-(3-methoxybenzyl)cyclopropyl) methoxy)phenyl)-2-methylpropanoate Intermediate 50 (120 mg, 0.29 mmol), chloro(2-dicyclohexylphosphino-2',4',6'-triisopropyl-1,1'-biphenyl)[2-(2'-amino-1,1'-biphenyl)]palladium (II), THF adduct (23 mg, 0.03 mmol) and 3-methoxybenzylzinc chloride (1.7 mL, 0.8 mmol, 0.5 M THF solution) were dissolved in anhydrous THF (1.5 mL). The mixture was degassed, purged with N$_2$ for 5 min, then heated at 60° C. for 3 h. The reaction was quenched with saturated NH$_4$Cl (10 mL), and extracted with EtOAc (2×20 mL). The combined EtOAc layers were washed with water (15 mL) and brine (15 mL), dried over MgSO$_4$ and evaporated. The resulting crude material was purified by ISCO (0~15% EtOAc in hexane) to afford the title compound.

Intermediate 52

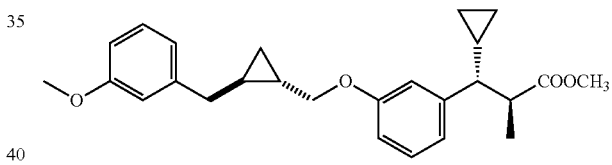

(2S,3R)-Methyl 3-cyclopropyl-3-(3-(((1S,2R)-2-(3-methoxybenzyl)cyclopropyl) methoxy)phenyl)-2-methylpropanoate Intermediate 52 was prepared in an analogous manner to Intermediate 51, starting with Intermediate 50.

Intermediate 53

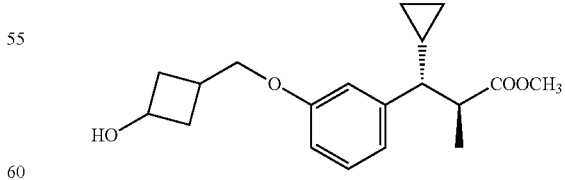

(2S,3R)-Methyl 3-cyclopropyl-3-(3-((3-hydroxycyclobutyl)methoxy)phenyl)-2-Methylpropanoate Intermediate 47 (480 mg, 1.2 mmol) and 10% palladium on carbon (125 mg, 1.2 mmol) were dissolved in MeOH (10 mL). The mixture was hydrogenated under H₂ balloon at rt for 2 h. Then the reaction mixture was filtered, evaporated, re-dissolved in DCM (3 mL), and purified by ISCO (0~100% EtOAc in hexane) to afford the title compound.

Intermediate 54

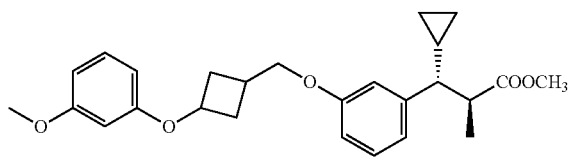 [SMILES: COC(=O)[C@@H](C)[C@H](c1cccc(OCC2CC(Oc3cccc(OC)c3)C2)c1)C1CC1]

(2S,3R)-Methyl 3-cyclopropyl-3-(3-((3-(3-methoxyphenoxy)cyclobutyl) methoxy)phenyl)-2-methylpropanoate Intermediate 54 was prepared in an analogous manner to Intermediate 43, starting with 3-methoxyphenol and Intermediate 53.

Intermediate 55

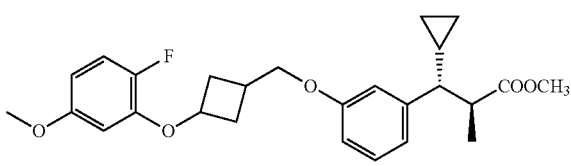 [SMILES: COC(=O)[C@@H](C)[C@H](c1cccc(OCC2CC(Oc3cc(OC)ccc3F)C2)c1)C1CC1]

(2S,3R)-Methyl 3-cyclopropyl-3-(3-((3-(2-fluoro-5-methoxyphenoxy)cyclobutyl) methoxy)phenyl)-2-methylpropanoate Intermediate 55 was prepared in an analogous manner to Intermediate 43, starting with 2-fluoro-5-methoxyphenol and Intermediate 53.

Intermediate 56

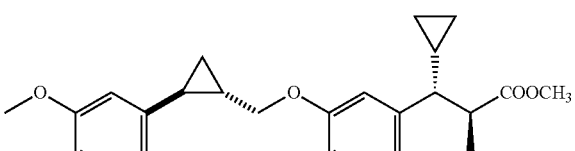

(2S,3R)-Methyl 3-cyclopropyl-3-(3-(((1 S,2S)-2-(2-fluoro-5-methoxyphenyl)cyclopropyl) methoxy)phenyl)-2-methylpropanoate Intermediate 50 (150 mg, 0.36 mmol), 2-fluoro-5-methoxyphenylboronic acid (92 mg, 0.54 mmol) and 1,1'-bis(di-tert-butylphosphino) ferrocenepalladium dichrolide (23 mg, 0.04 mmol) were dissolved in DMF (3 mL), and K₃PO₄ (0.46 mL, 1.0 mmol, 50% water) was added. The reaction mixture was degassed, purged with N₂ for 5 minutes and heated to 90° C. for 3 h. Then the reaction was quenched with water, and extracted with EtOAc (2×). The combined EtOAc layers were washed with water and brine, dried over MgSO₄ and evaporated. The resulting crude material was purified by silica gel chromatography (gradient elution, 0 to 20% EtOAc in hexane) to afford the title compound.

Intermediate 57

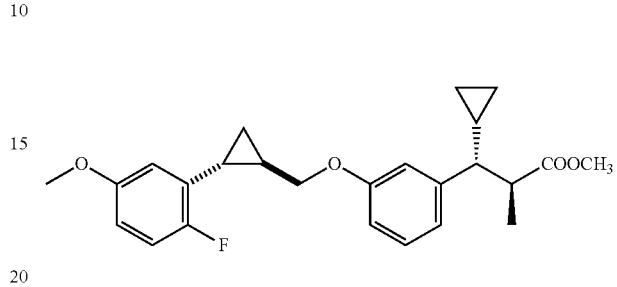

(2S,3R)-Methyl 3-cyclopropyl-3-(3-(((1R,2R)-2-(2-fluoro-5-methoxyphenyl)cyclopropyl) methoxy)phenyl)-2-methylpropanoate Intermediate 57 was prepared in an analogous manner to Intermediate 56, starting with Intermediate 49.

Intermediate 58

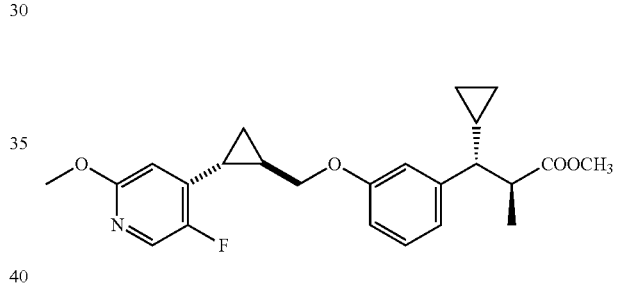

(2S,3R)-Methyl 3-cyclopropyl-3-(3-(((1R,2R)-2-(5-fluoro-2-methoxypyridin-4-yl)cyclopropyl)methoxy)phenyl)-2-methylpropanoate Intermediate 58 was prepared in an analogous manner to Intermediate 54 starting with Intermediate 49.

Intermediate 59A and 59B

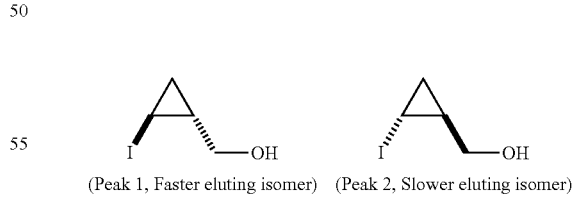

(Peak 1, Faster eluting isomer)   (Peak 2, Slower eluting isomer)

(+)-(1R,2S)-2-Iodocyclopropyl)methanol (Peak 1, Faster Eluting Isomer) and (−)-(1S,2R)-2-Iodocyclopropyl)methanol (Peak 2, Slower Eluting Isomer)

Step A: A solution of NaI (1203.5 g) in AcOH (5350 mL), methyl prop-2-ynoate (450 g, 5.35 mol, 1.00 equiv) was stirred overnight at 70° C., then cooled to room temperature, and diluted with 3000 mL of H$_2$O. The resulting solution was extracted with 2×2500 mL of ether.

The organic layers were combined, washed with 2×1000 mL of aqueous potassium hydroxide, dried over anhydrous sodium sulfate, filtered, concentrated under vacuum to afford (Z)-methyl 3-iodoacrylate.

Step B: A solution of methyl (Z)-methyl 3-iodoacrylate (977 g, 4.61 mol, 1.00 equiv) in toluene (2700 mL), HI (100 mL) was stirred overnight at 80° C. The reaction mixture was cooled to r.t and then quenched by the addition of 1500 mL of H$_2$O. The resulting solution was extracted with 2×1500 mL of ethyl acetate. The organic layers were combined, washed with 1×600 mL of aqueous sodium bicarbonate and 1×600 mL of aqueous Na$_2$S$_2$O$_3$ (10%) and 1×600 mL of brine, dried over anhydrous sodium sulfate, filtered and concentrated under vacuum. The resulting residue was triturated with hexane to afford (E)-methyl 3-iodoacrylate.

Step C: To a solution of methyl (E)-methyl 3-iodoacrylate (372 g, 1.75 mol, 1.00 equiv) in dichloromethane (3600 mL) was added dropwise diisobutylaluminum hydride (2296 g, 2.30 equiv, 25%) with stirring at 0° C. The resulting solution was stirred for 3 h at room temperature, then quenched by the addition of 1000 mL of aq. NH$_4$Cl (1M). The organic layer was washed with 1×800 mL of HCl (1M) and 1×800 mL of brine, dried over anhydrous sodium sulfate, filtered, concentrated under vacuum. The resulting residue was applied onto a silica gel column and eluted with ethyl acetate/petroleum ether (1:10) to afford (E)-3-iodoprop-2-en-1-ol.

Step D: To a solution of Et$_2$Zn (763 g, 4.00 equiv) in dichloromethane (400 mL) was added dropwise a solution of CF$_3$COOH (704 g, 6.17 mol, 4.00 equiv) in dichloromethane (460 mL) with stirring at −10° C. and this mixture was stirred for 20 min at −10° C. To this solution was added dropwise a solution of CH$_2$I$_2$ (1654 g, 4.00 equiv) in dichloromethane (500 mL) with stirring at −10° C. The resulting solution was stirred for 20 min at −10° C., then a solution of (E)-3-iodoprop-2-en-1-ol (284 g, 1.54 mol, 1.00 equiv) in dichloromethane (280 mL) was added dropwise with stirring at −10° C. The resulting solution was stirred for 1 h at room temperature, then quenched by the addition of 2400 mL of HCl (1M). The resulting solution was extracted with 2×2000 mL of dichloromethane. The organic layers were combined, washed with 1×1000 mL of brine, dried over anhydrous sodium sulfate, filtered, concentrated under vacuum. The resulting residue was applied onto a silica gel column and eluted with ethyl acetate/petroleum ether (1:30) to afford racemic trans-(2-iodocyclopropyl)methanol.

Step E: Racemic trans-(2-iodocyclopropyl)methanol was purified via Prep-SFC (Instrument: Thar preparative SFC 80, Column: ChiralPak AD-H, 250×30 mm I.D. 5 m. Mobile phases: A: CO$_2$ and B: methanol. Isocratic elution: 15% methanol. Flow rate: 55 mL/min, back pressure: 100 bar, column temperature: 40° C., wavelength: 254 nm, cycle time: 3.5 min. Sample preparation: Compound was dissolved in ethanol to ~30 mg/ml. Injection: 1 ml per injection.) to afford (+)-(1R,2S)-2-iodocyclopropylmethanol (Peak 1, faster eluting isomer, $[\alpha]_D^{20.1}$ +73.20 (C=0.410 g/100 mL in MeCN)) and (−)-(1S,2R)-2-iodocyclopropyl-methanol (Peak 2, slower eluting isomer, $[\alpha]_D^{18.9}$ −−74.5° (C=0.453 g/100 mL in MeCN)).

Analytical SFC Conditions: Instrument: Thar analytical SFC, Column: ChiralPak AD-H, 150×4.6 mm, 5 μm, Mobile phase: A for CO$_2$ and B for methanol, Gradient: B in A from 10% to 40% in 5 minutes, Flow rate: 4 mL/min, Back pressure: 100 bar, Column temperature: 30° C., Wavelength: 254 nm. The absolute stereochemistry of each enantiomer was confirmed by comparing the optical rotations of both compounds with the optical rotation for (+)-(1R,2S)-2-iodocyclopropyl-methanol, which was previously reported in *J. Am. Chem. Soc.*, Vol. 120, No. 46, 1998, p 11943.

Intermediate 60

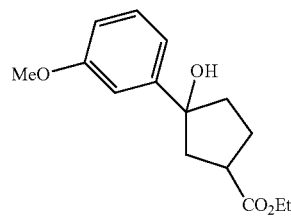 [SMILES: CCOC(=O)C1CCC(O)(c2cccc(OC)c2)C1]

Ethyl 3-hydroxy-3-(3-methoxyphenyl)cyclopentanecarboxylate

To a cooled (0° C.) solution of ethyl 3-oxocyclopentanecarboxylate (2.6 g, 16.65 mmol) in THF (50 mL) was added (3-methoxyphenyl)magnesium bromide (16.7 mL, 16.7 mmol). After 1 h at 0° C., the reaction was quenched by the addition of saturated NH$_4$Cl (50 mL). The mixture was extracted with EtOAc (2×50 mL). The combined organic layers were dried over MgSO$_4$ and concentrated. The resulting residue was purified by MPLC (ISCO 120 g, 0 to 50% EtOAc/Hex) to give the title compound as a clear oil. $^1$H NMR (500 MHz, CDCl$_3$): δ7.29 (t, 1H); 7.12 (s, 1H); 7.08 (d, 1H); 6.80 (d, 1H); 4.20 (q, 2H); 3.81 (s, 3H); 3.36 (br, 1H); 3.10 (m, 1H); 2.32-2.20 (m, 4H); 2.15-2.05 (m, 2H); 1.30 (t, 3H)

Intermediate 61

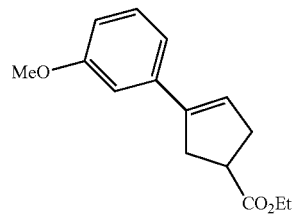 [SMILES: CCOC(=O)C1CC=C(c2cccc(OC)c2)C1]

Ethyl 3-(3-methoxyphenyl)cyclopent-3-enecarboxylate

To a solution of Intermediate 60 (250 mg, 0.9 mmol) in toluene (2 mL) was added TsOH (18 mg, 0.095 mmol). The reaction was then heated to 100° C. on a heating block. After 1 h, the reaction was cooled to rt and poured into saturated NaHCO$_3$ (25 mL). The mixture was extracted with EtOAc (2×25 mL). The combined organic layers were dried (MgSO$_4$) and concentrated. The resulting residue was purified by MPLC (ISCO 40 g, 0 to 40% EtOAc/Hex) to give the title compound. LC/MS: m/e 247.18 (M+H)$^+$

Intermediate 62

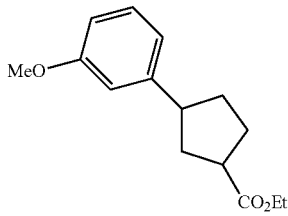 [SMILES: CCOC(=O)C1CCC(c2cccc(OC)c2)C1]

Ethyl 3-(3-methoxyphenyl)cyclopentanecarboxylate

To a solution of Intermediate 61(80 mg, 0.325 mmol) in MeOH (5 mL) was added Pd(OH)$_2$ (8 mg, 0.01 mmol). The reaction was then sealed in a Pyrex vessel and shaken on a Parr shaker under 40 psi of hydrogen gas. After 1 h, the reaction was vented. The mixture was then filtered through a pad of Celite™ and concentrated to give the title compound. $^1$H NMR (500 MHz, CDCl$_3$): δ7.22 (t, 1H); 6.90 (d, 1H); 6.85 (s, 1H); 6.75 (d, 1 h); 4.18 (q, 2H); 3.80 (s, 3H); 3.05 (m, 1H); 2.92 (m, 1H); 2.38 (m, 1H); 2.10 (m, 2H); 2.01 (m, 1H); 1.95 (m, 1H); 1.80 (m, 1H); 1.30 (t, 3H)

Intermediate 63

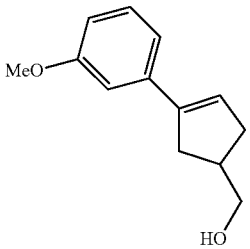 [SMILES: COc1cccc(C2=CCC(CO)C2)c1]

(3-(3-methoxyphenyl)cyclopent-3-en-1-yl)methanol

To a cooled (0° C.) solution of Intermediate 61 (80 mg, 0.33 mmol) in THF (3 mL) was added LAH (12 mg, 0.33 mmol) in a single portion. After 1 h, the reaction was quenched with Rochelle's salt solution (25 mL). The mixture was extracted with EtOAc (2×25 mL). The combined organic layers were dried over MgSO$_4$ and concentrated. The resulting residue was purified by MPLC (ISCO 40 g, 0 to 50% EtOAc/Hex) to give the title compound. LC/MS: m/e 205.15 (M+H)$^+$

Intermediate 64

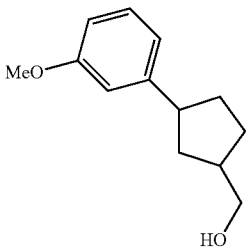 [SMILES: COc1cccc(C2CCC(CO)C2)c1]

(3-(3-methoxyphenyl)cyclopentyl)methanol

To a cooled (0° C.) solution of ethyl 3-(3-methoxyphenyl) cyclopentane-carboxylate (72 mg, 0.290 mmol) in THF (3 mL) was added LAH (11.00 mg, 0.290 mmol) in a single portion. After 1 h, the reaction was quenched with Rochelle's salt solution (25 mL). The mixture was extracted with EtOAc (2×25 mL). The combined organic layers were dried over MgSO$_4$ and concentrated. The resulting residue was purified by MPLC (ISCO 40 g, 0 to 50% EtOAc/Hex) to give the title compound. (500 MHz, CDCl$_3$): δ7.22 (t, 1H); 6.86 (d, 1H); 6.81 (s, 1H); 6.75 (d, 1H); 3.81 (s, 3H); 3.62 (d, 2H); 3.05 (m, 1H); 2.30 (m, 1H); 2.25 (m, 1H); 2.10 (m, 1H); 1.90 (m, 1H); 1.68 (m, 1H); 1.60 (m, 1H); 1.48 (br, 1H); 1.34 (q, 1H)

Intermediate 65

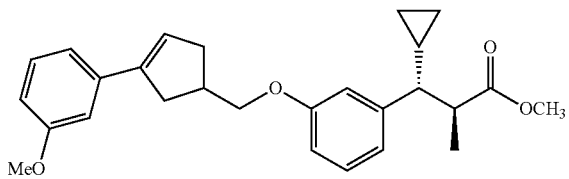 [SMILES: COC(=O)[C@@H](C)[C@H](c1cccc(OCC2CC=C(c3cccc(OC)c3)C2)c1)C1CC1]

(2S,3R)-Methyl 3-cyclopropyl-3-(3-((3-(3-methoxyphenyl)cyclopent-3-en-1-yl)methoxy)phenyl)-2-methylpropanoate To a solution of Intermediate 63 (70 mg, 0.34 mmol) and Intermediate 2 (80 mg, 0.34 mmol) in toluene (3 mL) was added PPh$_3$ (180 mg, 0.685 mmol) immobilized on a polystyrene support. The resulting slurry was cooled to 0° C. Then DIAD (0.13 mL, 0.685 mmol) was slowly added. After 1 h, the reaction was warmed to room temperature and filtered. The volatiles were removed in vacuo and the residue was purified by MPLC (ISCO 40 g, 0 to 40% EtOAc/Hex) to give the title compound. LC/MS: m/e 421.25 (M+H)$^+$

Intermediate 66

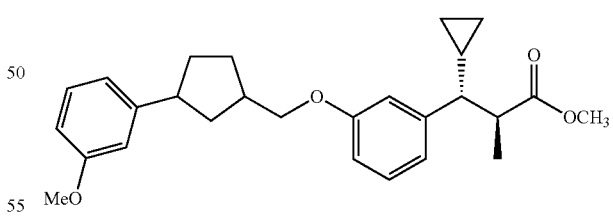

(2S,3R)-Methyl 3-cyclopropyl-3-(3-((3-(3-methoxyphenyl)cyclopentyl)methoxy)phenyl)-2-methylpropanoate To a solution of Intermediate 64 (50 mg, 0.24 mmol) and Intermediate 2 (57 mg, 0.24 mmol) in toluene (3 mL) was added PPh$_3$ (127 mg, 0.485 mmol) immobilized on a polystyrene support. The resulting slurry was cooled to 0° C. Then DIAD (0.094 ml, 0.485 mmol) was slowly added. After 1 h, the reaction was warmed to room temperature and filtered. The volatiles were removed in vacuo and the resulting residue was purified by MPLC (ISCO 40 g, 0 to 40% EtOAc/Hex) to give the title compound. LC/MS: m/e 423.28 (M+H)+

Intermediate 67

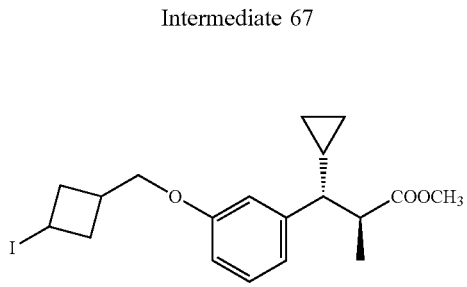

Methyl (2S,3R)-3-cyclopropyl-3-(3-((3-iodocyclobutyl)methoxy)phenyl)-2-methylpropanoate Intermediate 53 (790 mg, 2.481 mmol) was dissolved in toluene (10 ml) and imidazole (507 mg, 7.44 mmol). Then triphenylphosphine (1302 mg, 4.96 mmol) and iodine (945 mg, 3.72 mmol) were added at RT under a nitrogen atmosphere. The reaction was heated at 100° C. for 2 h, then diluted with EtOAc, and washed with saturated NaHCO$_3$. Iodine was added to the organic layer until the color was light yellow. Then the organic layer was washed with 5% Na$_2$S$_2$O$_3$, dried over anhydrous MgSO$_4$, filtered and evaporated. The resulting crude material was purified by silica gel chromatography (gradient elution, 0~20% EtOAc in hexanes) to give the title compound.

Intermediate 68

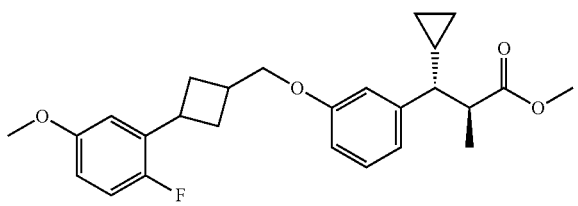

Methyl (2S,3R)-3-cyclopropyl-3-(3-((3-(2-fluoro-5-methoxyphenyl)cyclobutyl)methoxy)-phenyl)-2-methylpropanoate A solution of (2S,3R)-methyl 3-cyclopropyl-3-(3-((3-iodocyclobutyl)methoxy)phenyl)-2-methylpropanoate (250 mg, 0.584 mmol), (2-fluoro-5-methoxyphenyl)boronic acid (149 mg, 0.876 mmol) and 1,1'-bis(di-tert-butylphosphino)-ferrocene palladium dichloride (38.0 mg, 0.058 mmol) in DMF (4 ml) was treated with potassium phosphate tribasic (0.743 ml, 1.751 mmol, 50% water). The mixture was degassed, purged with nitrogen for 5 min, then heated at 90° C. for 3 h. The mixture was then cooled to room temperature, quenched with water and extracted with EtOAc (2×). The combined EtOAc layers were washed with water and brine, dried over anhydrous MgSO$_4$, filtered and evaporated. The resulting crude material was purified by silica gel chromatography (gradient elution, 0~15% EtOAc in hexanes) to afford the title compound.

Intermediate 69

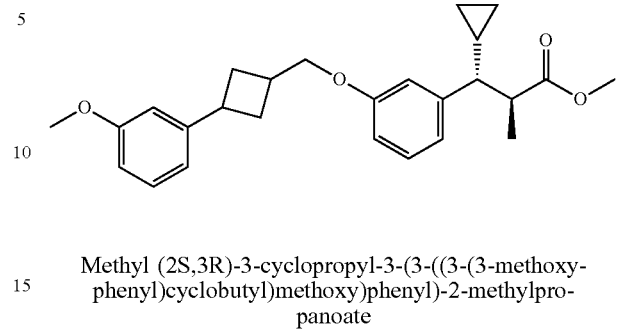

Methyl (2S,3R)-3-cyclopropyl-3-(3-((3-(3-methoxyphenyl)cyclobutyl)methoxy)phenyl)-2-methylpropanoate Intermediate 69 was prepared in an analogous manner to Intermediate 68, starting with 3-methoxyphenylboronic acid and Intermediate 67.

Intermediate 70

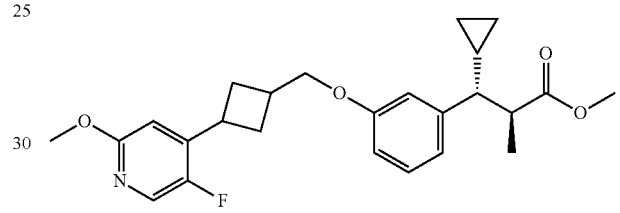

Methyl (2S,3R)-3-cyclopropyl-3-(3-((3-(5-fluoro-2-methoxypyridin-4-yl)cyclobutyl)-methoxy)phenyl)-2-methylpropanoate (2S,3R)-Methyl 3-cyclopropyl-3-(3-((3-iodocyclobutyl)methoxy)phenyl)-2-methylpropanoate (360 mg, 0.841 mmol), 5-fluoro-2-methoxypyridine-4-boronic acid (180 mg, 1.051 mmol) and 2nd generation S-Phos precatalyst (30.3 mg, 0.042 mmol) were dissolved in THF (6 mL) and potassium phosphate tribasic (1.070 ml, 2.52 mmol, 50% water solution) was added. The mixture was degassed, purged with nitrogen for 5 min, then heated at 75° C. for 2 h. Then the mixture was quenched with water, and extracted with EtOAc (2×). The combined EtOAc layers were washed with brine, dried over anhydrous MgSO$_4$, filtered and evaporated. The resulting crude material was purified by silica gel chromatography (40 g ISCO RediSep Rf Gold column, gradient elution 0~30% EtOAc in hexanes) to afford the title compound.

Intermediate 71

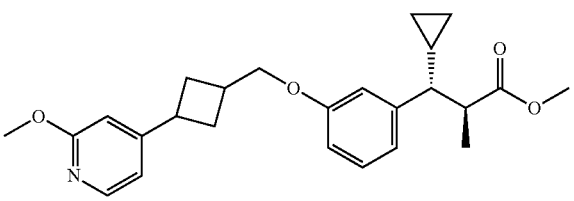

methyl (2S,3R)-3-cyclopropyl-3-(3-((3-(2-methoxy-pyridin-4-yl)cyclobutyl)methoxy)phenyl)-2-methyl-propanoate A solution of Intermediate 67 (342 mg, 0.80 mmol), 4-bromo-2-methoxypyridine (100 mg, 0.53 mmol), manganese (175 mg, 3.2 mmol), 4,4',4"-tri-tert-butyl-2,2':6',2"-terpyridine (85 mg, 0.21 mmol), pyridine (0.21 mL, 2.7 mmol) and nickel (II) chloride dimethoxyethane adduct (23 mg, 0.11 mmol) in N,N-dimethylacetamide (2 mL) was purged with nitrogen for 5 min., then sealed and microwaved at 100° C. for 1 h. The reaction mixture was quenched with water, and extracted with EtOAc (2×). The combined EtOAc layers were washed with brine, dried over anhydrous MgSO$_4$, filtered and evaporated. The resulting crude material was purified by silica gel flash chromatography (24 g ISCO RediSep R$^f$ Gold column, gradient elution, 0~20% EtOAc in hexanes) to afford the title compound.

Example 1

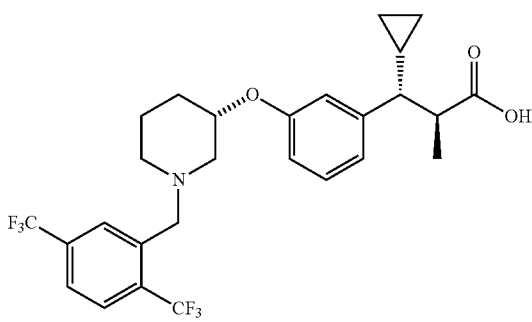 [SMILES: C[C@H](C(=O)O)[C@H](c1cccc(O[C@H]2CCCN(Cc3cc(C(F)(F)F)ccc3C(F)(F)F)C2)c1)C1CC1]

(2S,3R)-3-(3-(((S)-1-(2,5-bis(trifluoromethyl)ben-zyl)piperidin-3-yl)oxy)phenyl)-3-cyclopropyl-2-methylpropanoic acid Step A: To a solution of Intermediate 2 (59 mg, 0.252 mmol) in DMF (2 mL) at rt was added Cs$_2$CO$_3$ (164 mg, 0.504 mmol), and the reaction was stirred at rt for 10 minutes. Intermediate 16 (102 mg, 0.25 mmol) was added and the reaction mixture was stirred at 50° C. for 48 h. Then the solution was diluted with H$_2$O, extracted with EtOAc (3×15 mL), washed with brine solution, dried over MgSO$_4$, filtered, concentrated and purified by MPLC (ISCO 24 g, 0-15% EtOAc/hexanes) to give (2S,3R)-methyl 3-(3-(((R)-1-(2,5-bis(trifluoromethyl)benzyl) piperidin-3-yl)oxy)phenyl)-3-cyclopropyl-2-methylpropanoate as a colorless oil.

Step B: To (2S,3R)-methyl 3-(3-(((R)-1-(2,5-bis(trifluoromethyl)benzyl)piperidin-3-yl)oxy)phenyl)-3-cyclopropyl-2-methylpropanoate (98 mg, 0.180 mmol) in THF (1.5 mL)/MeOH (1.5 mL)/Water (1 mL) at rt was added LiOH (30 mg, 0.7 mmol). The resulting mixture was stirred at 60° C. for 12 h, then diluted with H$_2$O and acidified with 1N HCl to pH 4-5. The solution was extracted with EtOAc (3×50 mL). The combined EtOAc layers were washed with brine, dried over MgSO$_4$, filtered, concentrated and purified by MPLC (ISCO 4 g, 0-100% EtOAc/hexanes)) to give the title compound as a white foam. $^1$H NMR (500 MHz, CD$_3$OD): δ 8.32 (d, J=10.4 Hz, 1H); 7.91 (d, J=10.6 Hz, 1H); 7.89 (m, 1H); 7.22 (s, 1H); 6.80 (m, 1H); 6.75 (s, 1H); 6.68 (s, 1H); 4.49 (d, J=14.3 Hz, 1H); 3.84-4.02 (m, 2H); 2.99-3.20 (m, 2H); 2.78 (br s, 1H); 1.10-2.50 (m, 8H); 0.91 (s, 3H); 0.64 (s, 1H); 0.38 (s, 1H); 0.32 (br s, 1H); 0.01 (br s, 1H). LC/MS: m/e 530.41 (M+H)$^+$.

Example 2

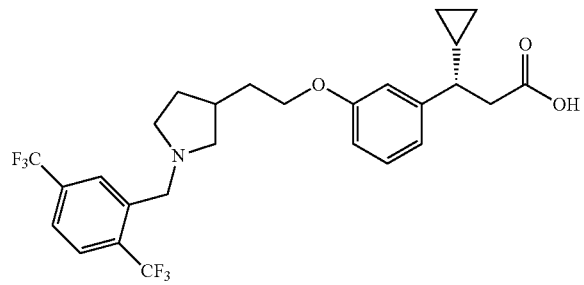 [SMILES: O=C(O)C[C@H](c1cccc(OCCC2CCN(Cc3cc(C(F)(F)F)ccc3C(F)(F)F)C2)c1)C1CC1]

(3S)-3-(3-(2-(1-(2,5-Bis(trifluoromethyl)benzyl) pyrrolidin-3-yl)ethoxy)phenyl)-3-cyclopropylpropanoic acid Step A: To Intermediate 20 (60 mg, 0.1 mmol) in DMF (1 mL) at rt was added 2,5-bis(trifluoromethyl)benzyl bromide (38 mg, 0.1 mmol) and K$_2$CO$_3$ (68 mg, 0.5 mmol). The resulting mixture was stirred at rt for 12 h, then diluted with H$_2$O (15 mL), and extracted with EtOAc (3×15 mL). The combined organic layers were washed with brine, dried over MgSO$_4$, filtered, concentrated and purified by MPLC (ISCO 24 g, 0-15% EtOAc/hexanes) to give (3S)-methyl 3-(3-(2-(1-(2,5-bis(trifluoromethyl)benzyl)-pyrrolidin-3-yl)ethoxy) phenyl)-3-cyclopropylpropanoate as a colorless oil.

Step B: To (3S)-methyl 3-(3-(2-(1-(2,5-bis(trifluoromethyl)benzyl)-pyrrolidin-3-yl)ethoxy)phenyl)-3-cyclopropylpropanoate (40 mg, 0.07 mmol) in THF (1.5 mL)/MeOH (1.5 mL)/water (1 mL) at rt was added LiOH (12 mg, 0.3 mmol). The resulting mixture was stirred at 60° C. for 12 h, then diluted with H$_2$O and acidified with 1N HCl to pH 4-5. The solution was extracted with EtOAc (3×10 mL). The combined EtOAc layers were washed with brine, dried over MgSO$_4$, filtered, concentrated and purified by MPLC (ISCO 4 g, 0-100% EtOAc/hexanes) to give the title compound as a colorless oil. 1H NMR (500 MHz, CD$_3$OD): δ 8.06 (s, 1H); 7.80 (d, J=8.3 Hz, 1H); 7.67 (d, J=8.2 Hz, 1H); 7.06 (t, J=7.9 Hz, 1H); 6.67-6.72 (m, 2H); 6.61 (d, J=8.2 Hz, 1H); 3.89 (m, 4H); 2.87 (s, 1H); 2.70 (t, J=8.2 Hz, 1H); 2.57-2.60 (m, 2H); 2.54 (t, J=10.1 Hz, 1H); 2.35 (m, 2H); 2.19 (t, J=8.5 Hz, 1H); 2.03 (br s, 1H); 1.78 (d, J=7.1 Hz, 2H); 1.51 (d, J=10.1 Hz, 1H); 0.92 (s, 1H); 0.46 (s, 1H); 0.27 (s, 1H); 0.18 (s, 1H); 0.02 (s, 1H). LC/MS: m/e 530.44 (M+H)$^+$.

Example 3

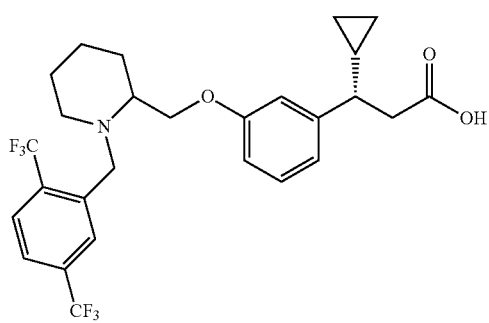 [SMILES: O=C(O)C[C@H](c1cccc(OCC2CCCCN2Cc2cc(C(F)(F)F)ccc2C(F)(F)F)c1)C1CC1]

(3S)-3-(3-((1-(2,5-Bis(trifluoromethyl)benzyl)piperidin-2-yl)methoxy)phenyl)-3-cyclopropylpropanoic acid The compound of Example 3 was prepared according to the procedure of Example 1 using Intermediate 37. $^1$H NMR (500 MHz, CD$_3$OD): δ 8.26 (s, 1H); 7.56-7.73 (m, 2H); 7.00 (m, 1H); 6.41-7.6.75 (m, 3H); 4.22-4.37 (m, 1H); 3.62-4.00 (m, 3H); 2.50-2.85 (m, 5H); 1.20-2.20 (m, 8H); 0.88 (m, 1H); 0.46 (br s, 1H); 0.25 (m, 1H); 0.17 (br s, 1H). LC/MS: m/e 530.40 (M+H)$^+$.

Example 4

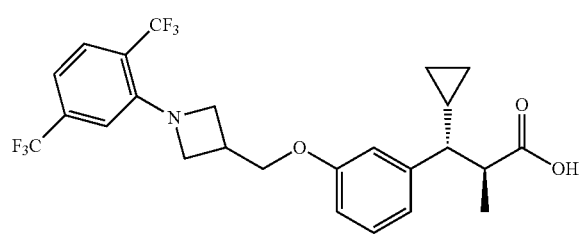 [SMILES: C[C@H](C(=O)O)[C@H](c1cccc(OCC2CN(c3cc(C(F)(F)F)ccc3C(F)(F)F)C2)c1)C1CC1]

(2S,3R)-3-(3-((1-(2,5-Bis(trifluoromethyl)phenyl)azetidin-3-yl)methoxy)phenyl)-3-cyclopropyl-2-methylpropanoic acid Step A: A vial was charged with 2,5-bis(trifluoromethyl)bromobenzene (64 mg, 0.22 mmol), Intermediate 29 (72 mg, 0.1 mmol), Pd$_2$dba$_3$ (6 mg, 7 μmol), X-Phos (14 mg, 0.03 mmol) and K$_3$PO$_4$ (124 mg, 0.6 mmol). The reaction mixture was purged with N$_2$, then 1,4-dioxane (2 mL) was added and the resulting mixture was heated to 100° C. for 12 h. Then the reaction was cooled to rt and filtered through a pad of Celite™, concentrated to dryness and purified by MPLC (ISCO 24 g, 0-15% EtOAc/hexanes) to give (2S,3R)-methyl 3-(3-((1-(2,5-bis(trifluoromethyl)phenyl)azetidin-3-yl)methoxy)phenyl)-3-cyclopropyl-2-methylpropanoate.

Step B: To (2S,3R)-methyl 3-(3-((1-(2,5-bis(trifluoromethyl)phenyl)azetidin-3-yl)methoxy)phenyl)-3-cyclopropyl-2-methylpropanoate (40 mg, 0.08 mmol) in THF (1.5 mL)/MeOH (1.5 mL)/water (1 mL) at rt was added LiOH (13 mg, 0.3 mmol). The resulting mixture was stirred at 60° C. for 12 h, then diluted with H$_2$O and acidified with 1N HCl to pH 4-5. The solution was extracted with EtOAc (3×10 mL). The combined EtOAc layers were washed with brine, dried over MgSO$_4$, filtered, concentrated and purified by MPLC (ISCO 4 g, 0-100% EtOAc/hexanes) to give the title compound as a yellow oil.

$^1$H NMR (500 MHz, CD$_3$OD): δ 7.68 (d, J=8.3 Hz, 1H); 7.23 (s, 1H); 7.02 (s, 1H); 6.84 (s, 1H); 6.80 (s, 3H); 4.28 (d, J=8.4 Hz, 2H); 4.22 (d, J=6.2 Hz, 2H); 4.02 (s, 2H); 3.17 (s, 1H); 2.79 (s, 1H); 1.95 (t, J=10.0 Hz, 1H); 1.30 (s, 1H); 0.92 (d, J=6.7 Hz, 3H); 0.60 (s, 1H); 0.34 (br s, 2H); 0.01 (s, 1H). LC/MS: m/e 502.35 (M+H)$^+$.

Example 5A and 5B

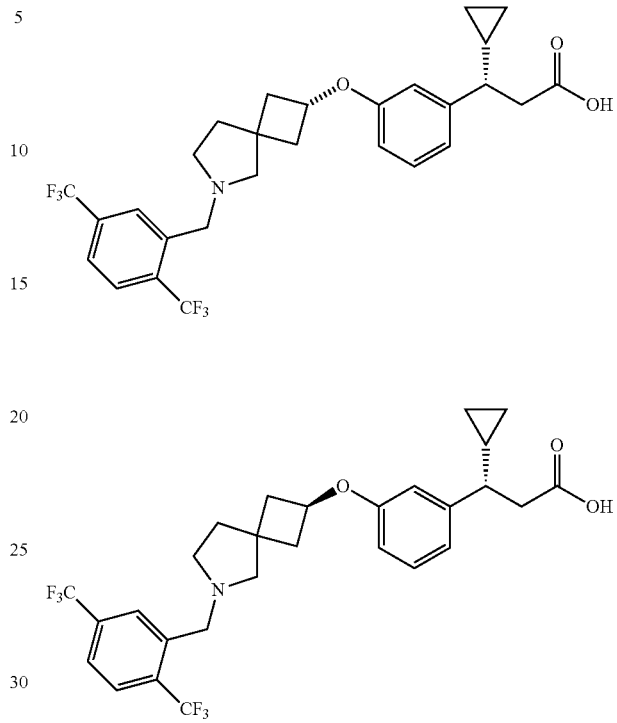

(3S)-3-(3-((6-(2,5-Bis(trifluoromethyl)benzyl)-6-azaspiro[3.4]octan-2-yl)oxy)phenyl)-3-cyclopropylpropanoic acid and (S)-3-(3-((6-(2,5-bis(trifluoromethyl)benzyl)-6-azaspiro[3.4]octan-2-yl)oxy)phenyl)-3-cyclopropylpropanoic acid The compounds of Examples 5A and 5B were prepared according to the procedure of Example 2 using Intermediates 21A and 21B.

Example 5A $^1$H NMR (500 MHz, CD$_3$OD): δ 8.07 (s, 1H); 7.78 (d, J=8.2 Hz, 1H); 7.64 (d, J=8.1 Hz, 1H); 7.02 (t, J=7.9 Hz, 1H); 6.68 (d, J=7.5 Hz, 1H); 6.57 (s, 1H); 6.51 (d, J=8.1 Hz, 1H); 4.64 (m, 1H); 3.81 (s, 2H); 2.43-2.62 (m, 8H); 2.16 (d, J=9.0 Hz, 1H); 2.02 (s, 2H); 1.88 (d, J=7.0 Hz, 2H); 0.90 (s, 1H); 0.45 (s, 1H); 0.26 (s, 1H); 0.16 (s, 1H); 0.01 (s, 1H). LC/MS: m/e 542.73 (M+H)$^+$.

Example 5B $^1$H NMR (500 MHz, CD$_3$OD): δ 8.02 (s, 1H); 7.76 (d, J=8.2 Hz, 1H); 7.63 (d, J=8.0 Hz, 1H); 7.03 (t, J=7.8 Hz, 1H); 6.69 (d, J=7.5 Hz, 1H); 6.58 (s, 1H); 6.52 (d, J=8.0 Hz, 1H); 4.56 (m, 1H); 3.78 (s, 2H); 2.40-2.62 (m, 8H); 2.17 (d, J=9.2 Hz, 1H); 2.03 (s, 2H); 1.94 (s, 2H); 0.90 (s, 1H); 0.45 (s, 1H); 0.26 (s, 1H); 0.16 (s, 1H); 0.00 (s, 1H). LC/MS: m/e 542.61 (M+H)$^+$.

Example 6

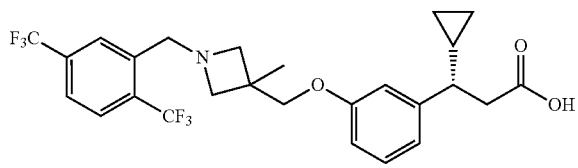 [SMILES: CC1(COc2cccc([C@@H](CC(=O)O)C3CC3)c2)CN(Cc2cc(C(F)(F)F)ccc2C(F)(F)F)C1]

(S)-3-(3-((1-(2,5-Bis(trifluoromethyl)benzyl)-3-methylazetidin-3-yl)methoxy)phenyl)-3-cyclopropylpropanoic acid The compound of Example 6 was prepared according to the procedure of Example 2 using Intermediate 30. $^1$H NMR (500 MHz, CD$_3$OD): δ 7.87 (s, 1H); 7.77 (d, J=8.2 Hz, 1H); 7.63 (d, J=8.1 Hz, 1H); 7.05 (d, J=8.3 Hz, 1H); 6.65-6.72 (m, 3H); 3.90 (s, 2H); 3.82 (s, 2H); 3.38 (m, 2H); 3.10 (m, 2H); 2.51-2.59 (m, 2H); 2.17 (d, J=9.0 Hz, 1H); 1.10 (s, 3H); 0.91 (s, 1H); 0.44 (s, 1H); 0.25 (s, 1H); 0.16 (s, 1H); 0.00 (s, 1H). LC/MS: m/e 516.65 (M+H)$^+$.

Example 7

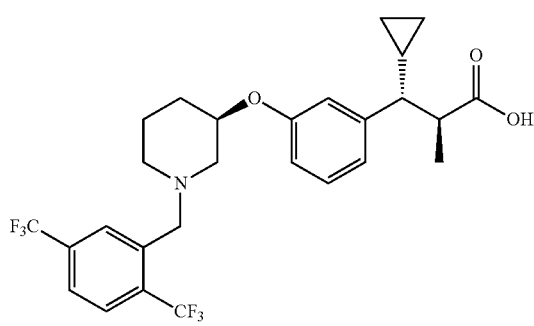

(2S,3R)-3-(3-(((R)-1-(2,5-bis(trifluoromethyl)benzyl)piperidin-3-yl)oxy)phenyl)-3-cyclopropyl-2-methylpropanoic acid Step A: To a solution of Intermediate 2 (53 mg, 0.3 mmol) in DMF (2 mL) at rt was added Cs$_2$CO$_3$ (147 mg, 0.45 mmol), followed by the addition of Intermediate 15 (92 mg, 0.226 mmol).

The resulting mixture was stirred at 50° C. for 48 hours, then diluted with H$_2$O (10 mL), and extracted with EtOAc (3×20 mL). The combined organic layers were washed with brine, dried over MgSO$_4$, filtered, concentrated and purified by MPLC (ISCO 24 g, 0-15% EtOAc/hexanes) to give (2S,3R)-methyl 3-(3-(((R)-1-(2,5-bis(tri-fluoromethyl)benzyl)piperidin-3-yl)oxy)phenyl)-3-cyclopropyl-2-methylpropanoate as a colorless oil.

Step B: To (2S,3R)-methyl 3-(3-(((R)-1-(2,5-bis(tri-fluoromethyl)benzyl)piperidin-3-yl)oxy)phenyl)-3-cyclopropyl-2-methylpropanoate (98 mg, 0.2 mmol) in THF (1.5 mL)/MeOH (1.5 mL)/water (1 mL) at rt was added LiOH (30 mg, 0.7 mmol). The resulting mixture was stirred at 60° C. for 12 h, then diluted with H$_2$O and acidified with 1N HCl to pH 4-5. The solution was extracted with EtOAc (3×10 mL). The combined EtOAc layers were washed with brine, dried over MgSO$_4$, filtered, concentrated and purified by MPLC (ISCO 4 g, 0-100% EtOAc/hexanes) to give the title compound as a white foam.

$^1$H NMR (500 MHz, CD$_3$OD): δ 8.32 (d, J=10.4 Hz, 1H); 7.91 (d, J=10.6 Hz, 1H); 7.79 (m, 1H); 7.22 (s, 1H); 6.80 (s, 1H); 6.75 (s, 1H); 6.68 (s, 1H); 4.49 (d, J=14.3 Hz, 1H); 3.82-4.02 (m, 2H); 2.97-3.21 (m, 2H); 2.78 (br s, 2H); 1.65-2.56 (m, 5H); 1.10-1.40 (m, 2H); 0.91 (s, 3H); 0.64 (s, 1H); 0.38 (m, 2H); 0.00 (br s, 1H). LC/MS: m/e 530.41(M+H)$^+$.

Example 8

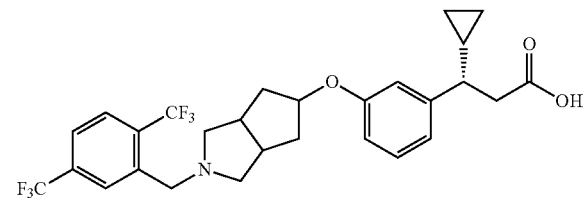 [SMILES: O=C(O)C[C@H](c1cccc(OC2CC3CN(Cc4cc(C(F)(F)F)ccc4C(F)(F)F)CC3C2)c1)C1CC1]

(3S)-3-(3-((2-(2,5-bis(trifluoromethyl)benzyl)octahydrocyclopenta[c]pyrrol-5-yl)oxy)phenyl)-3-cyclopropylpropanoic acid The compound of Example 8 was prepared according to the procedure of Example 2 using Intermediate 22. $^1$H NMR (500 MHz, CD$_3$OD): δ 8.08 (s, 1H); 7.79 (d, J=8.3 Hz, 1H); 7.65 (d, J=8.2 Hz, 1H); 7.07 (t, J=7.9 Hz, 1H); 6.63-6.72 (m, 3H); 4.84 (m, 1H); 3.75 (s, 2H); 2.57-2.71 (m, 5H); 2.33 (s, 2H); 2.20 (d, J=8.7 Hz, 1H); 2.04 (br s, 2H); 1.66 (d, J=12.7 Hz, 2H); 1.19 (s, 1H); 0.93 (s, 1H); 0.48 (s, 1H); 0.30 (s, 1H); 0.19 (s, 1H); 0.04 (s, 1H). LC/MS: m/e 542.45(M+H)$^+$.

Example 9

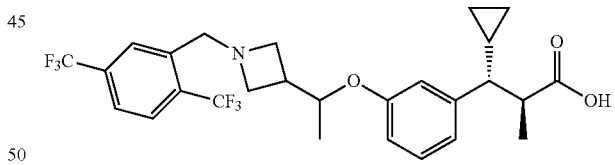

(2S,3R)-3-(3-(1-(1-(2,5-Bis(trifluoromethyl)benzyl)azetidin-3-yl)ethoxy)phenyl)-3-cyclopropyl-2-methylpropanoic acid The compound of Example 9 was prepared according to the procedure of Example 2 using Intermediate 38. $^1$H NMR (500 MHz, CD$_3$OD): δ 8.03 (s, 1H); 7.95 (d, J=8.2 Hz, 1H); 7.82 (d, J=8.3 Hz, 1H); 7.26 (t, J=7.9 Hz, 1H); 6.88 (m, 3H); 4.64 (t, J=6.3 Hz, 1H); 4.02 (s, 2H); 3.63 (t, J=7.8 Hz, 2H); 3.35-3.36 (m, 2H); 2.87-2.91 (m, 1H); 2.81 (ddd, J=9.9, 6.9, 3.8 Hz, 1H); 1.99 (t, J=9.9 Hz, 1H); 1.26 (d, J=6.1 Hz, 3H); 1.17 (m, 1H); 0.94 (d, J=6.6 Hz, 1H), 0.68 (m 1H); 0.60-0.65 (m, 1H); 0.32-0.40 (m, 2H); 0.00 (m, 1H). LC/MS: m/e 530.43(M+H)$^+$.

Example 10

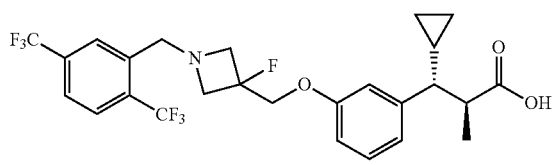 [SMILES: C[C@H](C(=O)O)[C@H](c1cccc(OCC2(F)CN(Cc3cc(C(F)(F)F)ccc3C(F)(F)F)C2)c1)C1CC1]

(2S,3R)-3-(3-((1-(2,5-Bis(trifluoromethyl)benzyl)-3-fluoroazetidin-3-yl)methoxy)-phenyl)-3-cyclopropyl-2-methylpropanoic acid The compound of Example 10 was prepared according to the procedure of Example 2 using Intermediate 36. $^1$H NMR (500 MHz, CD$_3$OD): δ 8.07 (s, 1H); 7.93 (d, J=8.2 Hz, 1H); 7.79 (d, J=8.3 Hz, 1H); 7.27 (t, J=7.9 Hz, 1H); 6.84-6.89 (m, 3H); 4.37 (s, 1H); 4.33 (s, 1H); 4.06 (s, 2H); 3.75 (dd, J=13.4, 9.2 Hz, 2H); 3.48 (m, 2H); 2.82 (dd, J=9.8, 6.8 Hz, 1H); 1.98 (t, J=9.9 Hz, 1H); 1.13-1.17 (m, 1H); 0.95 (d, J=6.9 Hz, 3H); 0.61-0.65 (m, 1H); 0.33-0.39 (m, 2H); 0.00 (m, 1H). LC/MS: m/e 534.82(M+H)$^+$.

Example 11

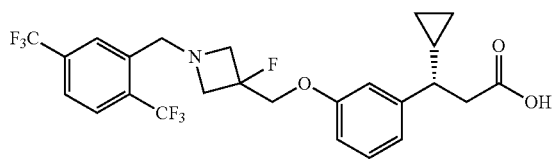 [SMILES: O=C(O)C[C@H](c1cccc(OCC2(F)CN(Cc3cc(C(F)(F)F)ccc3C(F)(F)F)C2)c1)C1CC1]

(S)-3-(3-((1-(2,5-Bis(trifluoromethyl)benzyl)-3-fluoroazetidin-3-yl)methoxy)phenyl)-3-cyclopropylpropanoic acid The above example was prepared in an analogous manner to example 2 using Intermediate 31. $^1$H NMR (500 MHz, CD$_3$OD): δ 7.89 (s, 1H); 7.76 (d, J=8.2 Hz, 1H); 7.62 (d, J=8.1 Hz, 1H); 7.07 (t, J=7.8 Hz, 1H); 6.73-6.75 (m, 2H); 6.68 (d, J=8.1 Hz, 1H); 4.18 (s, 1H); 4.14 (s, 1H); 3.88 (s, 2H); 3.57 (t, J=10.9 Hz, 2H); 3.32 (m, 2H); 2.52-2.63 (m, 2H); 2.17 (d, J=8.9 Hz, 1H); 0.91 (s, 1H); 0.44 (s, 1H); 0.25 (s, 1H); 0.15 (s, 1H); 0.00 (s, 1H). LC/MS: m/e 520.38(M+H)$^+$.

Example 12

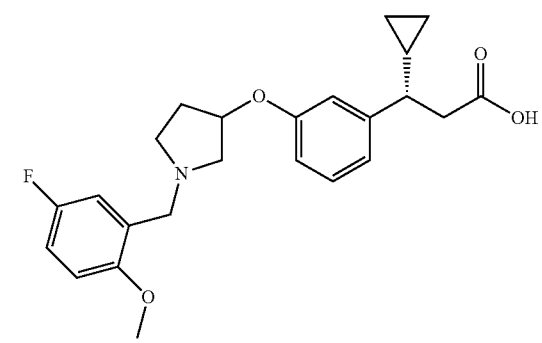 [SMILES: COc1ccc(F)cc1CN1CCC(Oc2cccc([C@@H](CC(=O)O)C3CC3)c2)C1]

(3S)-3-Cyclopropyl-3-(3-((1-(5-fluoro-2-methoxybenzyl)pyrrolidin-3-yl)oxy)phenyl)propanoic acid The compound of Example 12 was prepared according to the procedure of Example 2 using 2-(bromomethyl)-4-fluoro-1-methoxybenzene and Intermediate 17. $^1$H NMR (400 MHz, CD$_3$OD): δ 7.11-7.19 (m, 3H); 7.04 (d, J=8.6 Hz, 1H); 6.90 (d, J=7.5 Hz, 1H); 6.80 (s, 1H); 6.71 (d, J=8.4 Hz, 1H); 5.06 (m, 1H); 4.20 (s, 2H); 3.83 (s, 3H); 3.28-3.50 (m, 2H); 2.61-2.68 (m, 3H); 2.20-2.40 (m, 2H); 1.28 (m, 1H); 1.05 (m, 1H); 0.88 (m, 1H); 0.56 (s, 1H); 0.35 (m, 2H); 0.11 (s, 1H). LC/MS: m/e 414.37(M+H)$^+$.

Example 13

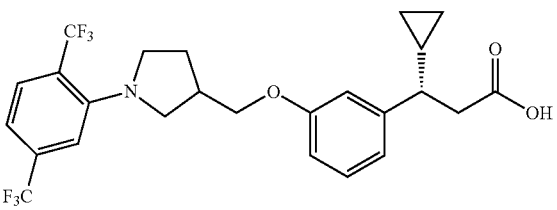 [SMILES: O=C(O)C[C@H](c1cccc(OCC2CCN(c3cc(C(F)(F)F)ccc3C(F)(F)F)C2)c1)C1CC1]

(3S)-3-(3-((1-(2,5-Bis(trifluoromethyl)phenyl)pyrrolidin-3-yl)methoxy)phenyl)-3-cyclopropylpropanoic acid The compound of Example 13 was prepared according to the procedure of Example 4 using 2,5-bis(trifluoromethyl)bromobenzene and Intermediate 18. $^1$H NMR (500 MHz, CD$_3$OD): δ 7.63 (d, J=8.3 Hz, 1H); 7.19 (s, 1H); 7.02-7.08 (m, 2H); 6.72 (d, J=6.9 Hz, 2H); 6.66 (d, J=8.3 Hz, 1H); 3.91 (t, J=8.7 Hz, 2H); 3.21-3.40 (m, 4H); 2.54-2.68 (m, 3H); 2.10-2.22 (m, 2H); 1.89 (m, 1H); 0.92 (s, 1H); 0.43-0.46 (m, 1H); 0.27 (d, J=7.8 Hz, 1H); 0.17 (dd, J=9.4, 5.0 Hz, 1H), 0.00 (m, 1H). LC/MS: m/e 502.34(M+H)$^+$.

Example 14

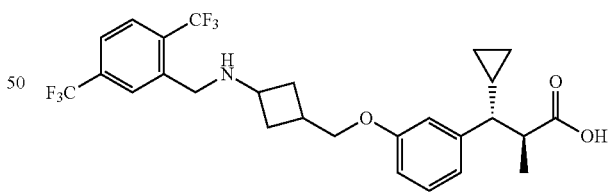

(2S,3R)-3-(3-((3-((2,5-Bis(trifluoromethyl)benzyl)amino)cyclobutyl)methoxy)phenyl)-3-cyclopropyl-2-methylpropanoic acid The compound of Example 14 was prepared according to the procedure of Example 2 using Intermediate 33. $^1$H NMR (500 MHz, CD$_3$OD): δ 8.16 (s, 1H); 7.98-8.00 (m, 1H); 7.86 (d, J=8.0 Hz, 1H); 7.24 (td, J=7.8, 5.1 Hz, 1H); 6.78-6.83 (m, 3H); 3.98-4.04 (m, 4H); 3.40 (m, 1H); 2.79-2.83 (m, 1H); 2.49 (t, J=7.6 Hz, 2H); 2.20-2.33 (m, 2H); 1.98 (m, 1H); 1.84

(m, 1H); 1.14 (m, 1H); 0.95 (dd, J=6.9, 3.4 Hz, 3H); 0.64 (s, 1H); 0.34-0.42 (m, 2H); 0.00 (m, 1H). LC/MS: m/e 530.79 (M+H)⁺.

Example 15

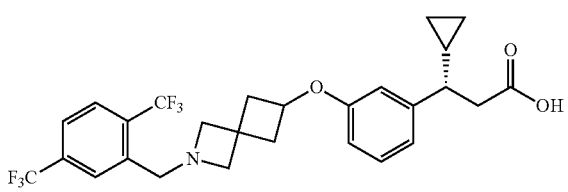 [SMILES: O=C(O)C[C@H](c1cccc(OC2CC3(C2)CN(Cc2cc(C(F)(F)F)ccc2C(F)(F)F)C3)c1)C1CC1]

(S)-3-(3-((2-(2,5-Bis(trifluoromethyl)benzyl)-2-azaspiro[3.3]heptan-6-yl)oxy)phenyl)-3-cyclopropylpropanoic acid The compound of Example 15 was prepared according to the procedure of Example 2 using Intermediate 32. ¹H NMR (500 MHz, CD₃OD): δ 7.86 (s, 1H); 7.78 (d, J=8.2 Hz, 1H); 7.65 (d, J=8.2 Hz, 1H); 7.03 (t, J=7.9 Hz, 1H); 6.69 (d, J=7.6 Hz, 1H); 6.57 (d, J=8.2 Hz, 1H); 6.51 (d, J=8.2 Hz, 1H); 4.48 (t, J=7.0 Hz, 1H); 3.82 (s, 2H); 3.40 (s, 2H); 3.32 (s, 2H); 2.54-2.64 (m, 4H); 2.15 (s, 3H); 0.90 (s, 1H); 0.44 (s, 1H); 0.26 (s, 1H); 0.16 (s, 1H), 0.00 (s, 1H). LC/MS: m/e 528.42(M+H)⁺.

Example 16

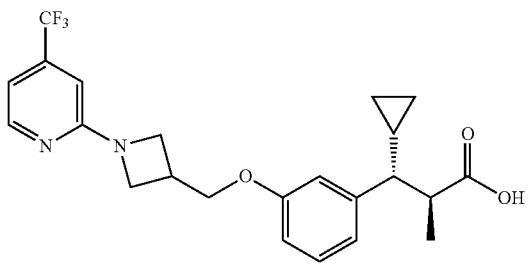 [SMILES: C[C@H](C(=O)O)[C@H](c1cccc(OCC2CN(c3cc(C(F)(F)F)ccn3)C2)c1)C1CC1]

(2S,3R)-3-Cyclopropyl-2-methyl-3-(3-((1-(4-(trifluoromethyl)pyridin-2-yl)azetidin-3-yl)methoxy)phenyl)propanoic acid Step A: To a solution of Intermediate 29 (88 mg, 0.2 mmol) in DMF (2 mL) at rt was added 2-chloro-4-trifluoromethylpyridine (36 mg, 0.2 mmol) and K₂CO₃ (109 mg, 0.8 mmol). The resulting mixture was stirred at rt for 12 h, then diluted with H₂O (10 mL) and extracted with EtOAc (3×20 mL). The combined organic layers were washed with brine, dried over MgSO₄, filtered and concentrated. The resulting oil was purified by MPLC (ISCO 12 g, 0-30% EtOAc/hexanes) to give a colorless oil.

Step B: To (2S,3R)-methyl 3-cyclopropyl-2-methyl-3-(3-((1-(4-(trifluoromethyl)pyridin-2-yl)azetidin-3-yl)methoxy)phenyl)propanoate (20 mg, 0.04 mmol) in THF (1.5 mL)/MeOH (1.5 mL)/Water (1 mL) at rt was added LiOH (7.5 mg, 0.2 mmol). The resulting mixture was stirred at 60° C. for 12 h, then diluted with H₂O and acidified with 1N HCl to pH 4-5. The solution was extracted with EtOAc (3×10 mL). The combined EtOAc layers were washed with brine, dried over MgSO₄, filtered, concentrated and purified by MPLC (ISCO 4 g, 0-100% EtOAc/hexanes) to give the title compound as a white solid.

¹H NMR (500 MHz, CD₃OD): δ 8.25 (d, J=5.4 Hz, 1H); 7.25 (t, J=7.9 Hz, 1H); 6.80-6.87 (m, 4H); 6.66 (s, 1H); 4.24-4.29 (m, 4H); 4.03 (dd, J=8.4, 5.3 Hz, 2H); 3.34-3.35 (m, 1H); 2.82 (dq, J=9.8, 6.9 Hz, 1H); 1.98 (m, 1H); 1.17 (m, 1H); 0.95 (d, J=6.9 Hz, 3H); 0.60-0.65 (m, 1H); 0.32-0.39 (m, 2H), 0.11 (m, 1H). LC/MS: m/e 435.35 (M+H)⁺.

Example 17

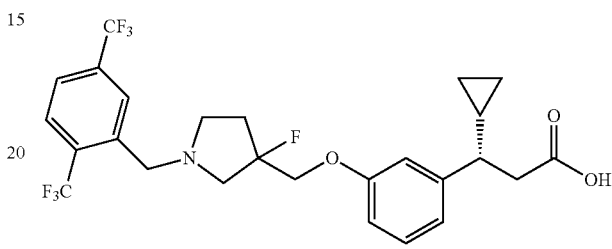

(3S)-3-(3-((1-(2,5-Bis(trifluoromethyl)benzyl)-3-fluoropyrrolidin-3-yl)methoxy)phenyl)-3-cyclopropylpropanoic acid The compound of Example 17 was prepared according to the procedure of Example 2 using Intermediate 23. ¹H NMR (500 MHz, CD₃OD): δ 8.09 (s, 1H); 7.80 (d, J=8.3 Hz, 1H); 7.66 (d, J=8.3 Hz, 1H); 7.10 (t, J=7.8 Hz, 1H); 6.76 (d, J=8.7 Hz, 2H); 6.69 (d, J=8.4 Hz, 1H); 4.01-4.09 (m, 2H); 3.85 (s, 2H); 2.83-2.90 (m, 3H); 2.56-2.68 (m, 3H); 2.12-2.24 (m, 3H); 0.93-0.96 (m, 1H); 0.46-0.50 (m, 1H); 0.26-0.31 (m, 1H); 0.20 (dt, J=9.4, 4.9 Hz, 1H); 0.02 (m, 1H). LC/MS: m/e 533.36 (M+H)⁺.

Example 18

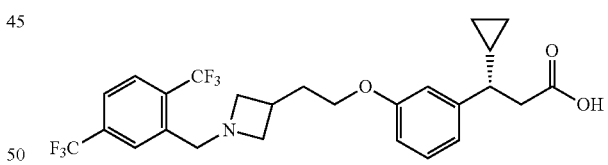

(S)-3-(3-(2-(1-(2,5-Bis(trifluoromethyl)benzyl)azetidin-3-yl)ethoxy)phenyl)-3-cyclopropylpropanoic acid The compound of Example 3 was prepared according to the procedure of Example 1 using Intermediate 34. ¹H NMR (500 MHz, CD₃OD): δ 7.89 (s, 1H); 7.80 (d, J=8.2 Hz, 1H); 7.67 (d, J=8.2 Hz, 1H); 7.04 (t, J=7.9 Hz, 1H); 6.71 (d, J=7.6 Hz, 1H); 6.66 (s, 1H); 6.59 (d, J=8.2 Hz, 1H); 3.90 (s, 2H); 3.86 (s, 2H); 3.59 (t, J=7.4 Hz, 2H); 3.10 (s, 2H); 2.69 (t, J=8.1 Hz, 1H); 2.60 (dd, J=14.7, 6.5 Hz, 1H); 2.52 (t, J=9.5 Hz, 1H); 2.18 (t, J=8.6 Hz, 1H); 1.89-1.94 (m, 2H); 0.91 (s, 1H); 0.45 (s, 1H); 0.25 (s, 1H); 0.17 (s, 1H); 0.00 (s, 1H). LC/MS: m/e 516.42 (M+H)⁺.

Example 19

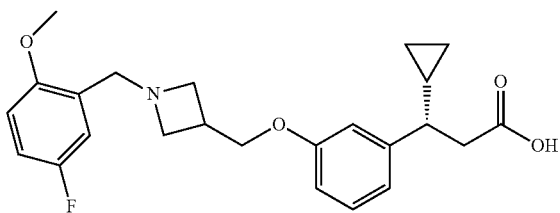 [SMILES: COc1ccc(F)cc1CN1CC(COc2cccc([C@@H](CC(=O)O)C3CC3)c2)C1]

(S)-3-Cyclopropyl-3-(3-((1-(5-fluoro-2-methoxybenzyl)azetidin-3-yl)methoxy)-phenyl)propanoic acid The compound of Example 19 was prepared according to the procedure of Example 2 using 2-(bromomethyl)-4-fluoro-1-methoxybenzene and Intermediate 28. $^1$H NMR (500 MHz, CD$_3$OD): δ 7.02-7.07 (m, 3H); 6.95 (dd, J=8.9, 4.2 Hz, 1H); 6.78-6.82 (m, 2H); 6.66 (d, J=8.2 Hz, 1H); 4.14 (s, 2H); 3.95 (m, 4H); 3.82 (m, 2H); 3.78 (s, 3H); 3.06 (s, 1H); 2.55-2.58 (m, 1H); 2.48 (t, J=10.8 Hz, 1H); 2.22-2.25 (m, 1H); 0.90 (s, 1H); 0.44 (m, 1H), 0.22 (m, 2H), 0.00 (m, 1H). LC/MS: m/e 414.42 (M+H)$^+$.

Example 20

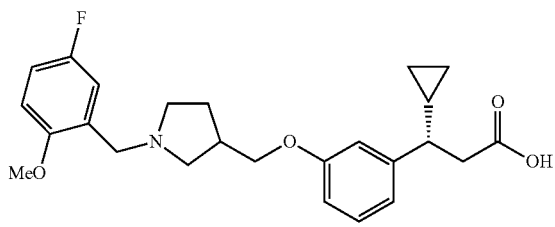 [SMILES: COc1ccc(F)cc1CN1CCC(COc2cccc([C@@H](CC(=O)O)C3CC3)c2)C1]

(3S)-3-Cyclopropyl-3-(3-((1-(5-fluoro-2-methoxybenzyl)pyrrolidin-3-yl)methoxy)phenyl)propanoic acid The compound of Example 20 was prepared according to the procedure of Example 2 using 2-(bromomethyl)-4-fluoro-1-methoxybenzene and Intermediate 18. $^1$H NMR (500 MHz, CD$_3$OD): δ 7.14 (d, J=8.6 Hz, 1H); 7.06 (t, J=8.1 Hz, 2H); 6.96 (dd, J=9.1, 4.3 Hz, 1H); 6.78 (d, J=7.6 Hz, 1H); 6.72 (s, 1H); 6.61 (d, J=8.2 Hz, 1H); 4.11 (s, 2H); 3.82 (m, 1H); 3.76 (s, 3H); 3.25 (m, 2H); 3.11 (s, 2H); 2.90 (m, 1H); 2.43-2.67 (m, 3H), 2.20 (m, 1H); 2.00 (m, 1H); 1.72 (m, 1H); 0.86-0.89 (m, 1H); 0.45 (d, J=7.5 Hz, 1H); 0.20-0.26 (m, 2H); 0.00 (m, 1H). LC/MS: m/e 428.31 (M+H)$^+$.

Example 21

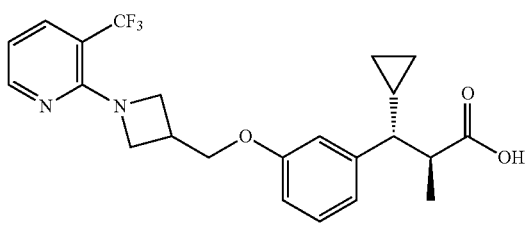 [SMILES: C[C@H](C(=O)O)[C@H](c1cccc(OCC2CN(c3ncccc3C(F)(F)F)C2)c1)C1CC1]

(2S,3R)-3-Cyclopropyl-2-methyl-3-(3-((1-(3-(trifluoromethyl)pyridin-2-yl)azetidin-3-yl)methoxy)phenyl)propanoic acid The compound of Example 21 was prepared according to the procedure of Example 16 using 2-chloro-3-trifluoromethyl pyridine and Intermediate 29. $^1$H NMR (500 MHz, CD$_3$OD): δ 8.30 (d, J=4.8 Hz, 1H); 7.87 (d, J=7.8 Hz, 1H); 7.25 (t, J=7.9 Hz, 1H); 6.85-6.92 (m, 3H); 6.78 (m, 1H); 4.38 (t, J=8.6 Hz, 2H); 4.22 (d, J=6.5 Hz, 2H); 4.11 (t, J=7.1 Hz, 2H); 3.18 (m, 1H); 2.82 (dq, J=9.8, 6.9 Hz, 1H); 1.98 (t, J=9.9 Hz, 1H); 1.15(m 1H); 0.95 (d, J=6.9 Hz, 3H); 0.62 (m, 1H); 0.36 (m, 2H); 0.02(m 1H). LC/MS: m/e 435.37 (M+H)$^+$.

Example 22

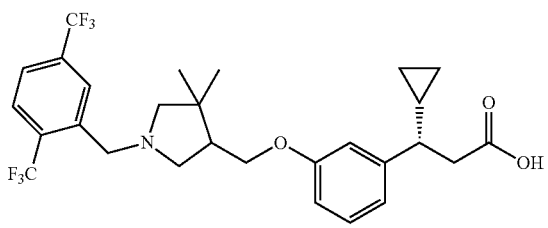 [SMILES: CC1(C)CN(Cc2cc(C(F)(F)F)ccc2C(F)(F)F)CC1COc1cccc([C@@H](CC(=O)O)C2CC2)c1]

(3S)-3-(3-((1-(2,5-Bis(trifluoromethyl)benzyl)-4,4-dimethylpyrrolidin-3-yl)methoxy)phenyl)-3-cyclopropylpropanoic acid The compound of Example 22 was prepared according to the procedure of Example 2 using Intermediate 24. $^1$H NMR (500 MHz, CD$_3$OD): δ 8.07 (s, 1H); 7.77 (d, J=8.2 Hz, 1H); 7.63 (d, J=8.3 Hz, 1H); 7.05 (m, 1H); 6.69-6.73 (m, 2H); 6.64 (d, J=8.3 Hz, 1H); 3.93 (t, J=8.0 Hz, 1H); 3.81 (d, J=10.2 Hz, 3H); 2.92 (m, 1H); 2.16-2.64 (m, 7H); 1.11 (s, 3H); 1.01 (s, 3H), 0.92 (m, 1H); 0.46 (m, 1H), 0.28 (m, 1H), 0.18 (m, 1H); 0.00 (m, 1H). LC/MS: m/e 544.41 (M+H)$^+$.

Example 23

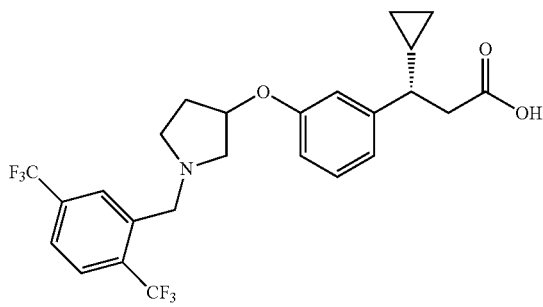 [SMILES: O=C(O)C[C@H](c1cccc(OC2CCN(Cc3cc(C(F)(F)F)ccc3C(F)(F)F)C2)c1)C1CC1]

(3S)-3-(3-((1-(2,5-Bis(trifluoromethyl)benzyl)pyrrolidin-3-yl)oxy)phenyl)-3-cyclopropylpropanoic acid The compound of Example 23 was prepared according to the procedure of Example 2 using Intermediate 17. $^1$H NMR (500 MHz, CDCl$_3$): δ 8.18 (s, 1H); 7.78(d, J=8.0 Hz, 1H); 7.64(d, J=8.0 Hz, 1H); 7.22(t, J=8.0 Hz, 1H); 6.85(d, J=7.5

Hz, 1H); 6.79 (s, 1H); 6.69(d, J=8.5 Hz, 1H); 4.86 (s, 1H); 3.96 (s, 2H); 3.16 (m, 1H); 2.72-2.85 (m, 5H); 2.09-2.40 (m, 2H); 2.06 (m, 1H); 1.04 (m, 1H); 0.60 (m, 1H); 0.45 (m, 1H); 0.32 (m, 1H); 0.19 (m, 1H). LC/MS: m/e 502.68 (M+H)+.

Example 24

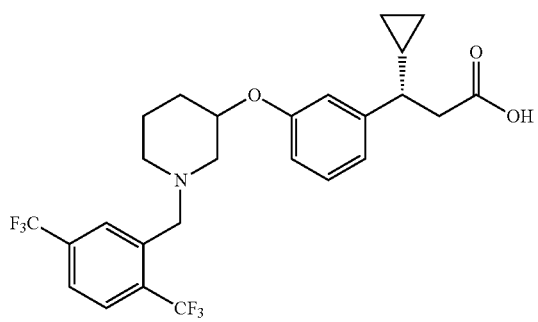 [SMILES: O=C(O)C[C@H](c1cccc(OC2CCCN(Cc3cc(C(F)(F)F)ccc3C(F)(F)F)C2)c1)C1CC1]

(3S)-3-(3-((1-(2,5-Bis(trifluoromethyl)benzyl)piperidin-3-yl)oxy)phenyl)-3-cyclopropylpropanoic acid The compound of Example 24 was prepared according to the procedure of Example 2 using Intermediate 12. ¹H NMR (500 MHz, CD₃OD): δ 8.22 (s, 1H); 7.82 (d, J=8.2 Hz, 1H); 7.68 (d, J=8.0 Hz, 1H); 7.09 (t, J=7.9 Hz, 1H); 6.67-6.75 (m, 3H); 4.37 (s, 1H); 3.73 (s, 2H); 2.89 (s, 1H); 2.60 (m, 3H); 2.26 (m, 3H); 2.00 (m, 1H); 1.82 (br s, 1H); 1.53-1.64 (m, 2H); 0.90 (m, 1H); 0.50 (s, 1H); 0.29 (s, 1H); 0.22 (s, 1H); 0.02 (m, 1H).
LC/MS: m/e 516.40 (M+H)+.

Example 25

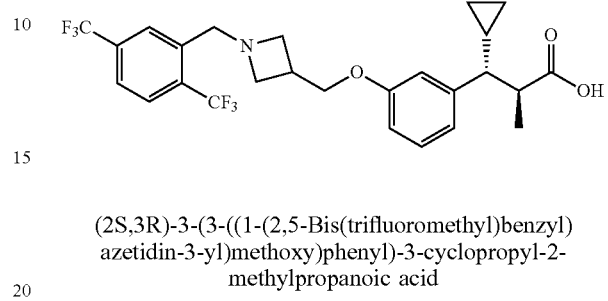

(2S,3R)-3-(3-((1-(2,5-Bis(trifluoromethyl)benzyl)azetidin-3-yl)methoxy)phenyl)-3-cyclopropyl-2-methylpropanoic acid The compound of Example 25 was prepared according to the procedure of Example 2 using Intermediate 29. ¹H NMR (500 MHz, CD₃OD): 8.04 (s, 1H); 7.94 (d, J=8.3 Hz, 1H); 7.80 (d, J=8.2 Hz, 1H); 7.23 (t, J=7.9 Hz, 1H); 6.81 (s, 3H); 4.14 (d, J=6.3 Hz, 2H); 4.04 (s, 2H); 3.66 (t, J=7.8 Hz, 2H); 3.38 (m, 2H); 3.06 (m, 1H); 2.79 (m, 1H); 1.97 (t, J=10.0 Hz, 1H); 1.13 (s, 1H); 0.93 (d, J=6.9 Hz, 3H); 0.60 (s, 1H), 0.33 (m, 2H); 0.00 (s, 1H). LC/MS: m/e 516.43 (M+H)+.

The compounds in Table 1 were prepared according to the procedure of Example 2 and the appropriate starting materials.

TABLE 1

| Example | | LCMS: found m/e (M + H) |
|---|---|---|
| 26 | ![structure] | 530.48 |
| 27 | ![structure] | 530.61 |

TABLE 1-continued
| Example | | LCMS: found m/e (M + H) |
|---|---|---|
| 28 | 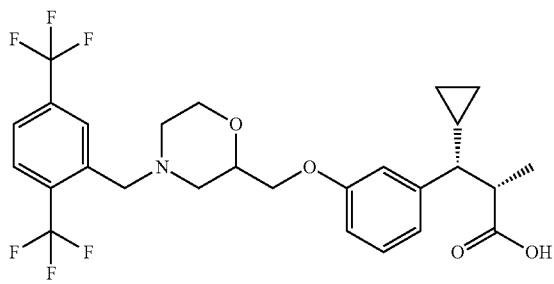 [SMILES: C[C@H](C(=O)O)[C@H](c1cccc(OCC2CN(Cc3cc(C(F)(F)F)ccc3C(F)(F)F)CCO2)c1)C1CC1] | 546.77 |
| 29 | 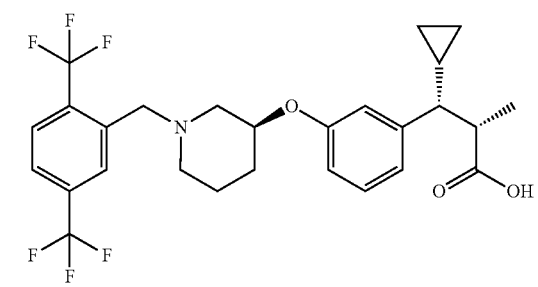 [SMILES: C[C@H](C(=O)O)[C@H](c1cccc(O[C@H]2CCCN(Cc3cc(C(F)(F)F)ccc3C(F)(F)F)C2)c1)C1CC1] | 530.41 |
| 30 | 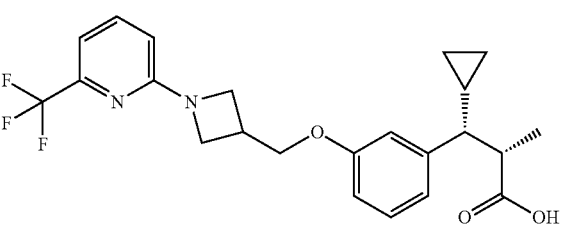 [SMILES: C[C@H](C(=O)O)[C@H](c1cccc(OCC2CN(c3cccc(C(F)(F)F)n3)C2)c1)C1CC1] | 435.28 |
| 31 | 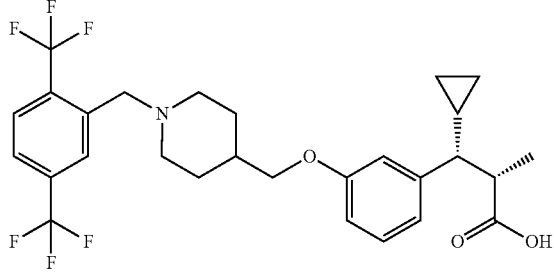 [SMILES: C[C@H](C(=O)O)[C@H](c1cccc(OCC2CCN(Cc3cc(C(F)(F)F)ccc3C(F)(F)F)CC2)c1)C1CC1] | 544.45 |
| 32 | 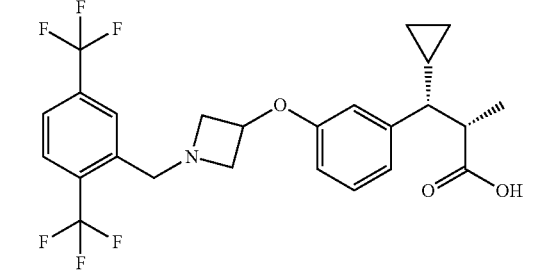 [SMILES: C[C@H](C(=O)O)[C@H](c1cccc(OC2CN(Cc3cc(C(F)(F)F)ccc3C(F)(F)F)C2)c1)C1CC1] | 502.33 |

TABLE 1-continued

| Example | | LCMS: found m/e (M + H) |
|---|---|---|
| 33 | | 530.43 |
| 34 | | 530.35 |
| 35 | | 558.78 |
| 36 | | 544.60 |
| 37 | | 463.53 |

TABLE 1-continued

| Example | | LCMS: found m/e (M + H) |
|---|---|---|
| 38 | | 463.51 |
| 39 | | 463.50 |
| 40 | | 544.56 |
| 41 | | 544.54 |
| 42 | | 468.11 |

TABLE 1-continued

| Example | | LCMS: found m/e (M + H) |
|---|---|---|
| 43 | [structure] | 530.44 |
| 44 | [structure] | 544.45 |
| 45 | [structure] | 434.20 |
| 46 | [structure] | 544.46 |
| 47 | [structure] | 516.34 |

TABLE 1-continued

| Example | | LCMS: found m/e (M + H) |
|---|---|---|
| 48 | [structure: 2,5-bis(trifluoromethyl)benzyl-piperidin-4-yloxy-phenyl cyclopropyl propanoic acid] | 516.40 |
| 49 | [structure: 2,5-bis(trifluoromethyl)benzyl-azetidin-3-ylmethoxy-phenyl cyclopropyl propanoic acid] | 502.54 |
| 50 | [structure: 2-(trifluoromethoxy)benzyl-azetidin-3-ylmethoxy-phenyl cyclopropyl propanoic acid] | 450.30 |
| 51 | [structure: 1-(2-chloro-5-fluorophenyl)ethyl-azetidin-3-ylmethoxy-phenyl cyclopropyl propanoic acid] | 432.3 |
| 52 | [structure: 1-(2-chlorophenyl)ethyl-azetidin-3-ylmethoxy-phenyl cyclopropyl propanoic acid] | 414.3 |

TABLE 1-continued

| Example | LCMS: found m/e (M + H) |
|---|---|
| 53 | 452.3 |
| 54 | 516.4 |
| 55 | 448.4 |
| 56 | 448.3 |
| 57 | 416.4 |
| 58 | 488.4 |

TABLE 1-continued

| Example | | LCMS: found m/e (M + H) |
|---|---|---|
| 59 | 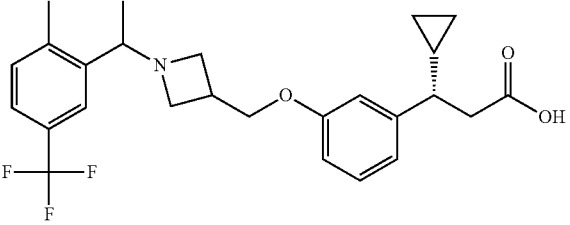 [SMILES: Cc1ccc(C(F)(F)F)cc1C(C)N1CC(COc2cccc([C@@H](CC(=O)O)C3CC3)c2)C1] | 462.3 |
| 60 | 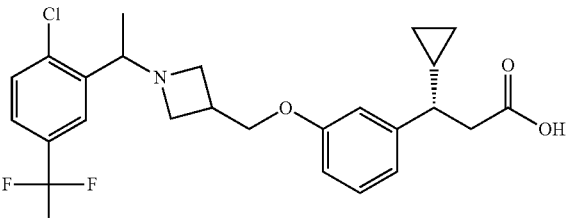 | 482.3 |

Example 61

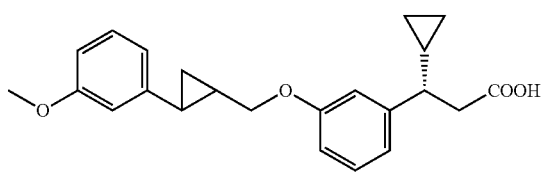 [SMILES: COc1cccc(C2CC2COc2cccc([C@@H](CC(=O)O)C3CC3)c2)c1]

(3 S)-3-cyclopropyl-3-(3-((2-(3-methoxyphenyl)cyclopropyl)methoxy)phenyl)propanoic acid To a solution of Intermediate 44 (200 mg, 0.526 mmol) in THF (2 mL)/MeOH (4 mL)/Water (2 mL) at rt was added LiOH (189 mg, 7.88 mmol). The resulting mixture was stirred at 60° C. for 12 h, then diluted with H₂O and acidified with 1N HCl to pH 4-5. The solution was extracted with EtOAc (3×20 mL), washed with brine, dried over MgSO₄, filtered, concentrated and purified by MPLC (ISCO 4 g, 0-100% EtOAc/hexanes)) to give the title compound as a colorless oil as a mixture of diastereomers at the cyclopropane. 1H NMR (500 MHz; CDCl₃): δ 7.20-7.15 (m, 2H), 6.90-6.80 (m, 5H), 4.03 (m, 1H), 3.86 (m, 1H), 3.81 (s, 3H), 2.80-2.75 (m, 2H), 2.38-2.32 (m, 1H), 1.84-1.80 (m, 1H), 1.05-1.00 (m, 3H), 0.69-0.65 (m, 1H), 0.51-0.44 (m, 1H), 0.36-0.30 (m, 1H), 0.20-0.16 (m, 1H). LC/MS: m/e 367 (M+1)⁺.

Example 62 AND 63

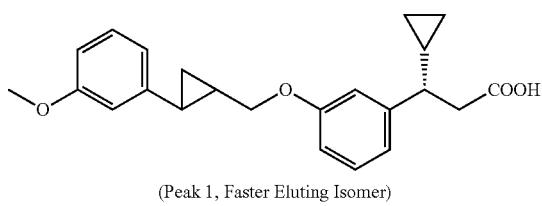

(Peak 1, Faster Eluting Isomer)

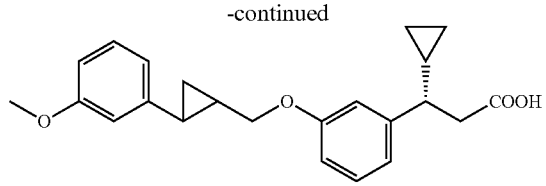

(Peak 2, Slower Eluting Isomer)

Separation of the diastereomers from Example 61 was performed by Chiral SFC (Column: Chiralpak AD-H, 21×250 mm, 55% IPA/CO₂, 50 mL/min, 40° C., 120 bar, 254 nm, 158 mg/20 mL in MeOH) to afford the following two isomers:

(3 S)-3-cyclopropyl-3-(3-((2-(3-methoxyphenyl)cyclopropyl)methoxy)phenyl)propanoic acid (Peak 1, Faster Eluting Isomer)

¹H NMR (500 MHz; CDCl₃): δ 7.20-7.15 (m, 2H), 6.90-6.80 (m, 5H), 4.03 (m, 1H), 3.86 (m, 1H), 3.81 (s, 3H), 2.80-2.75 (m, 2H), 2.38-2.32 (m, 1H), 1.84-1.80 (m, 1H), 1.05-1.00 (m, 3H), 0.69-0.65 (m, 1H), 0.51-0.44 (m, 1H), 0.36-0.30 (m, 1H), 0.20-0.16 (m, 1H). LC/MS: m/e 367 (M+1)⁺.

(3 S)-3-cyclopropyl-3-(3-((2-(3-methoxyphenyl)cyclopropyl)methoxy)phenyl)propanoic acid (Peak 2, Slower eluting isomer): ¹H NMR (500 MHz; CDCl₃): δ 7.20-7.15 (m, 2H), 6.90-6.80 (m, 5H), 4.03 (m, 1H), 3.86 (m, 1H), 3.81 (s, 3H), 2.80-2.75 (m, 2H), 2.38-2.32 (m, 1H), 1.84-1.80 (m, 1H), 1.05-1.00 (m, 3H), 0.69-0.65 (m, 1H), 0.51-0.44 (m, 1H), 0.36-0.30 (m, 1H), 0.20-0.16 (m, 1H). LC/MS: m/e 367 (M+1)⁺.

Example 64

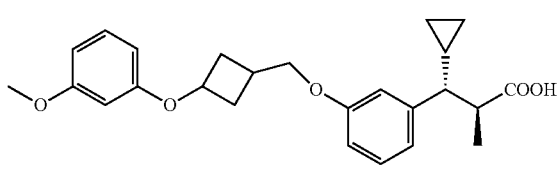 [SMILES: COc1cccc(OC2CC(COc3cccc([C@H](C4CC4)[C@H](C)C(=O)O)c3)C2)c1]

(2S,3R)-3-Cyclopropyl-3-(3-((3-(3-methoxyphenoxy)cyclobutyl)methoxy)phenyl)-2-methylpropanoic acid The compound of Example 64 was prepared as a mixture of cis and trans-cyclobutane isomers according to the procedure of Example 61 starting with Intermediate 54. ¹H NMR (500 MHz; CDCl₃): δ 7.25-7.18 (m, 2H), 6.80-6.75 (m, 3H), 6.53-6.50 (m, 1H), 6.43-6.38 (m, 2H), 4.90-4.86 (m, 0.5H), 4.64-4.60 (m, 0.5H), 4.06-4.02 (m, 2H), 3.80 (s, 3H), 2.91-2.87 (m, 1H), 2.72-2.68 (m, 1H), 2.46-2.40 (m, 2H), 2.16-2.12 (m, 1H), 2.02-1.98 (m, 1H), 1.19-1.15 (m, 1H), 1.03-0.98 (m, 3H), 0.72-0.68 (m, 1H), 0.45-0.41 (m, 2H), 0.20-0.16 (m, 1H).
LC/MS: m/e 411 (M+1)⁺.

Example 65 AND 66

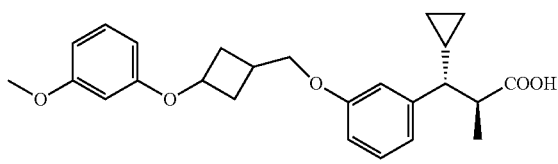

(Peak 1, Faster eluting isomer)

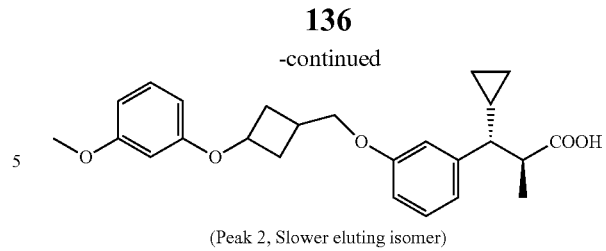

(Peak 2, Slower eluting isomer)

Separation of the cis and trans-cyclobutane isomers from Example 64 was performed by Chiral SFC (AD-H, 21×250 mm, 35% MeOH/CO₂, 40 mL/min, 40° C., 120 bar, 210 nm, 69 mg/15 mL in MeOH) to afford the following two isomers:
(2S,3R)-3-cyclopropyl-3-(3-((3-(3-methoxyphenoxy)cyclobutyl)methoxy)phenyl)-2-methylpropanoic acid (Peak 1, Faster eluting isomer): ¹H NMR (500 MHz; MeOD): δ 7.13-7.09 (br, 1H), 7.06-7.02 (m, 1H), 6.90-6.86 (m, 3H), 6.39-6.36 (m, 1H), 6.28-6.25 (m, 2H), 4.80-4.77 (m, 1H), 3.94 (d, J=6.23 Hz, 2H), 3.64 (s, 3H), 2.66 (br, 1H), 2.34 (br, 4H), 1.02(br, 1H), 1.03-0.98 (m, 3H), 0.72-0.68 (m, 1H), 0.45-0.41 (m, 2H), 0.20-0.16 (m, 1H). LC/MS: m/e 411 (M+1)⁺.

(2S,3R)-3-cyclopropyl-3-(3-((3-(3-methoxyphenoxy)cyclobutyl)methoxy)phenyl)-2-methylpropanoic acid (Peak 2, Slower eluting isomer): ¹H NMR (500 MHz; MeOD): δ 7.13-7.09 (br, 1H), 7.06-7.02 (m, 1H), 6.90-6.86 (m, 3H), 6.39-6.36 (m, 1H), 6.28-6.25 (m, 2H), 4.52-4.48 (m, 1H), 3.86 (d, J=5.76 Hz, 2H), 3.64 (s, 3H), 2.66 (br, 1H), 2.34 (br, 4H), 1.02(br, 1H), 1.03-0.98 (m, 3H), 0.72-0.68 (m, 1H), 0.45-0.41 (m, 2H), 0.20-0.16 (m, 1H). LC/MS: m/e 411 (M+1)⁺.

The compounds in Table 2 were prepared according to Step B of Example 2 or in a manner similar to that described in Example 61 using the appropriate starting materials.

TABLE 2

| Example | Compound | LCMS: found m/e (M + H) |
|---|---|---|
| 67 | ![structure] | 365.45 |
| 68 | ![structure] Mixture of cyclopropane isomers | 351.39 |

TABLE 2-continued

| Example | Compound | LCMS: found m/e (M + H) |
|---------|----------|-------------------------|
| 69 | mixture of cyclopropane isomers | 381.46 |
| 70 | | 395.23 |
| 71 | | 395.23 |
| 72 | cis/trans mixture at cyclobutane | 365.44 |
| 73 | cis/trans mixture of cyclobutane isomers | 429.25 |
| 74 | | 399.50 |

TABLE 2-continued

| Example | Compound | LCMS: found m/e (M + H) |
|---|---|---|
| 75 | ![structure] | 399.50 |
| 76 | ![structure] | 400.41 |
| 77 | ![structure] cis/trans mixture of cyclobutane isomers | 407.11 |

Example 78

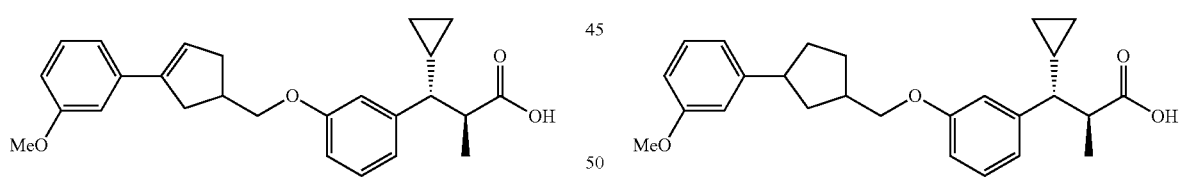

(2S,3R)-3-cyclopropyl-3-(3-((3-(3-methoxyphenyl)cyclopent-3-en-1 yl)methoxy)phenyl)-2-methylpropanoic acid To a solution of Intermediate 65 (80 mg, 0.190 mmol) in MeOH/THF/water (1:1:1, 1.5 mL total volume) was added LiOH (46 mg, 1.9 mmol). The mixture was heated (60° C.) and stirred on a heating block. After 16 h, the reaction was poured into 1N HCl (10 mL) and extracted with EtOAc (2×10 mL). The combined organic layers were dried (MgSO$_4$) and concentrated. The resulting residue was purified by HPLC (ISCO 40 g, 0 to 100% EtOAc/Hex) to give the title compound. LCMS: m/e 407.11 (M+H)$^+$

Example 79

(2S,3R)-3-cyclopropyl-3-(3-(((1R,3S)-3-(3-methoxyphenyl)cyclopentyl)methoxy)phenyl)-2-methylpropanoic acid To a solution of Intermediate 66 (50 mg, 0.118 mmol) in MeOH/THF/water (1:1:1, 1.5 mL total volume) was added LiOH (28 mg, 1.2 mmol). The mixture was heated (60° C.) and stirred on a heating block. After 16 h, the reaction was poured into 1N HCl (10 mL) and extracted with EtOAc (2×10 mL). The combined organic layers were dried (MgSO$_4$) and concentrated. The resulting residue was purified by HPLC (ISCO 40 g, 0 to 100% EtOAc/Hex) to give the title compound. LCMS: m/e 409.34 (M+H)$^+$

Examples 80 and 81

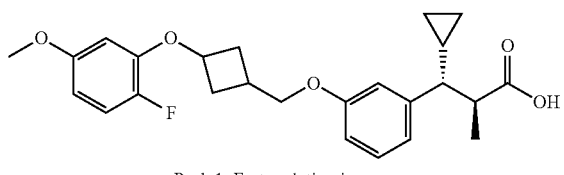

Example 79

Peak 1, Faster eluting isomer.

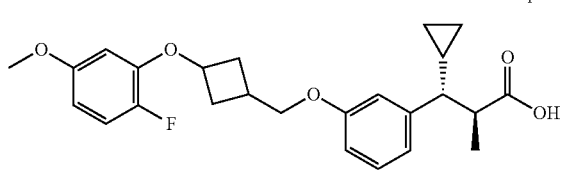

Example 80

Peak 2, Slower eluting isomer.

Separation of the cis and trans-cyclobutane isomers from Example 73 was performed by Chiral SFC (Column: AD-H, 21×250 mm, 30% i-PrOH/CO$_2$, 40 mL/min, 40° C., 120 bar, 254 nm, 120 mg/20 mL in MeOH, injection volume: 0.5 mL) to afford the following two isomers: Peak 1, Faster eluting isomer: (2S,3R)-3-cyclopropyl-3-(3-((3-(2-fluoro-5-methoxyphenoxy)cyclobutyl)methoxy)phenyl)-2-methylpropanoic acid 1H NMR (500 MHz, CHCl3-d): δ 0.04-0.10 (m, 1H), 0.42-0.38 (m, 2H), 0.70-0.61 (m, 1H), 1.02 (d, 3H), 1.18-1.10 (m, 1H), 1.99 (t, 1H), 2.51 (t, 4H), 2.92-2.80 (m, 2H), 3.78 (s, 3H), 4.03 (d, 2H), 4.88 (quintet, 1H), 6.40-6.36 (m, 2H), 6.84-6.76 (m, 3H), 7.03-6.98 (m, 1H), 7.26 (t, 1H). LC/MS: m/e 429 (M+1)$^+$.

Peak 2, Slower eluting isomer: (2S,3R)-3-cyclopropyl-3-(3-((3-(2-fluoro-5-methoxyphenoxy)cyclobutyl)methoxy)phenyl)-2-methylpropanoic acid 1H NMR (500 MHz, CHCl3-d): δ 0.07-0.04 (m, 1H), 0.42-0.34 (m, 2H), 0.67-0.62 (m, 1H), 1.00 (d, 3H), 1.13 (dtt, 1H), 1.97 (t, 1H), 2.20-2.14 (m, 2H), 2.53-2.43 (m, 1H), 2.74-2.67 (m, 2H), 2.89-2.82 (m, 1H), 3.78 (s, 3H), 4.00 (d, 2H), 4.64 (p, 1H), 6.39 (dt, 1H), 6.44 (dd, 1H), 6.80-6.73 (m, 3H), 7.00 (dd, 1H), 7.23 (t, 1H). LC/MS: m/e 429 (M+1)$^+$.

Examples 82 and 83

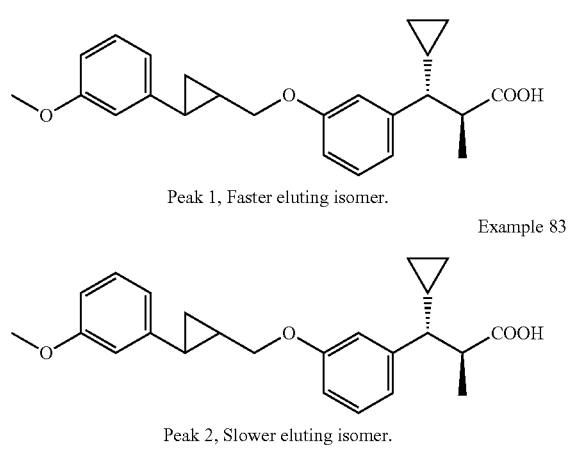

Example 82

Peak 1, Faster eluting isomer.

Example 83

Peak 2, Slower eluting isomer.

Separation of the two diastereomers from Example 69 was performed by Chiral SFC (Column: AD-H, 21×250 mm, 40% MeOH/CO$_2$, 50 mL/min, 40° C., 120 bar, 210 nm, 68 mg/16 mL in MeOH, injection volume: 0.5 mL) to afford the following two isomers:

Peak 1, Faster eluting isomer: (2S,3R)-3-cyclopropyl-3-(3-((2-(3-methoxyphenyl)cyclopropyl)methoxy)phenyl)-2-methylpropanoic acid LC/MS: m/e 381 (M+1)$^+$.

Peak 2, Slower eluting isomer: (2S,3R)-3-cyclopropyl-3-(3-((2-(3-methoxyphenyl)cyclopropyl)methoxy)phenyl)-2-methylpropanoic acid LC/MS: m/e 381 (M+1)$^+$.

The compounds in Table 3 were prepared in a manner similar to that described in Example 61 using the appropriate starting materials.

TABLE 3

| Example | Compound | LCMS: found m/e (M + H) |
|---|---|---|
| 84 | ![structure] cis/trans mixture of cyclobutane isomers | 413.4 |

TABLE 3-continued

| Example | Compound | LCMS: found m/e (M + H) |
|---|---|---|
| 85 | cis/trans mixture of cyclobutane isomers | 395.4 |
| 86 | cis/trans mixture of cyclobutane isomers | 396.1 |
| 87 | cis/trans mixture of cyclobutane isomers | 414.1 |

Examples 88 and 89

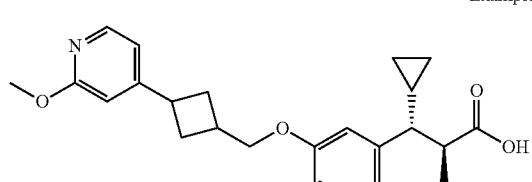

Peak 1, Faster eluting isomer.

Example 88

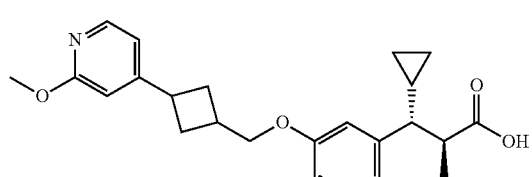

Peak 2, Slower eluting isomer.

Example 89

Separation of the cis and trans-cyclobutane isomers from Example 86 was performed by chiral SFC (Column: AD-H, 21×250 mm, 30% MeOH/CO$_2$, 50 mL/min, 40° C., 120 bar, UV detection: 210 nm, 75 mg/15 mL in MeOH, injection volume: 0.5 mL) to afford the following two isomers:

Example 88

Peak 1, Faster eluting isomer: (2S,3R)-3-cyclopropyl-3-(3-((3-(2-methoxy-pyridin-4-yl)cyclobutyl)methoxy)phenyl)-2-methylpropanoic acid; LC/MS: m/e 396.3 (M+1)$^+$.

Example 89

Peak 2, Slower eluting isomer: (2S,3R)-3-cyclopropyl-3-(3-((3-(2-methoxy-pyridin-4-yl)cyclobutyl)methoxy)phenyl)-2-methylpropanoic acid; LC/MS: m/e 396.3 (M+1)$^+$.

Examples 90 and 91

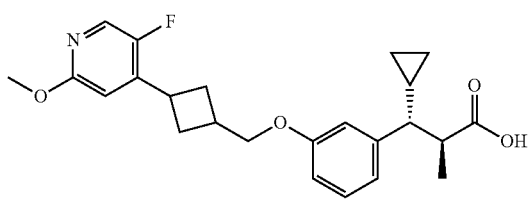 [SMILES: COc1cc(C2CC(COc3cccc([C@H](C4CC4)[C@H](C)C(=O)O)c3)C2)c(F)cn1]

Example 90

Peak 1, Faster eluting isomer.

Example 91

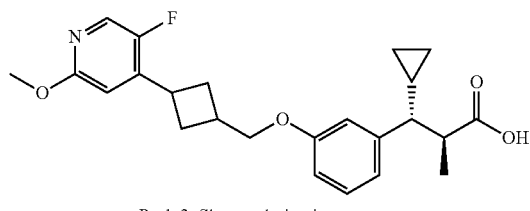

Peak 2, Slower eluting isomer.

Separation of the cis and trans-cyclobutane isomers from Example 87 was performed by chiral SFC (Column: AD-H, 21×250 mm, 30% MeOH/CO$_2$, 50 mL/min, 40° C., 120 bar, UV detection: 210 nm, 75 mg/15 mL in MeOH, injection volume: 0.5 mL) to afford the following two isomers:

Example 90

Peak 1, Faster eluting isomer: (2S,3R)-3-cyclopropyl-3-(3-((3-(5-fluoro-2-methoxypyridin-4-yl)cyclobutyl)methoxy)phenyl)-2-methylpropanoic acid; LC/MS: m/e 414.3 (M+1)$^+$.

Example 91

Peak 2, Slower eluting isomer: (2S,3R)-3-cyclopropyl-3-(3-((3-(5-fluoro-2-methoxypyridin-4-yl)cyclobutyl)methoxy)phenyl)-2-methylpropanoic acid; LC/MS: m/e 414.3 (M+1)$^+$.

Example 92

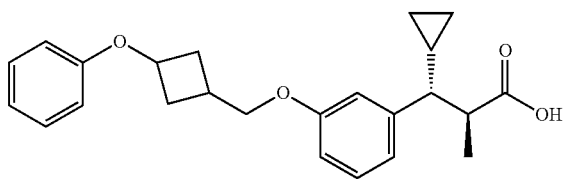 [SMILES: C[C@H](C(=O)O)[C@H](c1cccc(OCC2CC(Oc3ccccc3)C2)c1)C1CC1]

Step 1: Methyl (2S,3R)-3-cyclopropyl-2-methyl-3-(3-((3-phenoxycyclobutyl)methoxy)-phenyl)propanoate A 2-dram vial was charged with (2S,3R)-methyl 3-cyclopropyl-3-(3-((3-hydroxycyclobutyl)methoxy)phenyl)-2-methylpropanoate (25 mg, 0.079 mmol), phenol (22 mg, 0.236 mmol), and a solution of tri-N-butylphosphine (58.1 µL, 0.236 mmol) in anhydrous THF (0.85 ml). The mixture was stirred at r.t. for 10 min, then 1,1'-(azo-dicarbonyl)dipiperidine (59.4 mg, 0.236 mmol) was added. The resulting mixture was heated at 50° C. with stirring for 2 days. The reaction was then cooled to r.t. Water (1 mL) was added to the reaction mixture, and the mixture was stirred at r.t. for 10 min. Then the mixture was extracted with EtOAc (2 mL×2). The combined organic layers were collected into a 2 dram vial, and the volatiles were removed with a GeneVac. The resulting residue was used in the next step without further purification.

Step 2: (2S,3R)-3-cyclopropyl-2-methyl-3-(3-((3-phenoxycyclobutyl)methoxy)phenyl)-propanoic acid The residue from Step 1 was treated with THF (400 µL), MeOH (200 µL) and saturated aqueous LiOH (400 µL, 0.079 mmol). The mixture was heated at 50° C. overnight. Then the reaction was cooled to r.t., quenched with aq. 1N HCl (1 mL) and acidified with aq. 6N HCl until the reaction mixture turned homogeneous. The mixture was extracted with EtOAc (3 mL×2). The combined organic layers were transferred into a 2 dram vial, and the volatiles were removed with a GeneVac. The resulting residue was purified by reverse-phase chromatography (Waters XBridge C18, 5 um, 19×100 mm), eluting with 10-38% of acetonitrile (with 0.1% ammonium hydroxide) in water (with 0.1% ammonium hydroxide), 25 mL/min., 9 min.) to afford the title compound. 1H NMR (500 MHz, DMSO-d6) δ 7.26 (m, 2H), 7.20 (m, 1H), 6.94 (m, 1H), 6.82 (m, 5H), 4.92 (m, 0.5H), 4.64 (m, 0.5H), 4.02 (m, 2H), 2.71 (m, 1H), 2.64 (m, 1H), 2.40 (m, 1H), 2.26 (m, 1H), 1.94 (m, 2H), 1.08 (m, 1H), 0.85 (m, 1H), 0.80 (m, 3H), 0.54 (m, 1H), 0.28 (m, 2H), −0.06 (m, 1H). LC/MS (m/z): 379 (M−H)−.

The compounds in Table 4 were prepared in a manner similar to that described in Example 92 using the appropriate starting materials.

TABLE 4

| Example | Compound | LCMS: found m/e (M + H)+ | LCMS: found m/e (M − H)− |
|---|---|---|---|
| 93 | ![structure] | 412 | — |
| 94 | ![structure] | — | 397 |

TABLE 4-continued

| Example | Compound | LCMS: found m/e (M + H)+ | LCMS: found m/e (M − H)− |
|---|---|---|---|
| 95 | | 448 | — |
| 96 | | 413 | — |
| 97 | | 399 | — |
| 98 | More Polar Isomer | 371 | — |
| 99 | Less Polar Isomer | 371 | — |
| 100 | | 467 | — |
| 101 | | 385 | — |

Examples 102 and 103

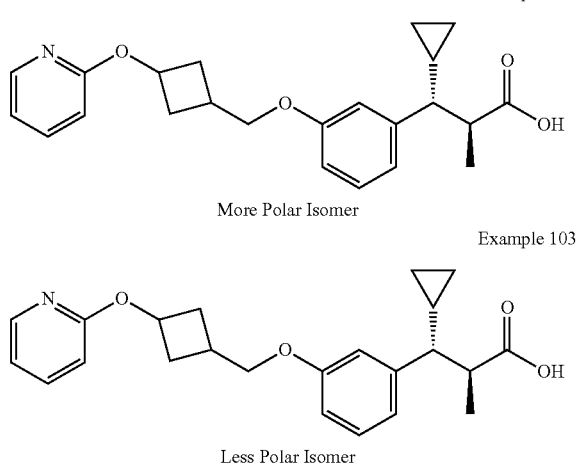

Example 102

More Polar Isomer

Example 103

Less Polar Isomer

Step 1: Methyl (2S,3R)-3-cyclopropyl-2-methyl-3-(3-((3-(pyridin-2-yloxy)cyclobutyl)-methoxy)phenyl)propanoate A 2-dram vial was charged with (2S,3R)-methyl 3-cyclopropyl-3-(3-((3-hydroxycyclobutyl)methoxy)phenyl)-2-methylpropanoate (18 mg, 0.057 mmol), pyridin-2-ol (16 mg, 0.170 mmol), PPh₃ (44.5 mg, 0.170 mmol) and anhydrous THF (0.61 ml). The mixture was stirred at r.t. for 10 min, then 1,1'-(azodicarbonyl)-dipiperidine (42.8 mg, 0.170 mmol) was added. The reaction mixture was shaken at 150 rpm at room temperature overnight. 1,1'-(Azodicarbonyl) dipiperidine (42.8 mg, 0.170 mmol) was added to a solution of PPh₃ (44.5 mg, 0.170 mmol) in anhydrous THF (0.180 ml), and the resulting mixture was stirred for 5 min. Then the PPh₃ mixture was added to the reaction mixture. The reaction was heated at 55° C. for 72 h, then cooled to r.t. The volatiles were removed with a GenVac. The resulting residue was partitioned between 1 mL of water and 2 mL of EtOAc. The layers were separated and the aqueous layer was extracted with EtOAc (2 mL). The combined organic layers were collected into a 2-dram vial, and the volatiles were removed with a GeneVac. The resulting residue was used in the next step without further purification.

Step 2: (2S,3R)-3-cyclopropyl-2-methyl-3-(3-((3-pyridin-2-yloxy)cyclobutyl)methoxy)-phenyl)propanoic acid The product from Step 1 was subjected to a method similar to that outlined in Step 2 of Example 92 and purified via reversed-phase chromatography (Waters XBridge C18, 5 um, 19×100 mm), eluting with 10-31% of acetonitrile (with 0.1% ammonium hydroxide) in water (with 0.1% ammonium hydroxide), 25 mL/min., 12 min. run time. to afford: 1) Example 102—the more polar isomer of (2S,3R)-3-cyclopropyl-2-methyl-3-(3-((3-pyridin-2-yloxy)cyclobutyl)methoxy)phenyl)propanoic acid, 1H NMR (500 MHz, DMSO-d6) δ 8.15 (m, 1H), 7.70 (m, 1H), 7.19 (m, 1H), 6.94 (m, 1H), 6.74 (m, 4H), 5.08 (m, 1H), 3.99 (m, 2H), 2.72 (m, 1H), 2.58 (m, 1H), 2.42 (m, 1H), 2.26 (m, 1H), 1.94 (m, 3H), 1.12 (m, 1H), 0.79 (m, 3H), 0.50 (m, 1H), 0.24 (m, 2H), −0.06 (m, 1H). LC/MS (m/z): 382 (M+H)⁺; and 2) Example 103—the less polar isomer, 1H NMR (500 MHz, DMSO-d6) δ 8.15 (m, 1H), 7.70 (m, 1H), 7.19 (m, 1H), 6.94 (m, 1H), 6.74 (m, 4H), 5.32 (m, 1H), 4.05 (m, 2H), 2.72 (m, 2H), 2.58 (m, 2H), 2.38 (m, 1H), 2.26 (m, 1H), 1.94 (m, 1H), 1.12 (m, 1H), 0.81 (m, 3H), 0.50 (m, 1H), 0.24 (m, 2H), −0.06 (m, 1H). LC/MS (m/z): 382 (M+H)⁺.

The compounds in Table 5 were prepared in a manner similar to that described in Examples 102 and 103 using the appropriate starting materials.

TABLE 5

| Example | Compound | LCMS: found m/e (M + H)+ | LCMS: found m/e (M − H)− |
|---|---|---|---|
| 104 | More Polar Isomer | 412 | — |
| 105 | Less Polar Isomer | 412 | — |

TABLE 5-continued

| Example | Compound | LCMS: found m/e (M + H)+ | LCMS: found m/e (M − H)− |
|---|---|---|---|
| 106 | (structure) | 430 | — |

Examples 107 and 108 in Table 6 were prepared in a manner similar to that described in the synthesis of Examples 102 and 103 using the appropriate starting materials, with the exception that diethylazodicarboxylate is used in place of 1,1'-(azodicarbonyl)dipiperidine in Step 1, and the reaction in Step 1 was heated at 50° C. The final compounds were purified Purified by reverse-phase chromatography (Waters XBridge C18, 5u, 19×100 mm), eluting with 40-75% of acetonitrile (with 0.1% trifluoroacetic acid) in water (with 0.1% trifluoroacetic acid), 25 mL/min., 12 min. run time).

TABLE 6

| Example | Compound | LCMS: found m/e (M + H)+ | LCMS: found m/e (M − H)− |
|---|---|---|---|
| 107 | (structure) More Polar Isomer | 437 | − |
| 108 | (structure) Less Polar Isomer | 437 | — |

The compounds in Table 7 were prepared in a manner similar to that described in Examples 102 and 103 using the appropriate starting materials, with the exception that resin-bound triphenylphosphine was used in place of triphenylphosphine in Step 1, and the reaction in Step 1 was heated at 60° C. The final compounds were purified by reverse-phase chromatography (Waters XBridge C18, 5 um, 19×100 mm), eluting with 8-40% of acetonitrile (with 0.1% ammonium hydroxide) in water (with 0.1% ammonium hydroxide), 25 mL/min., 12 min. run time).

TABLE 7

| Example | Compound | LCMS: found m/e (M + H)+ | LCMS: found m/e (M − H)− |
|---|---|---|---|
| 109 | Mixture of Isomers | 382 | — |
| 110 | Less Polar Isomer | 382 | — |
| 111 | | 440 | — |
| 112 | | — | 423 |
| 113 | | — | 423 |
| 114 | | — | 415 |
| 115 | | — | 415 |

TABLE 7-continued
| Example | Compound | LCMS: found m/e (M + H)+ | LCMS: found m/e (M − H)− |
|---|---|---|---|
| 116 | 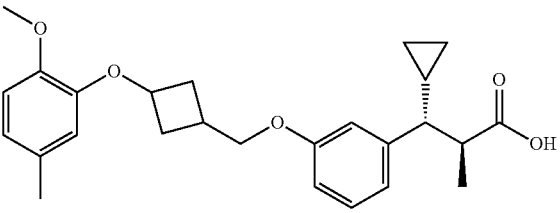 [SMILES: COc1ccc(C)cc1OC1CC(COc2cccc([C@H](C3CC3)[C@H](C)C(=O)O)c2)C1]<br>More Polar Isomer | — | 423 |
| 117 | 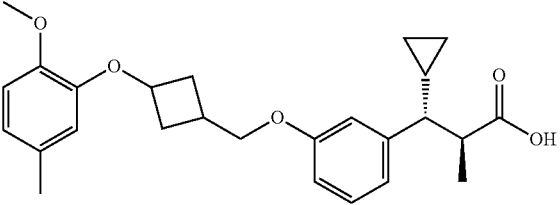 [SMILES: COc1ccc(C)cc1OC1CC(COc2cccc([C@H](C3CC3)[C@H](C)C(=O)O)c2)C1]<br>Less Polar Isomer | — | 423 |
| 118 | 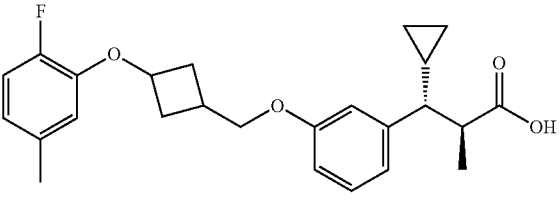 [SMILES: Cc1ccc(F)c(OC2CC(COc3cccc([C@H](C4CC4)[C@H](C)C(=O)O)c3)C2)c1]<br>More Polar Isomer | — | 411 |
| 119 | 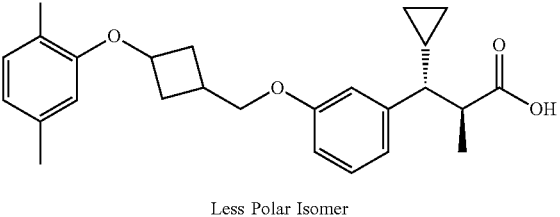<br>Less Polar Isomer | — | 411 |
| 120 | 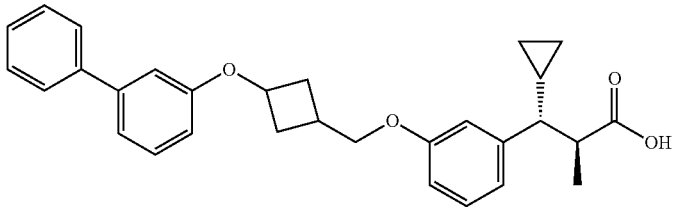 [SMILES: C[C@H](C(=O)O)[C@H](c1cccc(OCC2CC(Oc3cccc(-c4ccccc4)c3)C2)c1)C1CC1]<br>More Polar Isomer | — | 455 |
| 121 | 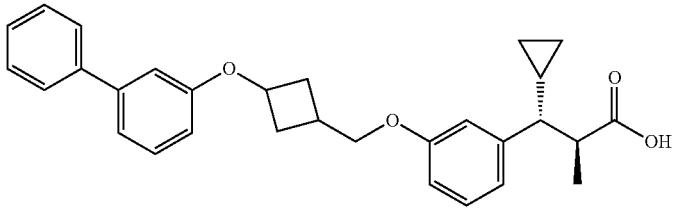 [SMILES: C[C@H](C(=O)O)[C@H](c1cccc(OCC2CC(Oc3cccc(-c4ccccc4)c3)C2)c1)C1CC1]<br>Less Polar Isomer | — | 455 |

TABLE 7-continued

| Example | Compound | LCMS: found m/e (M + H)+ | LCMS: found m/e (M − H)− |
|---|---|---|---|
| 122 | More Polar Isomer | — | 395 |
| 123 | Less Polar Isomer | — | 395 |
| 124 | More Polar Isomer | — | 409 |
| 125 | Less Polar Isomer | — | 409 |
| 126 | More Polar Isomer | — | 437 |
| 127 | Less Polar Isomer | — | 437 |

TABLE 7-continued

| Example | Compound | LCMS: found m/e (M + H)+ | LCMS: found m/e (M − H)− |
|---|---|---|---|
| 128 | | — | 409 |
| 129 | More Polar Isomer | — | 427 |
| 130 | Less Polar Isomer | — | 427 |
| 131 | | 425 | — |
| 132 | | — | 455 |
| 133 | More Polar Isomer | — | 413 |

TABLE 7-continued

| Example | Compound | LCMS: found m/e (M + H)+ | LCMS: found m/e (M − H)− |
|---|---|---|---|
| 134 | 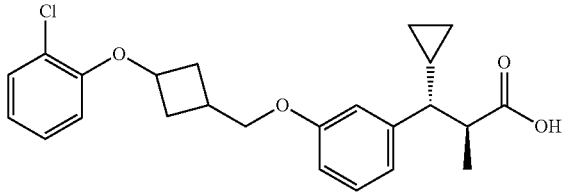 [SMILES: C[C@H](C(=O)O)[C@H](c1cccc(OCC2CC(Oc3ccccc3Cl)C2)c1)C1CC1]<br>Less Polar Isomer | — | 413 |
| 135 | 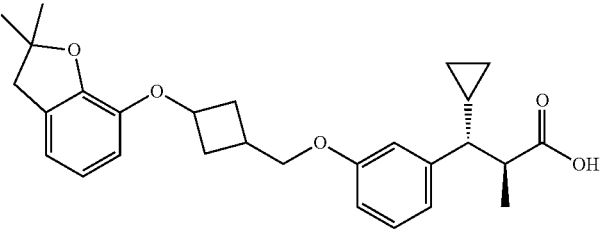 [SMILES: C[C@H](C(=O)O)[C@H](c1cccc(OCC2CC(Oc3cccc4c3OC(C)(C)C4)C2)c1)C1CC1] | 451 | — |
| 136 | 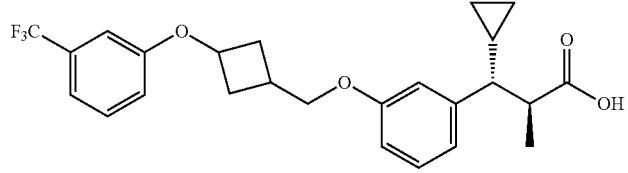 [SMILES: C[C@H](C(=O)O)[C@H](c1cccc(OCC2CC(Oc3cccc(C(F)(F)F)c3)C2)c1)C1CC1] | — | 447 |

General Method for Examples 137 to 159

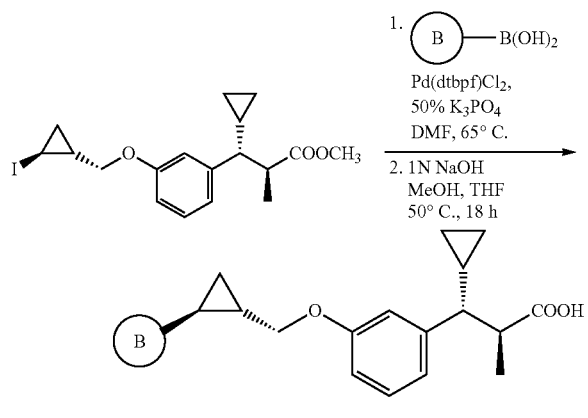

Examples 137 to 139

Into 24 two dram vials was added the requisite boronic acid (0.072 mmol), DMF (603 μl) solution of (2S,3R)- methyl 3-cyclopropyl-3-(3-(((1R,2S)-2-iodocyclopropyl) methoxy)-phenyl)-2-methylpropanoate (30 mg, 0.072 mmol) and 1,1'-bis(di-tert-butylphosphino)-ferrocene palladium dichloride (4.72 mg, 7.24 μmol), followed by addition of 50% aqueous potassium phosphate tribasic (92 μl, 0.217 mmol) under a stream of $N_2$. The reaction was heated at 65° C. for two hours. Then DMT-silica (3eq) was added and the solution was stirred at 45° C. for 1 hour. The mixture was filtered and the resulting solid was washed with EtOAc (2 ml) twice. The filtrate was concentrated on a Genevac to give a crude residue, which was dissolved in THF (0.4 mL), MeOH (0.3 mL) and 1N NaOH (0.4 mL, aq.). The resulting mixture was stirred at 50° C. overnight, then TFA (0.03 mL) was added. The mixture was then concentrated on a Genevac and the resulting residue was dissolved in DMSO (1.2 mL). The mixture was filtered, and subjected to C18 reverse-phase HPLC (Waters Sunfire C18, 5 micron, 19×100 mm, gradient elution over 10 min, weak solvent: 0.1% TFA in water, strong solvent: 0.1% TFA in MeCN, 25 ml/min) to afford the desired compound.

Examples 137 to 159 in Table 8 were prepared as described by the general method for Examples 137-159 described above.

TABLE 8

| Example | Compound | LCMS: found m/e (M + H)+ unless otherwise noted |
|---------|----------|---------|
| 137 | (structure: 3-(trifluoromethoxy)phenyl-cyclopropyl-CH2O-phenyl-CH(cyclopropyl)-CH(CH3)-COOH) | 435.1 |
| 138 | (structure: 3-cyclopropoxyphenyl-cyclopropyl-CH2O-phenyl-CH(cyclopropyl)-CH(CH3)-COOH) | 407.1 |
| 139 | (structure: 2,5-dimethoxyphenyl-cyclopropyl-CH2O-phenyl-CH(cyclopropyl)-CH(CH3)-COOH) | 433.2 (M + Na)+ |
| 140 | (structure: 2-fluoro-3-methoxyphenyl-cyclopropyl-CH2O-phenyl-CH(cyclopropyl)-CH(CH3)-COOH) | 399.2 |
| 141 | (structure: 3-fluoro-5-methoxyphenyl-cyclopropyl-CH2O-phenyl-CH(cyclopropyl)-CH(CH3)-COOH) | 399.2 |
| 142 | (structure: 2,6-difluoro-3-methoxyphenyl-cyclopropyl-CH2O-phenyl-CH(cyclopropyl)-CH(CH3)-COOH) | 417.2 |
| 143 | (structure: 2-chloro-5-(trifluoromethyl)phenyl-cyclopropyl-CH2O-phenyl-CH(cyclopropyl)-CH(CH3)-COOH) | 453.0 |

TABLE 8-continued

| Example | Compound | LCMS: found m/e (M + H)+ unless otherwise noted |
|---|---|---|
| 144 | | 437.2 |
| 145 | | 453.1 |
| 146 | | 469.1 |
| 147 | | 352.1 |
| 148 | | 383.2 |
| 149 | | 400.2 |
| 150 | | 382.1 |

TABLE 8-continued

| Example | Compound | LCMS: found m/e (M + H)+ unless otherwise noted |
|---|---|---|
| 151 | | 387.2 |
| 152 | | 403.2 |
| 153 | | 417.2 |
| 154 | | 399.1 |
| 155 | | 487.1 |
| 156 | | 453.1 |
| 157 | | 435.2 (M − H)− |

TABLE 8-continued

| Example | Compound | LCMS: found m/e (M + H)+ unless otherwise noted |
|---|---|---|
| 158 | (structure: 2-chloro-5-methoxyphenyl cyclopropyl-CH2-O-phenyl-CH(cyclopropyl)-CH(CH3)-COOH) | 415.2 |
| 159 | (structure: 4-methoxyphenyl cyclopropyl-CH2-O-phenyl-CH(cyclopropyl)-CH(CH3)-COOH) | 381.1 |

Biological Assays
Generation of GPR40-Expressing Cells:

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

FLIPR Assays:

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 μL medium/well. The cells were incubated with 20 μl/well of the assay buffer (HBSS, 0.1% BSA, 20 mM HEPES, 2.5 mM probenecid, pH 7.4) containing 8 μM fluo-4, AM, 0.08% pluronic acid at room temperature for 100 minutes. Fluorescence output was measured using FLIPR. Compounds were dissolved in DMSO and diluted to desired concentrations with assay buffer. 13.3 μL/well of compound solution was added.

The compounds of the present invention, including the compounds in Examples 1-159, have $EC_{50}$ values less than 2 micromolar (μM) in the FLIPR assay described above. The compounds in Examples 1-159 have the $EC_{50}$ values in the FLIPR assay listed in Table A.

Inositol Phosphate Turnover (IP1) Assay 1:

The assay was performed in 96-well format. HEK cells stably expressing human GPR40 were plated to be 60-80% confluent within 72 h. After 72 h, the plates were aspirated and the cells washed with inositol-free DMEM (ICN). The wash media was replaced with 150 μL of 3H-inositol labeling media (inositol-free media containing 0.4% human albumin or 0.4% mouse albumin, 1× pen/strep antibiotics, glutamine, 25 mM HEPES to which was added 3H-myo-inositol NEN #NET114A 1 mCi/mL, 25 Ci/mmol diluted 1:150 in loading media with a final specific radioactivity of 1 μCi/150 μL). Alternatively, the human and mouse albumin can be added after the overnight labeling step before the addition of LiCl.

The assay was typically run the next day after 18 h labeling. On the day of the assay, 5 μL of 300 mM LiCl was added to all wells and incubated at 37 degrees for 20 min. 0.75 μL of each compound was added and incubated with the cells for 60 min at 37 degrees. The media was then aspirated off and the assay terminated with the addition of 60 μL 10 mM formic acid. The cells were lysed for 60 min at room temperature. 15-30 μL of lysate was mixed with 70 μL/1 mg YSi SPA beads (Amersham) in clear bottom Isoplates. The plates were shaken for 2 h at room temperature. Beads were allowed to settle and the plates were counted in the Wallac Microbeta.

Inositol Phosphate Turnover (IP1) Assay 2:

The assay was performed in 384-well format. HEK cells stably expressing human GPR40 were plated at 15,000 cells per well in growth medium (DMEM/10% fetal calf serum). Cell plates were then incubated 16 hours at 37 degrees in a 5% $CO_2$ incubator.

Measurement of Inositol Phosphate Turnover (IP1) was performed using the CisBio IP-One kit (Part number 62IPA-PEB). After the 16 hour incubation, the cells were washed with HEPES buffer and 10 ul of stimulation buffer (prepared as described in the kit) was added to each well. In a separate plate, compounds were diluted in DMSO (400-fold over the final concentration in the assay well) and 25 nl was acoustically transferred to the appropriate well in the assay cell plate.

The plates were then incubated for 60 minutes at 37 degrees. 10 ul of detection buffer (also prepared as described in the IP-One kit) was added to each well and the plates were incubated for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP1 standard curve prepared at the time of the assay.

The compounds of the present invention, including the compounds in Examples 1-159, have $EC_{50}$ values less than 12 micromolar (μM) in the Inositol Phosphate Turnover (IP1) Assay 1 or in the Inositol Phosphate Turnover (IP1) Assay 2 described above. The compounds in Examples 1-159 have the $EC_{50}$ values in the Inositol Phosphate Turnover (IP1) Assay 1 and Inositol Phosphate Turnover (IP1) Assay 2 listed in Table A.

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

TABLE A $EC_{50}$ values in Human GPR40 FLIPR and IP1 Assays

| Example Number | Human GPR40 FLIPR, EC50, nM | Human GPR40 IP1, EC50, nM (Assay 1) | Human GPR40 IP1, EC50, nM (Assay 2) |
| --- | --- | --- | --- |
| 1 | 1.9 | 89 | ND |
| 2 | 173 | 1834 | ND |
| 3 | 126 | 8381 | ND |
| 4 | 77 | 485 | ND |
| 5A | 455 | 4154 | ND |
| 5B | 113 | 2135 | ND |
| 6 | 95 | 2725 | ND |
| 7 | 2 | 89 | ND |
| 8 | 15 | 866 | ND |
| 9 | 4 | 217 | ND |
| 10 | 0.9 | 102 | ND |
| 11 | 22 | 967 | ND |
| 12 | 111 | 4662 | ND |
| 13 | 129 | 1851 | ND |
| 14 | 26 | 956 | ND |
| 15 | 79 | 2083 | ND |
| 16 | 79 | 631 | ND |
| 17 | 285 | 2531 | ND |
| 18 | 359 | 3712 | ND |
| 19 | 497 | 4781 | ND |
| 20 | 266 | 10000 | ND |
| 21 | 13 | 297 | ND |
| 22 | 85 | 2612 | ND |
| 23 | 72 | 1045 | ND |
| 24 | 7.4 | 524 | ND |
| 25 | 1.4 | 79 | ND |
| 26 | 1.5 | 55 | ND |
| 27 | 0.3 | 7.6 | ND |
| 28 | 21 | 613 | ND |
| 29 | 51 | 711 | ND |
| 30 | 33 | 279 | ND |
| 31 | 1 | 77 | ND |
| 32 | 59 | 764 | ND |
| 33 | 5.3 | 158 | ND |
| 34 | 10 | 273 | ND |
| 35 | ND | 20 | ND |
| 36 | ND | 12 | ND |
| 37 | ND | 177 | ND |
| 38 | ND | 13 | ND |
| 39 | ND | 218 | ND |
| 40 | ND | 25 | ND |
| 41 | ND | 23 | ND |
| 42 | 94 | 1125 | ND |
| 43 | 231 | 952 | ND |
| 44 | 13 | 309 | ND |
| 45 | 387 | ND | ND |
| 46 | 108 | 1460 | ND |
| 47 | 42 | 560 | ND |
| 48 | 142 | 1025 | ND |
| 49 | 8.3 | 251 | ND |
| 50 | 55 | 5031 | ND |
| 51 | 58 | 449 | ND |
| 52 | 162 | 5638 | ND |
| 53 | 389 | 4567 | ND |
| 54 | 0.6 | 27 | ND |
| 55 | 7.3 | 904 | ND |
| 56 | 23 | 347 | ND |
| 57 | 480 | ND | ND |
| 58 | 113 | 366 | ND |
| 59 | 439 | 777 | ND |
| 60 | 184 | 527 | ND |
| 61 | 24 | 651 | ND |
| 62 | 5.7 | 166 | ND |
| 63 | 15 | 348 | ND |
| 64 | ND | 60 | ND |
| 65 | ND | 22 | ND |
| 66 | ND | 119 | ND |
| 67 | ND | 408 | ND |
| 68 | ND | 304 | ND |
| 69 | ND | 166 | ND |
| 70 | ND | 146 | ND |
| 71 | ND | 187 | ND |
| 72 | ND | 201 | ND |
| 73 | ND | 43 | ND |
| 74 | ND | 56 | ND |
| 75 | ND | 34 | ND |
| 76 | ND | 138 | ND |
| 77 | ND | 606 | ND |
| 78 | ND | 75 | ND |
| 79 | ND | 118 | ND |
| 80 | ND | 12 | ND |
| 81 | ND | 45 | ND |
| 82 | ND | 172 | ND |
| 83 | ND | 94 | ND |
| 84 | ND | 14 | ND |
| 85 | ND | 35 | ND |
| 86 | ND | 102 | ND |
| 87 | ND | 23 | 13 |
| 88 | ND | 930 | ND |
| 89 | ND | 61 | ND |
| 90 | ND | ND | 96 |
| 91 | ND | ND | 7.4 |
| 92 | ND | 208 | ND |
| 93 | ND | 181 | ND |
| 94 | ND | 110 | ND |
| 95 | ND | 1386 | ND |
| 96 | ND | 8233 | ND |
| 97 | ND | 7235 | ND |
| 98 | ND | 1480 | ND |
| 99 | ND | 2669 | ND |
| 100 | ND | 560 | ND |
| 101 | ND | 7221 | ND |
| 102 | ND | 643 | ND |
| 103 | ND | 187 | ND |
| 104 | ND | 564 | ND |
| 105 | ND | 56 | ND |
| 106 | ND | 54 | ND |
| 107 | ND | 3449 | ND |
| 108 | ND | 1973 | ND |
| 109 | ND | 7189 | ND |
| 110 | ND | 1961 | ND |
| 111 | ND | 3097 | ND |
| 112 | ND | 109 | ND |
| 113 | ND | 1208 | ND |

TABLE A-continued

EC$_{50}$ values in Human GPR40 FLIPR and IP1 Assays

| Example Number | Human GPR40 FLIPR, EC50, nM | Human GPR40 IP1, EC50, nM (Assay 1) | Human GPR40 IP1, EC50, nM (Assay 2) |
|---|---|---|---|
| 114 | ND | 107 | ND |
| 115 | ND | 110 | ND |
| 116 | ND | 77 | ND |
| 117 | ND | 50 | ND |
| 118 | ND | 156 | ND |
| 119 | ND | 98 | ND |
| 120 | ND | 975 | ND |
| 121 | ND | 561 | ND |
| 122 | ND | 597 | ND |
| 123 | ND | 324 | ND |
| 124 | ND | 577 | ND |
| 125 | ND | 565 | ND |
| 126 | ND | 147 | ND |
| 127 | ND | 182 | ND |
| 128 | ND | 72 | ND |
| 129 | ND | 109 | ND |
| 130 | ND | 139 | ND |
| 131 | ND | 119 | ND |
| 132 | ND | 150 | ND |
| 133 | ND | 152 | ND |
| 134 | ND | 85 | ND |
| 135 | ND | 307 | ND |
| 136 | ND | 262 | ND |
| 137 | ND | 176 | ND |
| 138 | ND | 74 | ND |
| 139 | ND | 188 | ND |
| 140 | ND | 225 | ND |
| 141 | ND | 109 | ND |
| 142 | ND | 78 | ND |
| 143 | ND | 175 | ND |
| 144 | ND | 385 | ND |
| 145 | ND | 223 | ND |
| 146 | ND | 111 | ND |
| 147 | ND | 4436 | ND |
| 148 | ND | 1159 | ND |
| 149 | ND | 802 | ND |
| 150 | ND | 4472 | ND |
| 151 | ND | 90 | ND |
| 152 | ND | 89 | ND |
| 153 | ND | 325 | ND |
| 154 | ND | 544 | ND |
| 155 | ND | 316 | ND |
| 156 | ND | 355 | ND |
| 157 | ND | 130 | ND |
| 158 | ND | 26 | ND |
| 159 | ND | 472 | ND |

ND is not determined

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

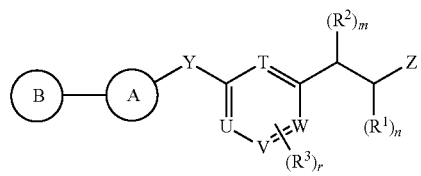

or a pharmaceutically acceptable salt thereof; wherein

A is selected from the group consisting of:
(1) —$C_{3-9}$cycloalkyl,
(2) —$C_{3-9}$cycloalkenyl, and
(3) —$C_{2-10}$cycloheteroalkyl,
wherein each cycloalkyl, cycloalkenyl and cycloheteroalkyl is unsubstituted or substituted with one, two or three substituents selected from $R^a$;

B is selected from the group consisting of:
(1) —$(CH_2)_u$-aryl,
(2) —$(CH_2)_u$-heteroaryl,
(3) —$(CH_2)_u$—$N(R^g)$—$(CH_2)_u$-aryl, and
(4) —$(CH_2)_u$—O—$(CH_2)_u$-aryl,
wherein each $CH_2$, aryl and heteroaryl is unsubstituted or substituted with one, two, three, four or five substituents selected from $R^b$;

T, U, V and W are CH;

Y is selected from: —O—, —$(CH_2)_x$O— and —O—$(CH_2)_x$, wherein $CH_2$ is unsubstituted or substituted with one or two substituents selected from $R^i$;

Z is —$CO_2H$;

$R^1$ is selected from the group consisting of:
(1) hydrogen, and
(2) —$C_{1-6}$alkyl,
wherein alkyl is unsubstituted or substituted with one, two or three halogens;

$R^2$ is —$C_{3-6}$cycloalkyl, wherein cycloalkyl is unsubstituted or substituted with one, two or three substituents selected from halogen, OH, —$C_{1-6}$alkyl and —$OC_{1-6}$alkyl;

each $R^3$ is independently selected from the group consisting of:
(1) hydrogen,
(2) halogen,
(3) —$(CH_2)_s$—$OC_{1-6}$alkyl,
(4) —$(CH_2)_s$—OH,
(5) —CN, and
(6) —$C_{1-6}$alkyl,
wherein $CH_2$ and alkyl are unsubstituted or substituted with one, two or three substituents selected from halogen, OH, and $OC_{1-6}$alkyl;

each $R^a$ is independently selected from the group consisting of:
(1) —$C_{1-6}$alkyl,
(2) halogen,
(3) —$(CH_2)_u$—$OC_{1-6}$alkyl,
(4) —$OR^e$,
(5) —$S(O)_uR^e$,
(6) —$S(O)_uNR^cR^d$,
(7) —$N(R^c)S(O)_pR^e$,
(8) —$NR^cR^d$,
(9) —$C(O)R^e$,
(10) —$OC(O)R^e$,
(11) —$CO_2R^e$,
(12) —$N(R^c)C(O)R^e$,
(13) —$N(R^c)C(O)OR^e$,
(14) —$N(R^c)C(O)NR^cR^d$,
(15) —$C(O)NR^cR^d$,
(16) —CN,
(17) —$CF_3$,
(18) —$OCF_3$,
(19) —$OCHF_2$,
(20) —$(CH_2)_r$aryl,
(21) —$(CH_2)_r$heteroaryl,
(22) —$(CH_2)_r$—$C_{3-6}$cycloalkyl,
(23) —$(CH_2)_r$—$C_{3-6}$cycloalkenyl,
(24) —$(CH_2)_r$—$C_{2-5}$cycloheteroalkyl, and
(25) —$(CH_2)_r$—O—$(CH_2)_r$—$C_{3-6}$cycloalkyl,
wherein each $CH_2$, alkyl, cycloalkyl, cycloalkenyl, cycloheteroalkyl, aryl and heteroaryl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl;
each $R^b$ is selected from the group consisting of:
1) —$C_{1-10}$alkyl,
2) —$C_{2-10}$alkenyl,
3) —$(CH_2)_v$—$CF_3$,
4) —$O(CH_2)_vCF_3$,
5) —$OCHF_2$,
6) halogen,
7) —$(CH_2)_v$CN,
8) —$(CH_2)_v$OH,
9) —$(CH_2)_v$$OC_{1-10}$alkyl,
10) —$CO_2R^e$,
11) —$NR^cR^d$,
12) —$(CH_2)_v$$C_{3-6}$cycloalkyl,
13) —$(CH_2)_v$$C_{2-10}$cycloheteroalkyl,
14) —$(CH_2)_v$-aryl, and
15) —$(CH_2)_v$-heteroaryl,
wherein each CH, $CH_2$, alkyl, alkenyl, cycloalkyl, cycloheteroalkyl, aryl and heteroaryl is unsubstituted or substituted with one, two or three substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl;
each $R^c$ is independently selected from the group consisting of:
(1) hydrogen,
(2) $C_{1-10}$alkyl,
(3) $C_{3-6}$cycloalkyl,
(4) $C_{2-5}$cycloheteroalkyl,
(5) aryl, and
(6) heteroaryl,
wherein each alkyl, cycloalkyl, cycloheteroalkyl, aryl and heteroaryl is unsubstituted or substituted with one to three substituents selected from $C_{1-6}$alkyl;

each $R^d$ is independently selected from the group consisting of:
(1) hydrogen,
(2) $C_{1-10}$alkyl,
(3) $C_{3-6}$cycloalkyl,
(4) $C_{2-5}$cycloheteroalkyl,
(5) aryl, and
(6) heteroaryl,
wherein each alkyl, cycloalkyl, cycloheteroalkyl, aryl and heteroaryl is unsubstituted or substituted with one to three substituents selected from $C_{1-6}$alkyl;
each $R^e$ is independently selected from the group consisting of:
(1) hydrogen,
(2) $C_{1-10}$alkyl,
(3) $C_{3-6}$cycloalkyl,
(4) $C_{2-5}$cycloheteroalkyl,
(5) aryl, and
(6) heteroaryl,
wherein each alkyl, cycloalkyl, cycloheteroalkyl, aryl and heteroaryl is unsubstituted or substituted with one to three substituents selected from $C_{1-6}$alkyl;
each $R^g$ is independently selected from the group consisting of:
(1) hydrogen,
(2) halogen,
(3) $C_{1-6}$alkyl, and
(4) $C_{3-6}$cycloalkyl;
each $R^i$ is independently selected from the group consisting of:
(1) hydrogen,
(2) halogen,
(3) —$C_{1-6}$alkyl,
(4) —$(CH_2)_s$—O—$C_{1-6}$alkyl,
(5) —$(CH_2)_s$OH,
(6) —$N(R^c)S(O)_2R^e$,
(7) —$S(C_{1-6}$alkyl),
(8) —$(CH_2)_sSO_2C_{1-6}$alkyl,
(9) —$(CH_2)_sSO_2$—$(CH_2)_t$—$C_{3-6}$cycloalkyl,
(10) —$S(O)_2NR^cR^d$,
(11) —$NR^cR^d$,
(12) —$C(O)R^e$,
(13) —$OC(O)R^e$,
(14) —$CO_2R^e$,
(15) —$(CH_2)_s$CN,
(16) —$C(O)NR^cR^d$,
(17) —$N(R^c)C(O)R^e$,
(18) —$N(R^c)C(O)OR^e$,
(19) —$N(R^c)C(O)NR^cR^d$,
(20) —$CF_3$,
(21) —$OCF_3$,
(22) —$OCHF_2$,
(23) —$C_{3-6}$cycloalkyl, and
(24) —$C_{2-5}$cycloheteroalkyl,
wherein each $CH_2$, alkyl, cycloalkyl and cycloheteroalkyl is unsubstituted or substituted with one, two, three or four substituents selected from: —$C_{1-6}$alkyl and halogen;
n is 1;
m is 1;
each p is independently selected from: 0, 1 and 2;
each q is independently selected from: 0, 1 and 2;
each r is independently selected from: 1, 2, 3 and 4;
each s is independently selected from: 0, 1, 2 and 3;
each t is independently selected from: 0, 1, 2, 3 and 4;
each u is independently selected from: 0, 1, 2 and 3;
each v is independently selected from: 0, 1, 2, 3 and 4;

each w is independently selected from: 0, 1, 2 and 3; and
each x is independently selected from: 0, 1 and 2.

2. A compound of structural formula I:

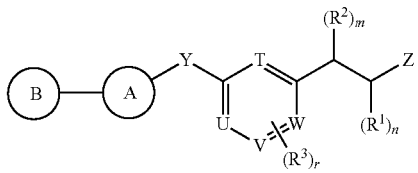

or a pharmaceutically acceptable salt thereof; wherein
A is —$C_{2-10}$cycloheteroalkyl, wherein each cycloheteroalkyl is unsubstituted or substituted with one, two or three substituents selected from $R^a$;
B is selected from the group consisting of:
(1) —$(CH_2)_u$-aryl, and
(2) -heteroaryl,
wherein each $CH_2$, aryl and heteroaryl is unsubstituted or substituted with one, two, three, four or five substituents selected from $R^b$;
T, U, V and W are CH;
Y is —$(CH_2)_xO$—, wherein $CH_2$ is unsubstituted or substituted with one or two substituents selected from $R^i$;
Z is —$CO_2H$;
$R^1$ is selected from the group consisting of:
(1) hydrogen, and
(2) —$C_{1-6}$alkyl,
wherein alkyl is unsubstituted or substituted with one, two or three halogens;
$R^2$ is —$C_{3-6}$ cycloalkyl, wherein cycloalkyl is unsubstituted or substituted with one, two or three substituents selected from halogen, OH, —$C_{1-6}$alkyl and —$OC_{1-6}$alkyl;
each $R^3$ is independently selected from the group consisting of:
(1) hydrogen,
(2) halogen,
(3) —$(CH_2)_s$—$OC_{1-6}$alkyl,
(4) —$(CH_2)_s$—OH,
(5) —CN, and
(6) —$C_{1-6}$alkyl,
wherein $CH_2$ and alkyl are unsubstituted or substituted with one, two or three substituents selected from halogen, OH, and $OC_{1-6}$alkyl;
each $R^a$ is independently selected from the group consisting of:
(1) —$C_{1-6}$alkyl,
(2) halogen,
(3) —$(CH_2)_u$—$OC_{1-6}$alkyl,
(4) —$OR^e$,
(5) —$S(O)_uR^e$,
(6) —$S(O)_uNR^cR^d$,
(7) —$N(R^c)S(O)_pR^e$,
(8) —$NR^cR^d$,
(9) —$C(O)R^e$,
(10) —$OC(O)R^e$,
(11) —$CO_2R^e$,
(12) —$N(R^c)C(O)R^e$,
(13) —$N(R^c)C(O)OR^e$,
(14) —$N(R^c)C(O)NR^cR^d$,
(15) —$C(O)NR^cR^d$,
(16) —CN,
(17) —$CF_3$,
(18) —$OCF_3$,
(19) —$OCHF_2$,
(20) —$(CH_2)_r$aryl,
(21) —$(CH_2)_r$heteroaryl,
(22) —$(CH_2)_r$—$C_{3-6}$cycloalkyl,
(23) —$(CH_2)_r$—$C_{3-6}$cycloalkenyl,
(24) —$(CH_2)_r$—$C_{2-5}$cycloheteroalkyl, and
(25) —$(CH_2)_r$—O—$(CH_2)_r$—$C_{3-6}$cycloalkyl,
wherein each $CH_2$, alkyl, cycloalkyl, cycloalkenyl, cycloheteroalkyl, aryl and heteroaryl is unsubstituted or substituted with one to four substituents selected from: halogen, —$C_{1-6}$alkyl, —$(CH_2)_w$—OH, —O—$C_{1-6}$alkyl, —$CF_3$, —CN, —$(CH_2)_v$—$C_{3-6}$cycloalkyl, SH, and —$SO_2$—$C_{1-6}$alkyl;
each $R^b$ is selected from the group consisting of:
1) —$C_{1-10}$alkyl,
2) —$C_{2-10}$alkenyl,
3) —$(CH_2)_v$—$CF_3$,
4) —$O(CH_2)_v CF_3$,
5) —$OCHF_2$,
6) halogen,
7) —$(CH_2)_v CN$,
8) —$(CH_2)_v OH$,
9) —$(CH_2)_v OC_{1-10}$alkyl, and
10) —$(CH_2)_v C_{3-6}$cycloalkyl,
wherein each CH, $CH_2$, alkyl, alkenyl and cycloalkyl is unsubstituted or substituted with one, two or three substituents selected from: halogen, —$C_{1-6}$alkyl, —$(CH_2)_w$—OH, —$CF_3$—CN, —$(CH_2)_v$—$C_{3-6}$cycloalkyl, SH, and —$SO_2$—$C_{1-6}$alkyl;
each $R^c$ is independently selected from the group consisting of:
(1) hydrogen,
(2) $C_{1-10}$alkyl,
(3) $C_{3-6}$cycloalkyl,
(4) $C_{2-5}$cycloheteroalkyl,
(5) aryl, and
(6) heteroaryl,
wherein each alkyl, cycloalkyl, cycloheteroalkyl, aryl and heteroaryl is unsubstituted or substituted with one to three substituents selected from $C_{1-6}$alkyl;
each $R^d$ is independently selected from the group consisting of:
(1) hydrogen,
(2) $C_{1-10}$alkyl,
(3) $C_{3-6}$cycloalkyl,
(4) $C_{2-5}$cycloheteroalkyl,
(5) aryl, and
(6) heteroaryl,
wherein each alkyl, cycloalkyl, cycloheteroalkyl, aryl and heteroaryl is unsubstituted or substituted with one to three substituents selected from $C_{1-6}$alkyl;
each $R^e$ is independently selected from the group consisting of:
(1) hydrogen,
(2) $C_{1-10}$alkyl,
(3) $C_{3-6}$cycloalkyl,
(4) $C_{2-5}$cycloheteroalkyl,
(5) aryl, and
(6) heteroaryl,
wherein each alkyl, cycloalkyl, cycloheteroalkyl, aryl and heteroaryl is unsubstituted or substituted with one to three substituents selected from $C_{1-6}$alkyl;
each $R^g$ is independently selected from the group consisting of:
(1) hydrogen,
(2) halogen, (3) $C_{1-6}$alkyl, and
(4) $C_{3-6}$cycloalkyl;
each $R^i$ is independently selected from the group consisting of:
(1) hydrogen,
(2) halogen,
(3) —$C_{1-6}$alkyl,
(4) —$(CH_2)_s$—O—$C_{1-6}$alkyl,
(5) —$(CH_2)_s$OH,
(6) —$N(R^c)S(O)_2R^e$,
(7) —$S(C_{1-6}$alkyl),
(8) —$(CH_2)_sSO_2C_{1-6}$alkyl,
(9) —$(CH_2)_sSO_2$—$(CH_2)_t$—$C_{3-6}$cycloalkyl,
(10) —$S(O)_2NR^cR^d$,
(11) —$NR^cR^d$,
(12) —$C(O)R^e$,
(13) —$OC(O)R^e$,
(14) —$CO_2R^e$,
(15) —$(CH_2)_sCN$,
(16) —$C(O)NR^cR^d$,
(17) —$N(R^c)C(O)R^e$,
(18) —$N(R^c)C(O)OR^e$,
(19) —$N(R^c)C(O)NR^cR^d$,
(20) —$CF_3$,
(21) —$OCF_3$,
(22) —$OCHF_2$,
(23) —$C_{3-6}$cycloalkyl, and
(24) —$C_{2-5}$cycloheteroalkyl,
wherein each $CH_2$, alkyl, cycloalkyl and cycloheteroalkyl is unsubstituted or substituted with one, two, three or four substituents selected from: —$C_{1-6}$alkyl and halogen;
each n is 1;
each m is 1;
each p is independently selected from: 0, 1 and 2;
each q is independently selected from: 0, 1 and 2;
each r is independently selected from: 1, 2, 3 and 4;
each s is independently selected from: 0, 1, 2 and 3;
each t is independently selected from: 0, 1, 2, 3 and 4;
each u is independently selected from: 0, 1, 2 and 3;
each v is independently selected from: 0, 1, 2, 3 and 4;
each w is independently selected from: 0, 1, 2 and 3; and
each x is independently selected from: 0, 1 and 2.

3. The compound according to claim 1 wherein Y is selected from: —O—, —$CH_2$—O—, and —O—$CH_2$— wherein $CH_2$ is unsubstituted or substituted with one or two substituents selected from $C_{1-6}$alkyl; or a pharmaceutically acceptable salt thereof.

4. The compound according to claim 1 wherein Y is selected from: —O— and —$CH_2$—O—, wherein $CH_2$ is unsubstituted or substituted with one or two substituents selected from $C_{1-6}$ alkyl; or a pharmaceutically acceptable salt thereof.

5. The compound according to claim 1 wherein $R^3$ is hydrogen; or a pharmaceutically acceptable salt thereof.

6. The compound according to claim 1 wherein
T, U, V and W are CH;
A is selected from the group consisting of:
(1) —$C_{3-6}$cycloalkyl,
(2) —$C_{3-6}$cycloalkenyl, and
(3) —$C_{2-10}$cycloheteroalkyl,
wherein each cycloalkyl, cycloalkenyl and cycloheteroalkyl is unsubstituted or substituted with one, two or three substituents selected from $R^a$;

Y is selected from: —O—, —$(CH_2)_xO$— and —O—$(CH_2)_x$, wherein $CH_2$ is unsubstituted or substituted with one or two substituents selected from $R^i$;
$R^3$ is hydrogen;
or a pharmaceutically acceptable salt thereof.

7. The compound according to claim 1 wherein
T, U, V and W are CH;
A is selected from the group consisting of:
(1) —$C_{3-6}$cycloalkyl,
(2) —$C_{3-6}$cycloalkenyl, and
(3) —$C_{2-10}$cycloheteroalkyl,
wherein each cycloalkyl, cycloalkenyl and cycloheteroalkyl is unsubstituted or substituted with one, two or three substituents selected from $R^a$;
B is selected from the group consisting of:
(1) —$(CH_2)_u$-aryl,
(2) —$(CH_2)_u$-heteroaryl,
(3) —$(CH_2)_u$—$NR^g(CH_2)_u$-aryl, and
(4) —$(CH_2)_u$—O—$(CH_2)_u$-aryl,
wherein each $CH_2$, aryl and heteroaryl is unsubstituted or substituted with one, two, three, four or five substituents selected from $R^b$;
Y is —$(CH_2)_xO$—, wherein $CH_2$ is unsubstituted or substituted with one or two substituents selected from $R^i$;
$R^3$ is hydrogen;
or a pharmaceutically acceptable salt thereof.

8. The compound according to claim 1 wherein
T, U, V and W are CH;
A is —$C_{2-10}$cycloheteroalkyl, wherein each cycloheteroalkyl is unsubstituted or substituted with one, two or three substituents selected from $R^a$;
B is selected from the group consisting of:
(1) —$(CH_2)_u$-aryl, and
(2) -heteroaryl,
wherein each $CH_2$, aryl and heteroaryl is unsubstituted or substituted with one, two, three, four or five substituents selected from $R^b$;
Y is selected from: —O— and —$CH_2$—O—, wherein $CH_2$ is unsubstituted or substituted with one or two substituents selected from $C_{1-6}$alkyl;
Z is —$CO_2H$;
$R^1$ is selected from the group consisting of:
(1) hydrogen, and
(2) —$C_{1-6}$alkyl,
wherein alkyl is unsubstituted or substituted with one, two or three halogens;
$R^2$ is —$C_{3-6}$cycloalkyl, wherein cycloalkyl is unsubstituted or substituted with one, two or three substituents selected from halogen, OH, —$C_{1-6}$alkyl and —$OC_{1-6}$alkyl;
$R^3$ is hydrogen;
or a pharmaceutically acceptable salt thereof.

9. A compound selected from:

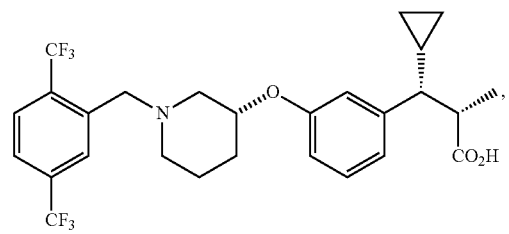

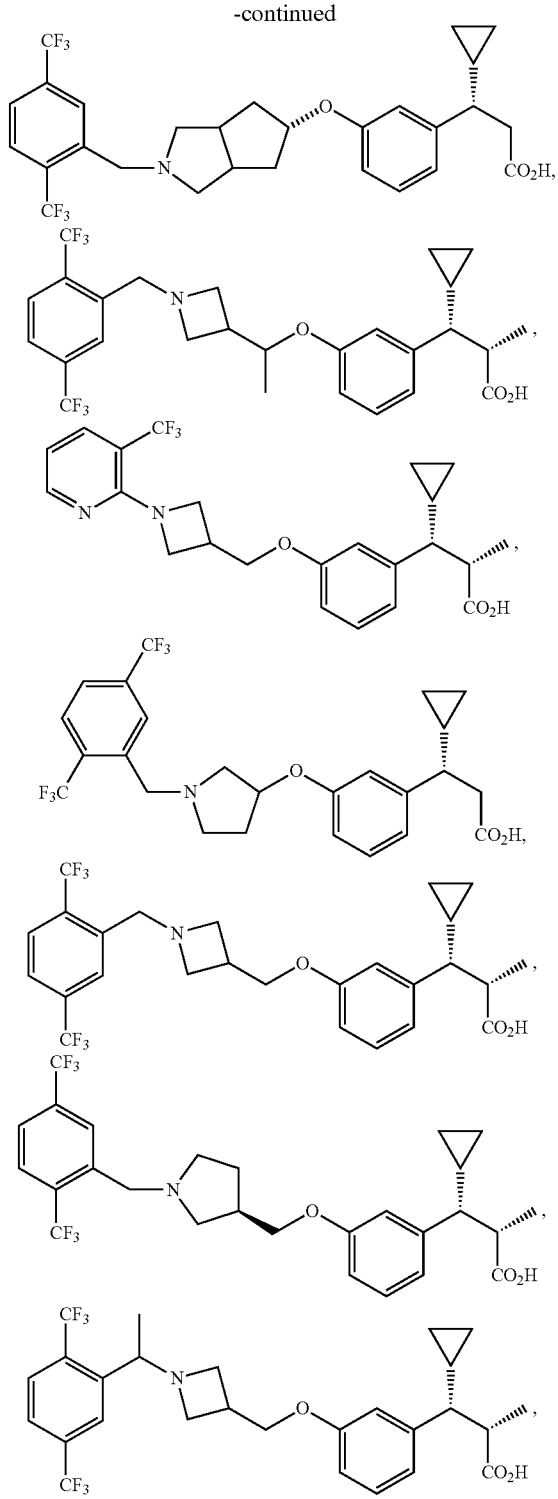
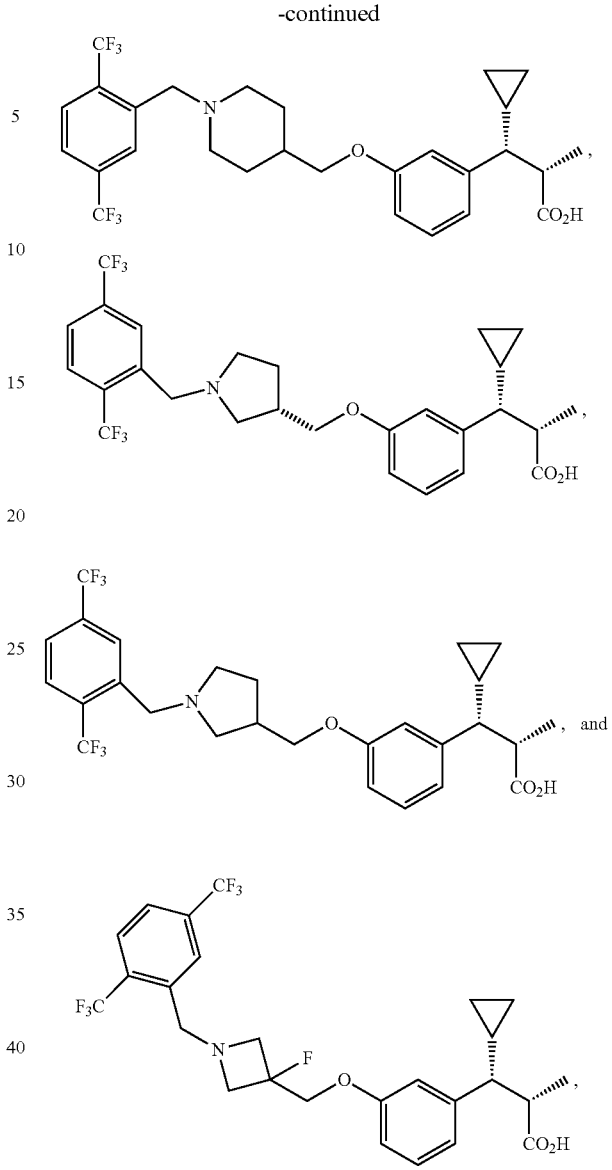

and pharmaceutically acceptable salts thereof.

10. A pharmaceutical composition comprising a compound of claim 1, or a pharmaceutically acceptable salt thereof, and a pharmaceutically acceptable carrier.

11. A method of treating type 2 diabetes mellitus in a patient in need of treatment comprising the administration to the patient of a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 10,059,667 B2  
APPLICATION NO. : 15/110894  
DATED : August 28, 2018  
INVENTOR(S) : Harry Chobanian et al.

Page 1 of 1

It is certified that error appears in the above-identified patent and that said Letters Patent is hereby corrected as shown below:

On the Title Page

At Item (72), add:  
-- Rui Zhang, Plainsboro, NJ (US) --

Signed and Sealed this  
Eleventh Day of June, 2019

Andrei Iancu  
*Director of the United States Patent and Trademark Office*